United States Patent
Lee et al.

(10) Patent No.: US 11,471,485 B2
(45) Date of Patent: Oct. 18, 2022

(54) METHOD OF GENERATING MULTI-LINEAGE POTENTIAL CELLS AND MULTI-LINEAGE POTENTIAL CELLS PRODUCED THEREFROM

(71) Applicant: JATT PTE. LTD., Singapore (SG)

(72) Inventors: Yi-Chen Lee, Keelung (CN); Tina Yu-Ming Pai, New South Wales (AU)

(73) Assignee: LAI CORPORATION PTY LTD

( * ) Notice: Subject to any disclaimer, the term of this patent is extended or adjusted under 35 U.S.C. 154(b) by 666 days.

(21) Appl. No.: 16/217,335

(22) Filed: Dec. 12, 2018

(65) Prior Publication Data
US 2019/0381096 A1    Dec. 19, 2019

(30) Foreign Application Priority Data
Jun. 18, 2018  (AU) ................................ 2018902168

(51) Int. Cl.
| | | |
|---|---|---|
| *A61K 35/15* | (2015.01) | |
| *A61K 35/545* | (2015.01) | |
| *C12N 5/078* | (2010.01) | |
| *C12N 5/0786* | (2010.01) | |
| *C12N 5/0787* | (2010.01) | |
| *C12N 5/0781* | (2010.01) | |
| *A61P 9/00* | (2006.01) | |
| *A61P 25/00* | (2006.01) | |
| *A61K 35/17* | (2015.01) | |
| *C12N 5/0783* | (2010.01) | |

(52) U.S. Cl.
CPC .............. *A61K 35/15* (2013.01); *A61K 35/17* (2013.01); *A61K 35/545* (2013.01); *A61P 9/00* (2018.01); *A61P 25/00* (2018.01); *C12N 5/0635* (2013.01); *C12N 5/0636* (2013.01); *C12N 5/0642* (2013.01); *C12N 5/0644* (2013.01); *C12N 5/0645* (2013.01)

(58) Field of Classification Search
None
See application file for complete search history.

(56) References Cited

U.S. PATENT DOCUMENTS

| | | | |
|---|---|---|---|
| 7,410,773 B2 * | 8/2008 | Abuljadayel | ........ C12N 5/0634 435/377 |
| 7,795,018 B2 | 9/2010 | Kuwana et al. | |
| 2010/0047908 A1 * | 2/2010 | Winnier | ............... C12N 5/0647 435/372 |
| 2015/0353897 A1 * | 12/2015 | Pai | ......................... A61K 35/15 424/93.71 |

FOREIGN PATENT DOCUMENTS

| | | | |
|---|---|---|---|
| WO | WO2006084672 | * | 8/2006 |
| WO | 2014/085871 A1 | | 6/2014 |
| WO | 2015/184506 A1 | | 12/2015 |

OTHER PUBLICATIONS

Alison et al., "Review—Hepatic stem cells", Journal of Hepatology, vol. 29, 1998, pp. 676-682. (Cited in specification on p. 1.).
Campagnoli et al., "Identification of mesenchymal stem/progenitor cells in human first-trimester fetal blood, liver, and bone marrow", Blood Journal, vol. 98, No. 8, Oct. 15, 2001, pp. 2396-2402. (Cited in specification on p. 1.).
Erices et al., "Mesenchymal progenitor cells in human umbilical cord blood", British Journal of Haematology, vol. 109, 2000, pp. 235-242. (Cited in specification on p. 1.).
Gage, "Mammalian Neural Stem Cells", Science, vol. 287, Feb. 25, 2000, pp. 1433-1438. (Cited in specification on p. 1.).
Pittenger et al., "Multilineage Potential of Adult Human Mesenchymal Stem Cells", Science, vol. 284, Apr. 2, 1999, pp. 143-147. (Cited in specification on p. 1.).
Weissman, "Translating Stem and Progenitor Cell Biology to the Clinic: Barriers and Opportunities", Science, vol. 287, Feb. 25, 2000, p. 1442 1446. (Cited in specification on p. 1.).
Zvaifler et al., "Mesenchymal precursor cells in the blood of normal individuals", Arthritis Research, vol. 2, No. 6, Aug. 31, 2000, pp. 1-12. (Cited in specification on p. 1.).

* cited by examiner

*Primary Examiner* — Michail A Belyavskyi
(74) *Attorney, Agent, or Firm* — Fresh IP PLC; Clifford D. Hyra; Aubrey Y. Chen

(57) ABSTRACT

The present invention is directed to a method of generating multilineage potential cells by de-differentiation of somatic leukocytes in a mixed leukocyte suspension from a blood sample. The present invention is also directed to the use of the generated multilineage potential cells to treat conditions in humans and mammals.

9 Claims, 134 Drawing Sheets

FIGURE 1 (continued)
6th day
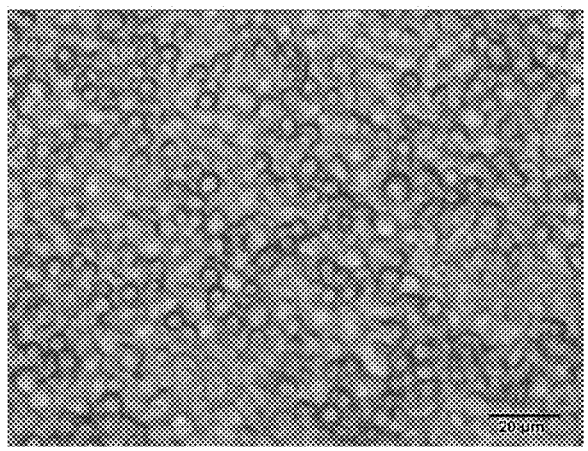
9th day
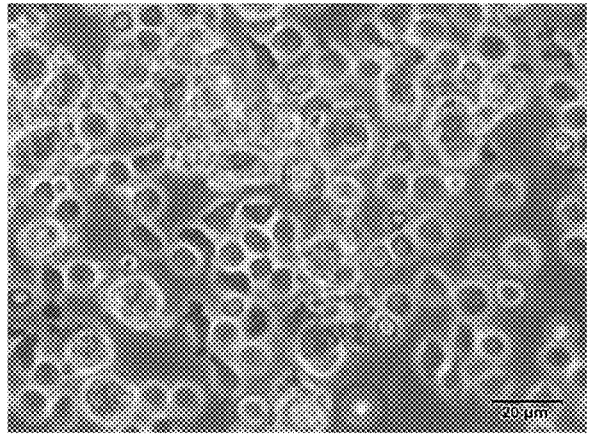
10th day
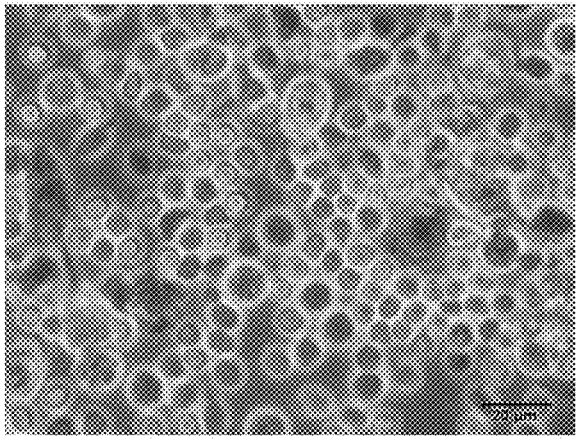

Synaptophysin

HIF-1 alpha

Figure 14
(A) First stage: 10$^{th}$ day
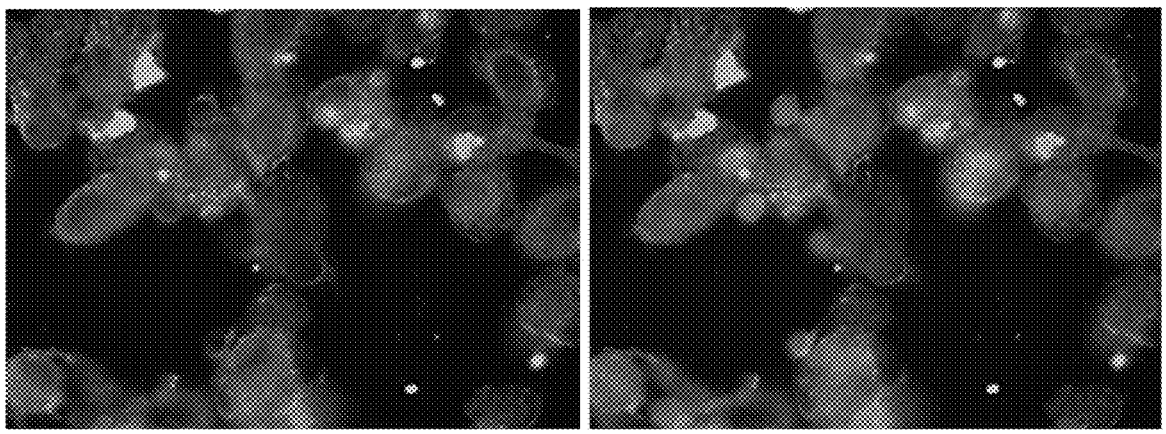
(B) Second stage: 12$^{th}$ day
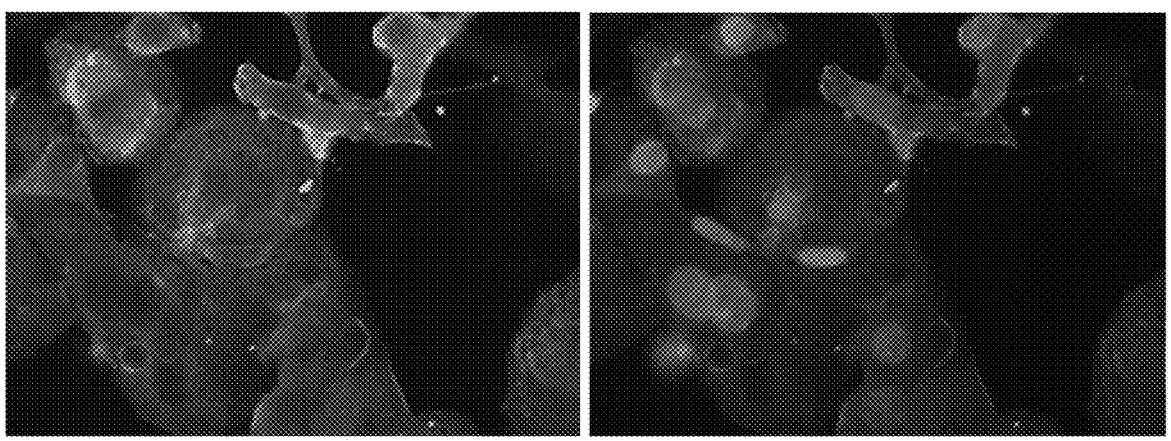
(C) Second stage: 16$^{th}$ day
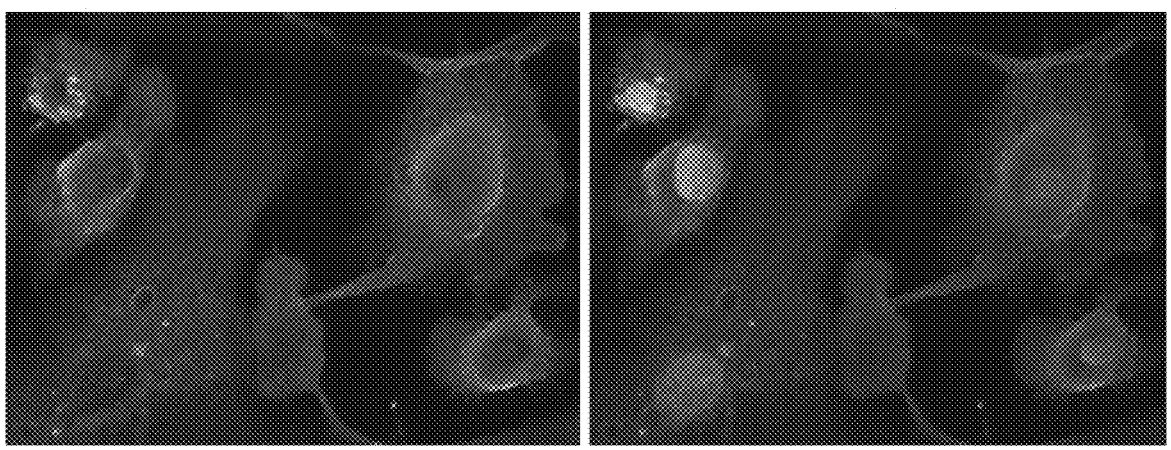

(D) Second stage: 20th day

Figure 15
(A) First stage: 10th day
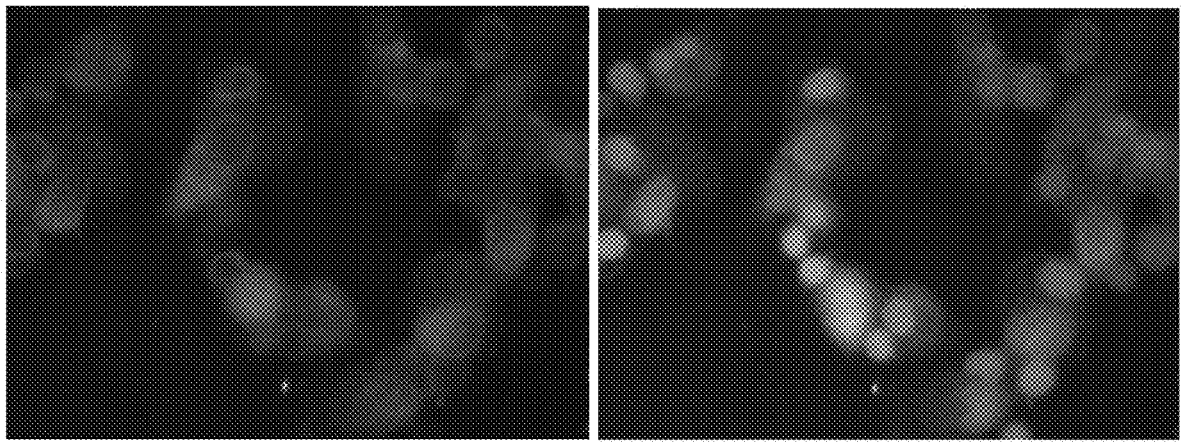
(B) Second stage: 12th day
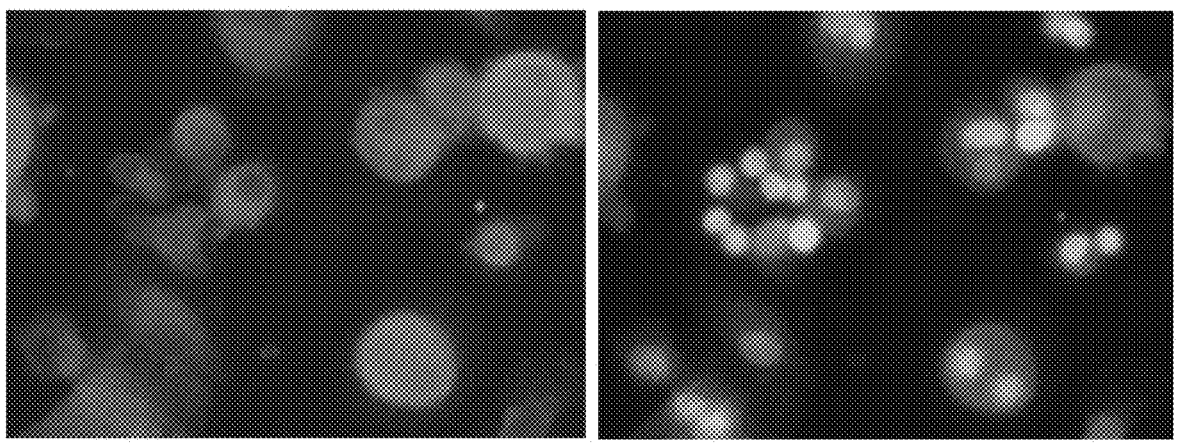
(C) Second stage: 16th day
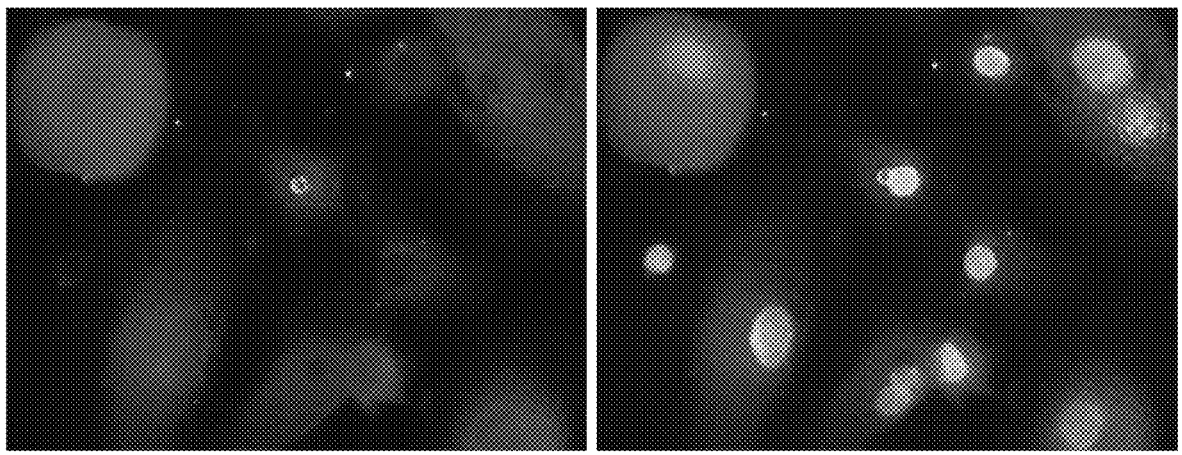

(D) Second stage: 20th day

Figure 16
(A) First stage: 10$^{th}$ day
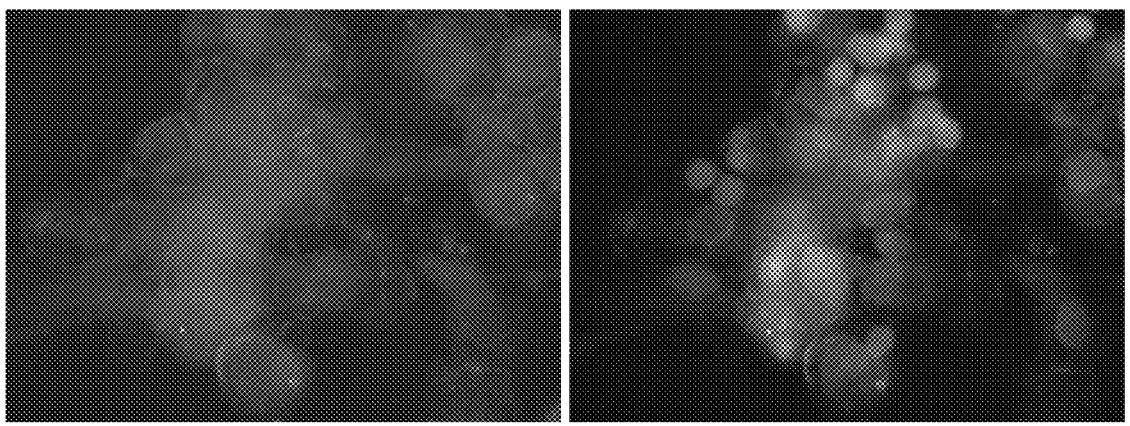
(B) Second stage: 12$^{th}$ day
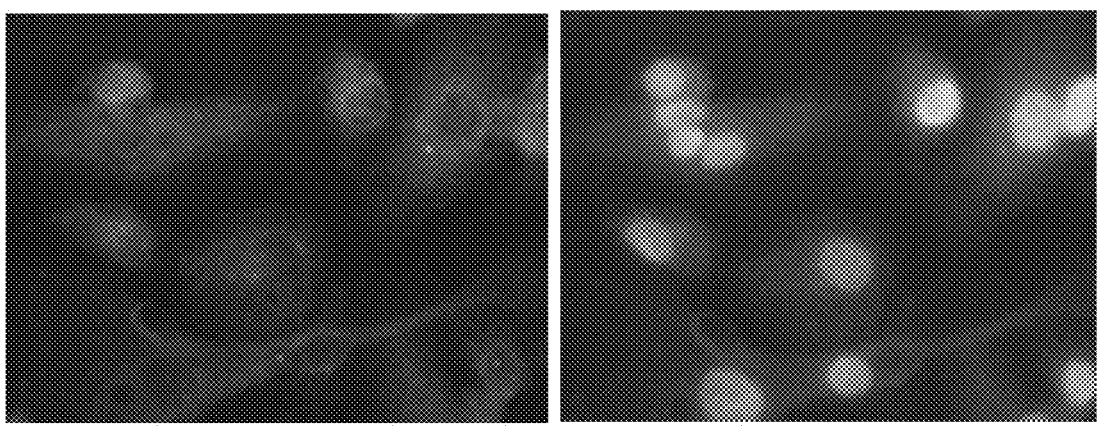
(C) Second stage: 16$^{th}$ day
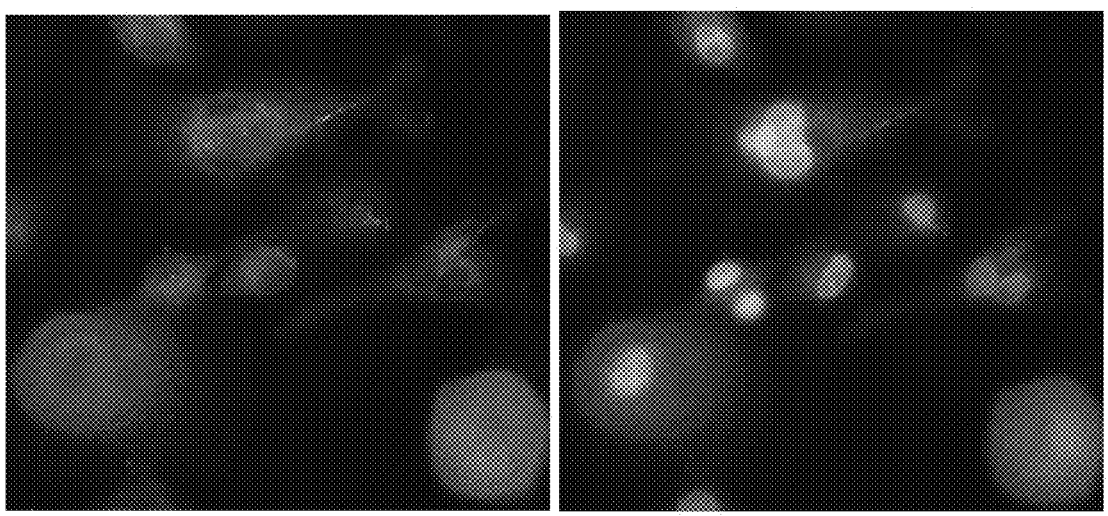

(D) Second stage: 20th day

Figure 17
(A) First stage: 10th day
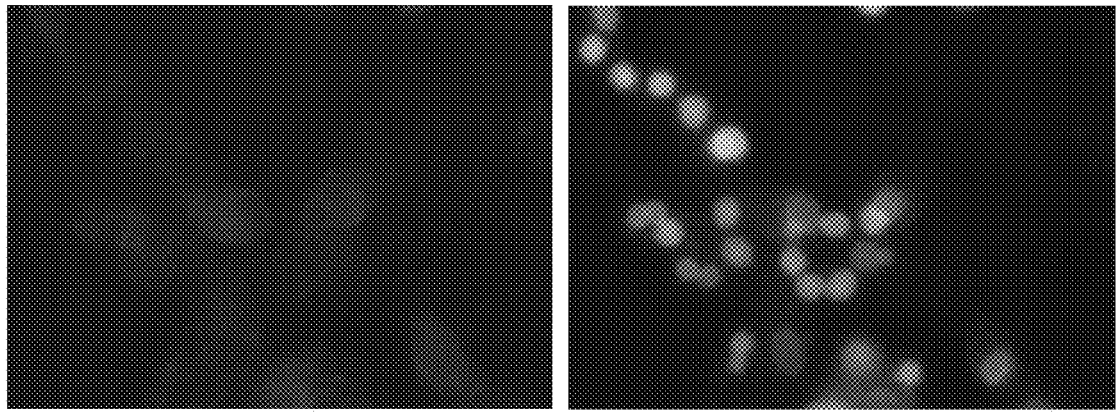
(B) Second stage: 12th day
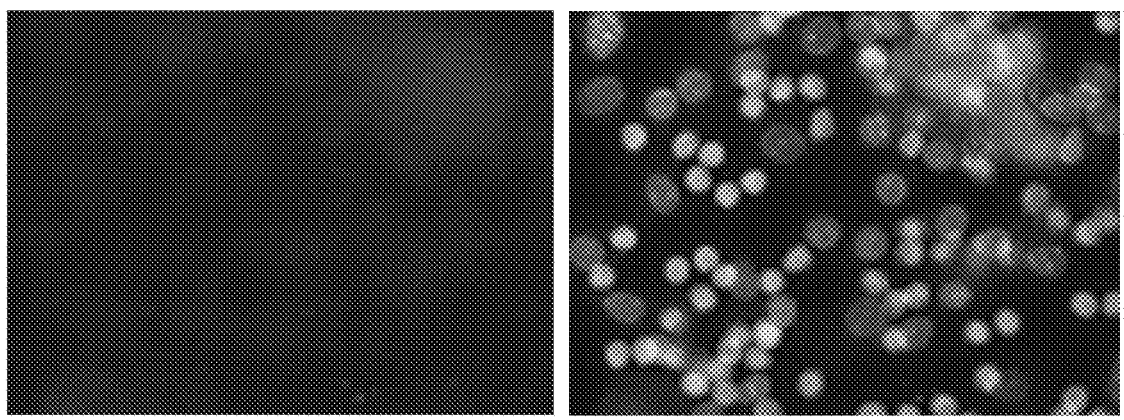
(C) Second stage: 16th day
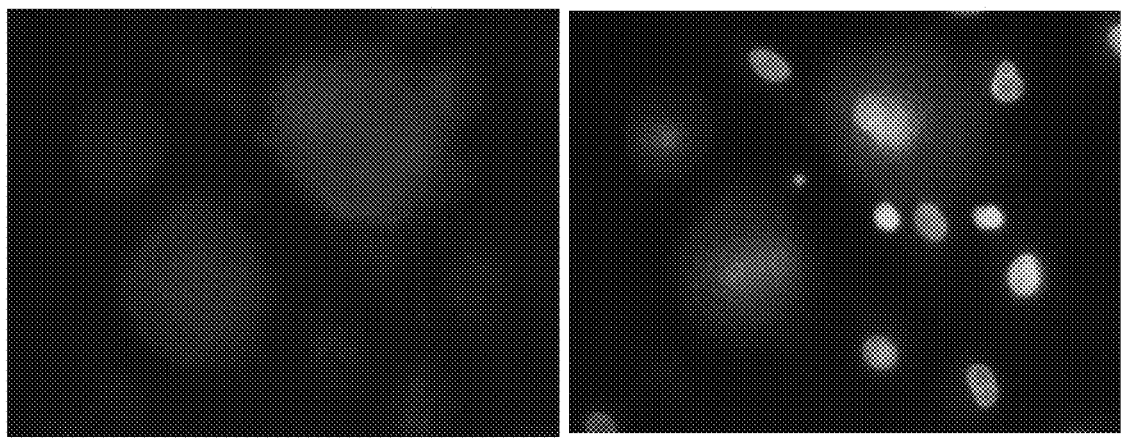

(D) Second stage: 20th day

Figure 19
(A) Second stage: 8th day
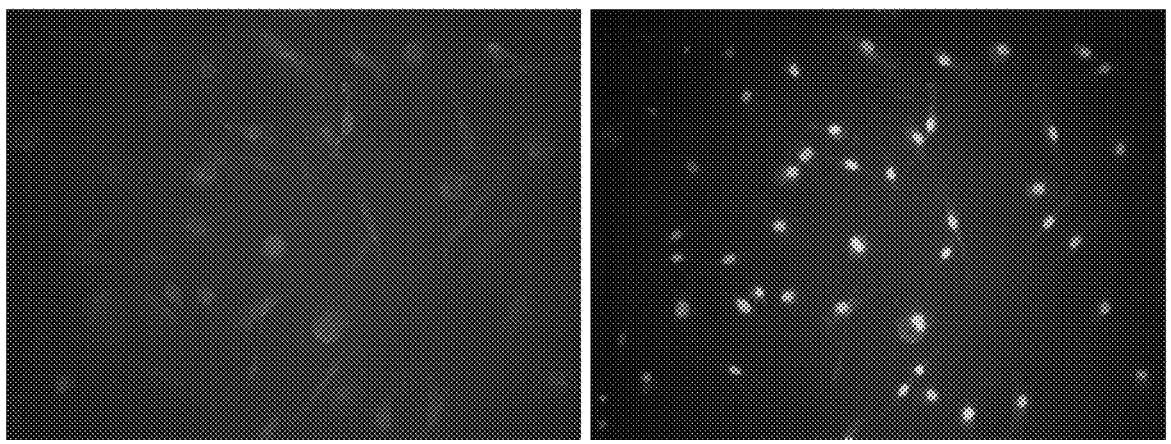
(B) Second stage: 12th day
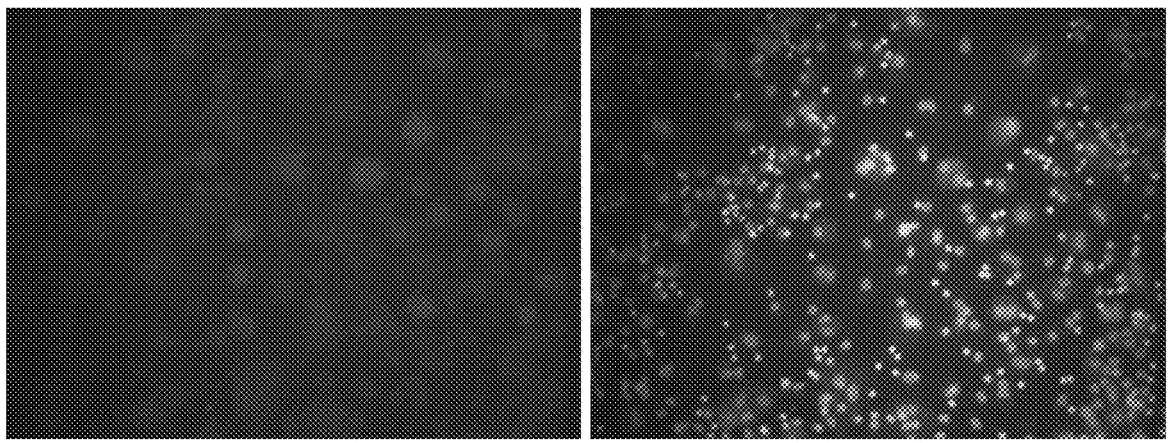

Figure 20
(A) Second stage: 8th day
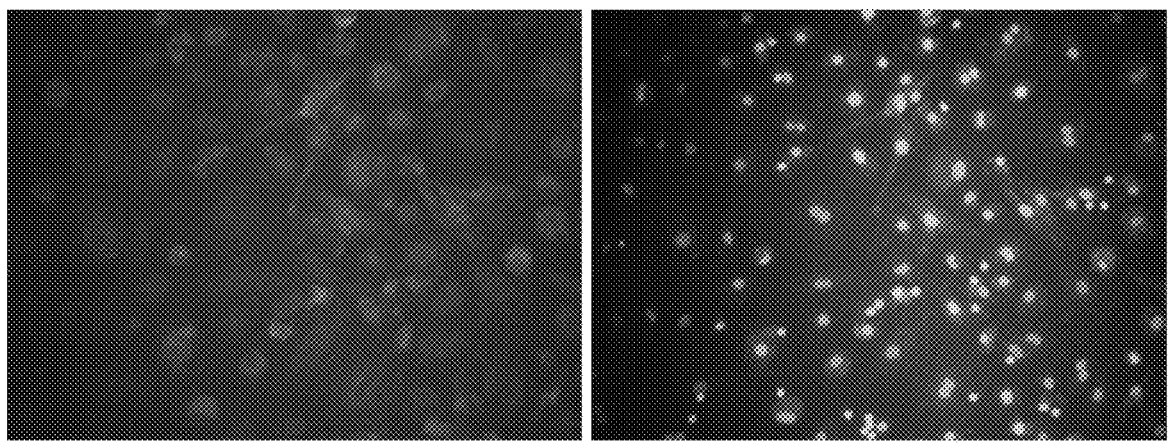
(B) Second stage: 12th day
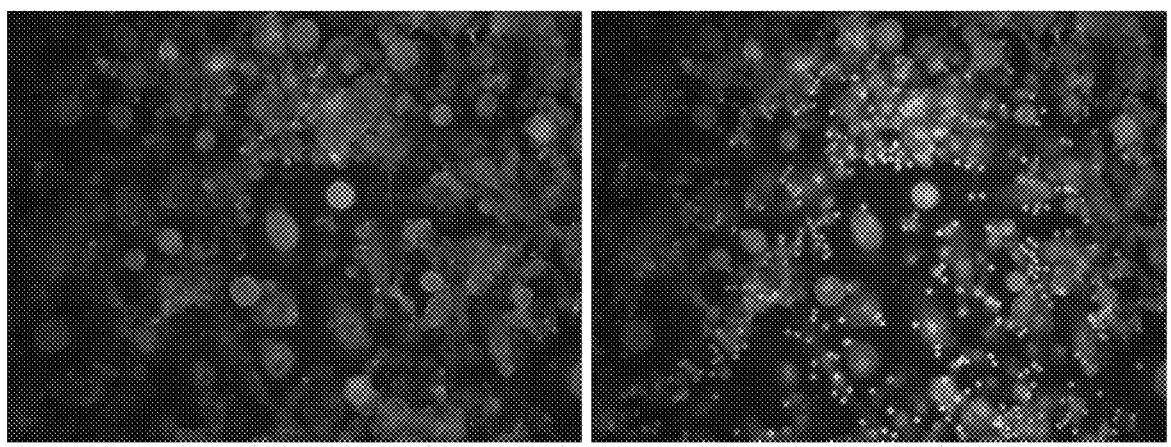

Figure 21
(A) Second stage: 12$^{th}$ day
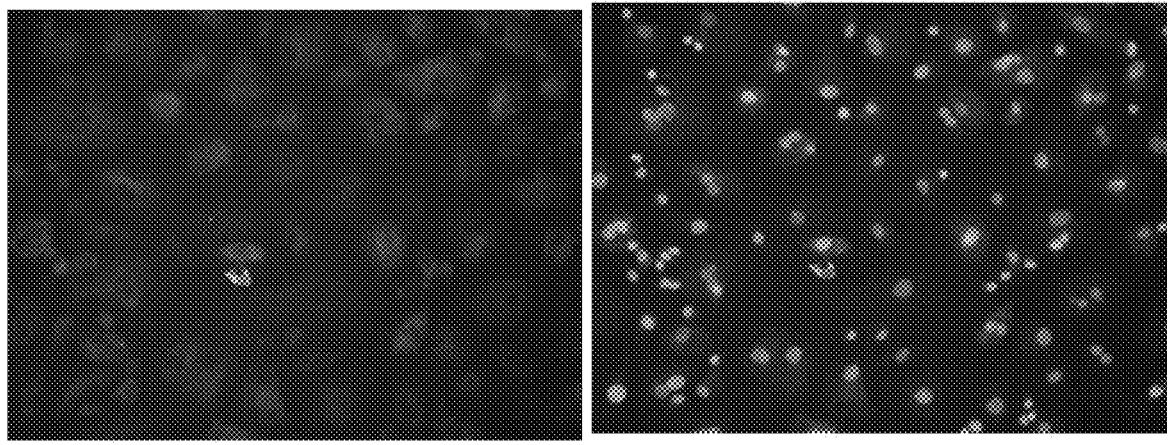
(B) Second stage: 16$^{th}$ day
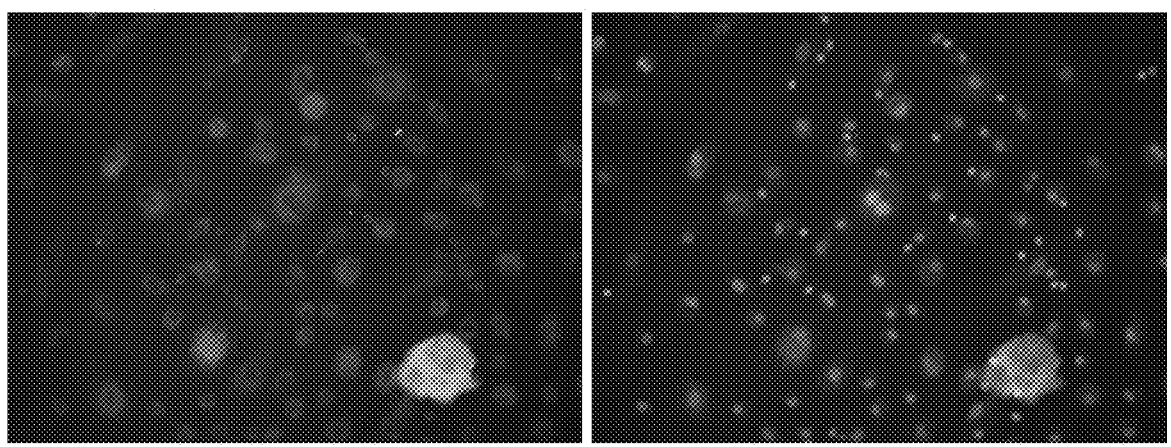
(C) Second stage: 19$^{th}$ day
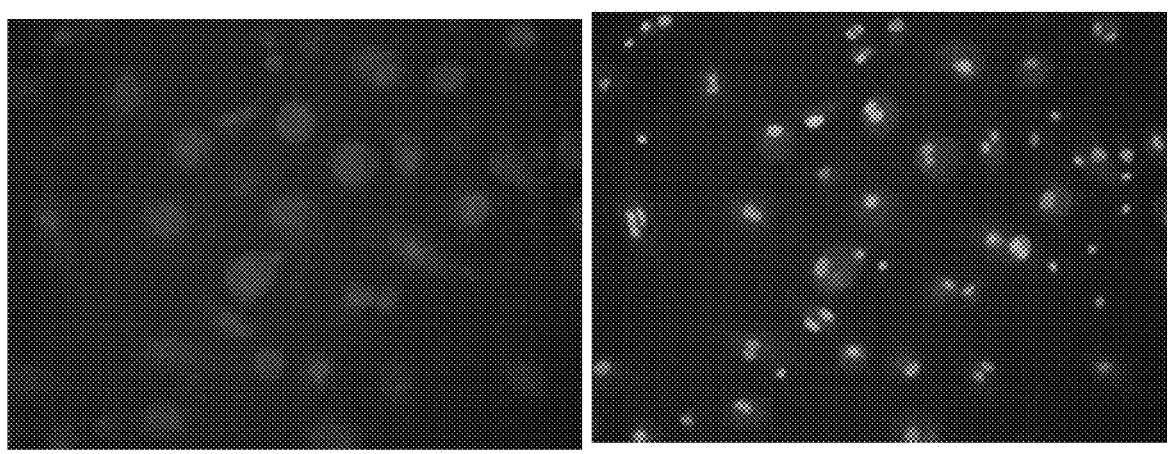

Figure 22
(A) Second stage: 12<sup>th</sup> day
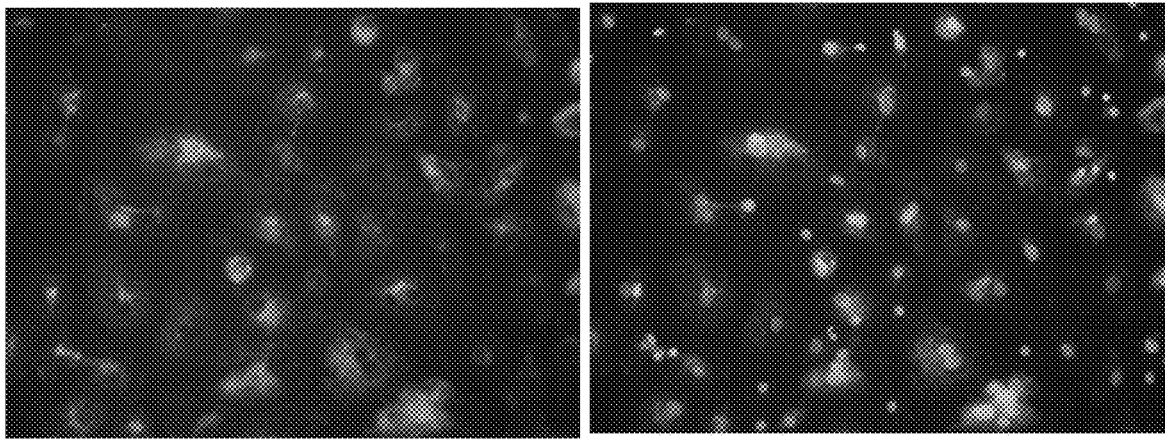
(B) Second stage: 16<sup>th</sup> day
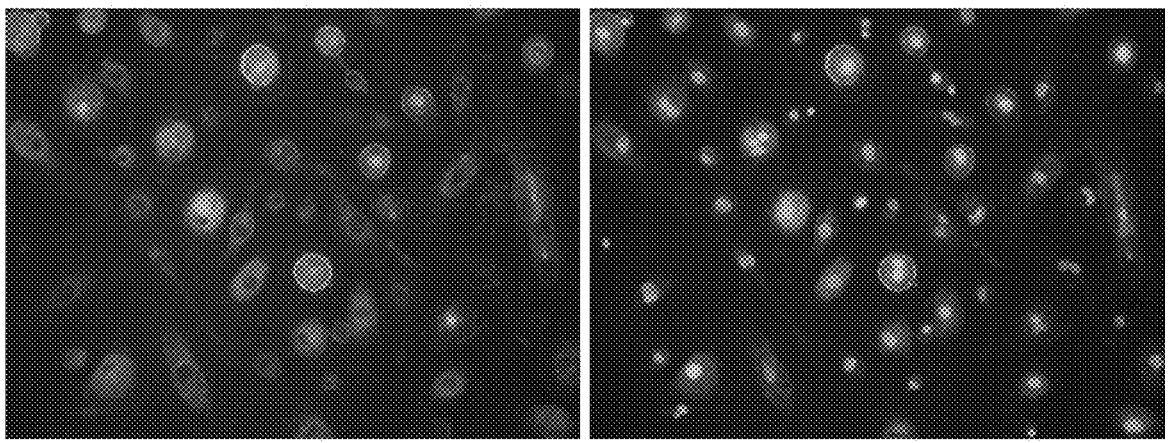
(C) Second stage: 19<sup>th</sup> day
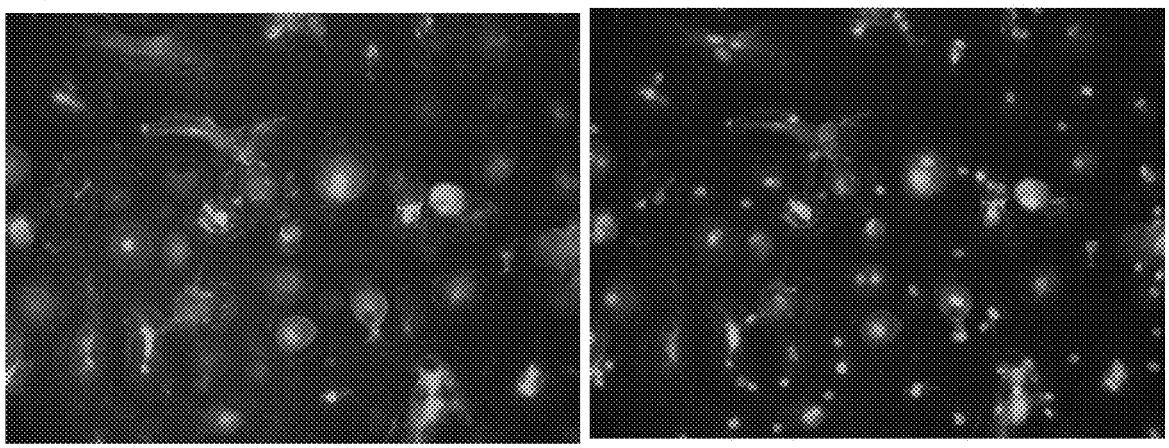

Figure 46
(A) Adherent cells
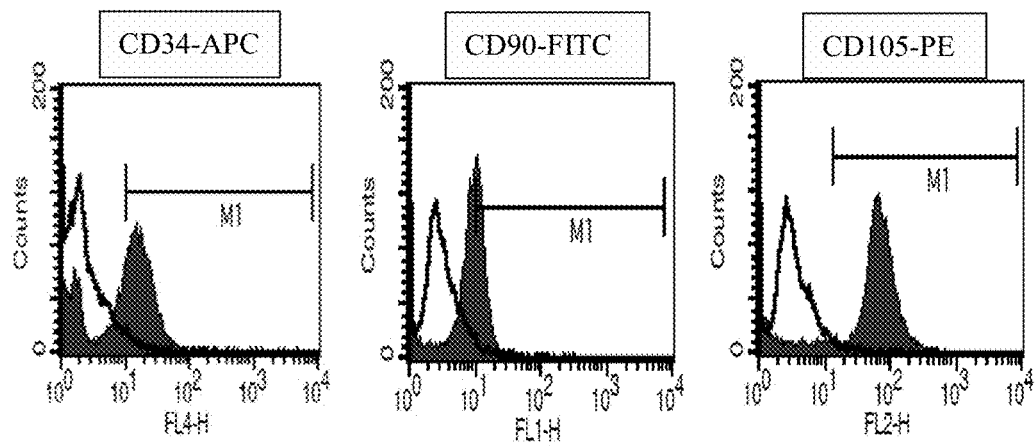
(B) Un-adherent cells
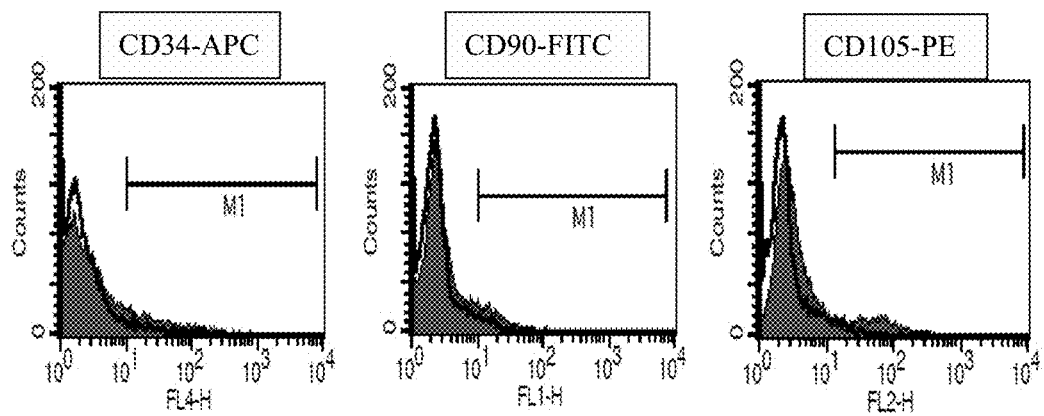

Figure 47
(A) First stage: Un-induction
$0^{st}$ day
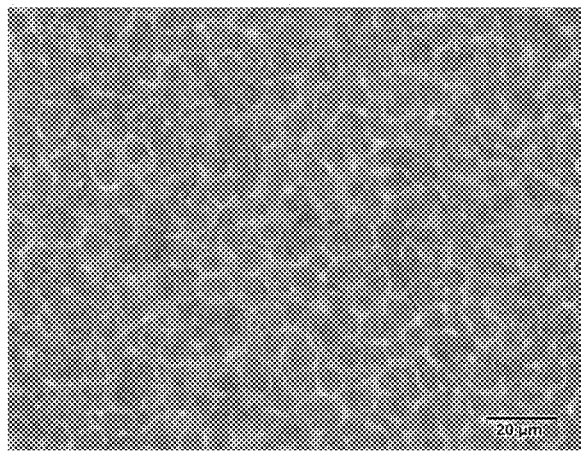
$4^{th}$ day
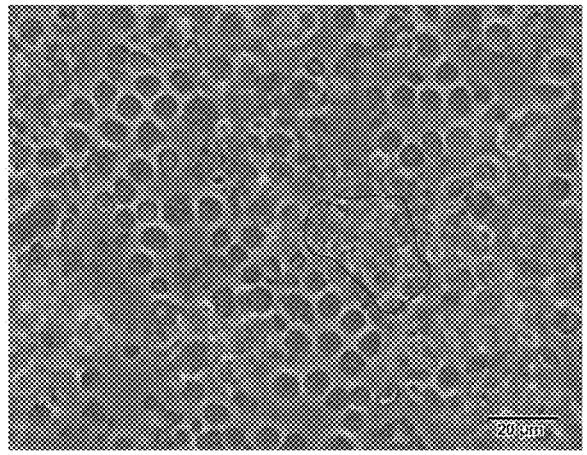
$6^{th}$ day
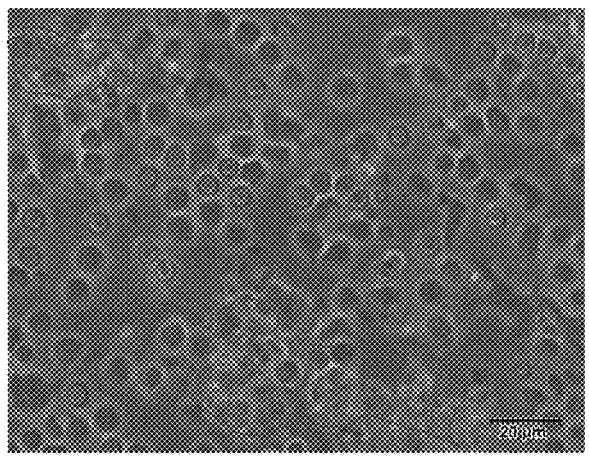
$10^{th}$ day
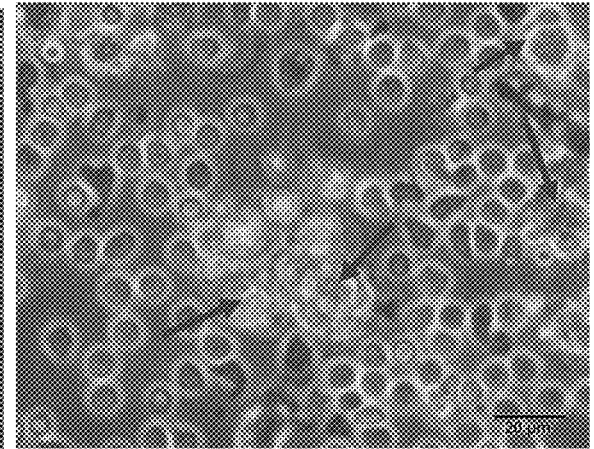

Figure 47 (continued)
(B) Second stage: Induction
12th day
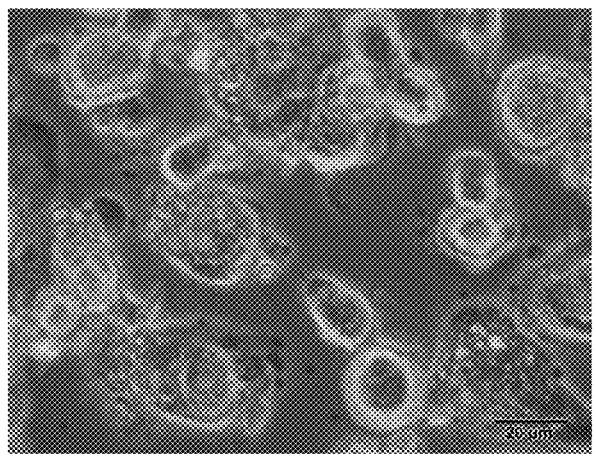
16th day
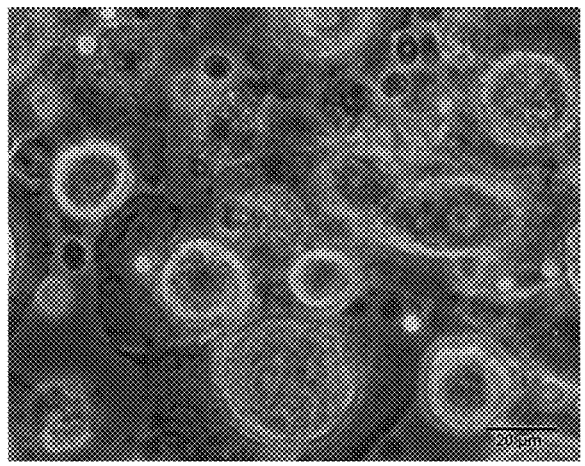
20th day
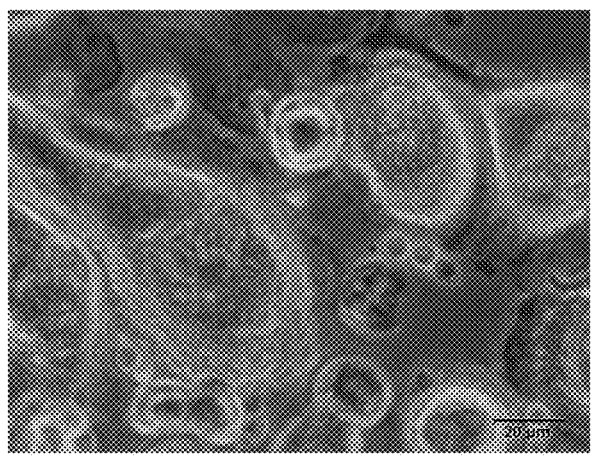

Figure 48
(A) First stage: 10$^{th}$ day
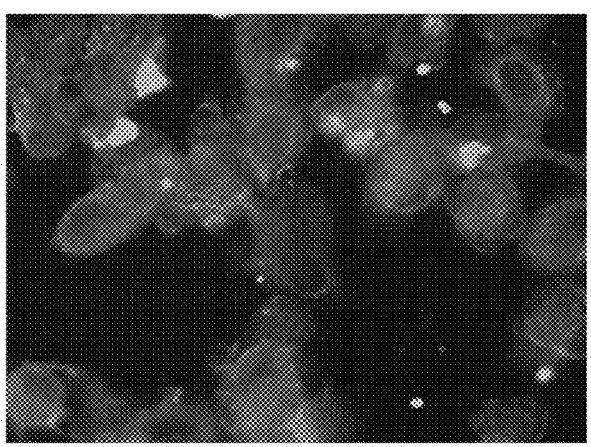 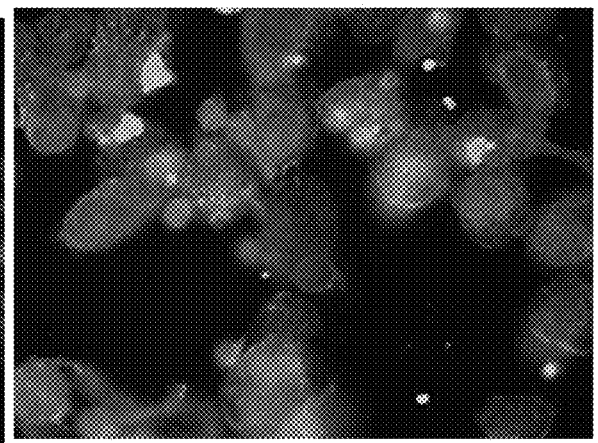
(B) Second stage: 12$^{th}$ day
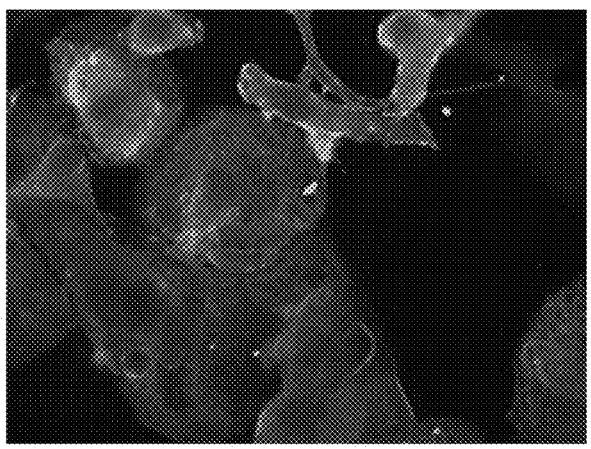 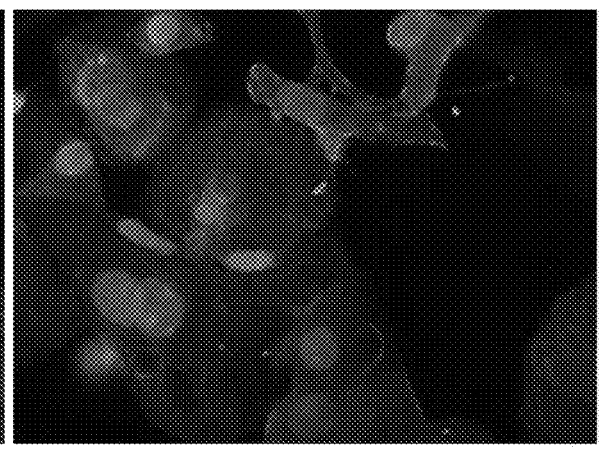
(C) Second stage: 16$^{th}$ day
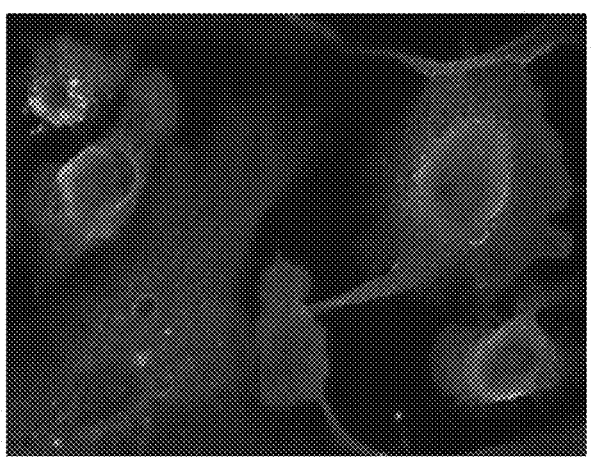 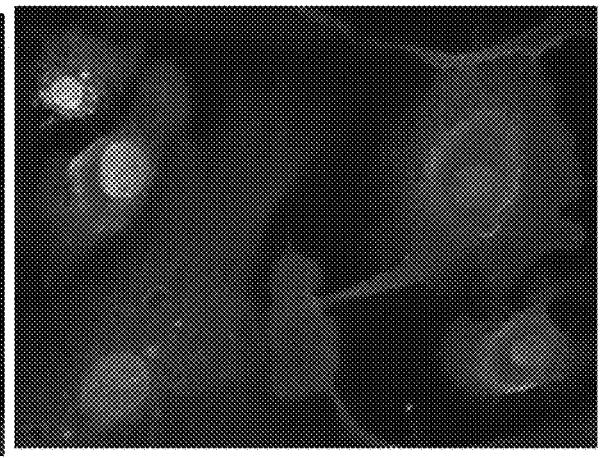

D) Second stage: $20^{th}$ day

Figure 49
(A) First stage: 10$^{th}$ day
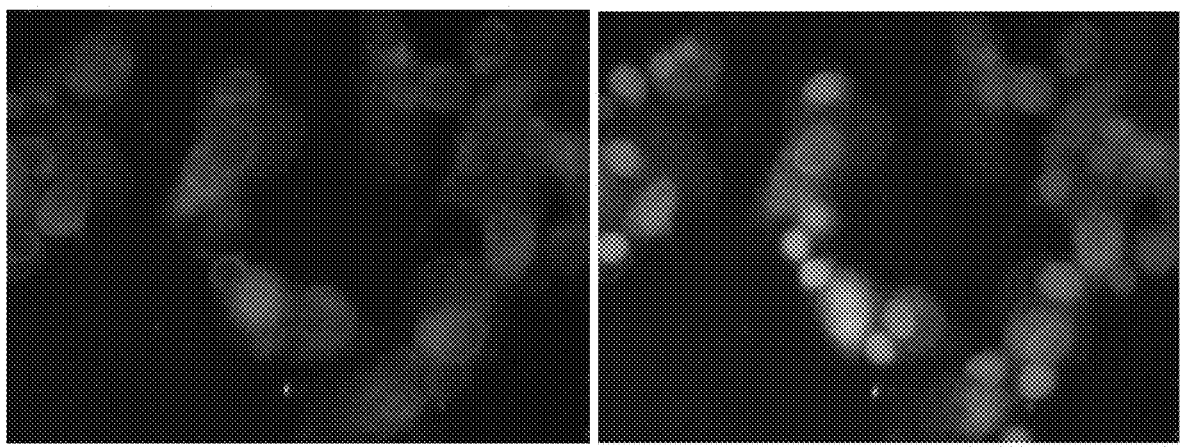
(B) Second stage: 12$^{th}$ day
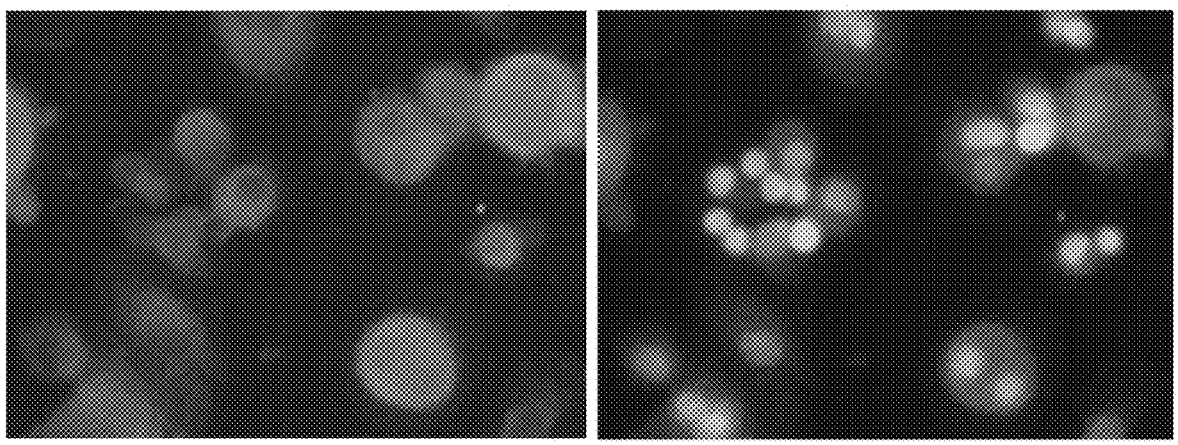

FIGURE 49 (continued)
(C) Second stage: 16th day
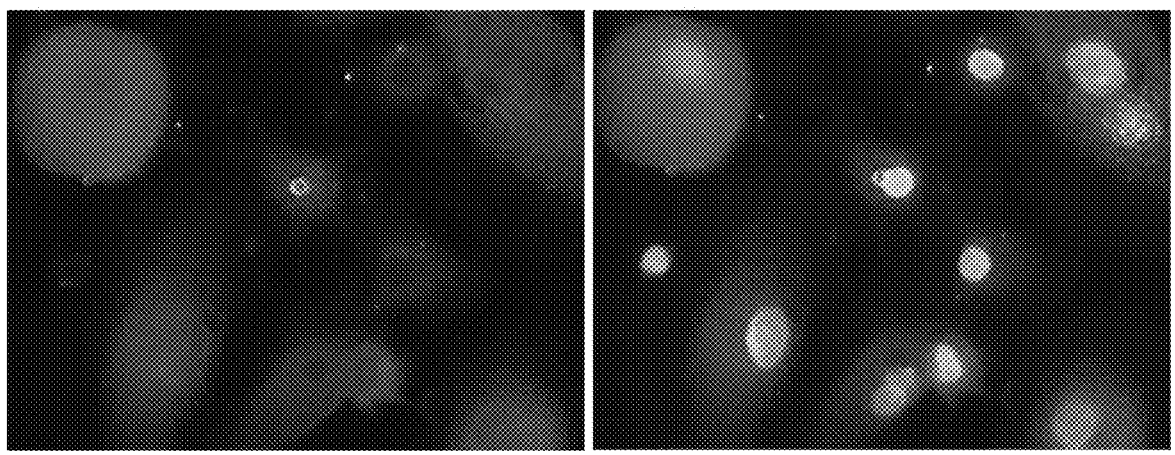
(D) Second stage: 20th day
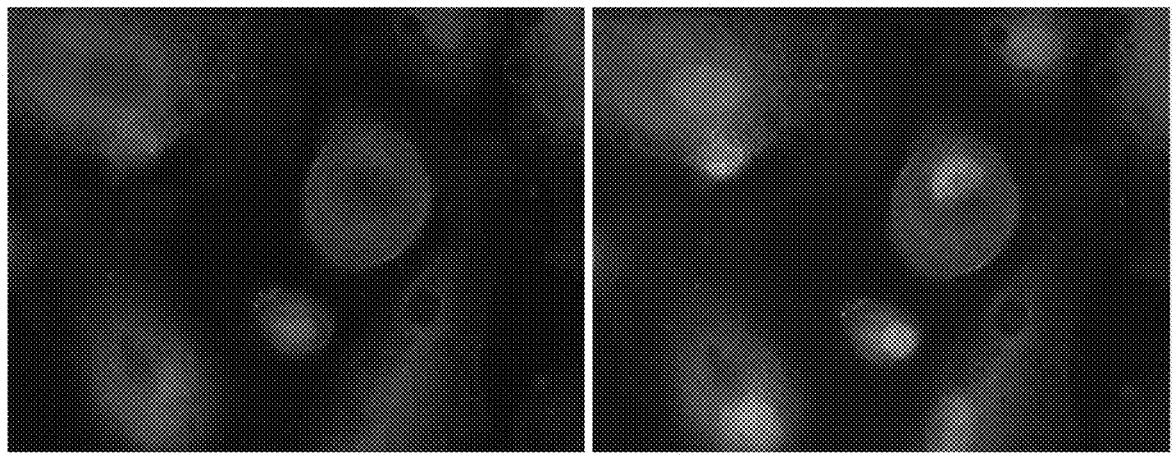

Figure 50
(A) First stage: 10<sup>th</sup> day
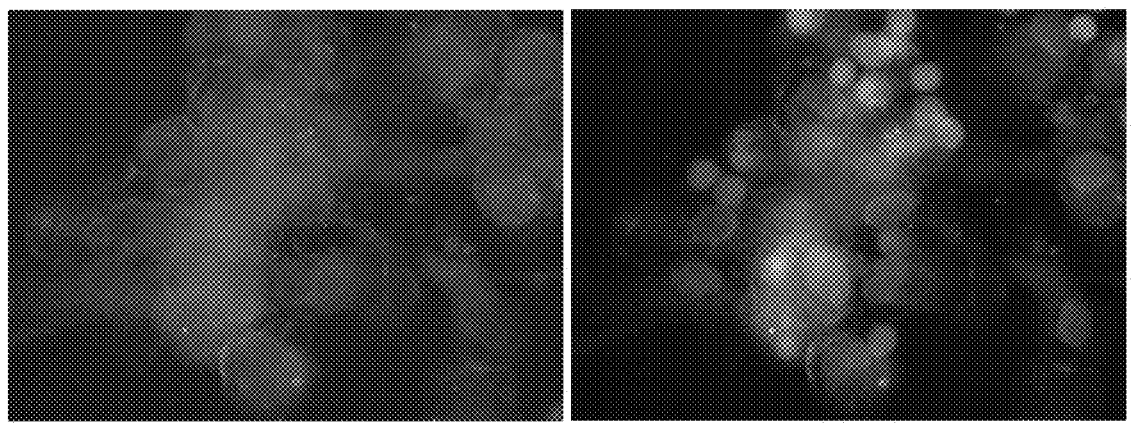
(B) Second stage: 12<sup>th</sup> day
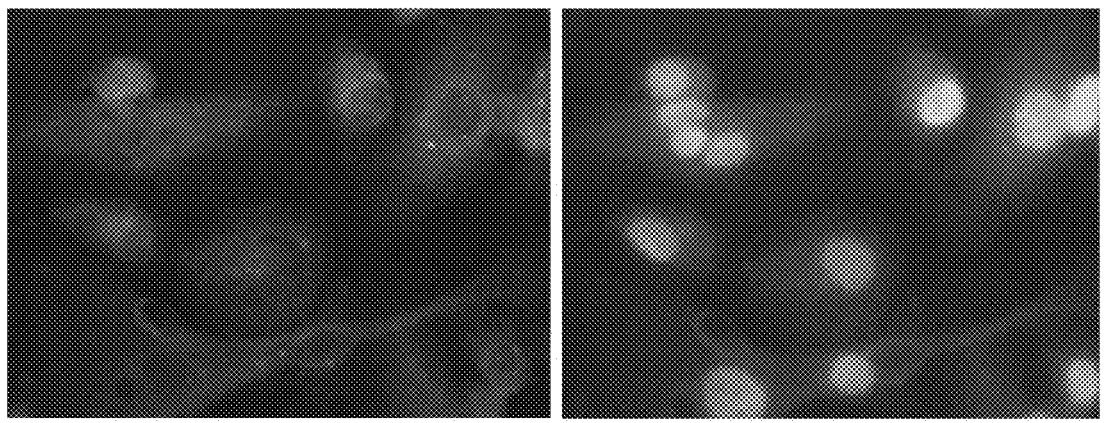
(C) Second stage: 16<sup>th</sup> day
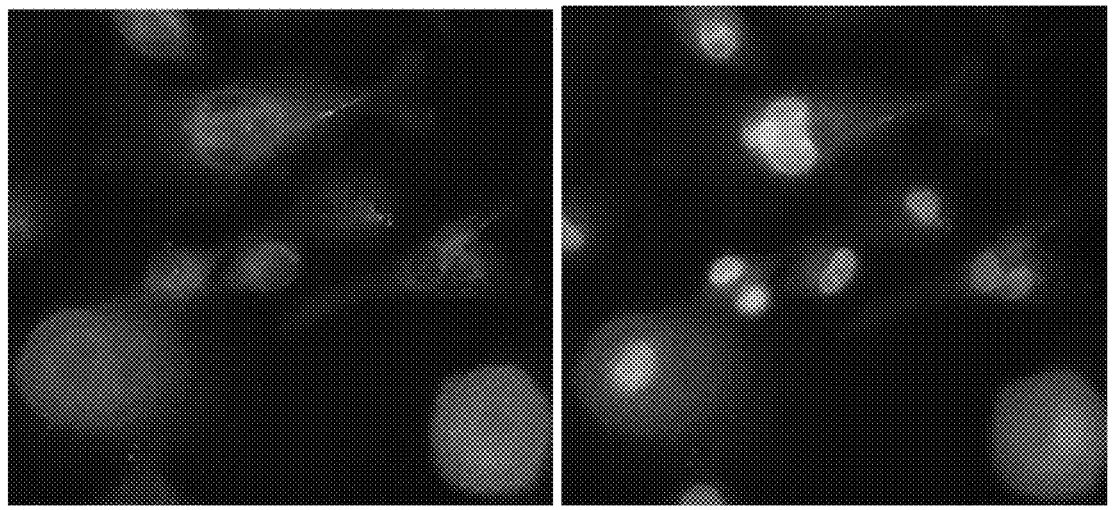

(D) Second stage: 20th day

Figure 51
(A) First stage: 10$^{th}$ day
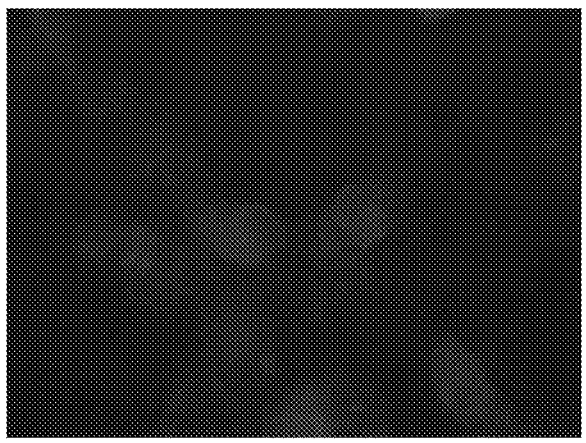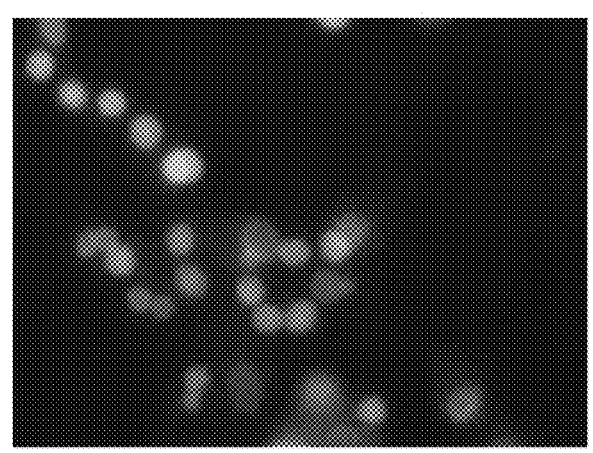
(B) Second stage: 12$^{th}$ day
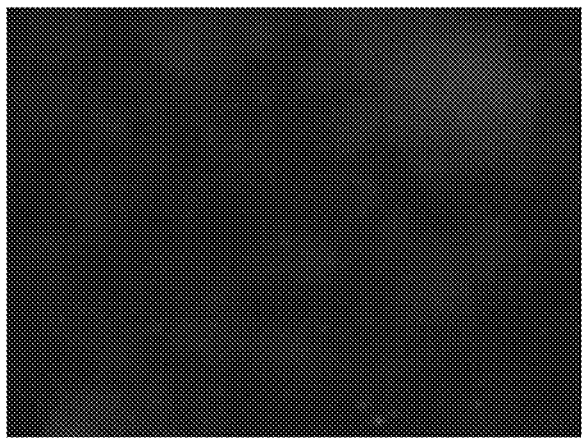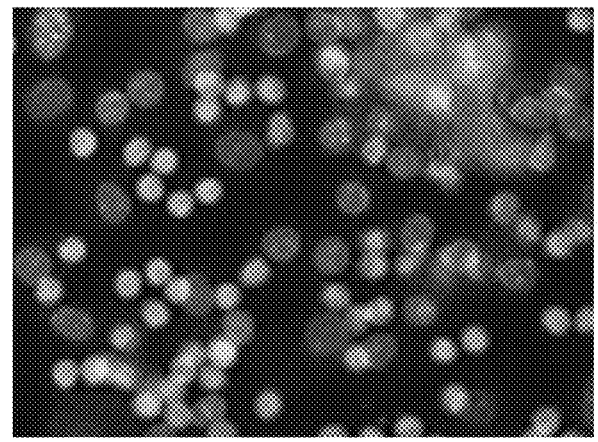
(C) Second stage: 16$^{th}$ day
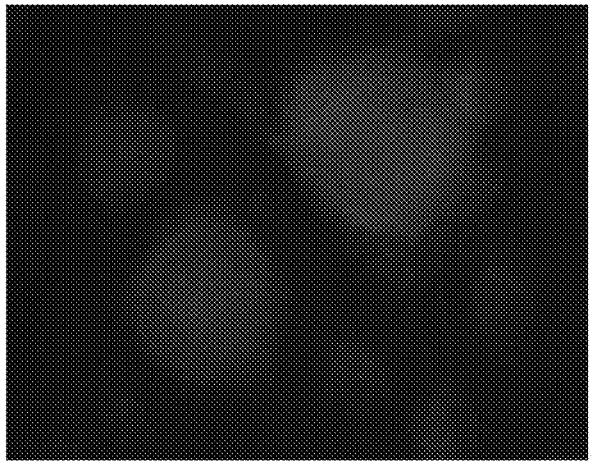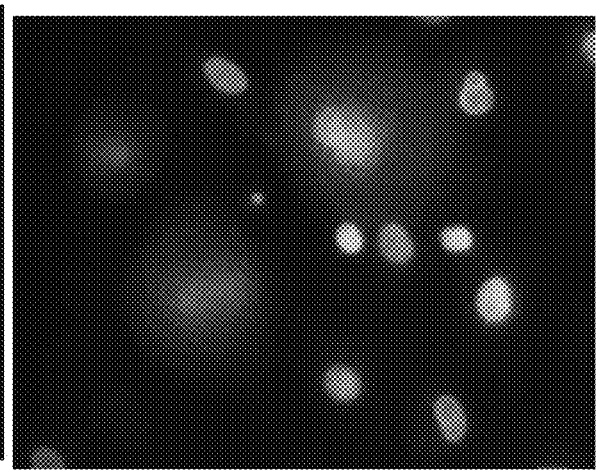

(D) Second stage: 20$^{th}$ day

FIGURE 103
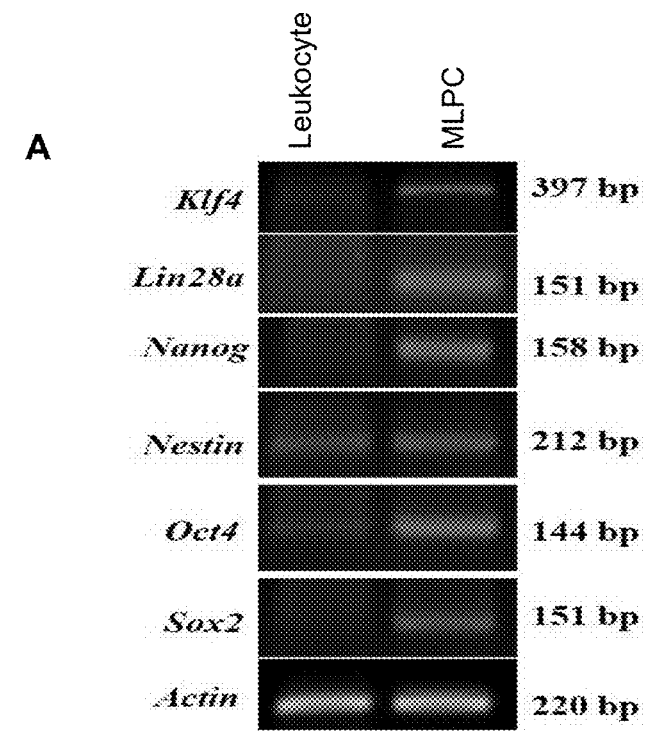
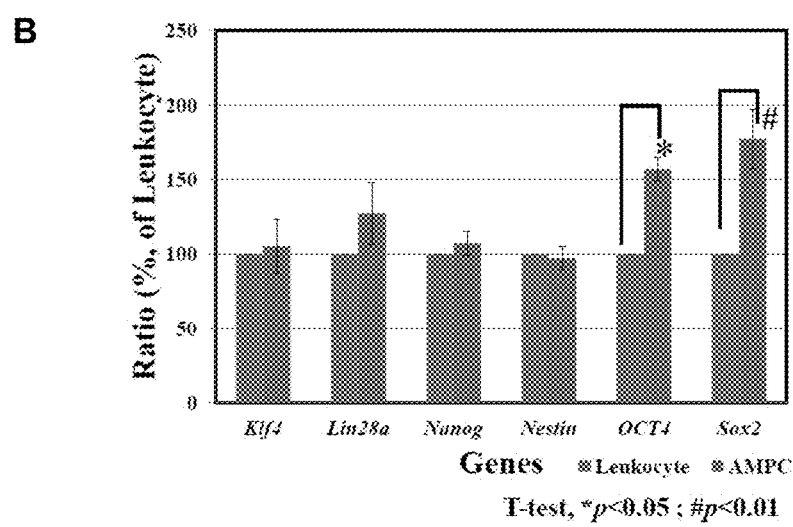

FIGURE 104
A
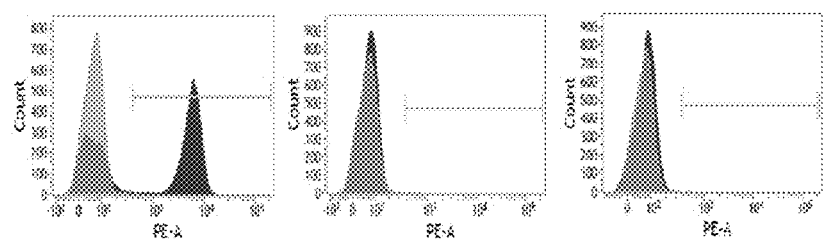
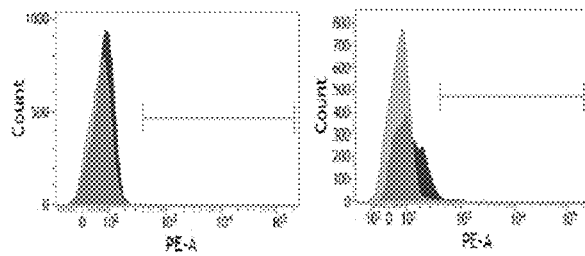
B
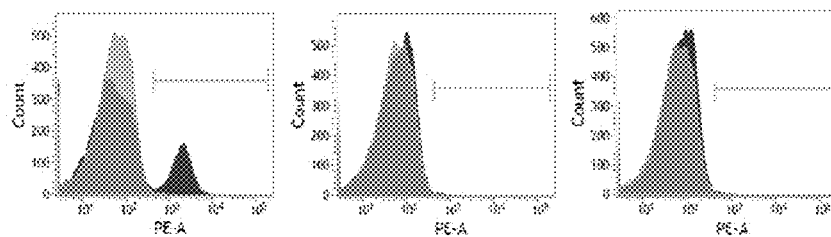
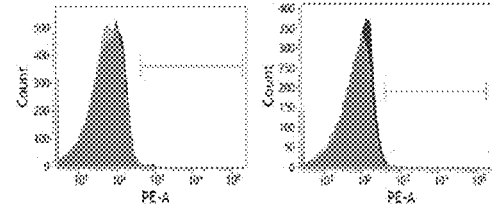

FIGURE 105
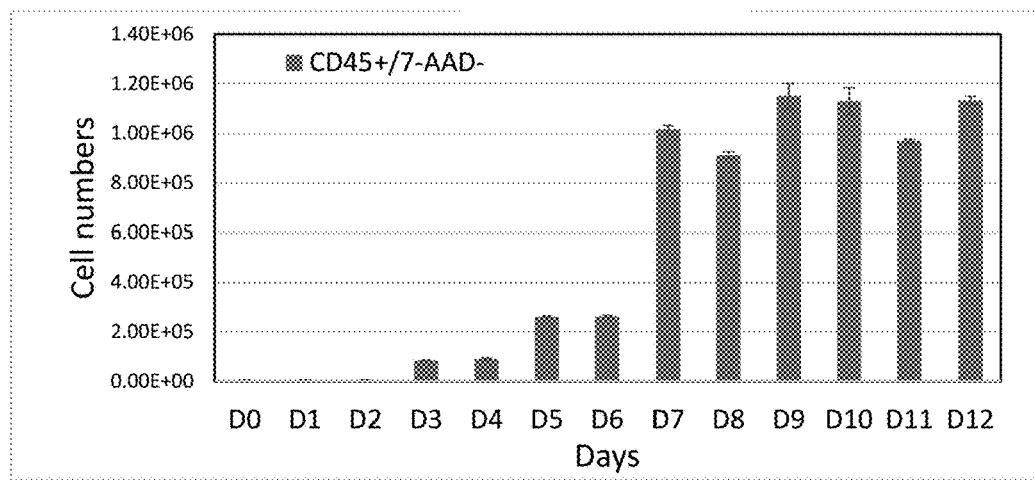
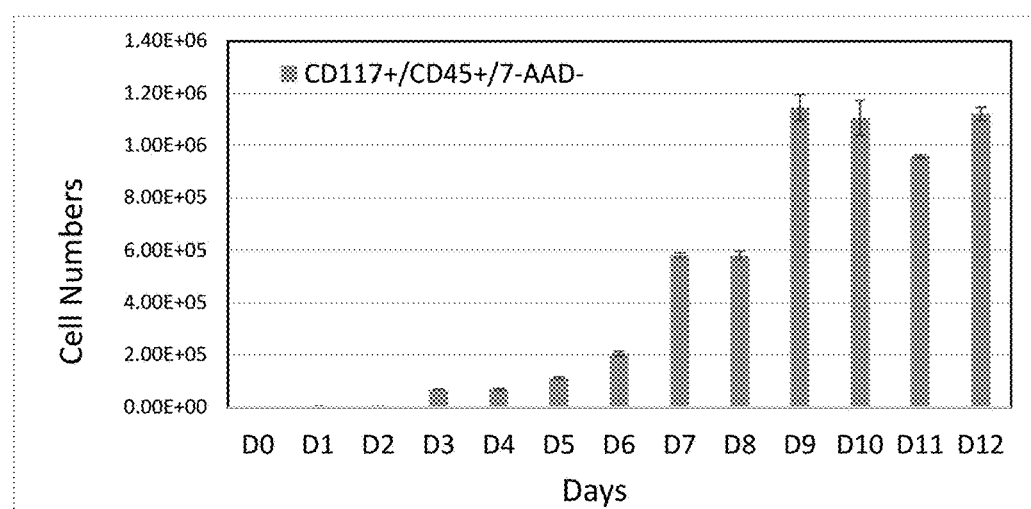
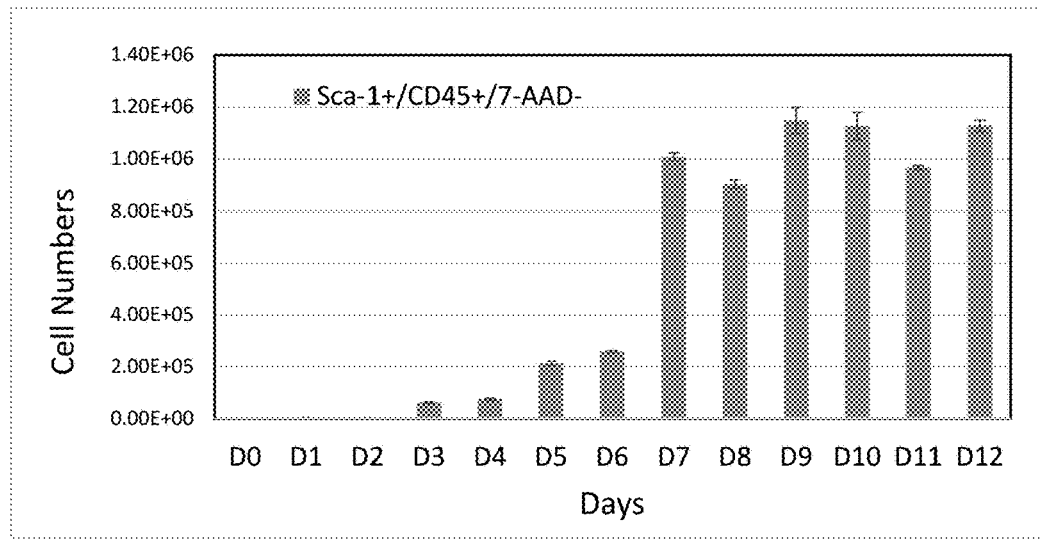

Figure 109
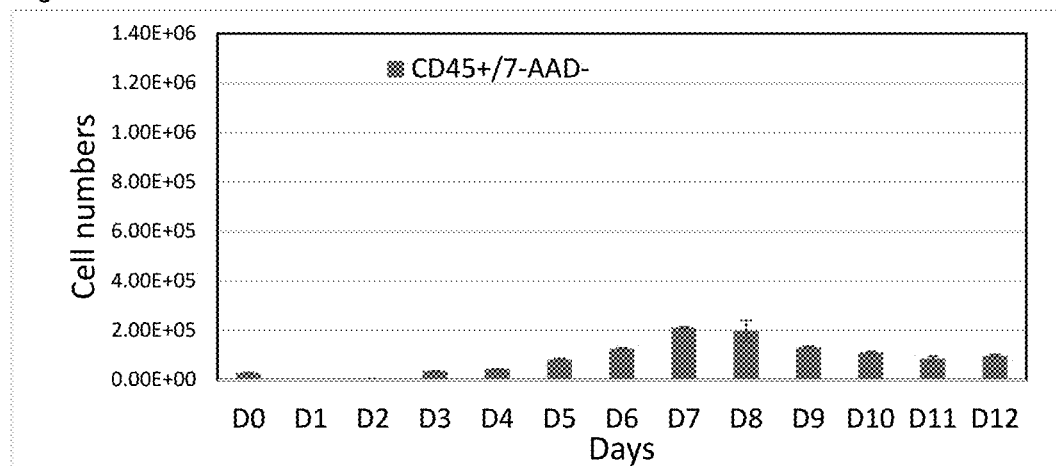
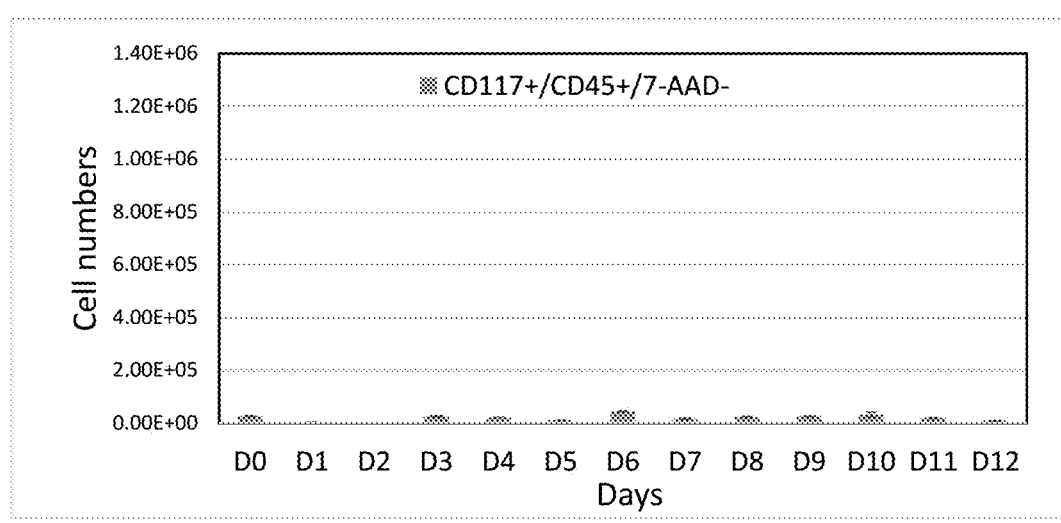
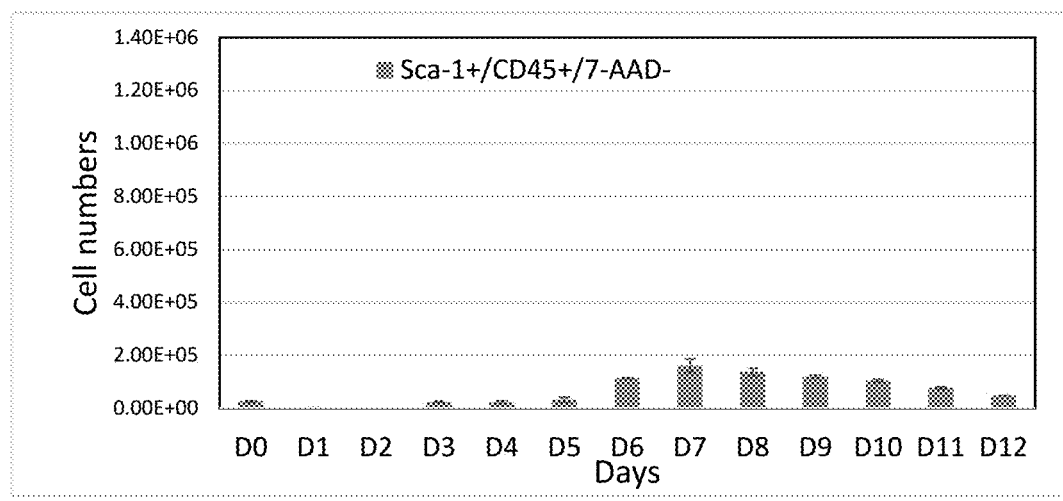

Figure 113 *POU5F1* amplification curve
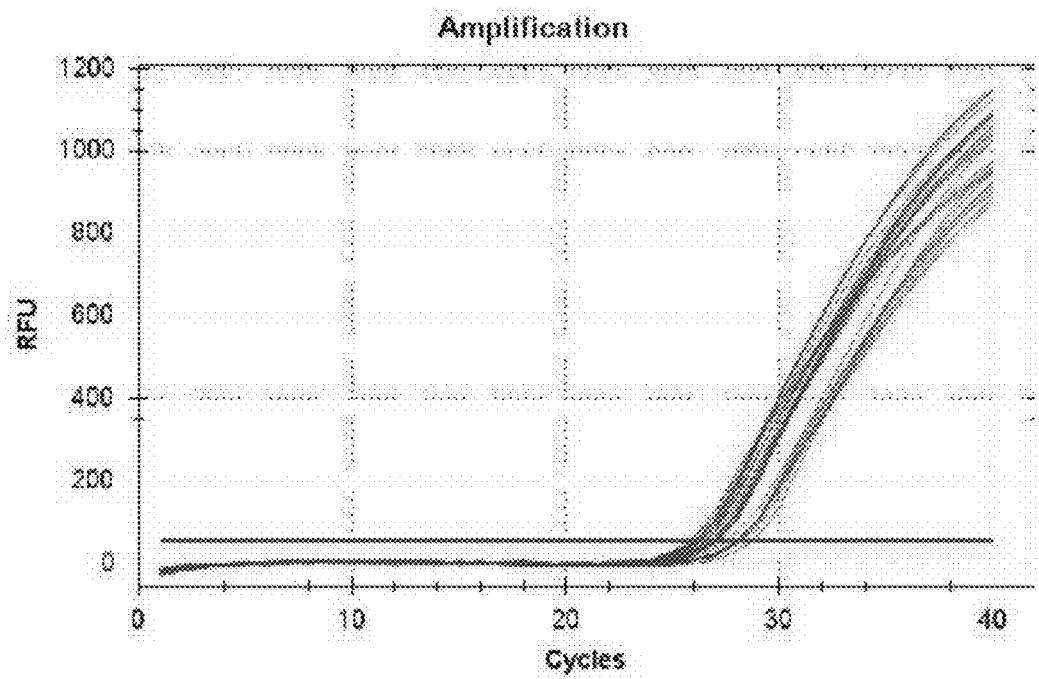
Figure 114 1.2 *sox-2* amplification curve
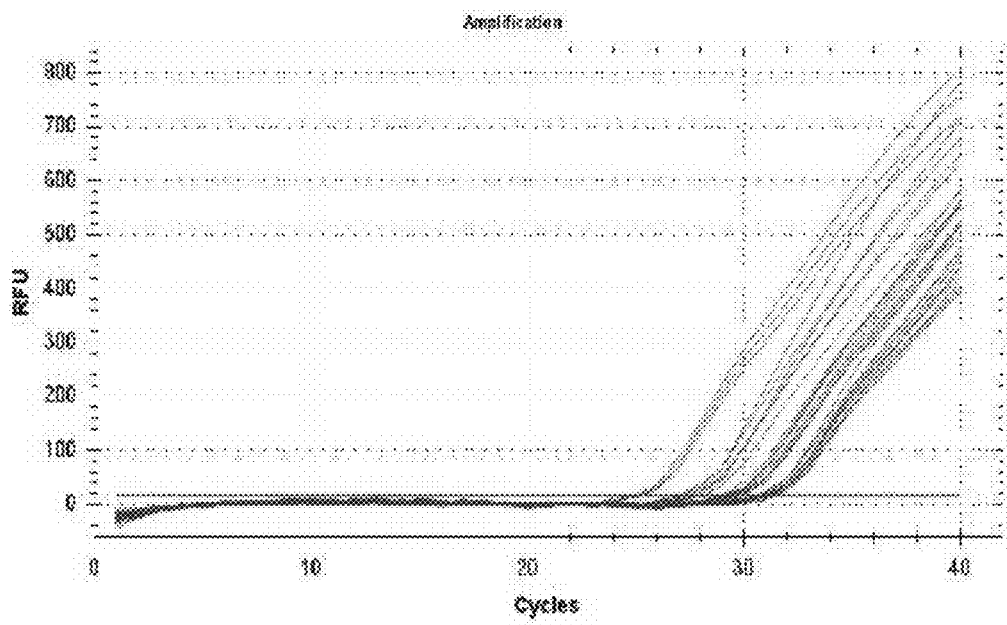

Figure 115  *nanog* amplification curve
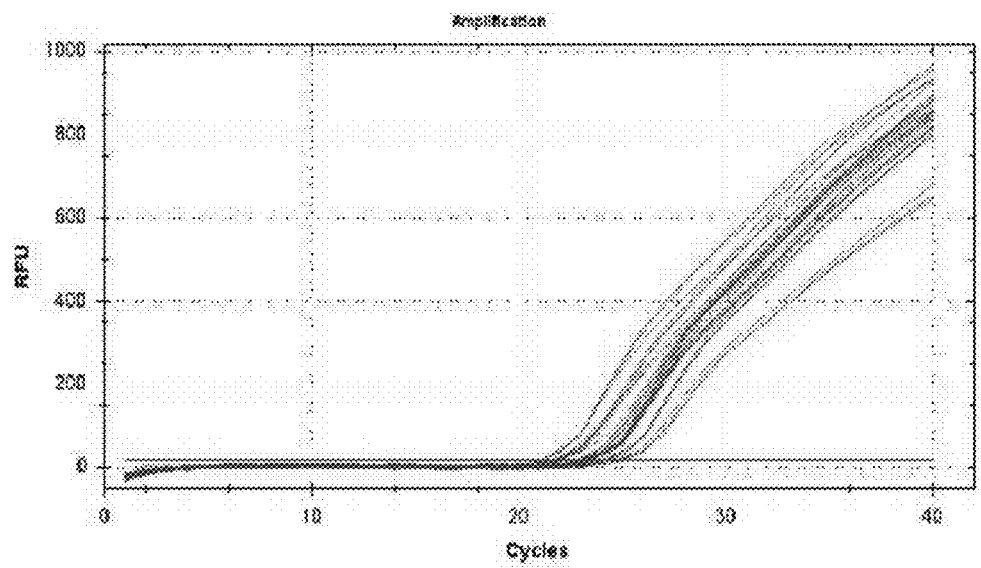
Figure 116  *actb* amplification curve
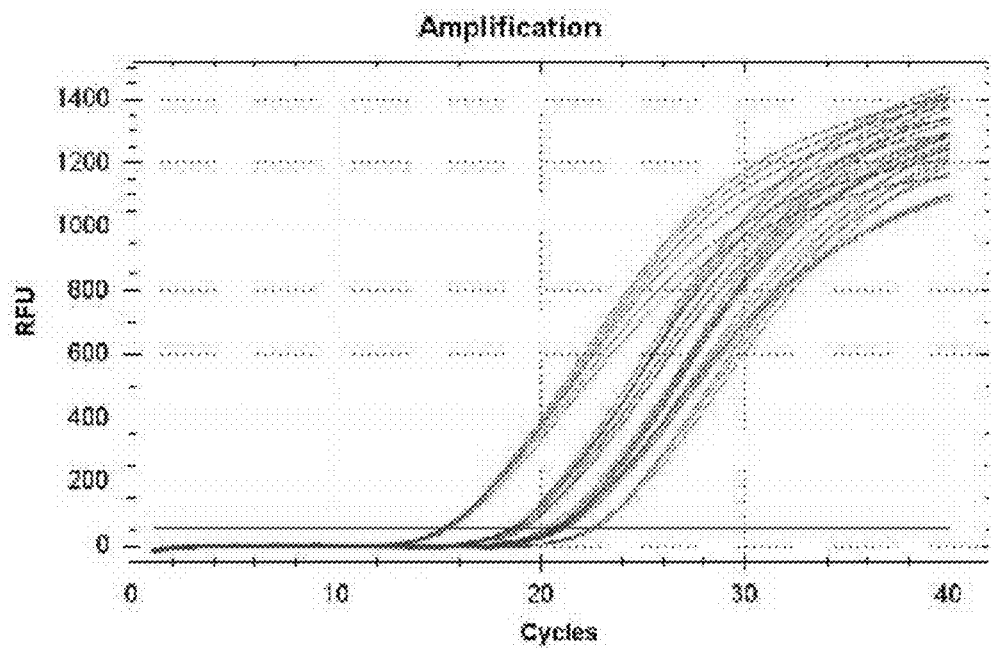

Figure 117   *POU5F1* melting curve
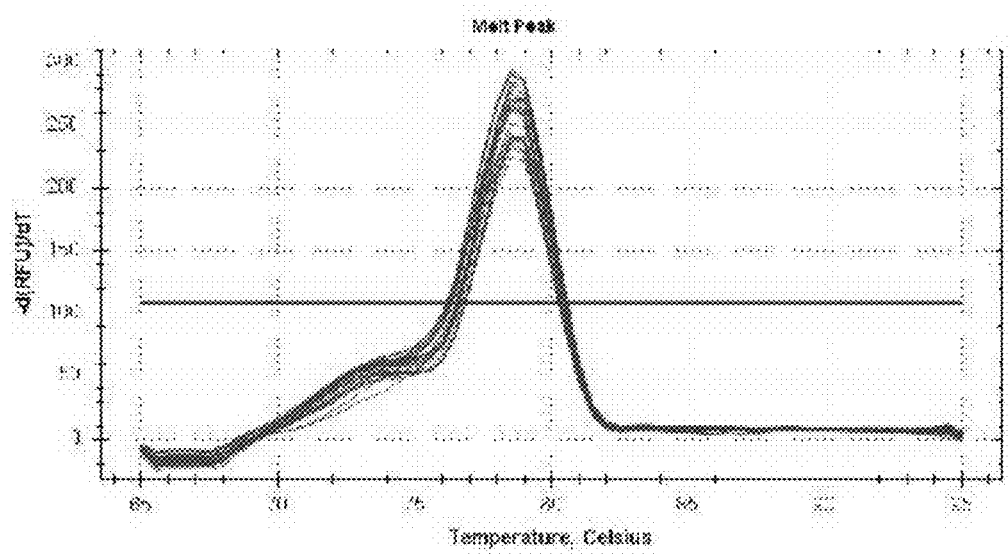
Figure 118   *sox-2* melting curve
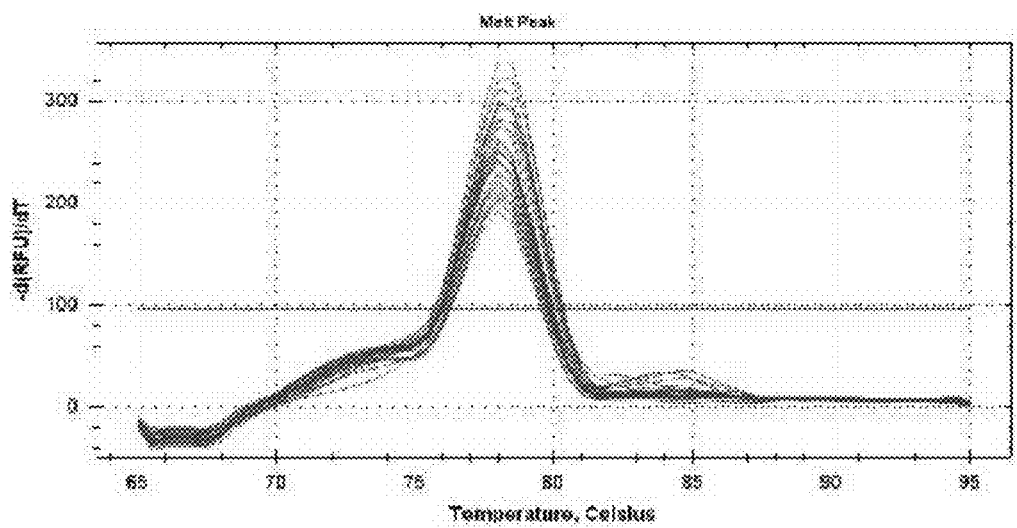

Figure 119  *nanog* melting curve
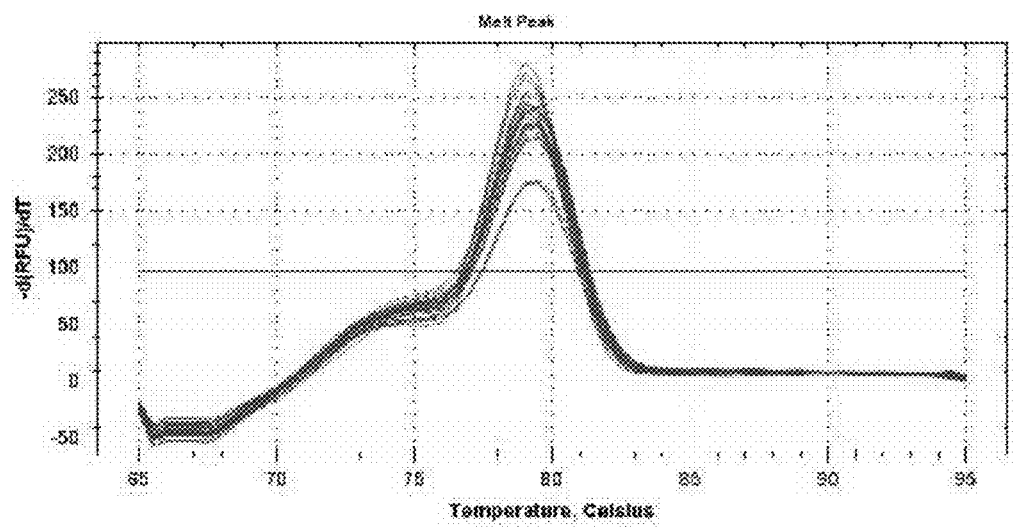
Figure 120  *actb* melting curve
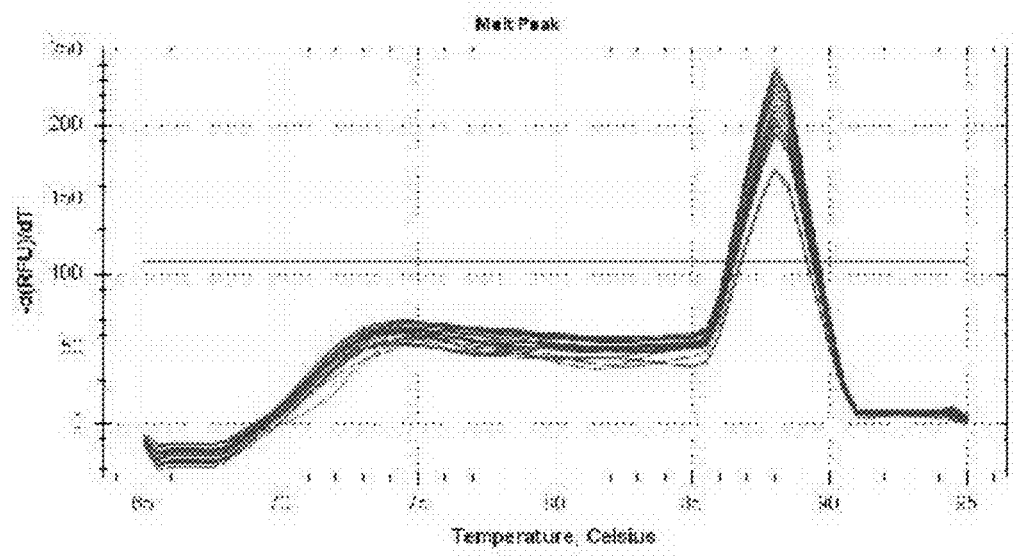

METHOD OF GENERATING MULTI-LINEAGE POTENTIAL CELLS AND MULTI-LINEAGE POTENTIAL CELLS PRODUCED THEREFROM

FIELD OF THE INVENTION

The present invention relates to multi-linage potential cells (MLPC) derived from leukocytes that have stem cell-like characteristics and methods of generation thereof.

BACKGROUND OF THE INVENTION

Adult tissues contain populations of stem cells that can self-replicate and give rise to daughter cells that undergo an irreversible terminal differentiation (Science, 287, 1442-1446, 2000). The best-characterized are hematopoietic stem cells and their progeny, but stem cells are identified in most of the tissues, including mysenchymal, neuron, and hemotopoietic cells (Science, 284, 143-147, 1999; Science, 287, 1433-1438, 2000; J. Hepatol., 29, 676-682, 1998). Mesenchymal stem cells (MSCs) are identified as adherent fibroblast-like cells in the bone marrow with differentiation potential into mesenchymal tissues, including bone, cartilage, fat, muscle, and bone marrow stroma (Science, 284, 143-147, 1999). Mesenchymal progenitors having morphologic and phenotypic features and differentiation potentials similar to MSCs have been reported at extremely low frequencies in umbilical cord blood (Br. J. Haematol., 109, 235-242, 2000), fetal (Blood, 98, 2396-2402, 2001) and adult peripheral blood (Arthritis Res., 2, 477-488, 2000). However, MSCs and circulating MSC-like cells do not express various hematopoietic markers or the stem cell/endothelial marker CD34 (Science, 284, 143-147, 1999; Br. J. Haematol., 109, 235-242, 2000; Blood, 98, 2396-2402, 2001).

US20060171928 discloses a method of producing multipotent cells from monocytes cultured on fibronectin-coated plastic plates for 7 to 10 days. These multipotent cells exhibited a fibroblast-like morphology with a unique phenotype of $CD14^+$, $CD45^+$, $CD34^+$ and type I collagen$^+$ markers. The specification disclosed that these multipotent cells could differentiate into mesenchymal cells including endothelial cells, myocardial cells, and neurons under particular culture conditions. The method however is complicated and the resultant multipotent cells appear to have a limited range of differentiation.

More recently, PCT publication WO2014085871 disclosed the use of $CD14^+$ monocytes to produce MLPC under experimental conditions to induce transitions. The PCT publication WO2015184506 described mononuclear cells that expressed the $CD^4$, $CD^8$, $CD^{25}$ or $CD^{19}$ genes that were able to transition to MLPC under certain experimental conditions. In both publications, the described experiments identified and separated each of the relevant cell types from a sample of peripheral blood. The methods used to generate MLPC were time consuming and expensive. Further the prolonged experimentation including the isolation of the relevant cell types had an adverse effect on the health and viability of the selected cells.

SUMMARY OF THE INVENTION

The inventors of the current invention conducted experiments to develop more efficient ways of isolating selected mononuclear cells and generating MLPC for use in therapeutic and prophylactic treatments. It was surprisingly discovered and then further investigated that MLPC which were induced to de-differentiate from somatic leukocytes demonstrated significantly better functional activity, and thereby provided better in vitro and in vivo treatment results, when a heterogeneous population of leukocyte subtypes were used. Where the proportion of leukocyte subtypes in a culture of a heterogeneous leukocyte subtypes used to produce MLPC, was approximately the same as occurs in in vivo peripheral blood, the inventors found that a proportionally greater number of cells were de-differentiated. The inventors obtained an unseparated leukocytes culture from a blood sample and used the culture to produce MLPC. The heterogeneous population of MLPC has been determined to provide better functional outcomes than if any one of these subpopulations were used in isolation.

Methods were subsequently developed that enabled the mixed population of leukocytes in blood to de-differentiate to multilineage potential cells.

This approach is different to current methods where homogenous or clonal stem cell lines or stem cells are produced from a single cell type. The homogenous or clonal stem cell lines or stem cells produced from a single cell type were preferentially used because of the perceived certainty in relation to the source of the stem cell and the desired phenotypic, functional and molecular characteristics of the induced MLPC.

In one aspect the invention broadly resides in a method of producing multilineage potential cells derived from a heterogeneous population of leukocyte subtypes, including having a suspension of leukocytes which comprise a heterogenous population of leukocyte subtypes and cultivating the leukocytes for 1 to 12 days at substantially 37° C. in a humidified incubator with between 1% to 10% $CO_2$ to form a cell suspension including multilineage potential cells.

Preferably the leukocytes are obtained from a blood sample. More preferably the leukocytes are obtained from a single blood sample from an individual. Preferably the suspension has unseparated leukocytes.

Preferably the leukocytes are incubated in a plastic container that allows the leukocyte cells to adhere to its surface. Preferably the plastic container is a gas permeable bag. Preferably the bag is a FEP (Fluro Ethylene Propylene) blood bag.

Preferably the leukocytes are incubated between 4 to 7 days and more preferably 5 or 6 days.

Preferably the leukocytes are incubated at 5% $CO_2$ with 90% humidity and at substantially 37° C.

Preferably the leukocytes are suspended in a nutrient medium. Preferably the nutrient medium contains albumin and more preferably serum albumin.

Following cultivation, the cultivated cell suspension is preferably harvested by separating the cells from the suspension media and resuspending the cells in nutrient media or physiological saline (0.9% saline solution). The cells are preferably harvested by removing them from the surface of the plastic container.

The heterogenous population of leukocytes can be obtained from a blood sample where red blood cells and platelets are separated from the leukocytes by centrifugation. In this embodiment, the platelet fraction or part thereof can be reintroduced to the leukocyte suspension to provide dilution and achieve suitable cell concentration and suspension viscosity.

In a preferred embodiment the suspension includes up to 10% of red blood cells and plasma when compared with the original sample concentration of red blood cells and plasma.

The inventors have discovered that a minor portion of red blood cells and plasma in the mixed leukocyte suspension is beneficial in the de-differentiation of the leukocytes to MPLC. The amount of red blood cells and or plasma is preferably at a level that does not interfere with or restrict the de-differentiation process.

In an alternative embodiment, leukocytes can be separated in a sample, based on subtype identification. Each subtype of leukocytes can be suitably identified by optical detection methods. Where leukocyte subtypes are identified and sorted, it is then possible to select the preferred ratio of leukocyte subtypes for the leukocyte cultivation so to achieve the de-differentiated cell population for the desired treatment result.

Agents such as insulin, fibronectin and other additives, can be added to assist with de-differentiation to MLPC and or MLPC with a particular phenotype. In an embodiment to differentiate into osteoblasts using osteogenic induction medium including dexamethasone, β-glycerophosphate and absorbic acid 2-phosphate; neuroectodermal cells using a co-culture induction system where induction cells secreted neural growth factors; cardiomyogenic cells using cardiomyogenic lineage induction medium including human insulin, human EGF and human β-FGF; and neo-hepatocytes using neo-hepatocyte lineage induction medium including dexamethasone, human HGF and human β-FGF.

In a further aspect, the invention broadly resides in the MLPC produced from the above mentioned method.

Preferably the leukocyte suspension is a heterogeneous population in relative proportions which mimics the natural in vivo differential ratios of somatic peripheral blood leukocyte subpopulations. More preferably the leukocyte suspension includes the substantially complete heterogeneous leukocyte population taken from a blood sample.

In another aspect the invention broadly resides in a treatment with the introduction of the harvested MLPC to a patient. Preferably the harvested MLPC are intravenously introduced. Alternatively, the harvested MLPC are introduced locally at the site or tissue for treatment. Preferably the introduced MLPC were initially derived from cells from the same patient. Preferably the use of a patient's own blood sample and introducing the treated cell suspension (that is autologous cell treatment with respect to the patient) will reduce incompatibility problems. The introduction of the harvested MLPC to a patient from where the initial leukocyte suspension was derived avoids possible histocompatibility problems.

In another aspect of the present invention is directed to an isolated heterogeneous population of mammalian multilineage potential cells, which multilineage potential cells have been induced to de-differentiate from lymphocytes, monocytes and granulocytes, said population of multilineage potential cells comprising 40%-60% multilineage potential cells induced from granulocytes; 20%-40% multilineage potential cells induced from lymphocytes; and 2%-8% multilineage potential cells induced from monocytes; wherein the multilineage potential cells were de-differentiated after cultivation for 1 to 12 days at substantially 37° C. in a humidified incubator with between 1% to 10% $CO_2$.

The ratio of the leukocyte subtypes can vary between individuals and an individual's health status. For example, an increase in neutrophil population in the blood can result from acute stress, infection, gout, rheumatoid arthritis, thyroiditis, trauma and pregnancy and a decrease in the proportion of neutrophils can result from anemia, chemotherapy, viral based infection and radiation exposure. An increase in lymphocyte population in the blood can result from chronic infection, and leukemia and a decrease in the proportion of lymphocytes can result from chemotherapy, HIV infection, sepsis and radiation exposure. An increase in monocyte population in the blood can result from tuberculosis, viral infections and chronic inflammatory disease and a decrease in the proportion of monocytes can result from chemotherapy, skin infections and bone marrow disorder.

Preferably the lymphocytes, granulocytes and monocytes are derived from peripheral blood.

In an alternative embodiment the ratio of de-differentiated cells can change depending on the treatment and the condition being treated. Where the ratio of de-differentiated cells differs from the ratio of the leukocyte subtypes, the ratio of leukocyte subtypes in the initial culture will be changed accordingly. The leukocyte preparation will preferably always include the subtypes, granulocytes, monocytes and lymphocytes.

A further aspect of the present invention is directed to a method of therapeutically and/or prophylactically treating a condition in a mammal, said method comprising administering to said mammal an effective number of multilineage potential cells of the present invention.

Said condition can include cardiac damage, hepatic disease, neural disorders and/or osteopathies.

Yet another aspect of the present invention is directed to the use of a population of multilineage potential cells or MLPC-derived cells, which cells have been generated in accordance with the method of the present invention, in the manufacture of a medicament for the treatment of a condition in a mammal.

The features described with respect to one aspect also apply where applicable to all other aspects of the invention. Furthermore different combinations of described features are herein described and claimed even when not expressly stated.

BRIEF DESCRIPTION OF THE DRAWINGS

FIG. 19—Alpha fetal protein expressed (AFP-FITC) in MLPC in the second stage (A)~(B) respectively. Left: fluorescence, Right: merged fluorescence & DAPI images. Original magnification: ×200.

FIG. 20—Albumin expressed (Albumin-FITC) in MLPC in the second stage (A)~(B) respectively. Left: fluorescence, Right: merged fluorescence & DAPI images. Original magnification: ×200.

FIG. 21—Connexin 32 expressed (Connexin 32-FITC) in MLPC in the second stage (A)~(C) respectively. Left: fluorescence, Right: merged fluorescence & DAPI images. Original magnification: ×200.

FIG. 22—CYP1A1 expressed (CYP1A1-FITC) in MLPC in the second stage (A)~(C) respectively. Left: fluorescence, Right: merged fluorescence & DAPI images. Original magnification: ×400.

FIG. 46—CD34, CD90, CD105 expression of adherent cells of MLPC. Adherent and un-adherent cells of MLPC were respectively collected and analyzed for surface markers expression (CD34-APC, CD90-FITC, and CD105-PE) by flow cytometry after 6 days culture in first stage. Surface marker analysis for (A) adherent cells of MLPC, (B) un-adherent cells of MLPC by flow cytometry (BD).

FIG. 47—Cardiomyogenic lineage trans-differentiation of MLPC—Cells morphology of MLPC were observed on (A) in the first stage (1-10 days) (B) in the second stage (1-20 days) under an invert microscple (OLYMPUS). Adherent and cluster of MLPC: see red circle, some adherent cells became bigger and the nuclear margin become blurring: see red arrow. Original magnification: ×400.

FIG. 49—Myogenin expressed (Myogenin-FITC) in MLPC in the first stage (A) and in the second stage (B)~(D) respectively. Left: fluorescence, Right: merged fluorescence & DAPI images. Original magnification: ×400.

FIG. 52—FIG. 44 MLPC derived stem-like cells ATA6, 47 genes were significantly involved lysosomes by KEGG database analysis. Red colour indicated 43 genes of up regulation and green colour indicated 4 genes of down-regulation.

FIG. 103: Gene expression between leukocytes and MLPC

FIG. 104: Marker expression

FIG. 105—CD45+/7-AAD−, CD117+-PECy7 and Sca-1-APCCy7 cell numbers of P from the day 0 to the day 12

FIG. 109—CD45+/7-AAD−, CD117+-PECy7 and Sca-1-APCCy7 cell numbers of L from the day 0 to the day 12.

FIG. 113 POU5F1 amplification curve.

FIG. 114 sox-2 amplification curve.

FIG. 115 nanog amplification curve.

FIG. 116 actb amplification curve.

FIG. 117 POU5F1 melting curve.

FIG. 118 sox-2 melting curve.

FIG. 119 nanog melting curve.

FIG. 120 actb melting curve.

Figure 121:
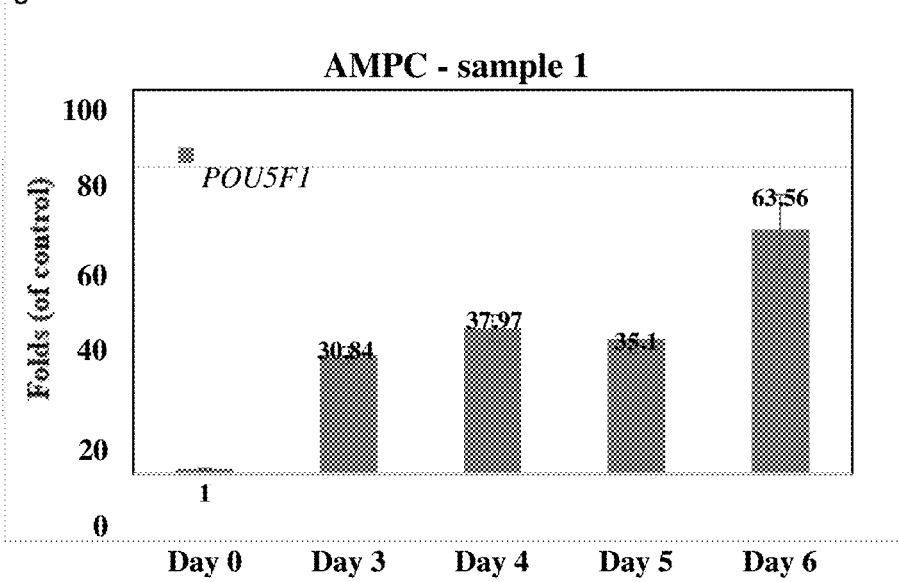
Figure 122:
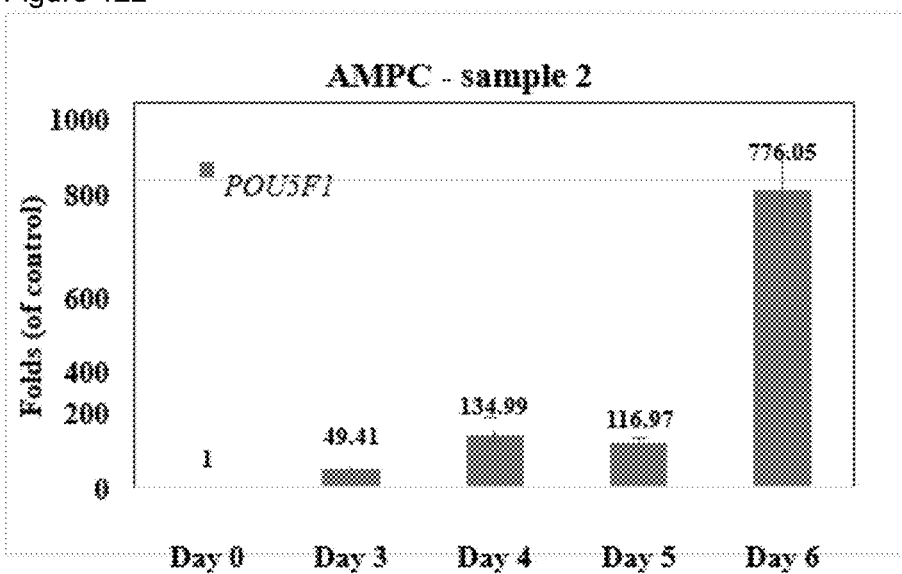

FIGS. 121 and 122: POU5F1 gene fold changes.

Figure 123:
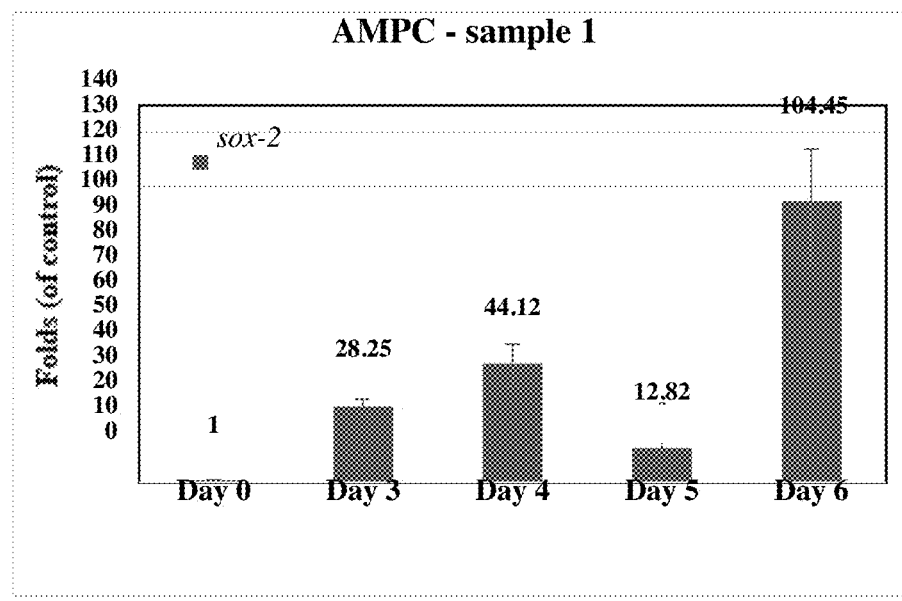
Figure 124:
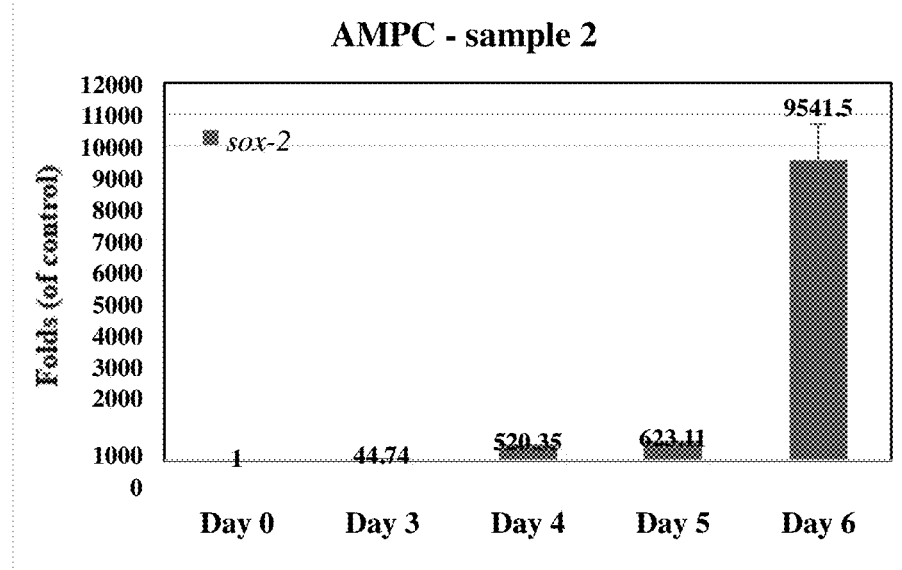

FIGS. 123 and 124: sox-2 gene fold changes.

Figure 125:
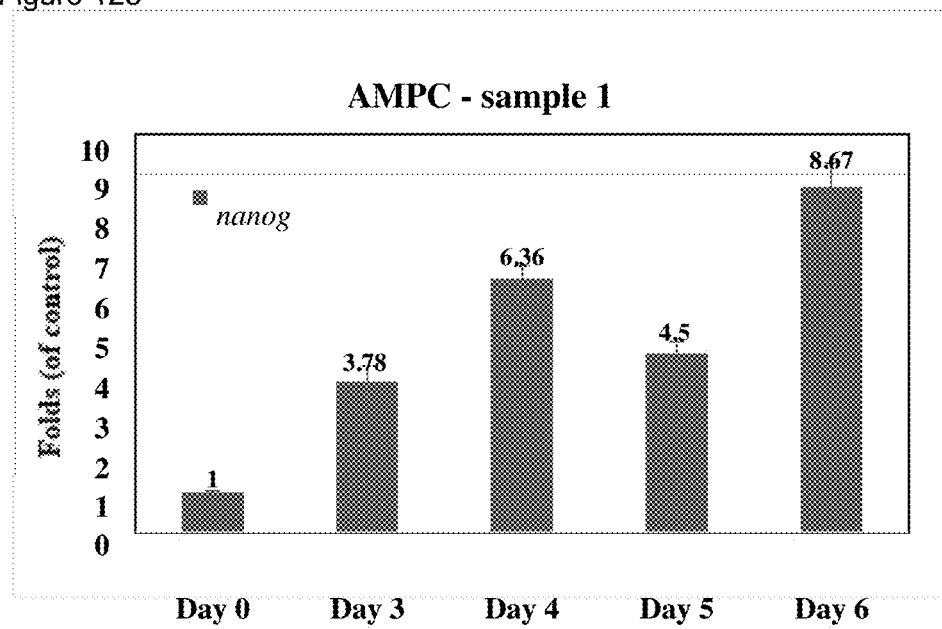
Figure 126:
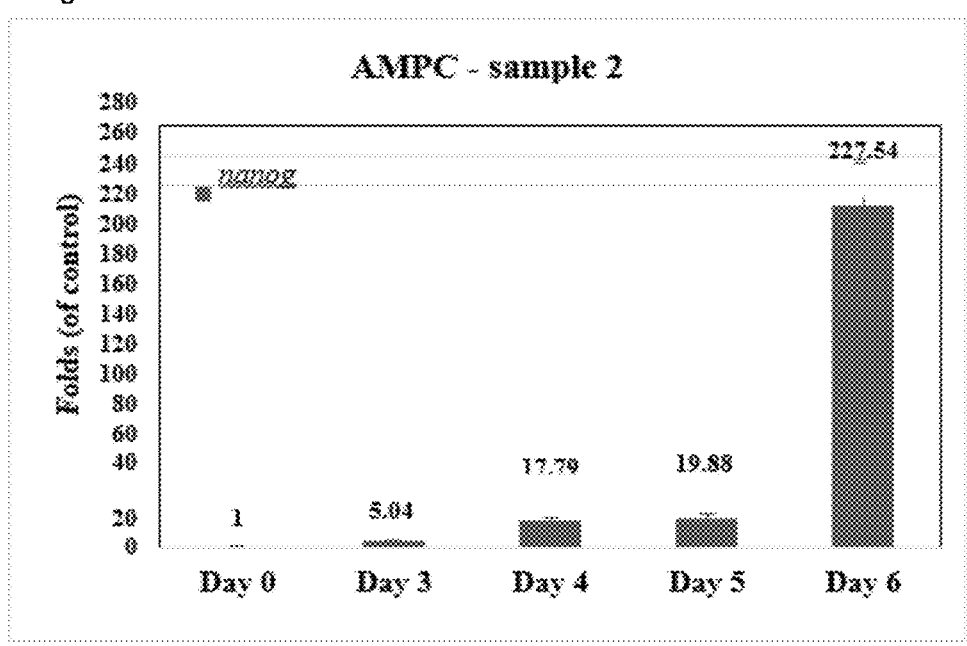

FIGS. 125 and 126: nanog gene fold changes.

Figure 127:
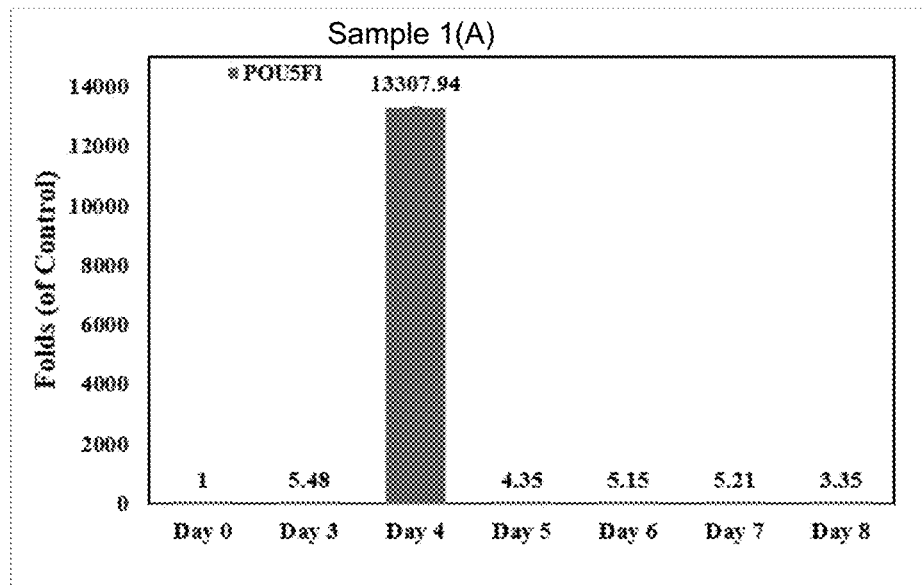

FIG. 127: POU5F1 gene fold change of Sample 1(A).

Figure 128:
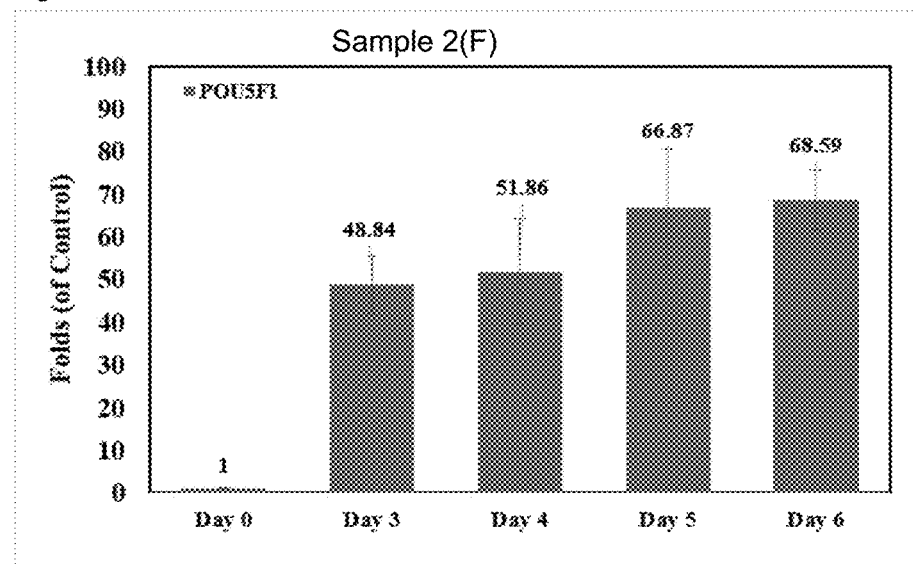

FIG. 128: POU5F1 gene fold change of Sample 2(F).

Figure 129:
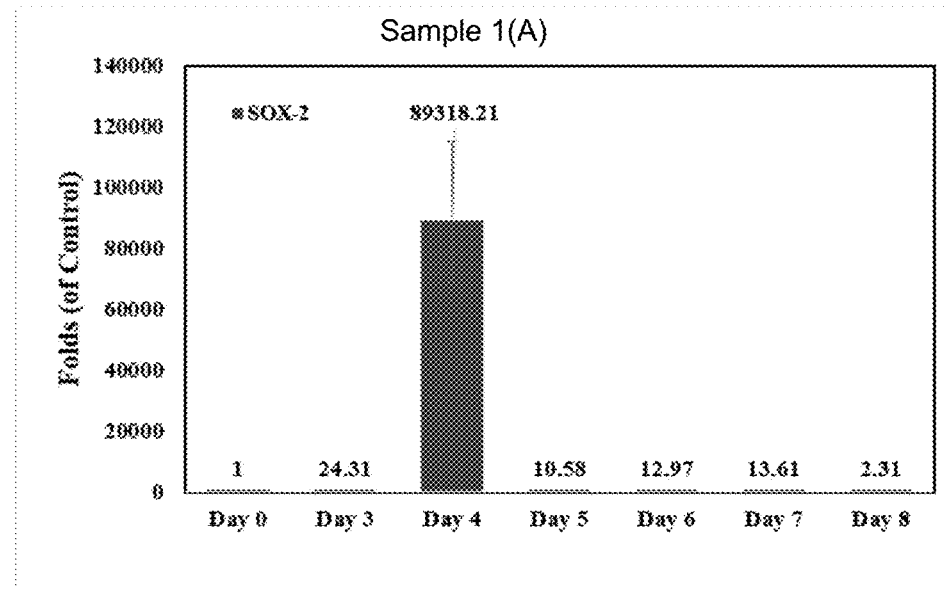

FIG. 129: sox-2 gene fold change of Sample 1(A).

Figure 130:
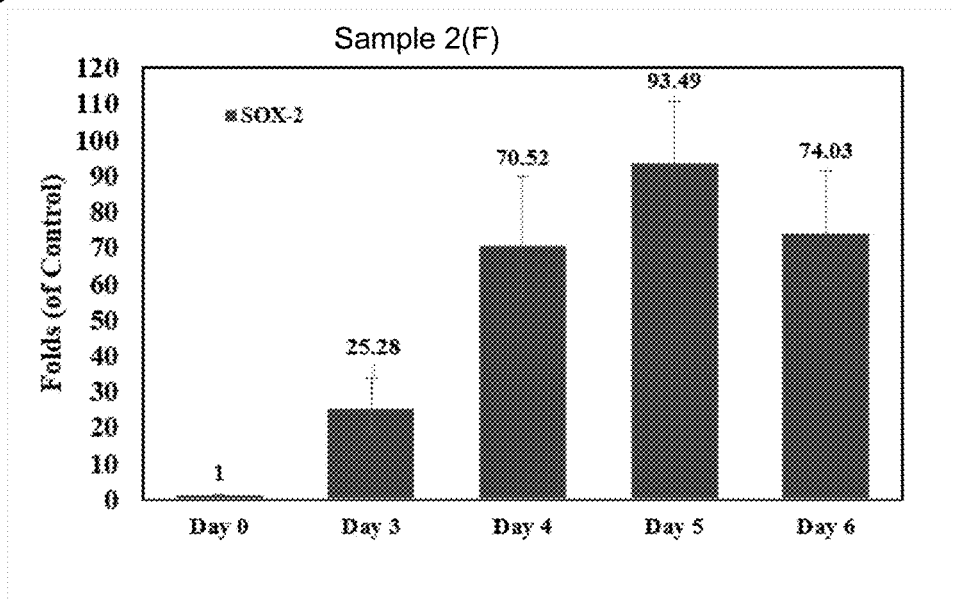

FIG. 130: sox-2 gene fold change of Sample 2(F).

Figure 131:
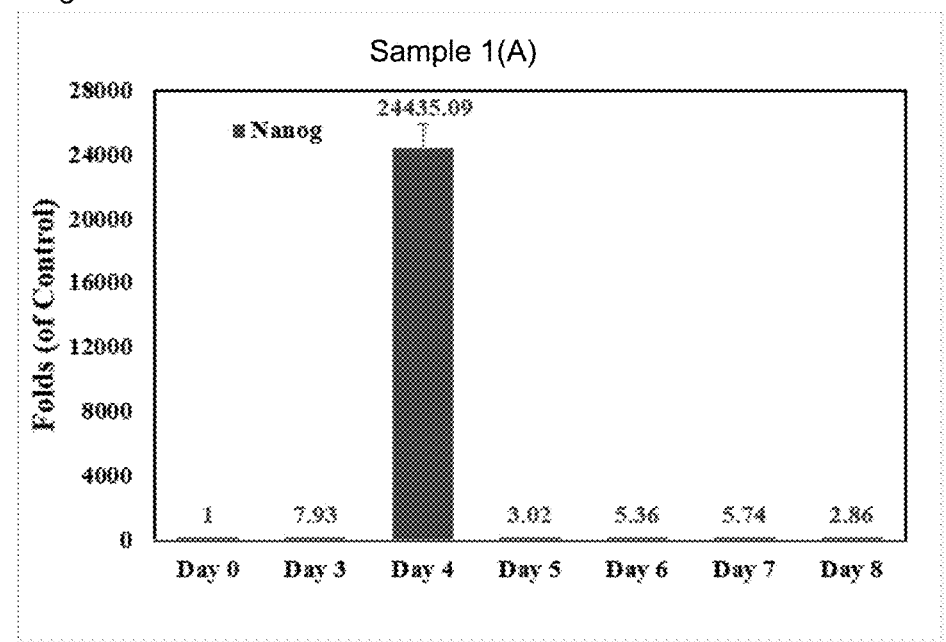

FIG. 131: nanog gene fold change of Sample 1(A).

Figure 132:
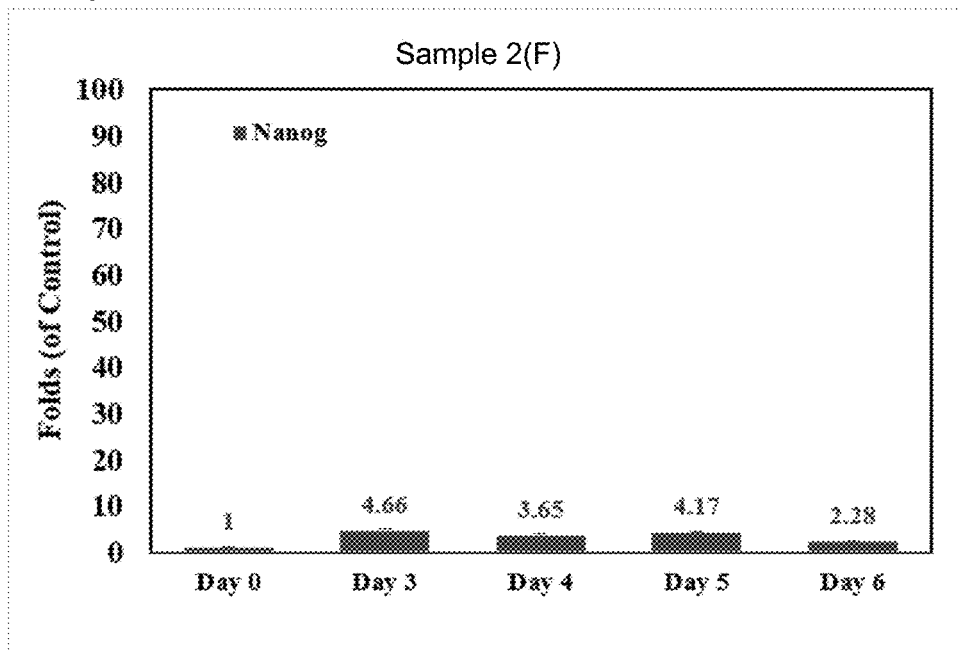

FIG. 132: nanog gene fold change of Sample 2(F).

Figure 133:
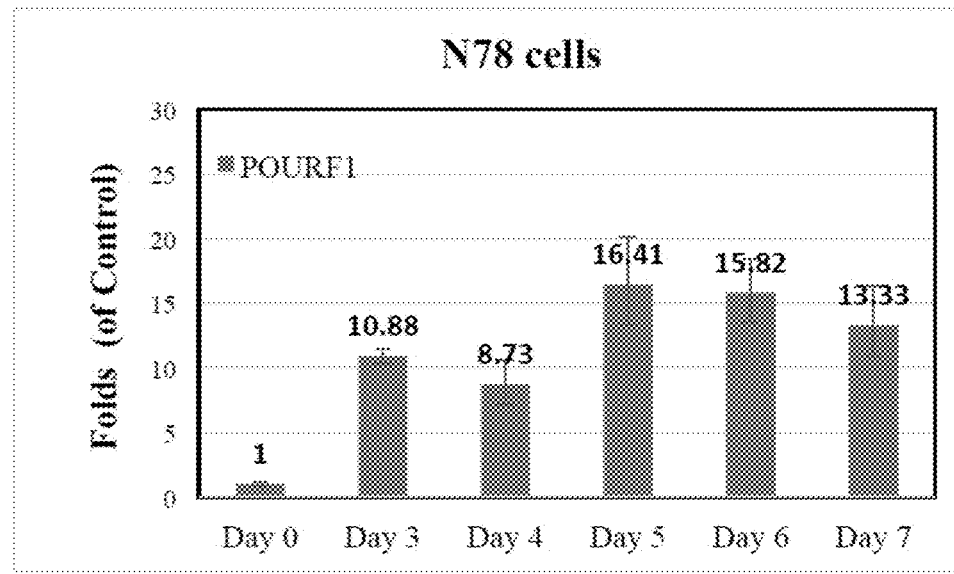

FIG. 133: POU5F1 gene fold change of N78 cells.

Figure 134:
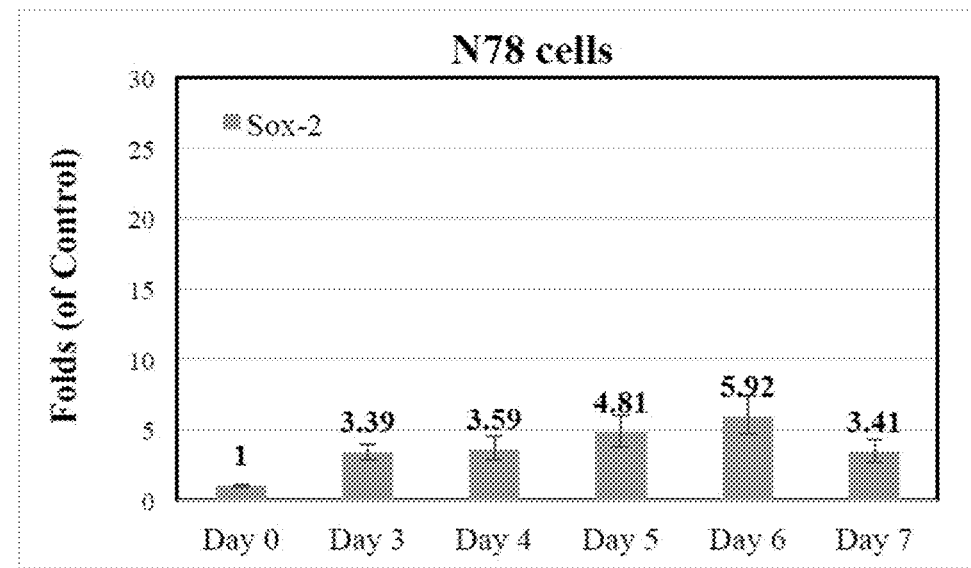

FIG. 134: sox-2 gene fold change of N78 cells.

Figure 135:
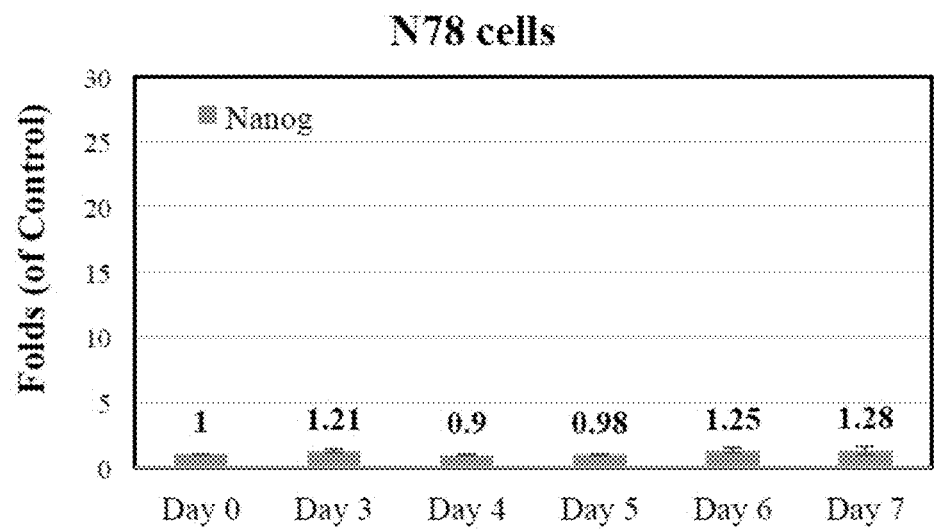

FIG. 135: nanog gene fold change of N78 cells.

DETAILED DESCRIPTION OF THE INVENTION

The present invention is based on the determination that multilineage potential cells which are de-differentiated from somatic leukocytes exhibit superior functional outcomes if they are derived from each of the lymphocytic, monocytic and granulocytic cellular subtype populations in a mixed leukocyte suspension. The proportion of leukocyte subpopulations in the leukocyte suspension is preferably similar to the natural in vivo differential ratios of somatic peripheral blood leukocyte subpopulations. Preferably the leukocyte suspension is a heterogeneous population in relative proportions which mimics the natural in vivo differential ratios of somatic peripheral blood leukocyte subpopulations. More preferably the leukocyte suspension includes the substantially complete mixed leukocyte population taken from a blood sample. In a preferred embodiment the suspension includes approximately less than or equal to 10% of red blood cells and or plasma when the percentage of red blood cells/plasma is compared with the original concentration of red blood cells and plasma in the sample. Examples 3 and 4 provide experimental support for the increased survival and de-differentiation when red blood cells are with the leukocytes during the de-differentiation incubation.

The present invention therefore provides for improved outcomes where these cells are used, both in vitro and in vivo, relative to the outcomes which would otherwise be achieved using a multilineage potential cell generated from any one of these leukocyte subtypes alone.

Accordingly, the potential in vivo and in vitro applications of these findings are extremely widespread including, but not limited to, the in vitro generation of multilineage potential cell populations; directed differentiation of the subject multilineage potential cells; therapeutic or prophylactic treatment regimes based on the generated MLPC.

The term "mammal" and "mammalian" as used herein include humans, primates, livestock animals (e.g. horses, cattle, sheep, pigs, donkeys), laboratory test animals (e.g. mice, rats, guinea pigs), companion animals (e.g. dogs, cats) and captive wild animal (e.g. kangaroos, deer, foxes). Preferably, the mammal is a human or a laboratory test animal. Even more preferably, the mammal is a human.

The multilineage potential cells of the present invention have been induced to de-differentiate from mature somatic lymphocytes, monocytes and granulocytes. In this regard, reference to "inducing de-differentiation" should be understood as a reference to inducing the genetic, morphologic and/or functional changes which are required to transition a somatic phenotype to a multilineage potential phenotype.

Reference to a cell exhibiting "multilineage differentiation potential" or "multilineage potential" should be understood as a reference to a cell which exhibits the potentiality to develop along more than one somatic differentiative path. For example, the cell may be capable of generating a range of somatic cell types, such cells usually referred to as pluripotent or multipotential. These cells exhibit commitment to a more limited range of lineages than a totipotent cell, the latter being a cell which can develop in any of the differentiation directions inherently possible including all the somatic lineages and the gametes. Many cells that are classically termed "progenitor" cells or "precursor" cells may also fall within the scope of the definition of "multilineage differentiation potential" on the basis that, under appropriate stimulatory conditions, they can give rise to cells of more than one somatic lineage. To the extent that reference to "stem cell" is made herein in terms of the cells generated by the method of the invention, this should be understood as a reference to a cell exhibiting multilineage differentiative potential phenotypes as herein defined.

The de-differentiation method of the present invention has been developed to specifically enable the induction of de-differentiation of leukocytes, in particular lymphocytes, monocytes and granulocytes, to multilineage potential cells. This method is based on the in vitro culturing of somatic leukocytes under specific culture conditions of starting cell concentration, albumin concentration and cell culture medium concentration.

In terms of inducing the in vitro de-differentiation of lymphocytes, monocytes and granulocytes to a multilineage potential cell, this can be achieved either in the context of small scale in vitro tissue culture or large scale bioreactor production.

The transition of lymphocytes, monocytes or granulocytes to a cell of multilineage potential can be achieved in vitro by subjecting said cells to a unique cell culture regime. Specifically, a starting sample of cells are cultured in specific proportions together with albumin and a cell culture medium. This is a particular advantage of the method since unlike most cell culture systems, the establishment of this culture is not based on culturing a specific concentration of cells, which entails determination of cell numbers and appropriate adjustment of cell concentration, but is based on designing the culture around volume proportions, irrespective of the actual number of cells within that volume. This renders the present method very simple and routine to perform based on whatever starting volume of lymphocytes, monocytes or granulocytes are either available or convenient to work with.

The in vitro cell culture system is therefore established around the starting volume of lymphocytes, monocytes or granulocytes suspension. These cells may be contained in any suitable medium such as an isotonic solution (e.g. PBS, saline, Hank's balanced salt solution or other balanced salt solution variations), cell culture medium, bodily fluid (e.g. serum) or the like which will maintain the cells in a viable state. The subject cells may have undergone enrichment or treatment by other methods, such as positive or negative magnetic bead separation, which would result in the final suspension of lymphocytes, monocytes or granulocytes being contained in any one of a variety of different isotonic solutions, depending upon the nature of the method which is utilized. Irrespective of the actual concentration of cells which are obtained, any suitable volume of this suspension can be used to establish the culture. This volume will be selected based on the type of culture system which is sought to be used. For example, if one is culturing in a flask-based system, bag-based system or roller bottle-based system, it is likely that smaller volumes, up to about one litre, will form the totality of the cell culture. However, in the context of a bioreactor, significantly larger volumes of cell culture can be accommodated and thereby larger starting volumes can be used. It is well within the skill of the person in the art to determine an appropriate final cell culture volume for use in the context of the particular cell culture system which will be utilized.

In terms of initially establishing the cell culture, the final volume of the cell culture which will undergo culturing comprises about 15% v/v of a lymphocyte, monocyte and/or granulocyte suspension together with about 15% v/v of a 5%-85% albumin solution and about 70% v/v of a cell culture medium. As detailed herein, references to these percentage values are approximate to the extent that some deviation from these specific percentages is acceptable and provides a functionally equivalent proportion. For example, it is to be expected that from about 10% to 20% v/v of the leukocyte cell suspension and the 5%-85% albumin solution may be effective, in particular 11%-19%, 12%-18%, 13%-17% or 14%-16%. In relation to the subject albumin solution, a solution of from about 4% to 90%, or 5%-86% or preferably 5%-7% may be equally effective.

Without limiting the present invention in any way, an albumin concentration across a very wide range is effective. Accordingly, one may use a concentration range of 5%-85%, 5%-85%, 5%-80%, 5%-75%, 5%-70%, 5%-65%, 5%-60%, 5%-50%, 5%-45%, 5%-40%, 5%-35%, 5%-30%, 5%-25%, 5%-20%, 5%-15%, 5%-10%. In one embodiment, said concentration is 5%-20%.

In another embodiment, said albumin concentration is 5%, 6%, 7%, 8%, 9%, 10%, 11%, 12%, 13%, 14%, 15%, 16%, 17%, 18%, 19% or 20%.

The present method should not be limited by reference to strict adherence to reference to 15% v/v cells, 5%-20% v/v albumin or 70% cell culture medium, as appears herein, for example, but includes within its scope variation to these percentages which retain functionality and which can be routinely and easily assessed by the person of skill in the art.

The concentration of lymphocytes, monocytes or granulocytes within the starting cell suspension can be any number of cells. Whether that cell number is relatively low or relatively high, it is preferred that the starting cell suspension is approximately 15% v/v of the total volume of the starting cell culture, irrespective of the concentration of cells within that suspension. Nevertheless, in a preferred embodiment, although there is neither a lower limit nor an upper limit to the starting cell concentration, the cell number should not be so high that there is insufficient surface area in the culture container for these cells to adhere to during culture. Although the method will nevertheless succeed in producing cells exhibiting multilineage differentiative potential, to the extent that the starting cell concentration is so high that there may be insufficient surface area for these cells to adhere. Accordingly, the preferred cell concentration of the starting cell culture is at a concentration where substantially all of the cells present are able to adhere to the culture container. For example, where one is using a culture bag container, a cell concentration of not more than $10^6$ cells/ml is suitable.

In terms of the albumin solution which is used, a 6% albumin solution is commonly commercially available but may otherwise be made up in any suitable isotonic solution, such as saline. It should be understood that reference to "albumin" is intended as a reference to the group of globular proteins which are soluble in distilled water and solutions of half-saturated ammonium sulphate, but insoluble in fully saturated ammonium sulphate solution. For example, serum albumin, which is a major protein of serum, may be used in the context of the cell culture. However, it should be understood that any albumin molecule may be utilized such as lactalbumin or ovalbumin. It would be appreciated by the person of skill in the art that by using the 6% albumin solution, for example, in the proportion of 15% v/v of the starting culture volume, an effective concentration of 0.9% albumin is achieved.

The remainder of the starting culture volume is comprised of cell culture medium being approximately 70% v/v of the starting cell culture volume. Reference to "cell culture medium" should be understood as a reference to a liquid or gel which is designed to support the growth of mammalian cells, in particular medium which will support stem cell culturing. To this end, any suitable cell culture medium may be used including minimal media, which provide the minimum nutrients required for cell growth, or enriched media, which may contain additional nutrients to promote maintenance of viability and growth of mammalian cells. Examples of media suitable for use include Nutriflex peri solution, DMEM and RPMI. Alternatively, a supplementary minimal medium which contains an additional selected agent such as an amino acid or a sugar to facilitate maintenance of cell viability and growth can be used. The medium may also be further supplemented with any other suitable agent, for example antibiotics. In another example the cell culture medium is supplemented inducing agents such as insulin to assist with de-differentiation. In still another example, where autologous MLPC are prepared for a particular patient, the culture medium may be supplemented with serum harvested from the blood of that patient. It should be understood that reference to the 70% v/v cell culture medium is a stand-alone requirement which is not impacted upon by the nature of the solutions, whether they be isotonic solutions such as saline or minimal culture media, which the starting lymphocytes, monocytes or granulocytes or albumin are suspended in. It is in fact a particular advantage that irrespective of the nature of the solution within which the mononuclear cells are initially suspended, prior to their introduction to the culture system, or in which the albumin is dissolved, the requirement for the 70% v/v cell culture medium as a percentage of the total volume of the starting cell culture population remains unchanged.

In one embodiment, said cell culture additionally comprises 10 mg/L insulin.

As detailed hereinbefore, the method of generating multilineage potential cells is based on culturing a population of lymphocytes, monocytes and/or granulocytes in specific proportions together with a cell culture medium and a 5%-85% albumin solution to induce de-differentiation of the cells to a stem cell phenotype. Said lymphocytes, monocytes or granulocytes are cultured in vitro until such time as the subject stem cell like phenotype is achieved. In one embodiment, a culture period of 3-12 days, in particular 4-7 days, has been determined to be appropriate for generating the subject MLPC cells.

It has been determined that 4 to 6 days of incubation is particularly suitable when culturing human lymphocytes, monocytes or granulocytes for de-differentiation. The culturing can proceed under conditions as deemed appropriate to maintain good cell viability and growth over the culture period of several days. The cells in the culture are believed to become stressed during the incubation and the stress is believed to contribute to inducing de-differentiation.

As detailed herein, the multilineage potential cells of the present invention are induced to de-differentiate from lymphocytes, monocytes and granulocytes. In this regard, reference to a "lymphocyte" should be understood as a reference to any one of three subtypes of small leukocytes found in the blood and lymphatic systems which exhibit a single round nucleus, specifically B cells, T cells and NK cells. In one embodiment, said lymphocyte expresses CD4, CD8, CD25 or CD19. Reference to a cell which expresses CD4, CD8, CD25 or CD19 should be understood as a reference to a mononuclear cell which expresses either or both of the CD4 and CD8 antigens or which expresses CD25 or CD19. The expression of these cell surface molecules may be transient, such as the double-positive expression of CD4 and CD8 on thymocytes during T cell differentiation, or ongoing. CD4 is a glycoprotein found on the surface of T helper cells, monocytes, macrophages and dendritic cells. It is a member of the immunoglobulin superfamily and comprises four immunoglobulin domains, $D_1$ to $D_4$. CD4 also has alternatively been known as leu-3 and T4. CD8 is predominantly expressed on the surface of cytotoxic T cells but can also be found on natural killer cells, natural killer T cells, cortical thymocytes and dendritic cells. CD8 takes the form of a dimer consisting of a pair of CD8 chains, most commonly a CD8-$\alpha$ and a CD8-$\beta$ chain. Both these chains are also members of the immunoglobulin super family. Although CD8 is most commonly expresses as a heterodimer, homodimers are also expressed on some cells, such as CD8-$\alpha$ homodimers. CD25 is the alpha chain of the IL-2 receptor. It is a type I transmembrane protein present on activated T cells, activated B cells, some thymocytes, myeloid precursors, and oligodendrocytes that associate with CD122 to form a heterodimer that can act as a high-affinity receptor for IL-2. Although CD25 has been used as a marker to identify regulatory T cells, it has been found that a proportion of resting memory T cells constitutively express CD25 in humans. The CD19 gene encodes a cell surface molecule that assembles with the antigen receptor of B lymphocytes in order to decrease the threshold for antigen receptor-dependent stimulation. It is expressed on follicular dendritic cells and B cells. It is present on B cells from the earliest recognizable B-lineage cells during development to B-cell blasts. However, it is lost on maturation to plasma cells. It primarily acts as a B cell co-receptor in conjunction with CD21 and CD81. Upon activation, the cytoplasmic tail of CD19 becomes phosphorylated, which leads to binding by Src-family kinases and recruitment of PK-3 kinase.

Accordingly, in one embodiment, said CD4$^+$ and/or CD8$^+$ lymphocyte is a thymocyte, T cell, natural killer cell, natural killer T cell, macrophage or dendritic cell. In another embodiment, said CD25$^+$ cell is a regulatory T cell or a memory T cell. In still another embodiment, said CD19$^+$ cell is a B cell of any stage of differentiation.

As detailed herein the CD4, CD8, CD25 and CD19 molecules are predominantly expressed extensively on lymphocytes and NK cells. Reference to "lymphocyte" should be understood as a reference to any lymphocyte or NK cell, irrespective of its developmental stage of differentiation or level of expression of the relevant CD molecule.

Monocytes constitute between three to eight percent of the leukocytes in the blood. Approximately half are stored as a reserve in the spleen in clusters in the red pulp's Cords of Billroth. In the tissues, monocytes mature into different types of macrophages at different anatomical locations. There are at least three types of monocytes in human blood:

(a) the classical monocyte is characterized by high level expression of the CD14 cell surface receptor (CD14++ CD16− monocyte)
(b) the non-classical monocyte shows low level expression of CD14 and with additional co-expression of the CD16 receptor (CD14+CD16++ monocyte).
(c) the intermediate monocyte shows high level expression of CD14 and low level expression of CD16 (CD14++ CD16+ monocytes).

Reference to "granulocytes" should be understood as reference to the leukocyte subpopulation, also known as polymorphonuclear leukocytes, which are characterized by the presence of granules in their cytoplasm. The cells typically falling within this class of cells are neutrophils, eosinophils, basophiles and mast cells.

In one preferred embodiment, said lymphocytes, monocytes and granulocytes are isolated from peripheral blood.

Accordingly, in another embodiment there is provided an isolated heterogeneous population of mammalian multilineage potential cells, which multilineage potential cells have been induced to de-differentiate from peripheral blood lymphocytes, monocytes and granulocytes, said population of multilineage potential cells comprising:
(i) about 40%-60% multilineage potential cells induced from granulocytes;
(ii) about 20%-40% multilineage potential cells induced from lymphocytes; and
(iii) about 2%-8% multilineage potential cells induced from monocytes.

In another embodiment, said lymphocytes include T cells, B cells and NK cells, preferably CD4+, CD8+, CD25+ and/or CD19+ cells.

In still another embodiment, said monocytes are CD14+ cells.

As detailed hereinbefore, the present invention is predicated on the determination that where multilineage potential cells have been derived from each of lymphocytes, monocytes and granulocytes which are in a heterogeneous leukocyte suspension with a leukocyte subtype profile being similar to the profile in a patient's blood. In a preferred embodiment, the leukocyte suspension is taken from a blood sample and includes a minor proportion of red blood cells and or plasma of up to 10% of red blood cells and plasma when compared with the original sample concentration of red blood cells and plasma. The red blood cells and or plasma are taken concurrently when the mixed leukocytes are taken from the blood sample.

The subject lymphocytes, monocytes and granulocytes can be taken from a blood sample of an individual who is the subject of treatment or they can be sourced from a non-fresh source, such as from a culture (for example, where cell numbers were expanded and/or the cells were cultured so as to render them receptive to differentiative signals) or a frozen stock of cells, which had been isolated at some earlier time point either from an individual or from another source.

To the extent that the multilineage potential cells of the present invention are generated from starting populations of separated leukocyte subpopulations, it is preferred that the subject multilineage potential cells are recombined in relative proportions which reflect the differential ratios of leukocytes which are found in the peripheral blood.

In a preferred and convenient embodiment, the subject multilineage potential cells can be generated in a single step by inducing the de-differentiation of the whole leukocyte population isolated from peripheral blood. In terms of the in vitro culture based de-differentiation method exemplified herein, this method is effective to induce de-differentiation of approximately all of the subpopulations of leukocytes present in a peripheral blood derived sample.

According to this preferred embodiment there is therefore provided an isolated population of multilineage potential cells, which multilineage potential cells have been induced to de-differentiate from peripheral blood derived leukocytes.

Reference to "peripheral blood derived leukocytes" should be understood as a reference to the whole leukocyte population of a peripheral blood sample.

To the extent that the leukocytes which are de-differentiated in accordance with the present invention are derived from whole blood, for example unfractionated, fractioned or enriched samples, it is preferred that red blood cells are present in the starting leukocyte suspension, such as residual red blood cells which remain after fractionation or enrichment. It has been unexpectedly determined that the presence of red blood cells assists with the de-differentiation and or ongoing survival of the MLPC which are generated from the leukocytes. Accordingly, in one preferred embodiment said isolated populations of multilineage potential cells includes subpopulation of red blood cells. The experimental results of demonstrating the positive effects of including red blood cells in the starting leukocyte suspension are described in Example 4 which is provided herein.

The isolated multilineage potential cells of the present invention are useful in a range of in vitro and in vivo applications. As detailed hereinbefore, it has been determined that the functionality of multilineage potential cells in terms of their directed differentiation and therapeutic/prophylactic utility, either in vitro or in vivo, is significantly better where the isolated multilineage potential cell population is derived from a mixed leukocyte suspension and, in particular, from one where the leukocyte subtype proportions are similar to those found in the peripheral blood. Example 6 described herein provides experimental support that multilineage potential cells derived from a mixed leukocyte suspension is therapeutically better than use of a leukocyte suspension having only a few leukocyte subtypes.

As described herein, the comparative leukocyte subtype proportions will vary between individuals. In an embodiment where a blood sample is taken from two or more different individuals, each blood sample will have a substantially different leukocyte subtype profile and consequently the number, type and profile of the MLPC derived each blood sample (from a different individual) will be different. Example 5 provides experimental support that different individuals have different mixed leukocyte profiles and a different MLPC profile following de-differentiation.

In one embodiment, said multilineage potential cell may be induced, in vitro, to undergo directed differentiation to a desired somatic phenotype. For example, and exemplified herein, cardiomyogenic, osteogenic, neuronal and neo-hepatocyte induction can be achieved. In another example, haematopoietic stem cells give rise to all the blood cells (e.g. red blood cells, platelets, lymphocytes, monocytes and the granulocytes) while mesenchymal stem cells give rise to a wide variety of connective tissues including bone, cartilage, smooth muscle, tendon, ligament, stroma, marrow, dermis and fat. To the extent that the method of the present invention produces multilineage potential cells with both mesenchymal and haematopoietic potential, the method of the invention can be adapted, either in vitro or in vivo, to include a further step which introduces the subject multilineage potential cell population to the specific stimuli required to effect partial or full differentiation along the lineage of interest.

Accordingly, in a related aspect of the present invention there is provided a method of facilitating the generation of mammalian MLPC-derived cells, said method comprising establishing an in vitro cell culture system which proportionally comprises:

(i) about 40%-60% multilineage potential cells induced from granulocytes;
(ii) about 20%-40% multilineage potential cells induced from lymphocytes; and
(iii) about 2%-8% multilineage potential cells induced from monocytes and contacting said multilineage potential cell with a stimulus to direct the differentiation of said multilineage potential cell to a MLPC-derived phenotype.

In one embodiment, said lymphocytes include T cells, B cells and NK cells, preferably $CD4^+$, $CD8^+$, $CD25^+$ and/or $CD19^+$ cells.

In another embodiment, said monocytes are $CD14^+$ cells.

In still another embodiment, said in vitro culture system comprises peripheral blood derived leukocytes.

In yet another embodiment said multilineage potential cell exhibits both hematopoietic and mesenchymal potential.

In still another embodiment, said MLPC-derived cells are cardiomyocytes, osteocytes, neurons or hepatocytes.

In another embodiment, said MLPC-derived cells are red blood cells, lymphocytes, monocytes, neutrophils, basophils or eosinophils.

In yet still another embodiment, said MLPC-derived cells are connective tissue cells such as cells of the bone, cartilage, smooth muscle, tendon, ligament, stroma, marrow, dermis or fat.

In the context of this aspect of this invention, it should be understood that there may be produced both cellular aggregates such as tissues (for example, muscular or dermal tissue), or cell suspensions (for example, hematopoietic cell suspensions).

In terms of either enriching a mature somatic cell population for one or more of lymphocytes, monocytes or granulocytes prior to culturing in accordance with the method of the invention or isolating or enriching a multilineage potential cell population derived therefrom there are various well known techniques which can be performed.

(i) Detection of Cell Lineage Specific Structures.

Detection of cell lineage specific structures can be performed, for example, via light microscopy, fluorescence affinity labelling, fluorescence microscopy or electron microscopy, depending on the type of structure to be identified. Light microscopy can be used to detect morphologic characteristics such as lymphocyte vs polymorphonuclear vs red blood cell nuclear characteristics or multinucleate skeletal muscle cells. In another example, mononuclear cells which are about 10-30 μm in diameter, with round or rod-shaped morphology characteristic of immature cardiomyocytes can be identified. Electron microscopy can be used to detect structures such as sarcomeres, X-bands, Z-bodies, intercalated discs, gap junctions or desmosomes. Fluorescence affinity labelling and fluorescence microscopy can be used to detect cell lineage specific structures by fluorescently labelling a molecule, commonly an antibody, which specifically binds to the structure in issue, and which is either directly or indirectly conjugated to a fluorophore. Automated quantitation of such structures can be performed using appropriate detection and computation systems.

(ii) Detection of Cell Lineage Specific Proteins.

Detection of cell lineage specific proteins, such as cell surface proteins or intracellular proteins, can be conveniently effected via fluorescence affinity labelling and fluorescence microscopy, for example. Specific proteins can be detected in both whole cells and tissues. Briefly, fluorescently labelled antibodies are incubated on fixed cells to detect specific cardiac markers. Alternatively, techniques such as Western immunoblotting or hybridization micro arrays ("protein chips") may be employed. The proteins which can be detected via this method may be any protein which is characteristic of a specific population of cells. For example, classes of precursor/progenitor cell types can be distinguished via the presence or absence of expression of one or more cell surface molecules. In this regard, this method can be utilised to identify cell types via either a positive or negative selection step based on the expression of any one or more molecules. More mature cells can usually be characterised by virtue of the expression of a range of specific cell surface or intracellular proteins which are well defined in the literature. For example, the differentiative stages of all the hematopoietic cell types have been well defined in terms of cell surface molecule expression patterns. Similarly, muscle cells and other mesenchymal-derived cell types are also well documented in the context of protein expression profiles through the various differentiative stages of development. To this end, the MLPCs of the present invention typically express a range of cell surface markers which are exemplified herein, these being cell surface markers characteristic of monocytic stem cells generally, mesenchymal stem cells, hematopoietic stem cells, multilineage potential cells and neuronal stem cells.

(iii) Detection of Cell Lineage Specific RNA or DNA.

This method is preferably effected using RT-PCR or real-time (qRT-PCR). Alternatively, other methods, which can be used include hybridization microarray ("RNA chip") or Northern blotting or Southern blotting. RT-PCR can be used to detect specific RNAs encoding essentially any protein, such as the proteins detailed in point (ii) above, or proteins which are secreted or otherwise not conveniently detectable via the methodology detailed in point (ii). For example, in the context of early B cell differentiation, immunoglobulin gene rearrangement is detectable at the DNA level prior to cell surface expression of the rearranged immunoglobulin molecule.

(iv) Detection of Cell Lineage Specific Functional Activity.

Although the analysis of a cell population in terms of its functioning is generally regarded as a less convenient method than the screening methods of points (i)-(iii), in some instances this may not be the case. For example, to the extent that one is seeking to generate cardiac cells, one may simply screen, under light microscopy, for cardiac specific mechanical contraction.

As detailed above, antibodies and other cell surface binding molecules, such as lectins, are particularly useful for identifying markers associated with particular cell lineages and/or stages of differentiation. The antibodies may be attached to a solid support to allow for separation. However, other cell separation techniques include those based on differences in physical characteristics (density gradient centrifugation, continuous flow centrifugation and counter-flow centrifugal elutriation) and vital staining properties (mitochondria-binding dye rhodamine 123 and DNA-binding dye Hoechst 33342).

Procedures for separation may include magnetic separation, using antibody or lectin-coated magnetic beads, affinity chromatography, "panning" with antibody attached to a solid matrix or any other convenient technique. Other techniques providing particularly accurate separation include fluorescence activated cell sorting, this technique also being applicable to the separation of cells based on morphological characteristics which are discernible by forward vs side light scatter. Whereas these techniques can be applied in the context of either positive or negative selection, additional negative selection techniques include, but are not limited to, the site-directed administration of a cytolytic, apoptotic or otherwise toxic agent.

This may be most conveniently achieved via the coupling of such an agent to a monoclonal antibody in order to facilitate its directed delivery. In another example, opsonization with an antibody followed by complement administration may achieve the same outcome.

These techniques can be performed as either a single-step or multi-step protocol in order to achieve the desired level of purification or enrichment.

Since the proliferative capacity of the cells and tissues of the present invention may be essential to a given use, for example to repair damaged tissue, or to test the effects of a therapeutic treatment regime, it may be desirable to screen for cells which are displaying an adequate level of proliferative capacity. Determining the proliferative capacity of cells can be performed by numerous standard techniques.

Preferably, determination of proliferation is effected via $^3$[H]-thymidine or $^{125}$I-iododeoxyuridine uptake assay. Alternatively, colourimetric assays employing metabolic dyes such as XTT or direct cell counting may be employed to ascertain proliferative capacity. Proliferation capacity can also be evaluated via the expression of cell cycle markers such as Ki-67.

The development of the present invention has now facilitated the development of means for therapeutically or prophylactically treating subjects. To date, the stem cells that have been used for therapy have been homogenous (or even clonal) populations. The determination that an isolated population of multilineage potential cells as defined herein exhibit superior functional outcomes relative to any one of the lymphocytic, granulocytic or monocytic populations used alone was unexpected and counterintuitive relative to current practice and dogma.

This method can be applied to a wide range of conditions including, but not limited to hematopoietic disorders, circulatory disorders, stroke, myocardial infarction, hypertension bone disorders, type II diabetes, infertility, cardiac disorders, hepatic disorders, neural disorders, damaged or morphologically abnormal cartilage or other tissue, hernia repair, pelvic floor prolapse surgery using supportive mesh and biological scaffolds, cell therapy for other musculoskeletal disorders and replacement of defective supportive tissues in the context of aging, surgery or trauma.

Accordingly, another aspect of the present invention is directed to a method of therapeutically and/or prophylactically treating a condition in a mammal, said method comprising administering to said mammal an effective number of multilineage potential cells of the present invention.

In one embodiment, said condition is cardiac damage, hepatic disease, neuronal disorders and/or osteopathy.

Reference to "administering" to an individual an effective number of the cells of the invention should be understood as a reference to introducing into the mammal an ex vivo population of cells which have been generated according to the method of the invention.

In accordance with the present invention, the subject multilineage potential cells or MLPC-derived cells are preferably autologous cells which are identified and transplanted back into the individual from which they were originally harvested. In accordance with the present invention, peripheral blood is preferably harvested, the leukocytes enriched for and de-differentiated to multilineage potential cells. However, it should be understood that the present invention nevertheless extends to the use of cells derived from any other suitable source where the subject cells exhibit the same major histocompatability profile as the individual who is the subject of treatment.

Accordingly, such cells are effectively autologous in that they would not result in the histocompatability problems which are normally associated with the transplanting of cells exhibiting a foreign MHC profile. Such cells should be understood as falling within the definition of "autologous". For example, under certain circumstances it can be desirable, necessary or of practical significance that the subject cells are isolated from a genetically identical twin. The cells may also have been engineered to exhibit the desired major histocompatability profile. The use of such cells overcomes the difficulties which are inherently encountered in the context of tissue and organ transplants.

As detailed hereinbefore, multilineage potential cell transition is performed in vitro. In this situation, the subject cell will then require introduction into an individual. For example, cell suspensions may be introduced by direct injection or inside a blood clot whereby the cells are immobilized in the clot thereby facilitating transplantation. The cells may also be encapsulated prior to transplantation. Encapsulation is a technique which is useful for preventing the dissemination of cells which may continue to proliferate (i.e. exhibit characteristics of immortality) or for minimizing tissue incompatibility rejection issues. However, the usefulness of encapsulation will depend on the function which the transplanted cells are required to provide. For example, if the transplanted cells are required primarily for the purpose of secreting a soluble factor, a population of encapsulated cells will likely achieve this objective. However, if the transplanted cells are required for their contractile properties, for example, the cells will likely be required to integrate with the existing tissue scaffold of the muscle, encapsulated cells would not be able to do this efficiently.

The cells which are administered to the patient can be administered as single or multiple doses by any suitable route. Preferably, and where possible, a single administration is utilised. Administration via injection can be directed to various regions of a tissue or organ, depending on the type of repair required.

Another aspect of the present invention is directed to the use of a population of multilineage potential cells or MLPC-derived cells, which cells have been generated in accordance with the method of the present invention, in the manufacture of a medicament for the treatment of a condition in a mammal.

In a related aspect of the present invention, the subject undergoing treatment or prophylaxis may be any human or animal in need of therapeutic or prophylactic treatment. Accordingly, treatment and prophylaxis include amelioration of the symptoms of a particular condition or preventing or otherwise reducing the risk of developing a particular condition. The term "prophylaxis" may be considered as reducing the severity of the onset of a particular condition. "Treatment" may also reduce the severity of an existing condition.

The cells of the present invention may be administered to the patient by any suitable method. For example, cell suspensions may be introduced by direct injection or inside a blood clot whereby the cells are immobilised in the clot thereby facilitating transplantation. The cells may also be encapsulated prior to transplantation. Encapsulation is a technique which is useful for preventing the dissemination of cells or for minimising tissue incompatibility rejection issues.

In one embodiment of the present invention the subject cells are administered systemically.

In another embodiment, said cells are administered locally to the site of the tissue or area to be treated.

The cells which are administered to the patient can be administered as single or multiple sequential doses by any suitable route. Administration via injection can be directed to various regions of a tissue or organ, depending on the type of treatment or repair required.

It would be appreciated that in accordance with these aspects of the present invention, the cells which are administered to the patient may take any suitable form, such as being in a cell suspension or cell aggregate. In terms of utilising a cell suspension, it may also be desirable to select out specific subpopulations of cells for administration to a patient. To the extent that it is desired that a cell aggregate or encapsulated cells are transplanted into a patient, this will usually require surgical implantation (as opposed to administration via a needle or catheter).

In accordance with the method of the present invention, other proteinaceous or non-proteinaceous molecules may be co-administered either with the introduction of the subject cells or prior or subsequently thereto. By "co-administered" is meant simultaneous administration in the same formulation or in different formulations via the same or different routes or sequential administration via the same or different routes. By "sequential" administration is meant a time difference of from seconds, minutes, hours or days between the introduction of these cells and the administration of the proteinaceous or non-proteinaceous molecules or the onset of the functional activity of these cells and the administration of the proteinaceous or non-proteinaceous molecule. Examples of circumstances in which such co-administration may be required include, but are not limited to:

(i) When administering non-syngeneic cells or tissues to a subject, there usually occurs immune rejection of such cells or tissues by the subject. In this situation it would be necessary to also treat the patient with an immunosuppressive regimen, preferably commencing prior to such administration, so as to minimize rejection. Immunosuppressive protocols for inhibiting allogeneic graft rejection, for example via administration of cyclosporin A, immunosuppressive antibodies, and the like are widespread and standard practice.

(ii) Depending on the nature of the condition being treated, it may be necessary to maintain the patient on a course of medication, such as pain killers, to alleviate the symptoms of the condition until such time as the transplanted cells become fully functional. Alternatively, at the time that the condition is treated, it may be necessary to commence the long term use of medication to prevent re-occurrence of the condition, such as hormonal treatment after breast cancer treatment.

It should also be understood that the method of the present invention can either be performed in isolation to treat the condition in issue or it can be performed together with one or more additional techniques designed to facilitate or augment the subject treatment. These additional techniques may take the form of the co-administration of other proteinaceous or non-proteinaceous molecules, for example radiation therapy or chemotherapy. In one embodiment, the method of the present invention is performed by:

(i) coadministering the MLPC together with chemotherapy; or (ii) administering the MLPC in sequence with chemotherapy.

This can be done as a two stage process where either the chemotherapy step is performed first and followed by administration of MLPC or vice versa.

In one embodiment, said MLPC are administered simultaneously with chemotherapy.

In another embodiment said MLPC are administered in a two-stage sequential protocol wherein the MLPC are administered in the first stage and the chemotherapy in the second stage.

In still another embodiment, said MLPC are administered in a two-stage sequential protocol wherein the chemotherapy is administered in the first stage and the MLPC in the second stage.

In one embodiment, said method is performed with 1 cycle, 2 cycles, 3 cycles, 4 cycles, 5 cycles or 6 or more cycles.

Still without limiting the present invention in any way, the MLPC of the present invention may be administered in multiple sequential doses, with each administration being termed a "cycle". Similarly, to the extent that the MLPC are administered simultaneously with chemotherapy, one such administration is one "cycle". Where the MLPC and chemotherapy are administered in a two-stage method, one such two-stage administration step is one "cycle". Accordingly, it should be understood that multiple cycles can be performed as needed to effect the desired end-point in the patient.

The present invention is further described by reference to the following non-limiting examples.

Example 1

Multiple Differentiations of Autologous Multilineage Potential Cells (MLPC)

Materials and Methods

1. MLPC Preparation

Leukocytes were isolated from peripheral blood collected from healthy subjects aged 20 to 40. Cells were grown for 4 to 7 days at 37° C. in a humidified incubator with 5% $CO_2$. After cultivation in the lab, the cells were named autologous multi-lineage potential cells (MLPC). Continually, MLPC may be isolated and collected by Ficoll-Paque™ PLUS (GE Healthcare) or Polymorphprep™ (Fresenius Kabi Norge AS for Axis-Shield PoC AS, Oslo, Norway) which were composed of various populations of lymphocytes, monocytes, and granulocytes. These multilineage potential stem cells were present in final population about 20%-70% induced from granulocytes, 20%-60% induced from lymphocytes, and 1%-15% induced from lymphocytes and were investigated to determine whether MLPC express stemness genes and can differentiate into osteoblasts, neurons, hepatocytes and cardiomyocytes various lineages.

2. RNA Extraction and RT-PCR

RNA was respectively extracted from total, un-adherent and adherent cells of MLPC after 6 days culture on first stage. Total cellular RNA is extracted from MLPC, both adherent and un-adherent cells, using the TRIzol (Invitrogen) reagent. Reverse transcriptions (RT) of total RNA, 3 micrograms from each sample, were performed in a 20 microliter volume, using the 2-fold RT master mix (Zymeset). The Polymerase chain reaction (PCR) is started from an initial denaturation at 94° C. for 5 min, followed by 40 cycles for annealing, and stay at 72° C. for 5 min finally, using Actin as internal control. The PCR products are analyzed by 2% (w/v) agarose gel electrophoresis which was stained with 0.015% RedSafe (iNtRON). PCR was performed in a 20 microliter of a reaction mixture containing 2 micrograms cDNA and 500 nM each primers. After RT-PCR, they were analyzed for nestin, nanog, oct-4, sox-2 and actin expression.

3. Surface-Marker Determination by Flow Cytometry

Cells were harvested from flasks and washed with phosphate buffered saline (PBS) containing 2% FBS, then centrifuged at 1500 rpm (640 g) at 4° C. for 5 min and the cell pellets were collected. We used 2.5-3×106 cells per sample for each flow cytometry assay. The cells were labeled with fluorochrome antibodies, and then the cell pellets were added to a 100-µL fixation buffer (BD), standing at 4° C. for 20 min, and then stored at 4° C. without light until flow cytometry analysis (Bacton Dickinson). Viable cells were identified using the CellQuest software. The data are shown as logarithmic histograms.

4. Induction Culture and Immune-Fluorescence Staining for Multi-Lineages Differentiation 4.1 Osteogenic Induction and Staining of MLPC MLPC were seeded in 12-well plates and cultured in the induction medium. The osteogenic induction medium included dexamethasone (Sigma), β-glycerophosphate (Sigma), and ascorbic acid 2-phosphate (Sigma), and the induction medium was changed every 4 days. After 12-day or 18-day induction periods, cells were respectively fixed with citrate/acetone/formaldehyde (20%/50%/30%) and 10% formaldehyde and then stained with alkaline-dye mixture (12-day induction) or 2% Alizarin Red S (ARS) (18-day induction) (Sigma).

The alkaline-dye mixture was prepared by adding 40 µl of sodium nitrite solution to 40 µl of FRV-Alkaline solution and then mixed by gentle inversion. This mixture was allowed to stand for 2 minutes, then 1.8 ml de-ionized water was added to prepare diazonium salt solution. Finally, 40 µl of naphthol AS-BI alkaline solution was added to create the working solution of alkaline-dye mixture.

4.2 Neuronal Induction and Immune-Fluorescence Staining of MLPC

MLPC were grown in co-culture system in 24-well plates coated with fibronectin (10 microg/mL). The coculture system was established by inserting 0.4 micron transwells (CORING) onto the 24-well plates. The upper deck (transwell) seeded the induction cells, 7×10⁴ of PC-12 cells per well, which secrete neural growth factors to induce differentiation of MLPC grown in the lower deck (24-well plate). The co-culture induction cells were replaced every 3 days.

Antibody Paired box-5 (PAX-5), was obtained from Epitomic Inc., Nestin, Synaptophysin, Hypoxia-inducible factor-1 alpha (HIF-1 alpha), Achaete-scute homolog 1 (MASH1), Actin, from Merck Millipore Headquarters (Billerica, Mass., USA), Neurogenin 3 (E-8) from Santa Cruz Biotechnology (Santa Cruz, Calif., USA) and NeuN, FITC and DAPI from Abcam.

After differentiation induction, the cells were fixed in cold methanol for 10 minutes. These fixed cells were treated with 0.1% Triton X-100 solution for 10 minutes at room temperature, and washed two times in D-PBS for 5 min each to be subjected to permeabilization. Nonspecific binding sites were blocked with blocking buffer (containing 5% bovine calf serum in 1% bovine serum albumin solution) and then incubated for 1 hour at room temperature.

Primary antibodies were diluted in 1% bovine serum albumin solution. These permeabilized cells were incubated with the primary antibody overnight at 4° C. cold room, then washed for five minutes for three times with D-PBS. The secondary antibodies were diluted in 1% bovine serum albumin solution. Cells were incubated with the secondary antibodies for one hour at room temperature in the dark, and washed for five minutes for three times with D-PBS.

The DAPI's stock solution was diluted in D-PBS solution. The permeabilized cells were incubated in the DAPI solution for five min at room temperature in the dark, and then washed for five minutes for three times with D-PBS. The immune-staining was observed under a fluorescent microscope using the appropriate filters for each fluorophore.

4.3 Cardio Myogenic Induction and Immune-Fluorescence Staining of MLPC

The directed cardio myogenic lineage differentiation induction includes two stages. In stage I, the MLPC were cultured and adhered to the fibronectin (10 micro g/mL) culture system and then in the second stage, the culture medium was changed to cardiomyogenic lineage induction medium which contains insulin (Life), EGF (eBioscience), and β-FGF (eBioscience).

Figure 1:
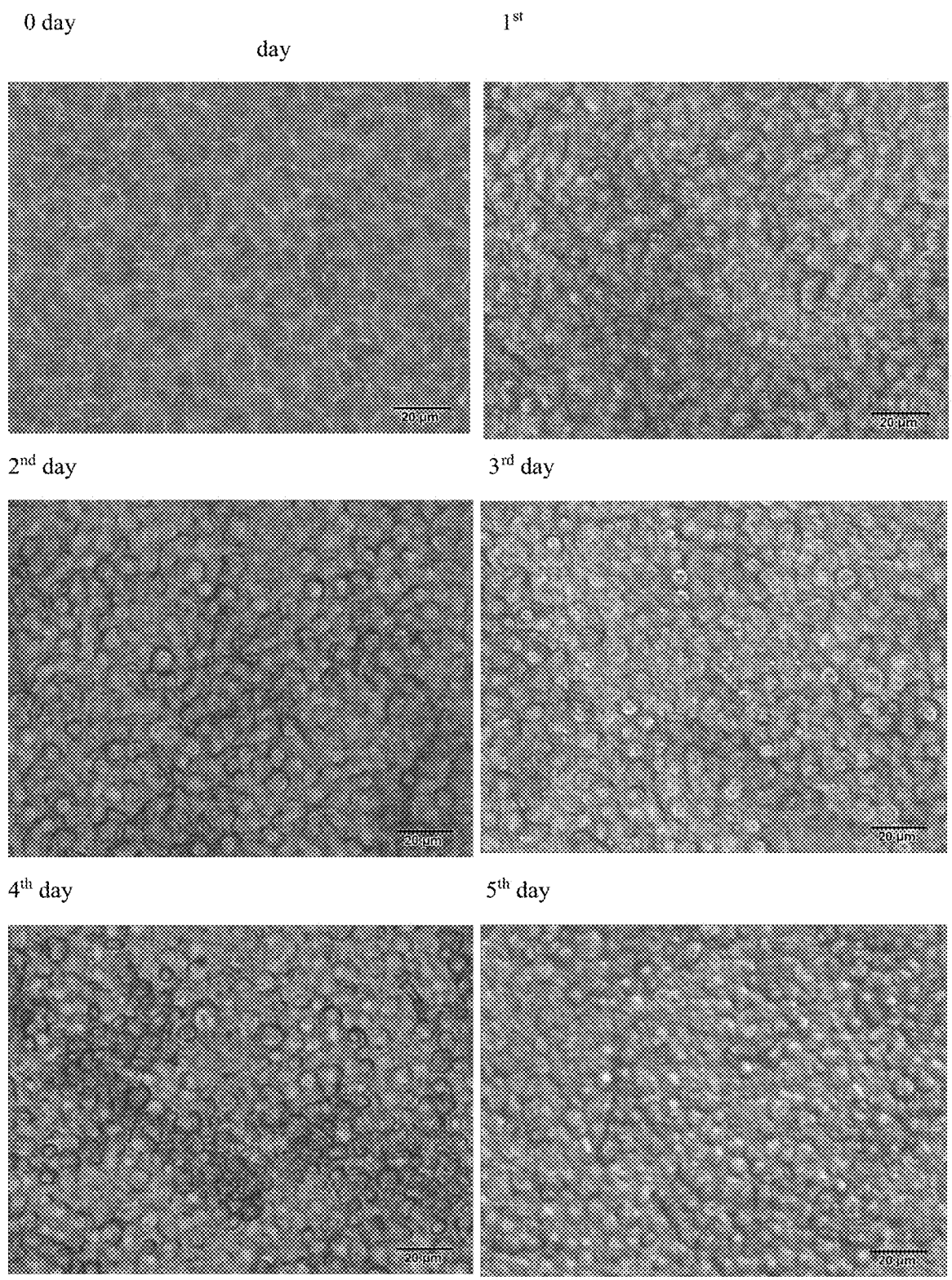
FIG. 1—Cell morphology of MLPC—Cells morphology of MLPC were observed between 1 to 10 days under an invert microscope (OLYMPUS). Original magnification: ×400.

Induced MLPC of second stage were assayed for cardiomyogenic lineage markers expression, including alpha-Actinic, Myogenic, GATA-4, and Troponin I by immune-fluorescence staining at various times from 10 to 20 days (FIG. 1).

Cells fixed steps, dilution buffer of primary antibodies and secondary antibodies, and DAPI reagent were similar as neuron markers staining steps. Antibodies against various proteins were purchased from commercially available sources. These include alpha-Actinin, GATA binding factor-4 (GATA4), Myogenin (Merck Millipore Headquarters) and Troponin I (Abnova).

These cells were observed under a fluorescent microscope for these immunostaining using the appropriate filters for each fluorophore.

4.4 Neo-Hepatocyte Induction and Immune-Fluorescence Staining of MLPC

The directed neo-hepatocyte lineage differentiation induction includes two stages. In stage I, the MLPC were cultured and adhered to the fibronectin (10 micro g/mL) culture system and then in the second stage, the culture medium was changed to neo-hepatocyte lineage induction medium which contains Dexamethasone (Sigma), human HGF (eBioscience), and human β-FGF (eBioscience).

Induced MLPC of second stage were assayed for neo-hepatocyte lineage markers expression, including albumin, alpha fetal protein (AFP), connexion 32, and cytochrome P450 (CYP1A1) by immune-fluorescence staining at various times from 8 to 19 days (FIG. 1).

Cells fixed steps, dilution buffer of primary antibodies and secondary antibodies, and DAPI reagent were similar as neuron markers staining steps. Antibodies against various proteins were purchased from commercially available sources. These include albumin (Sigma), alpha fetal protein (AFP) (Sigma), connexion 32 (Merck Millipore Headquarters), and cytochrome P450 (CYP1A1) (Abnova).

These cells were observed under a fluorescent microscope for these immunostaining using the appropriate filters for each fluorophore.

5. Microarray Analysis

Leukocytes were isolated from 3-5 peripheral blood collected from healthy subjects aged 20 to 40. Cells were grown for 4 to 7 days at 37° C. in a humidified incubator with 5% $CO_2$. Collection cells and extraction RNA before and after 6 days culture in I stage, including no culture (A0) and after 6 days culture total (PA6), attached (ATA6), and un-attached (UATA6) MLPC respectively.

The fold change distribution of all probes excluded control and flagged probes. Fold changes were calculated by Rosetta Resolver 7.2 with error model adjusted by Amersham Pairwise Ration Builder for signal comparison of sample. The number of differentially expressed genes for each comparison is shown in the experiments, including PA6 verse A0, ATA6 verse A0, and UATA6 verse A0. Standard selection criteria to identify differentially expressed genes were as follows: (1) log 2|Fold change|≥1 and P<0.05 (2) log 2 ratios="NA" and the differences of intensity between the two samples ≥1000. For advanced data analysis, intensity data were pooled and calculated to identify differentially expressed genes based on the threshold of fold change and p-value. The correlation of expression profiles between samples and treatment conditions was demonstrated by unsupervised hierarchical clustering analysis. A gene set enrichment analysis of pathways, Gene Ontology (GO) terms were performed using the differentially expressed gene lists as input.

Results

1. Cell Morphology of MLPC

Cells morphology of MLPC were observed in first stage (1-10 days) and second stage (1-20 days) by inverted microscope (OLYMPUS). Cells were adherent and formed cluster from the 4th day on, then the morphology of most of the adherent cells changed remarkably and formed more clusters on the 6th day. On the 10th day, more than 90% of the adherent cells became bigger and the nucleus margin blurred, a phenomenon of cell differentiation (FIG. 1).

2. Stemness Genes Expression of MLPC

Figure 2:
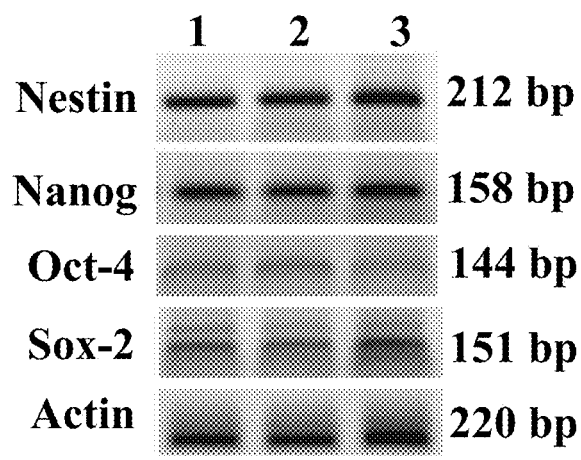
FIG. 2—Nestin, nanog and sox-2 genes of adherent cells of MLPC remark expression—Lane 1, 2, 3 were total, un-adherent and adherent cells of MLPC respectively. The PCR products are analyzed with 2% (w/v) agarose gel electrophoresis and stained with 1.5% RedSafe (iNtRON). PCR was performed in 20 microliter of a reaction mixture containing 2 micrograms cDNA and 500 nM each primers (Table 3).

Collection and extraction RNA of MLPC from culture 6 days cells, sox-2 gene expression was more marked on adherent cells, compared with total and un-adherent cells, while nestin and nanog gene expressions were similar in these 3 settings (FIG. 2).

3. Stem Cell Markers Expression of MLPC

In the literature, CD34, CD90, and CD105 expressions were related to differentiation potentials of mesenchymal stem cells. Adherent and un-adherent cells of MLPC were respectively collected and analyzed for surface markers CD34-APC, CD90-FITC, and CD105-PE expression by flow cytometry after 6 days culture in first stage. In these studies, CD34, CD90, and CD105 were respectively expressed in 55%, 32% and 73% of the adherent MLPCs, but almost none in the un-adherent cells (Table 2). These adherent cells of MLPC were allowed to progress to trans-differentiation induction in the second stage.

4. Osteoblast Differentiation of MLPC

The differentiation of osteoprogenitor cells to osteoblast can be divided into 4 phases, preosteoblast proliferation, matrix maturation, mineralization, and osteoblast formation. In preosteoblast proliferation phase, cells secrete collagen 1, and the proliferation is regulated by parathyrin, prostaglandin E2, transforming growth factor beta, 1, 25(OH) vitamin D3 and interleukin-1. The cell nuclei become larger and round in shape. When the cells enter the matrix maturation phase, the cells secrete alkaline phosphatase (ALP), platelet-derived growth factor, and vascular endothelial growth factor in an autocrine fashion. Then these cells progress to mineralization phase and finally osteoblast phase, in which the cells present with calcium and phosphate ions accumulation. The cell nuclei become flat progressively, and the cells secrete osteocalcin and osteopontin. Finally, the nuclei of osteoblast cells becomes very flat to less than tenth of the original size.

Figure 3:
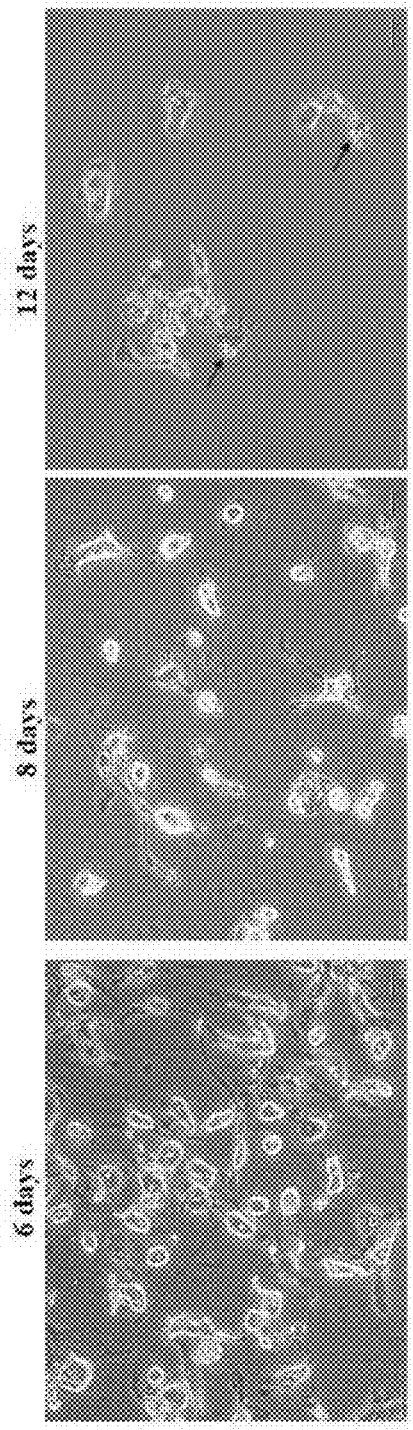
FIG. 3—Osteogenic differentiation of MLPC between 6 to 12 days of induction, and the respective alkaline phosphatase expression (arrow: alkaline mixture staining on the twelfth day). Original magnification: ×400.

MLPC were respectively harvested after 6, 8, 12 days of induction, and were fixed in citrate/acetone/formaldehyde solution and then stained with alkaline-dye mixture. MLPC were observed via invert microscope (OLYMPUS) for ALP expression, and we found commencement of alkaline phosphatase (ALP) expression after 12 days of induction (FIG. 3).

Figure 4:
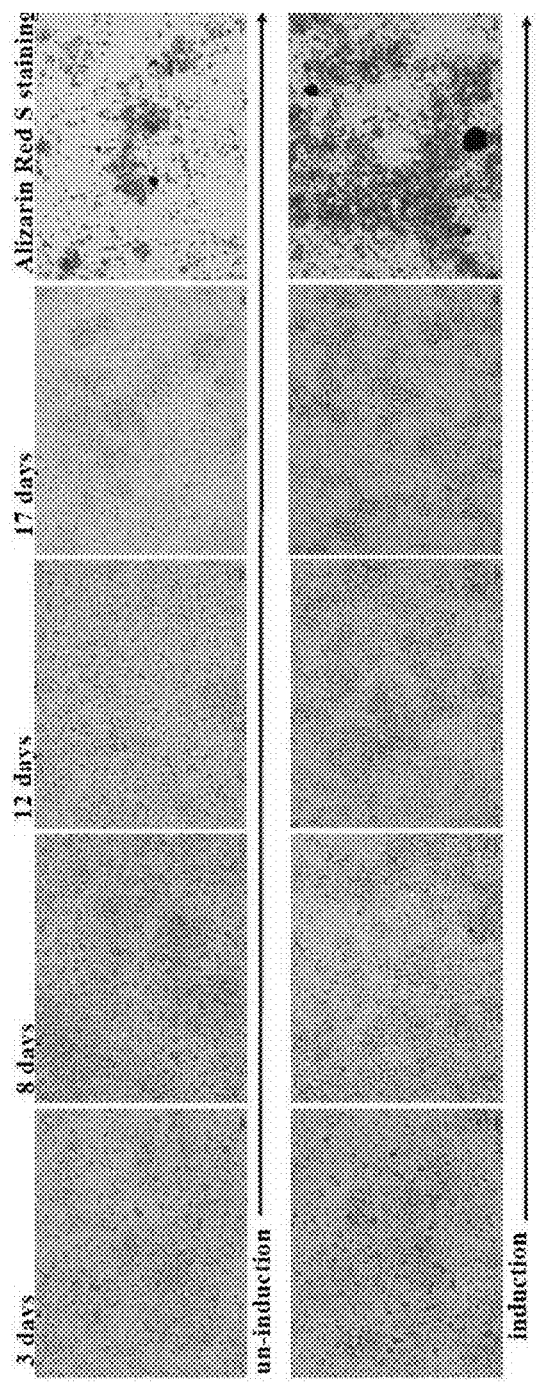
FIG. 4—Calcium accumulation byARS staining in Osteogenic differentiation of MLPC between 3 to 18 days of induction. Original magnification: ×400 [0038].

MLPC were observed for cell morphology between 3 and 18 days after induction. MLPCs present with progressively increasing mineralization from the third day of induction and the cells flattened progressively. On the 18th day, MLPC showed abundant calcium accumulation by ARS staining (FIG. 4).

5. Neural Differentiation of MLPC

Figure 5:
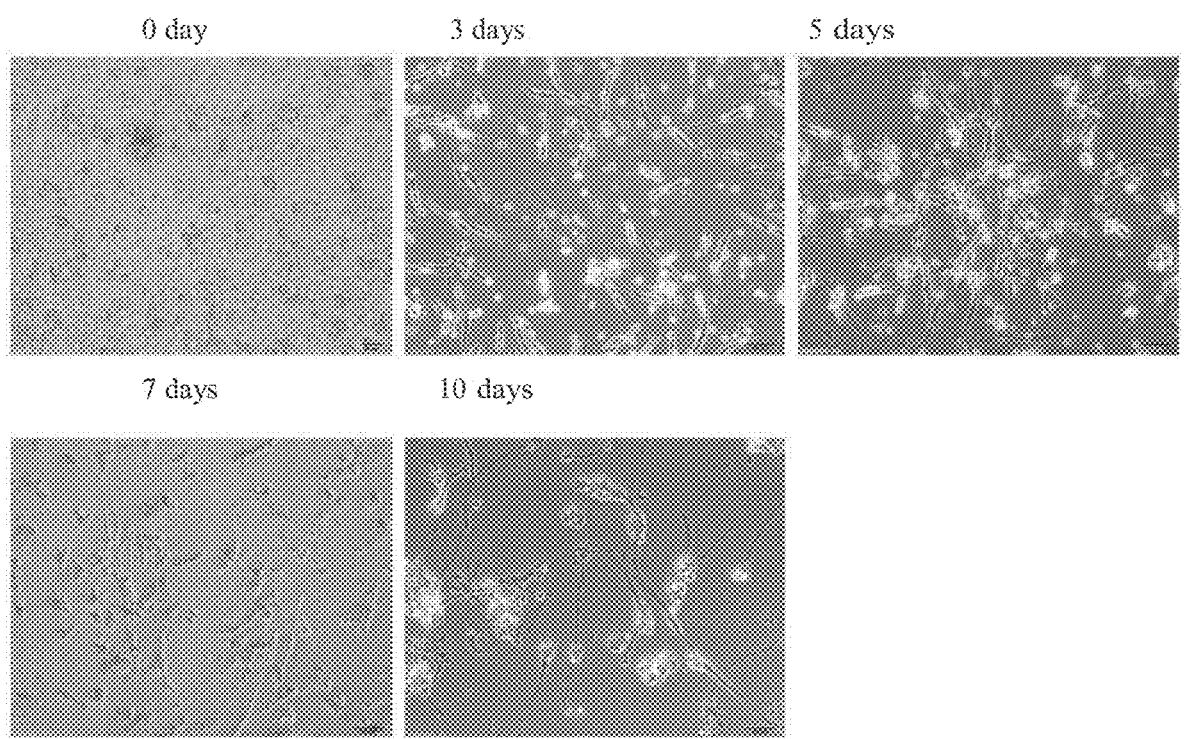
FIG. 5—Neurogenic differentiation of MLPC in co-culture between 0 to 10 days of induction. Original magnification: ×200.
Figure 6:
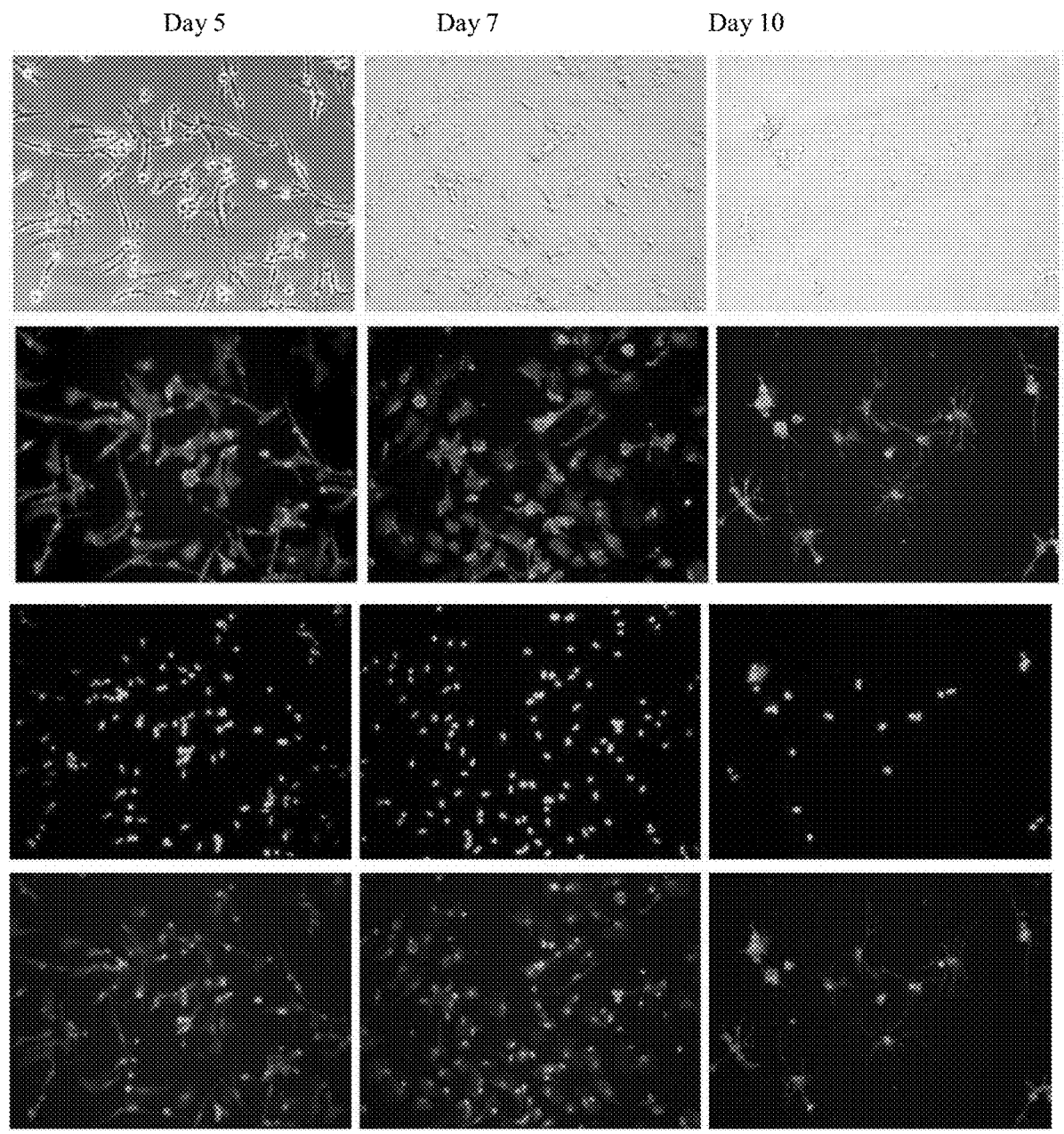
FIG. 6—Actin expression (Actin-FITC) in MLPC after 5, 7 and 10 day of induction. First row: invert microscopic view, second: fluorescence, third: DAPI, fourth: merged fluorescence & DAPI images. Original magnification: ×200.

These studies showed that MLPC can differentiate into neuroectodermal lineage after 10 days of co-culture induction. Partial MLPC displayed a multipolar elongated morphology (FIG. 5). MLPC showed marked actin expression after induction and displayed specifically neural multipolar morphology on seventh day and tenth day (FIG. 6), similar to neurons and astrocytes. Neural progenitor markers expressions, including HIF-1 alpha, Nestin, Neurogenin 3, and Pax 5 were observed on the seventh day, and early neuroectodermal marker display of MASH 1 on the tenth day respectively. Furthermore, synaptophysin involved in progressive formation of the synapse, was expressed.

Figure 7:
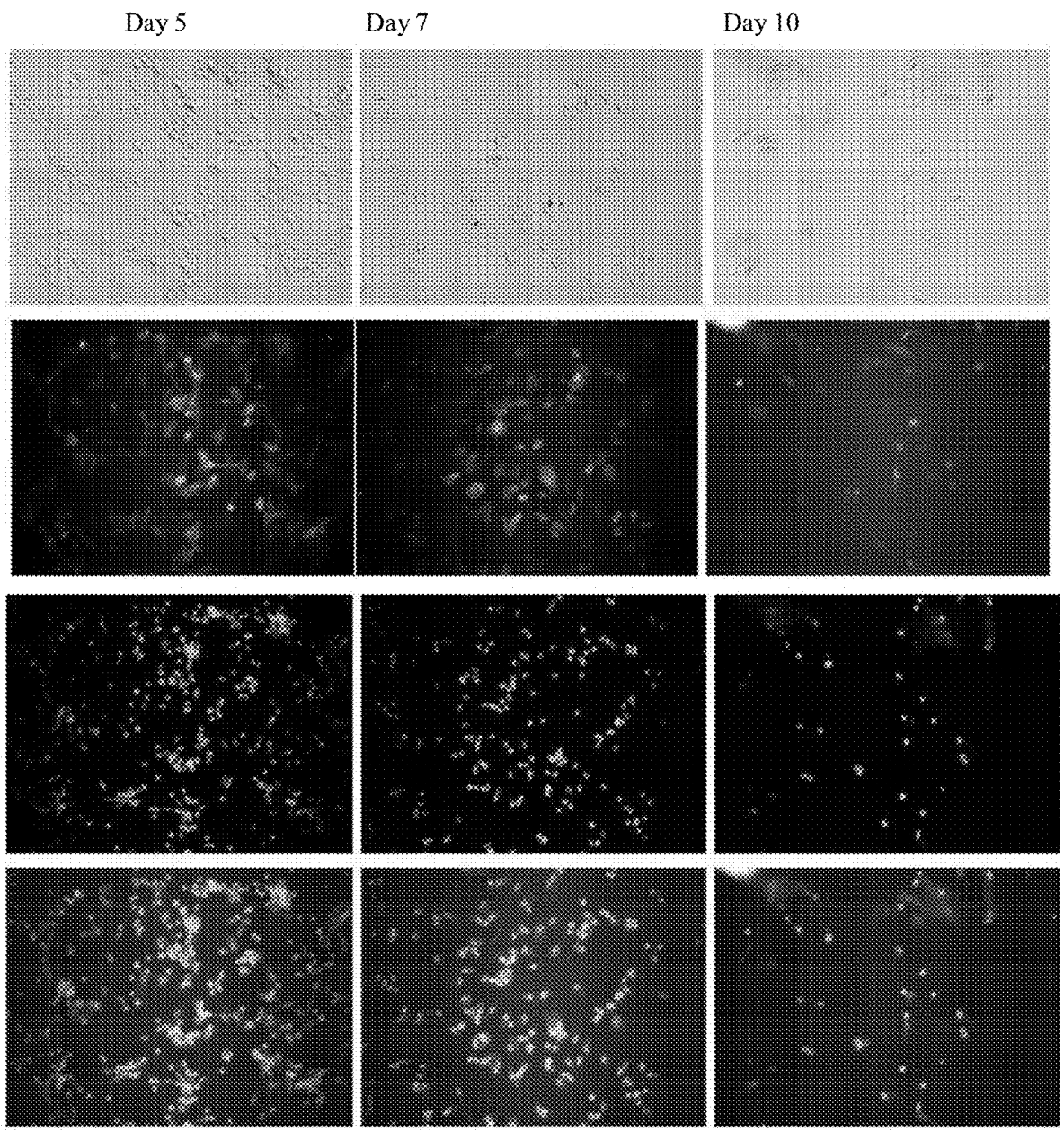
FIG. 7—Nestin expression (Nestin-FITC) in MLPC after 5, 7, and 10 days of induction. First row: invert microscopic view, second: fluorescence, third: DAPI, fourth: merged fluorescence & DAPI images Original magnification: ×200.

Nestin, a class VI intermediate filament protein, is expressed in the stem cells of the central nervous system (CNS) cells. Nestin plays an important role for B-cell differentiation as well as neural development (Genes Dev. 1992 September; 6(9):1589-607). Nestin expression is used extensively as a marker for CNS stem cells in the developing nervous system. Its transient expression is a critical step in the neural differentiation. MLPC expressed Nestin-FITC on days 5 and 7 (FIG. 7).

Figure 8:
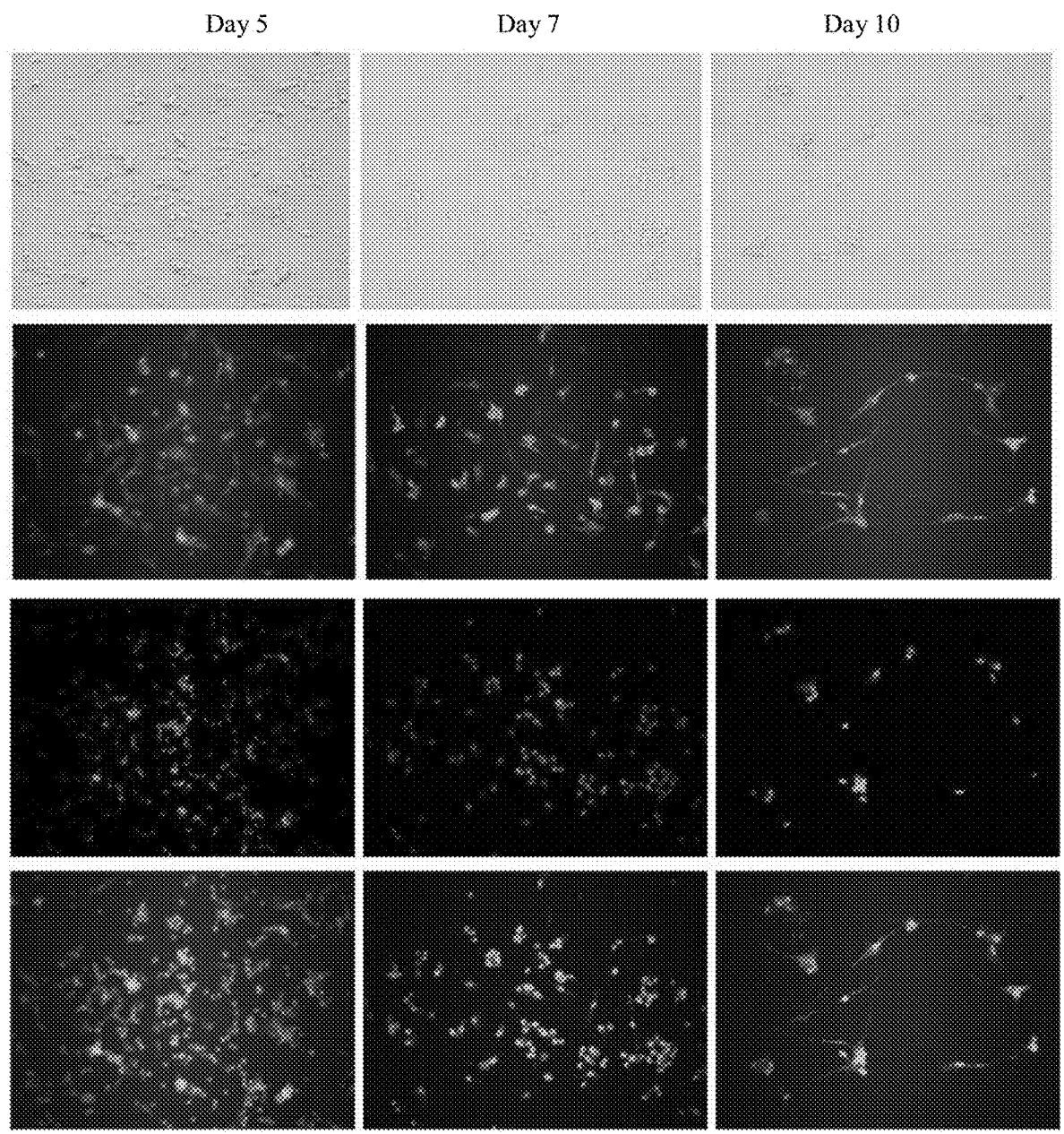
FIG. 8—Nemogenin-3 expression (Nemogenin-3-FITC) in MLPC after 5, 7, and 10 days of induction. First row: invert microscopic view, second: fluorescence, third: DAPI, fourth: merged fluorescence & DAPI images Original magnification: ×200.

The neurogenin family of proteins consists of Neurogenin 1, 2 and 3. The neurogenin family of proteins belongs to transcriptional regulators and can determine cell fate. Neurogenin 3 is expressed in discrete regions of developing neurons. It is involved in the initial differentiation of the four islets cell types, but many transcription factors are required simultaneously, including HIxb9, Isl1, Neuro D, Nkx-2.2, Nkx-6.4, Pax-4, Pax-6, PDX-1 and Mash1for final differentiation. Neurogenin 3 acts upstream of Neuro D in a neuron mature program, and can activate the expression of Neuro D for differentiation (Proc Natl Acad Sci USA. Feb. 15, 2000; 97(4): 1607-1611). MLPC displayed Neurogenin 3-FITC protein expression during induction (FIG. 8).

Figure 9:
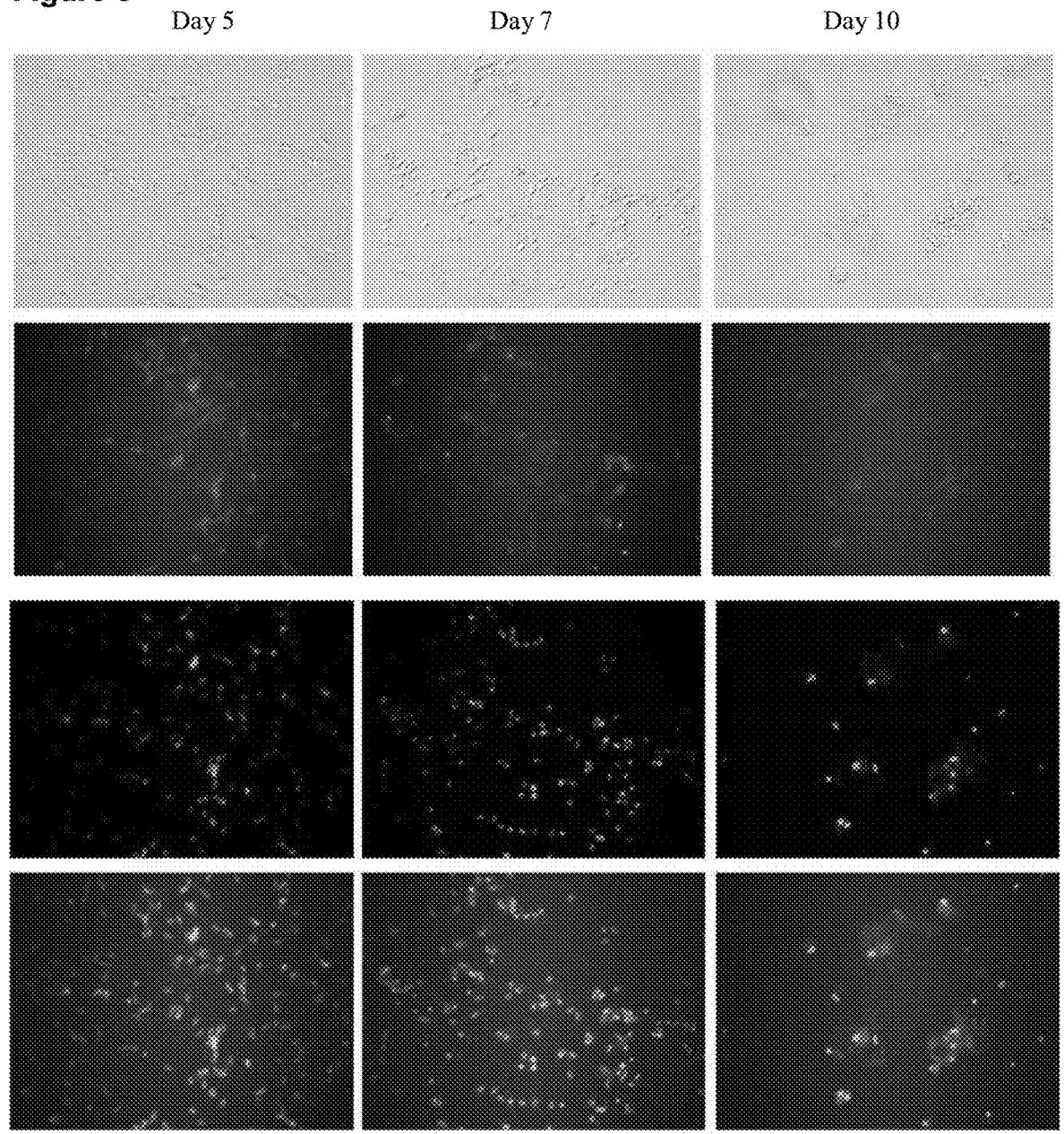
FIG. 9—Pax expression (Pax -FITC) in MLPC after 5, 7, and 10 days of induction. First row: invert microscopic view, second: fluorescence, third: DAPI, fourth: merged fluorescence & DAPI images Original magnification: ×200.

Pax 5 is an intermediate filament protein expressed in dividing cells during the early stages of development in the CNS and peripheral nervous system. Pax 5 can help differentiation, and nestin becomes down-regulated and is replaced by tissue-specific intermediate filament proteins. In the formation of the glial scar after CNS injury, Pax 5 can help nestin re-induced in the adult for regeneration therapy (Histol Histopathol, 2005, 20:665-671). T h e data showed that MLPC expressed clearly Pax 5-fluorescence image on initial induction, with decreased expression on the tenth day (FIG. 9).

Figure 10:
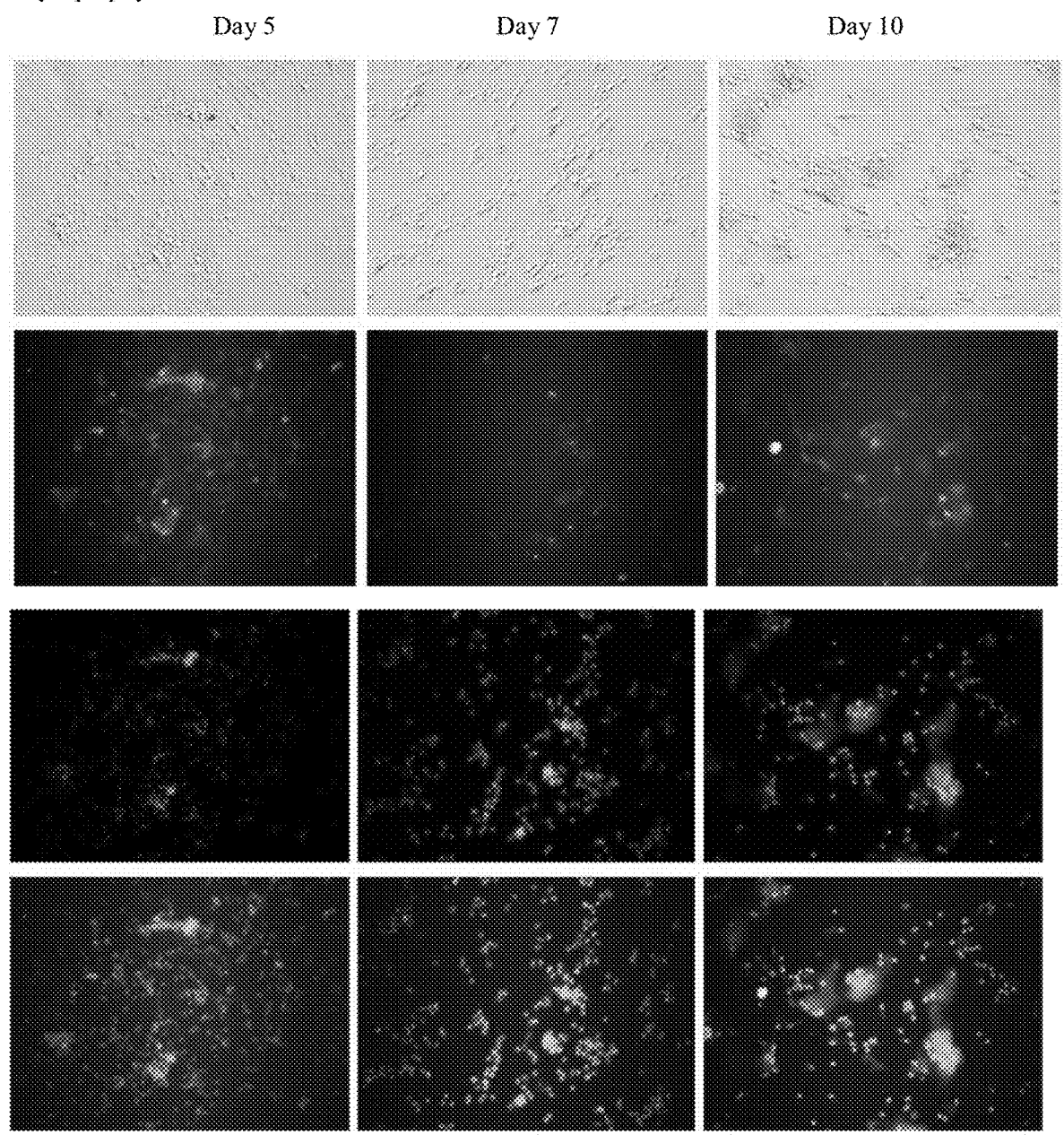
FIG. 10—Synaptophysin expression (Synaptophysin-FITC) in MLPC after 5, 7, and 10 days of induction. First row: invert microscopic view, second: fluorescence, third: DAPI, fourth: merged fluorescence & DAPI images. Original magnification: ×200.

Synaptophysin is the major synaptic vesicle protein p38, a synaptic vesicle glycoprotein. It is expressed in neural endocrine cells and in virtually all neurons in the CNS that participate in synaptic transmission. Synaptophysin expression is related to normal development, aging, as well as a variety of neurological disorders (Journal of Neurocytology, 1996, 25: 821-828). MLPC displayed Synaptophysin-FITC expression during induction, especially on the fifth day (FIG. 10).

Figure 11:
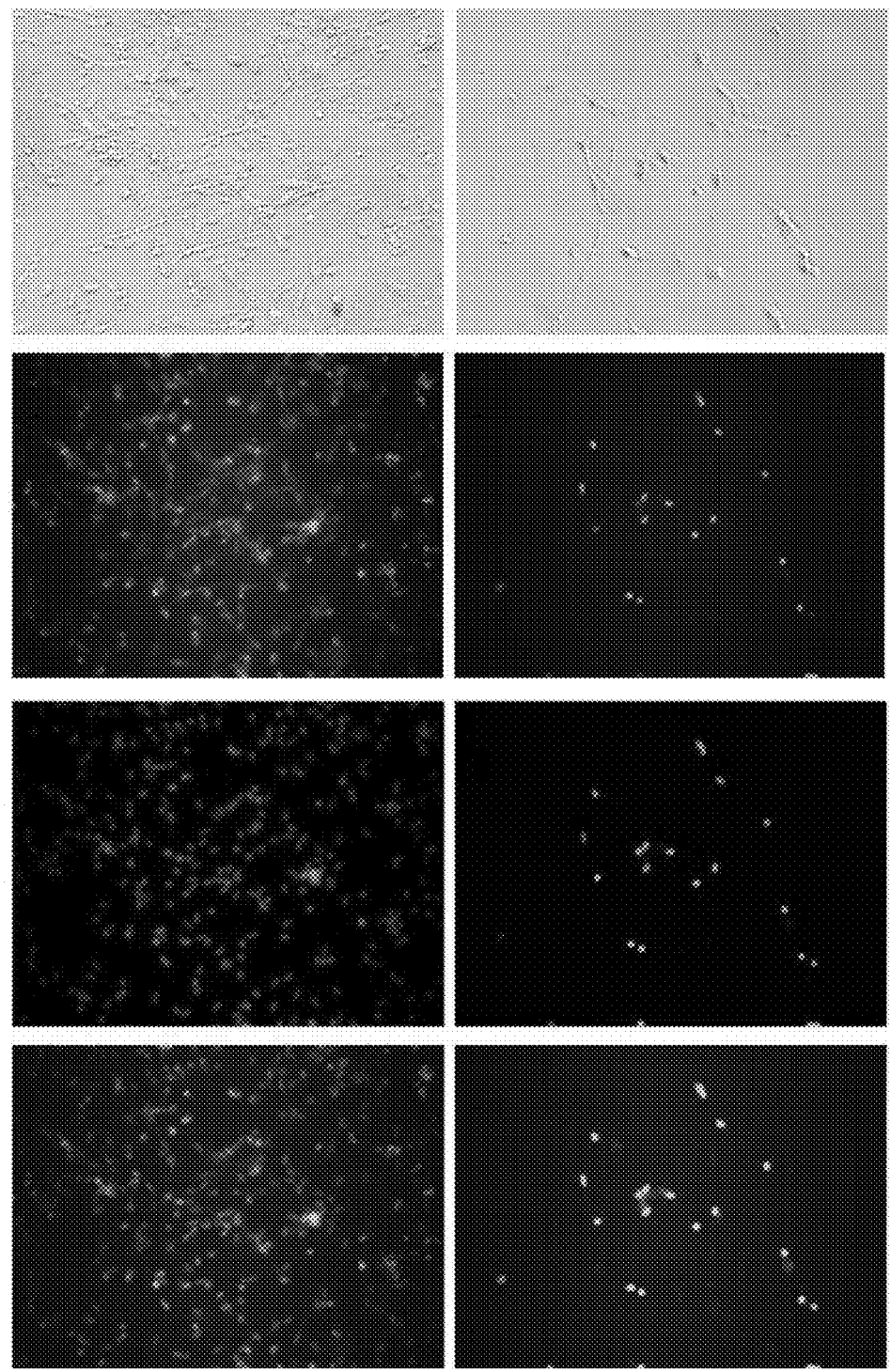
FIG. 11—HIF-1 alpha expression (HIF-1 alpha-FITC) in MLPC after 5 and 10 days of induction. First row: invert microscopic view, second: fluorescence, third: DAPI, fourth: merged fluorescence & DAPI images. Original magnification ×200.

Under hypoxic conditions, mammalian cells up regulate the expression of hypoxic genes, including induction of angiogenesis and a switch to anaerobic metabolism to survive. HIF-1 (Hypoxia Inducible Factor-1) is one of the key regulators of the transcriptional response to oxygen deprivation. HIF-1 is composed of two subunits, HIF-1α and HIF-1β also known as aryl hydrocarbon receptor nuclear translocator (ARNT)) that are members of the basic helix-loop-helix (βHLH) Per-Arnt-Sim (PAS) (βHLH-PAS) family of transcription factors. HIF-1 is essential for angiogenesis, embryonic development, erythropoiesis, vascular development/remodeling, vasodilation, it is also implicated in pathophysiology of ischemic disease and glucose/energy metabolism. Interestingly, on the fifth day of induction, HIF-1α protein was evidently expressed in MLPC, but limited to the nuclei on the tenth day (FIG. 11).

Figure 12:
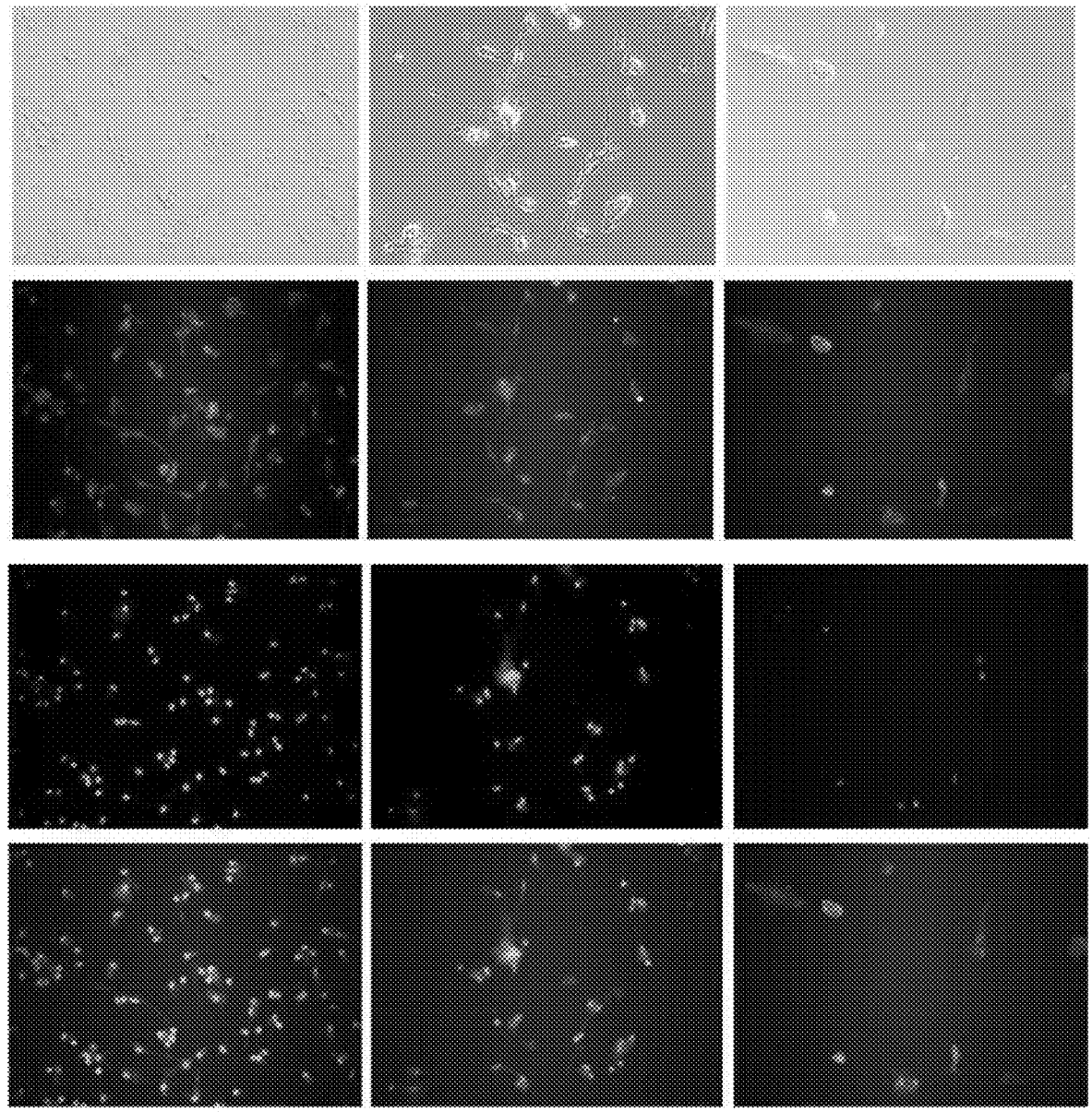
FIG. 12—MASH1 expression (MASH1-FITC) in MLPC after 7, 10 and 20 days of induction. First row: invert microscopic view, second: fluorescence, third: DAPI, fourth: merged fluorescence & DAPI images. Original magnification: ×200.

MASH 1, also named Achaete-scute homolog 1 (ASCL1), is a basic helix-loop-helix transcription factor. MASH 1 proteins may also be involved in the fate of neuronal precursors in the central and peripheral nervous systems. It is expressed in fetal brain and is essential for neuronal commitment and differentiation. MLPC expressed MASH 1 protein days 7 and 10 after induction, and displayed specifically neural-like morphology on day 10 (FIG. 12).

Figure 13:
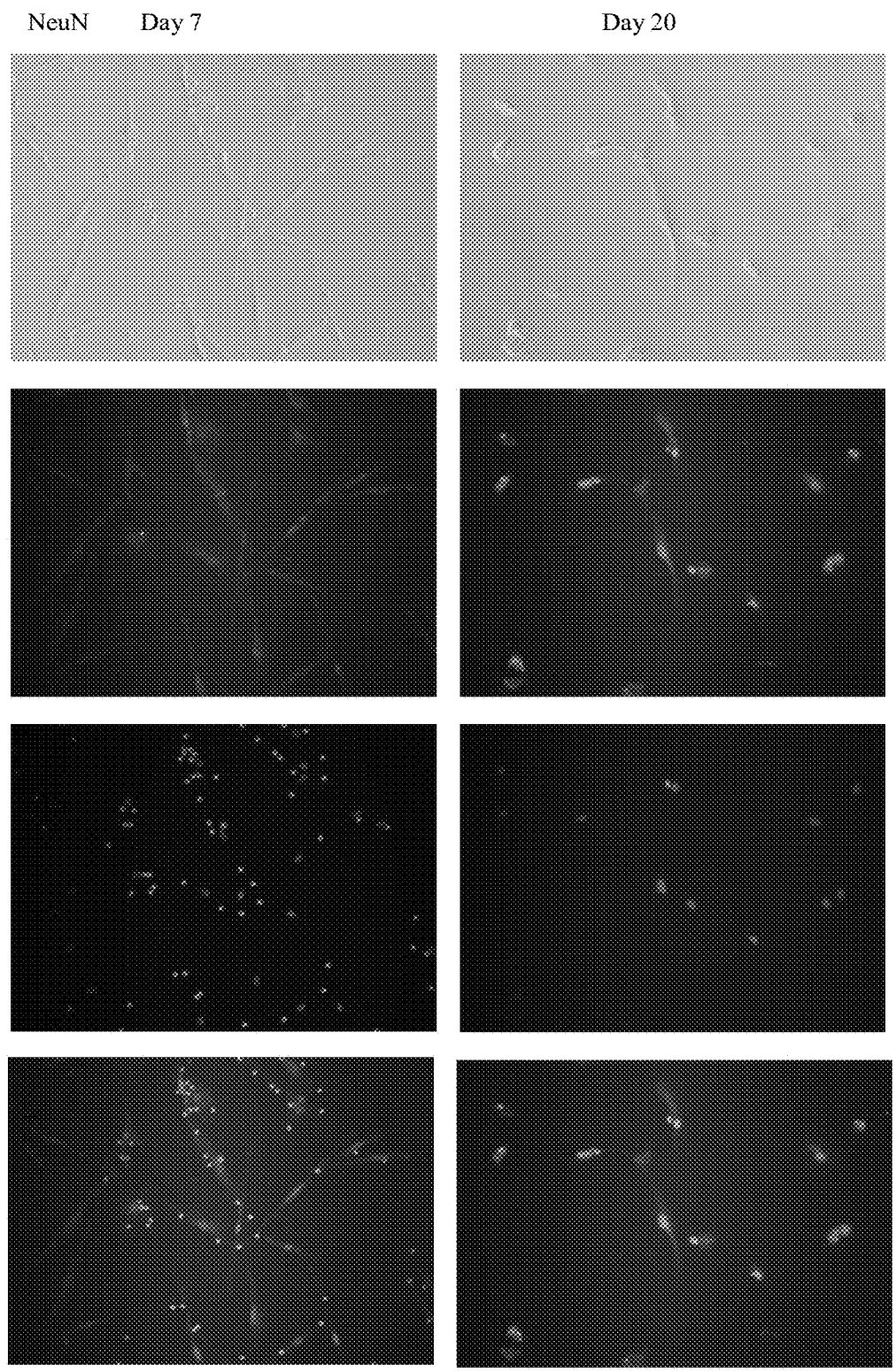
FIG. 13: NeuN expression (NeuN-FITC) in MLPC after 7 and 20 day of induction. First row: invert microscopic view, second: fluorescence, third: DAPI, fourth: merged fluorescence & DAPI image. Original magnification: ×200.

NeuN was proved to express only in neuronal nuclei and to a lesser extent the cytoplasm of neuronal cells. It is a neuronal nuclear antigen and as a biomarker of neurons. The vast majority of neurons are strongly NeuN positive, and NeuN immunoreactivity has been widely used to identify neurons in tissue culture and in sections and to measure the neuron/glia ratio in brain regions. After induction, MLPC expressed NeuN protein on the seventh and twentieth day, and most cells expressed NeuN at the nuclei on the twentieth day (FIG. 13). The data suggested that MLPC, in co-culture, can differentiate into neuroectodermal lineage.

6. Induced Differentiation of MLPC to Potentially Facilitate Cardiac Repair and Regeneration The endothelial cells play an essential role in neovascularization, which is the most important process in cardiac repair after an ischemic event. Hence an ample supply of endothelial progenitor cells facilitates the cardiac repair. In addition, skeletal myoblasts, which has the potential to transdifferentiate to cardiomyocytes, may contribute to cardiac regeneration.

Alpha-Actinins belong to the spectrin gene superfamily which represents a diverse group of cytoskeletal proteins, including the alpha and beta spectrins and dystrophins. Alpha-Actinin is an actin-binding and microfilament protein with multiple roles, where it is involved in binding actin to the membrane in non-muscle cells. In skeletal muscle cells, alpha-Actinin helps actin filaments attachment and contractions.

Figure 14:
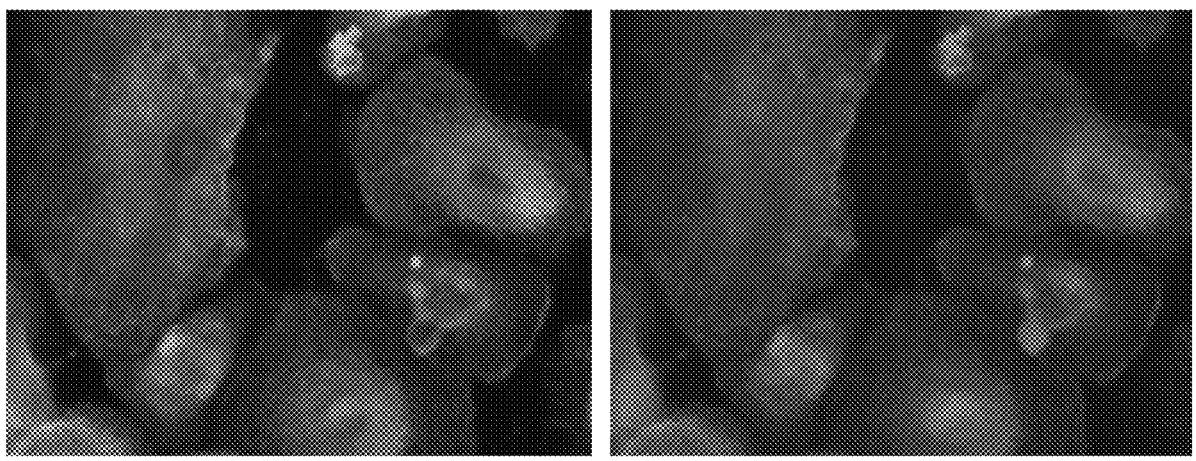
FIG. 14—Alpha-Actinin expressed (Alpha-Actinin-FITC) in MLPC in the first stage (A) and in the second stage (B)~(D) respectively. Left: fluorescence, Right: merged fluorescence & DAPI images. Original magnification: ×400.

In our experiments, alpha-actinin expression was homogeneously distributed in the first sage, but actin filaments of adherent cells developed gradually in the second stage. After 20 days of induction, alpha-actinin was found to trans-locate to nucleus on most adherent cells (FIG. 14).

Figure 15:
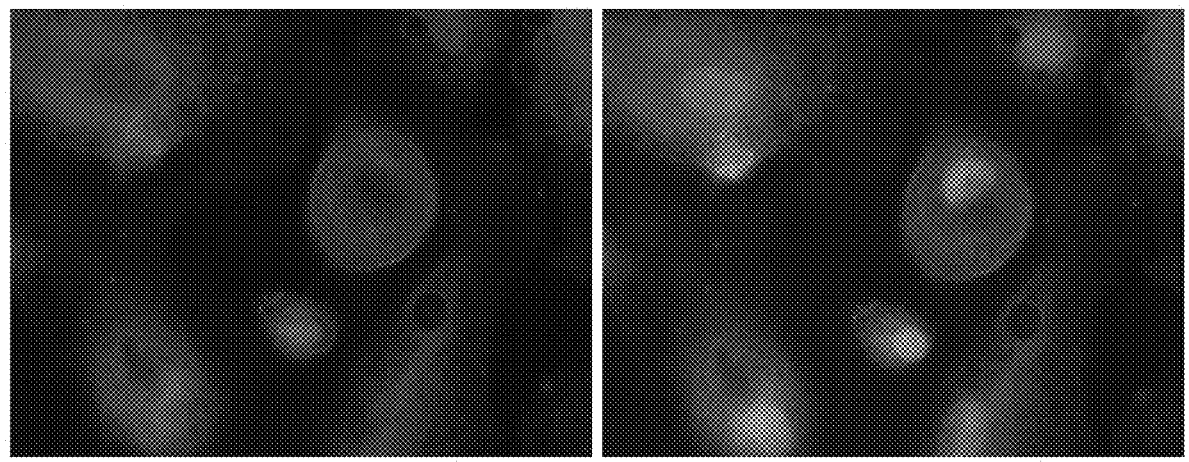
FIG. 15—Myogenin expressed (Myogenin-FITC) in MLPC in the first stage (A) and in the second stage (B)~(D) respectively. Left: fluorescence, Right: merged fluorescence & DAPI images. Original magnification: ×400.

Myogenin (myogenic factor 4), is a muscle-specific basic-helix-loop-helix transcription factor involved in the coordination of skeletal muscles development or myogenesis repair. Myogenin is involved myogenic precursor cells binding to fibers during the process of differentiation in myogenesis. In cell culture, myogenin can induce myogenesis in a variety of non-muscle cell types. In our adherent cells of MLPC, myogenin expression was inactive before induction. After 10 days of induction, myogenin expression became activated and localized in the cytoplasm of adherent cells (FIG. 15).

Figure 16:
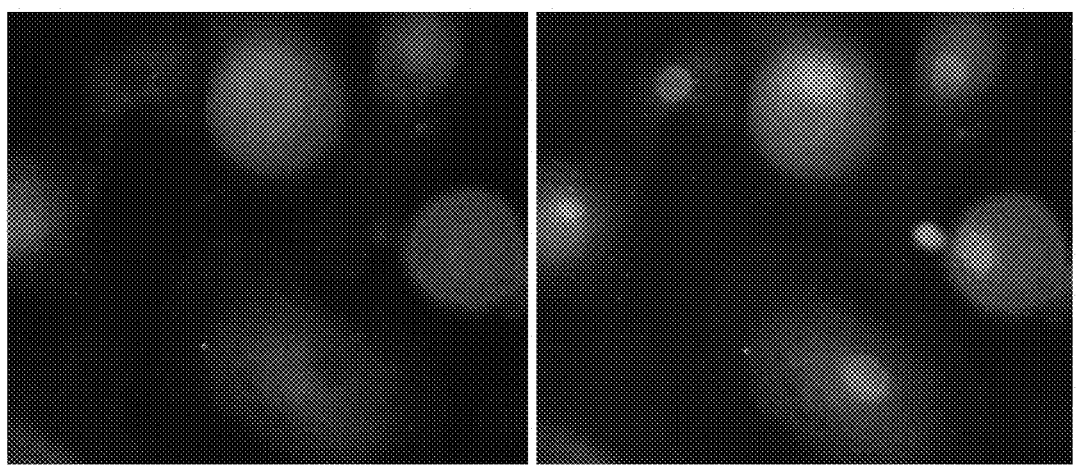
FIG. 16—Troponin I expressed (Troponin I -FITC) in MLPC in the first stage (A) and in the second stage (B)~(D) respectively. Left: fluorescence, Right: merged fluorescence & DAPI images. Original magnification: ×400.

Troponin is a complex of three regulatory proteins, troponin C (TnC), troponin I (TnI), and troponin T (TnT), is integral to muscle contraction in skeletal muscle and cardiac muscle. Troponin is attached to the protein tropomyosin to bind actin filaments in muscle tissue causes cross bridge formation, and contraction of the muscle begins. Troponin usually pertain a diagnostic marker or therapeutic target for various heart disorders, such as myocardial infarction, heart muscle cell death. In the induced differentiation of MLPC, troponin I protein expression increased in the cytoplasm and nucleus after 10 days induction (FIG. 16).

Figure 17:
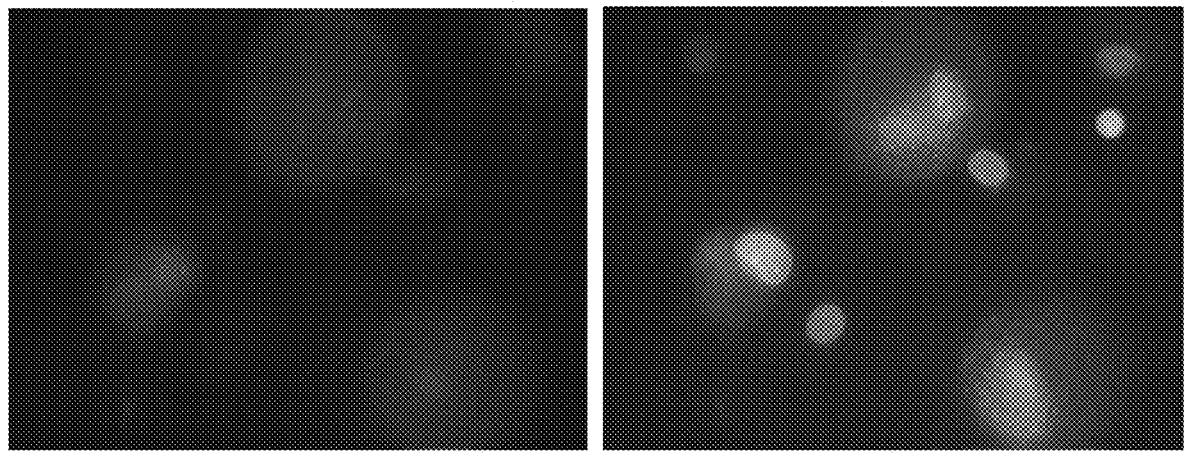
FIG. 17—GATA-4 expressed (GATA-4-FITC) in MLPC in the first stage (A) and in the second stage (B)~(D) respectively. Left: fluorescence, Right: merged fluorescence & DAPI images. Original magnification: ×400.

Transcription factor GATA-4 (GATA-4) protein is a critical transcription factor, involved in myocardial differentiation and function, and is expressed on adult cardiomyocytes. GATA4 promotes cardiac morphogenesis, cardiomyocytes survival, and maintains cardiac function in the adult heart. GATA4 expression is important for atrioventricular (AV) formation and function, and help endocardial cells undergo epithelial to mesenchymal transitions (EMT) into the AV cushions during development. GATA-4 regulated many cardiac genes, such as Nkx2-5 and Tbx5. In our studies, GATA-4 expression was found in the induced differentiated cells of MLPC after 16 days of induction (FIG. 17).

In summary, the results indicated that the MLPC possesses the potentials, of trans-differentiation into skeletal muscle and cardiac muscle, shown by increased alpha-actinin and myogenin expression and activated troponin I and GATA-4 proteins after induction. The induced differentiated MLPC might enhance cardiomyocytes regeneration and repair.

7. Neo-Hepatocyte Differentiation of MLPC

Mature hepatocytes can express markers and functional characterization, including albumin, glycogen storage, drug transporters activation, and cytochrome P450 activity, these cells will be useful for the therapeutic medicine. Blood monocyte-derived neohepatocytes expressed important drug-metabolizing enzymes, cytochrome P450 isoforms (CYP1A1, 1A2, 2A6, 2B6, 2C8, 2C9, 2D6, 2E1, and 3A4), can help drug metabolism.

Human umbilical cord blood (UCB) and bone marrow (BM) can generate hepatocyte lineage cells, which mRNAs of albumin (ALB), and alpha-fetoprotein were expressed in both the UCB- and BM-derived cells.

Figure 18:
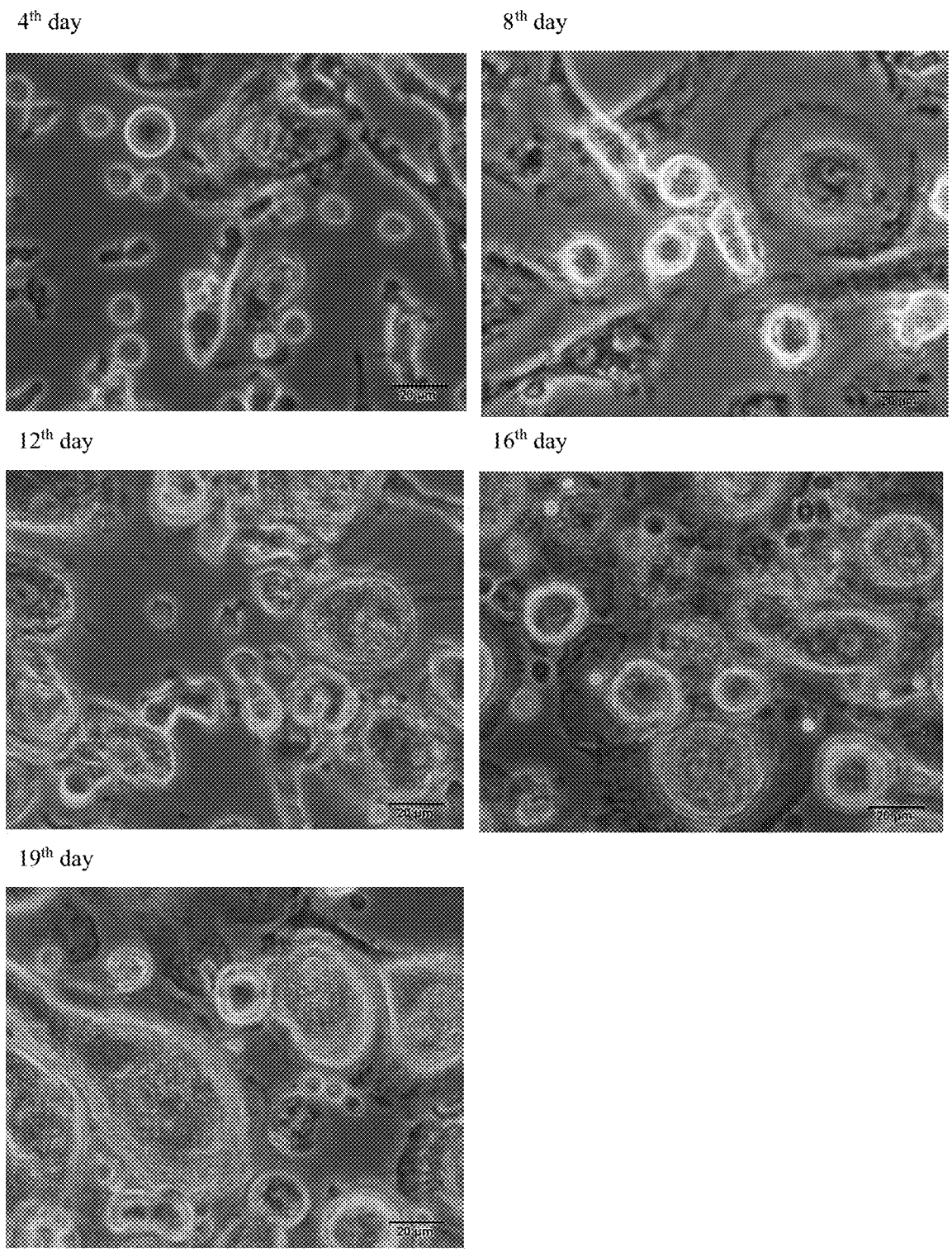
FIG. 18—Neo-hepatocyte lineage trans-differentiation of MLPC—Cells morphology of MLPC were observed in the second stage under an invert microscope (OLYMPUS). Original magnification: ×400.
Figure 23:
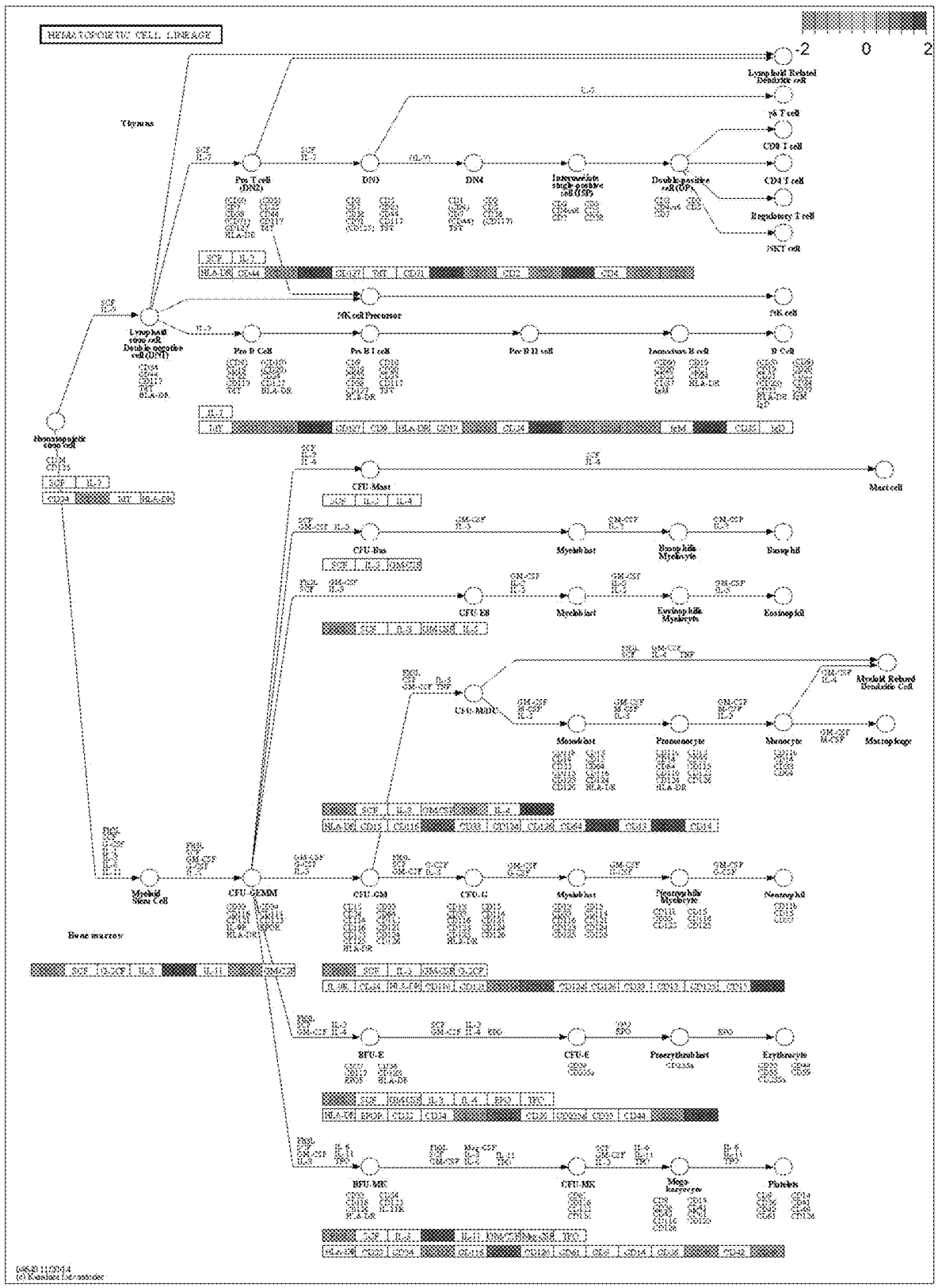
FIG. 23—MLPC derived stem-like cells ATA6, 36 genes were significantly involved hematopoietic cell lineage by KEGG database analysis. Red colour indicated 11 genes of up regulation and green colour indicated 25 genes of down-regulation.
Figure 24:
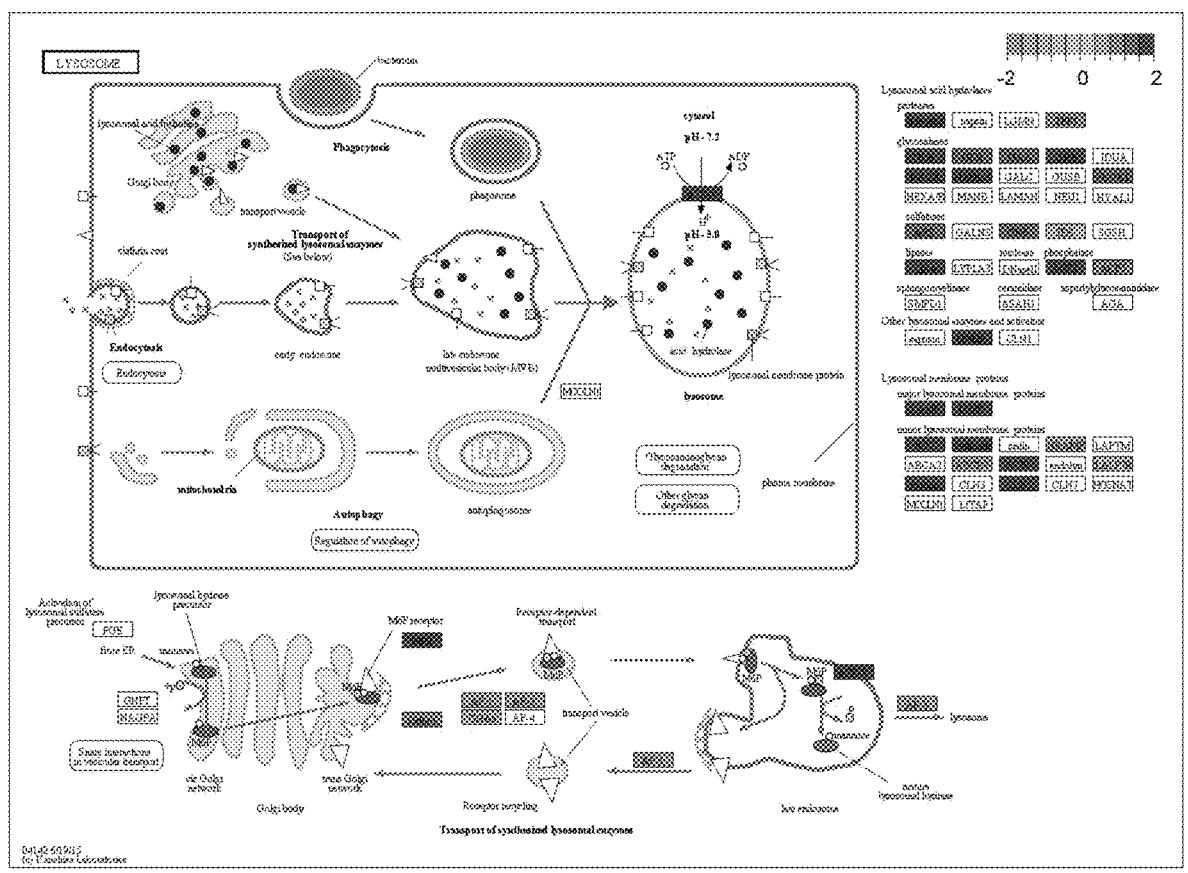
FIG. 24—MLPC derived stem-like cells PA6, 42 genes were significantly medicated lysosome biological processes by KEGG database analysis. Red colour indicated up-regulation genes, green colour indicated down-regulation genes FIG. 25—MLPC derived stem-like cells PA6, 16 genes were significantly medicated biological processes of citrate cycle (TCA cycle) by KEGG database analysis. Red colour indicated up-regulation genes, green colour indicated down-regulation genes.
Figure 25:
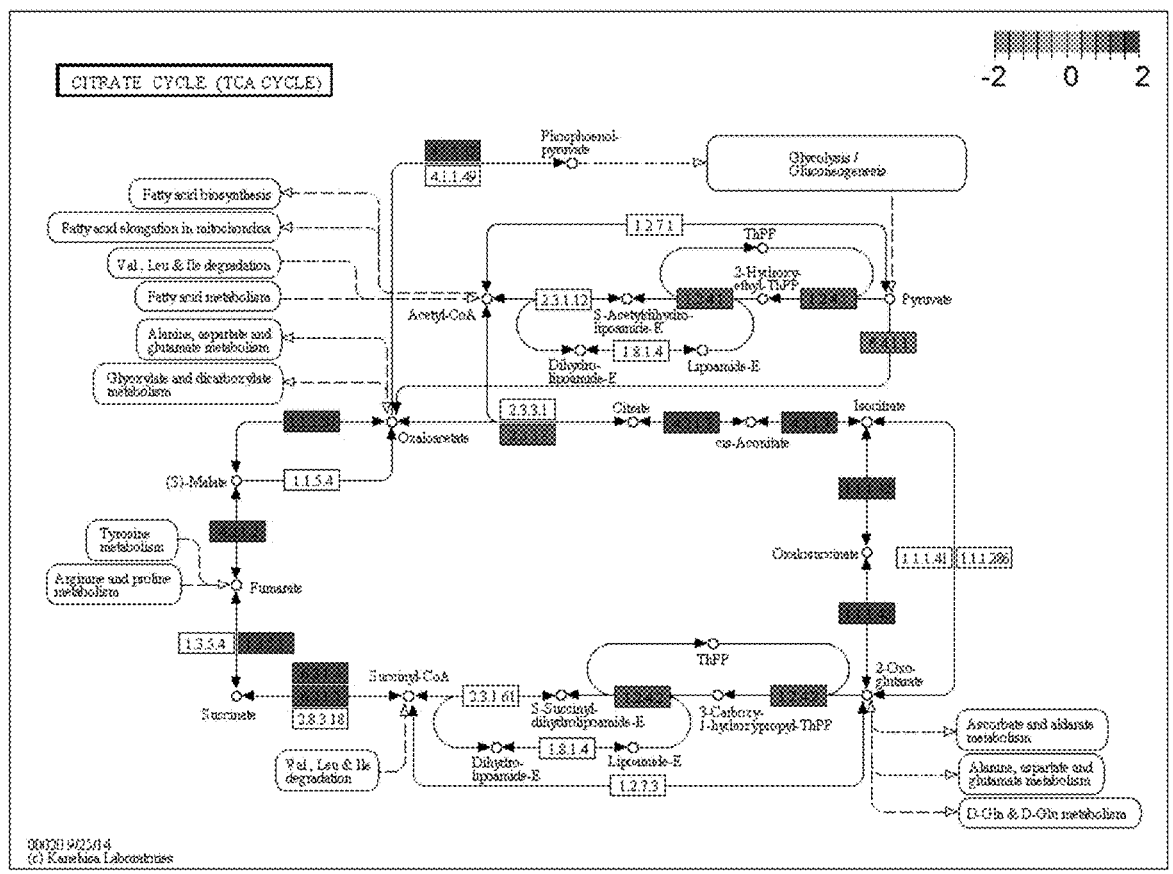
Figure 26:
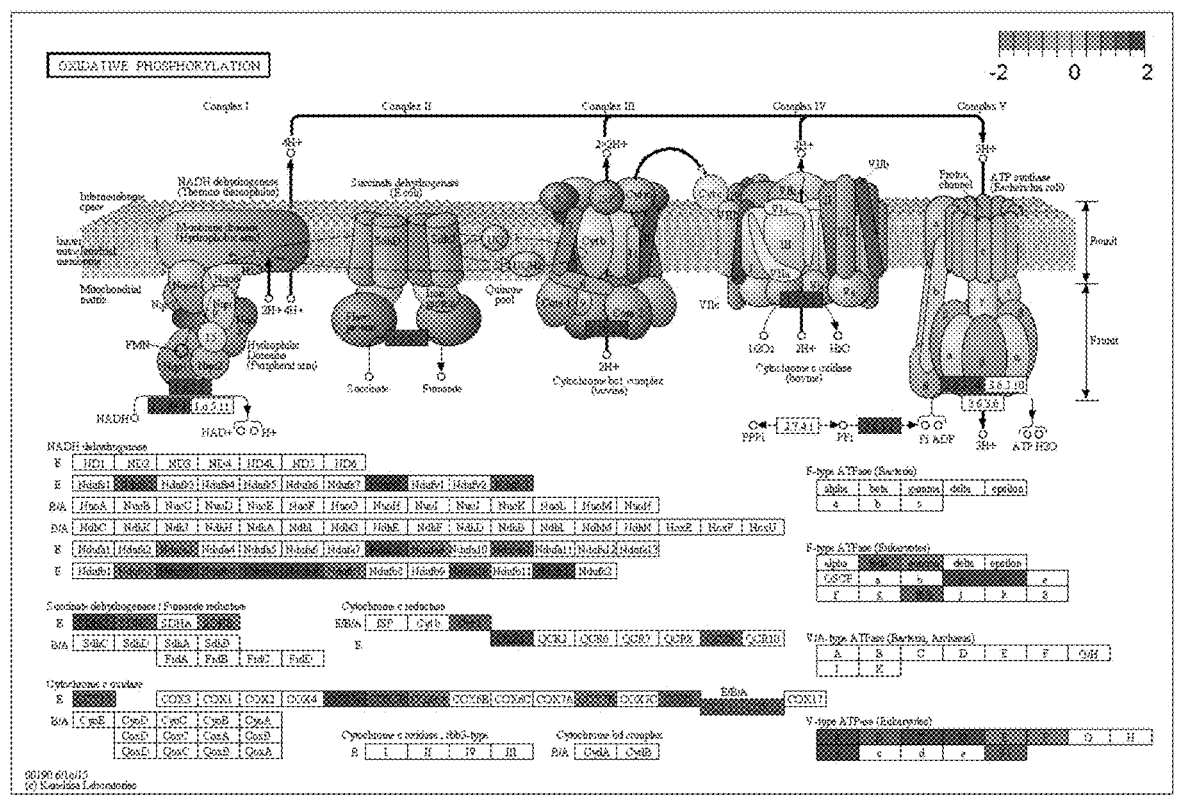
FIG. 26—MLPC derived stem-like cells PA6, 43 genes were significantly medicated biological processes of oxidative phosphorylation by KEGG database analysis. Red colour indicated up-regulation genes, green colour indicated down-regulation genes.
Figure 27:
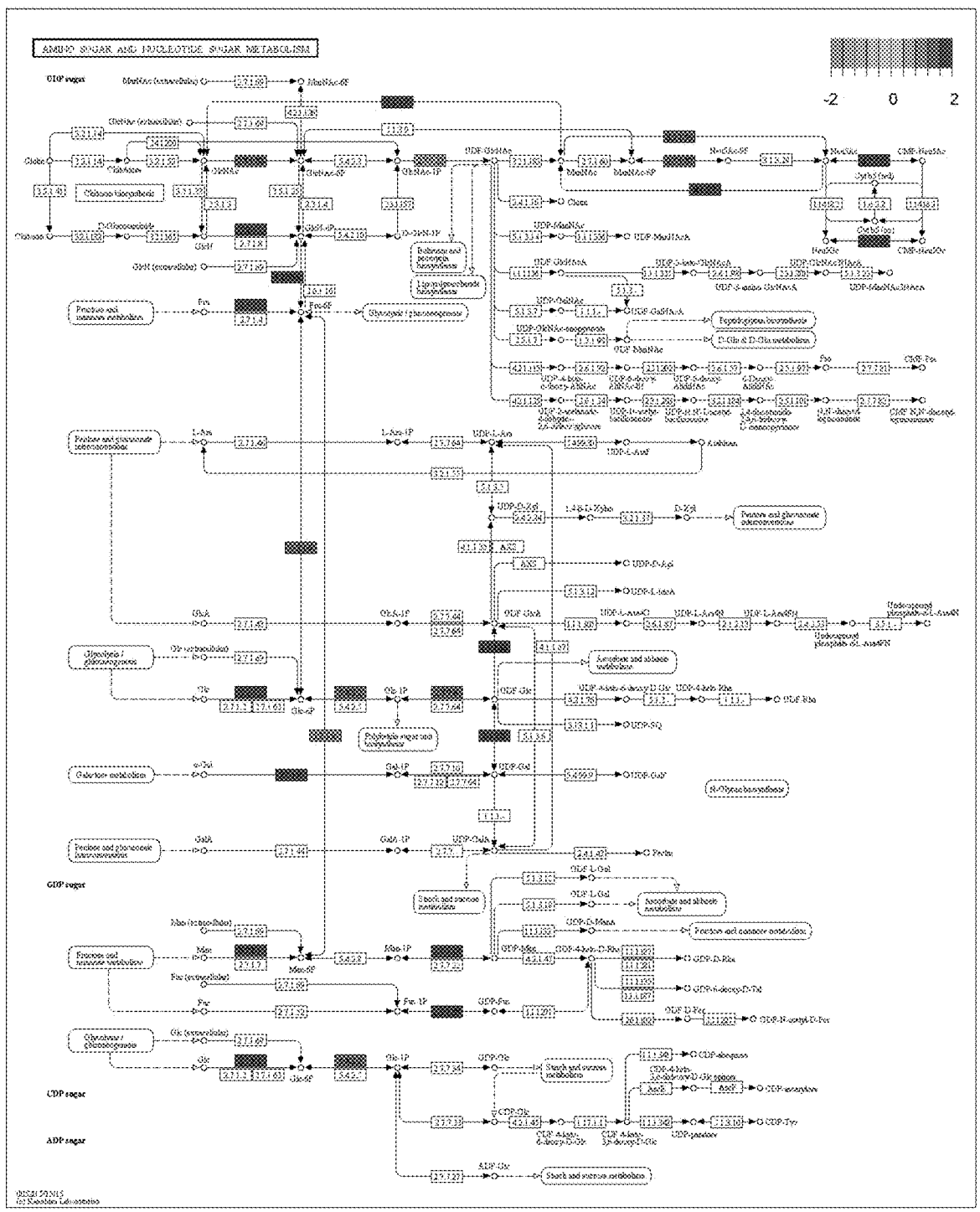
FIG. 27—MLPC derived stem-like cells PA6, 19 genes were significantly medicated amino sugar and nucleotide sugar metabolism by KEGG database analysis. Red colour indicated up-regulation genes, green colour indicated down-regulation genes.
Figure 28:
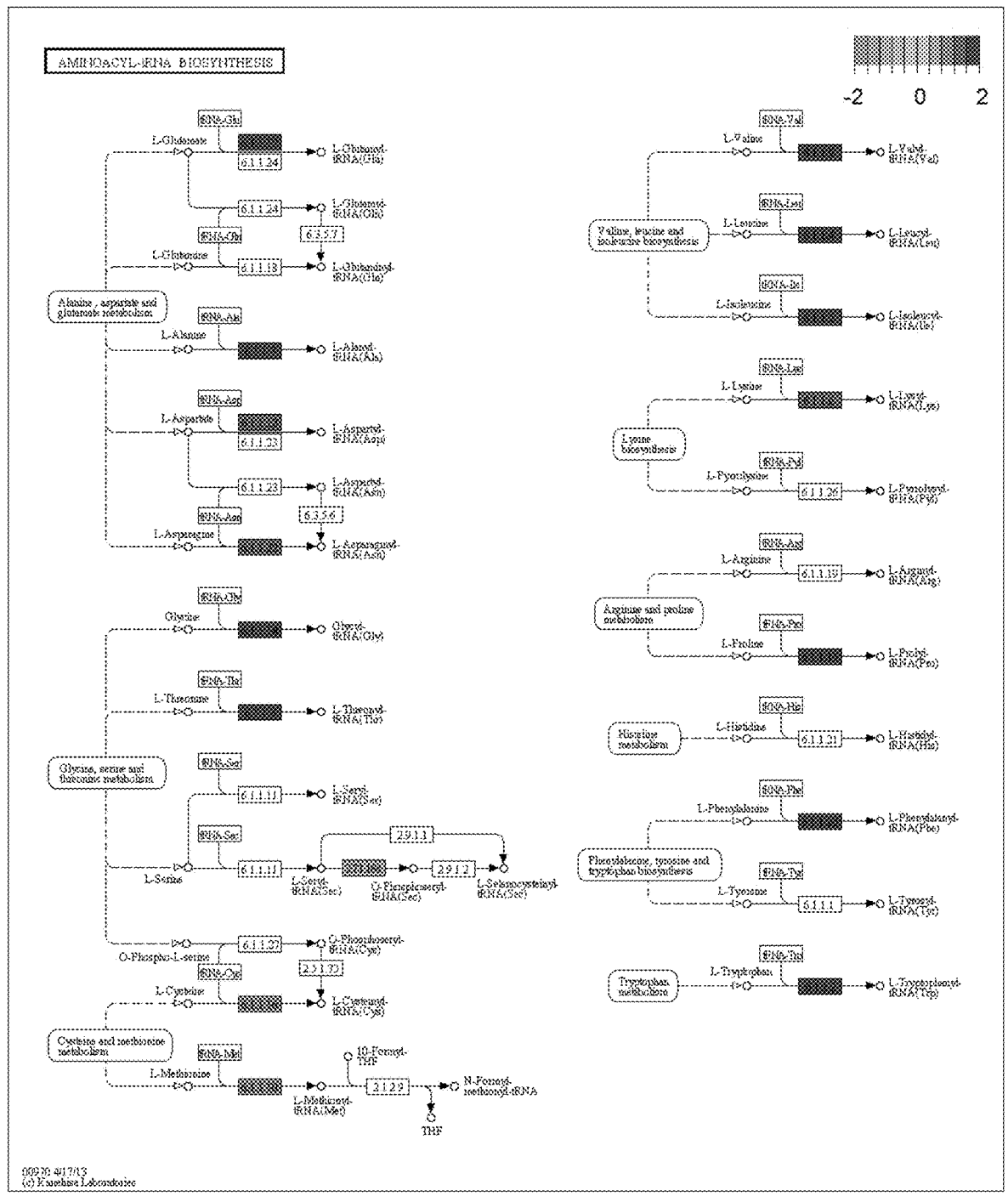
FIG. 28—MLPC derived stem-like cells PA6, 18 genes were significantly medicated aminoacyl-tRNA biosynthesis by KEGG database analysis. Red colour indicated up-regulation genes, green colour indicated down-regulation genes.
Figure 29:
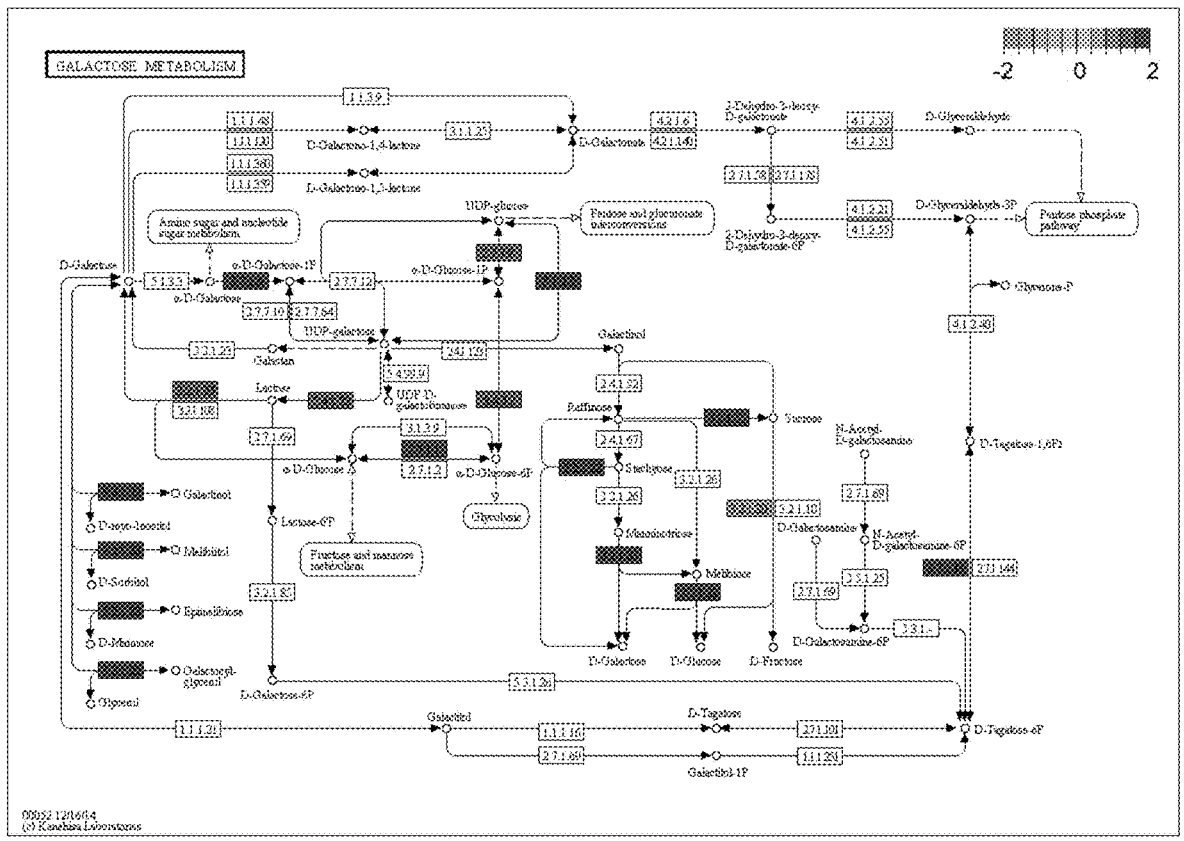
FIG. 29—MLPC derived stem-like cells PA6, 13 genes were significantly mediated galactose metabolism by KEGG database analysis. Red colour indicated up-regulation genes, green colour indicated down-regulation genes.
Figure 30:
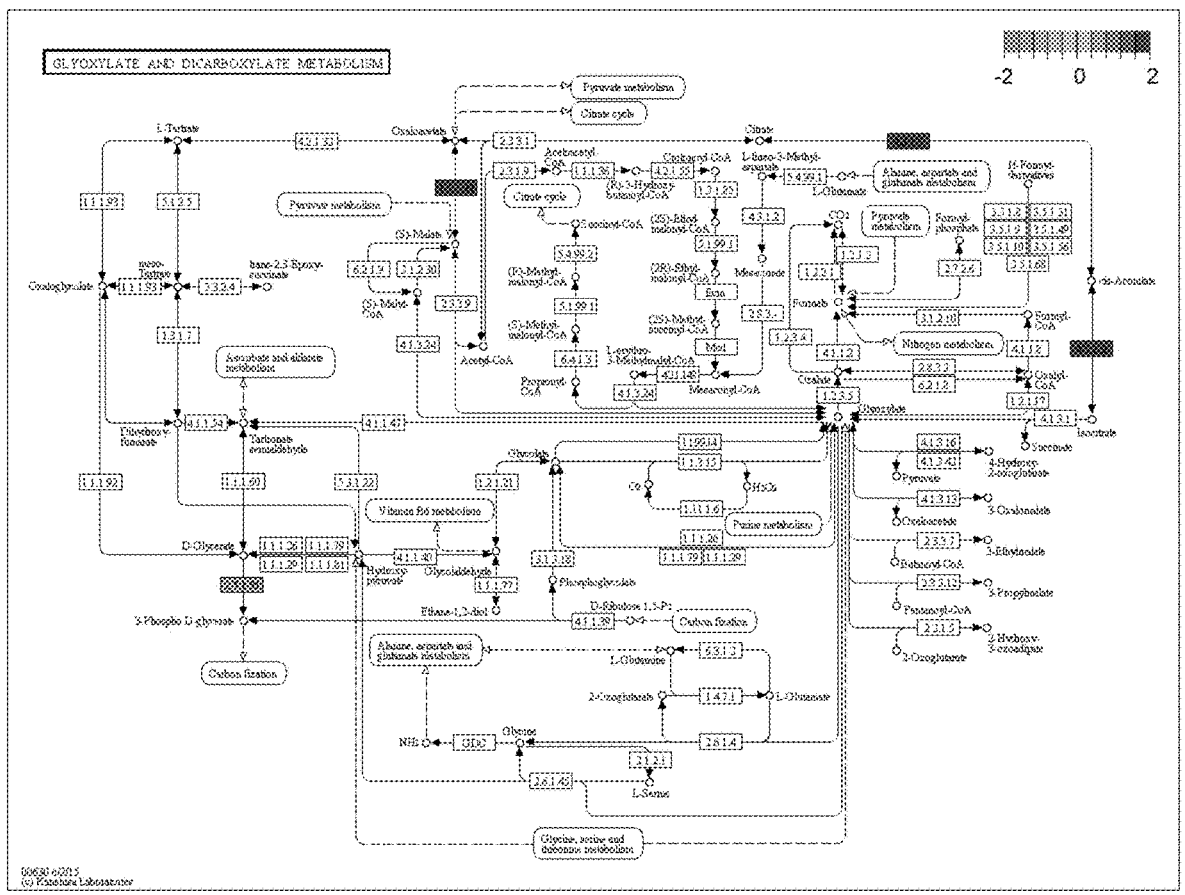
FIG. 30—MLPC derived stem-like cells PA6, 9 genes were significantly medicated glyoxylate and dicarboxylate metabolism by KEGG database analysis. Red colour indicated up-regulation genes, green colour indicated down-regulation genes.
Figure 31:
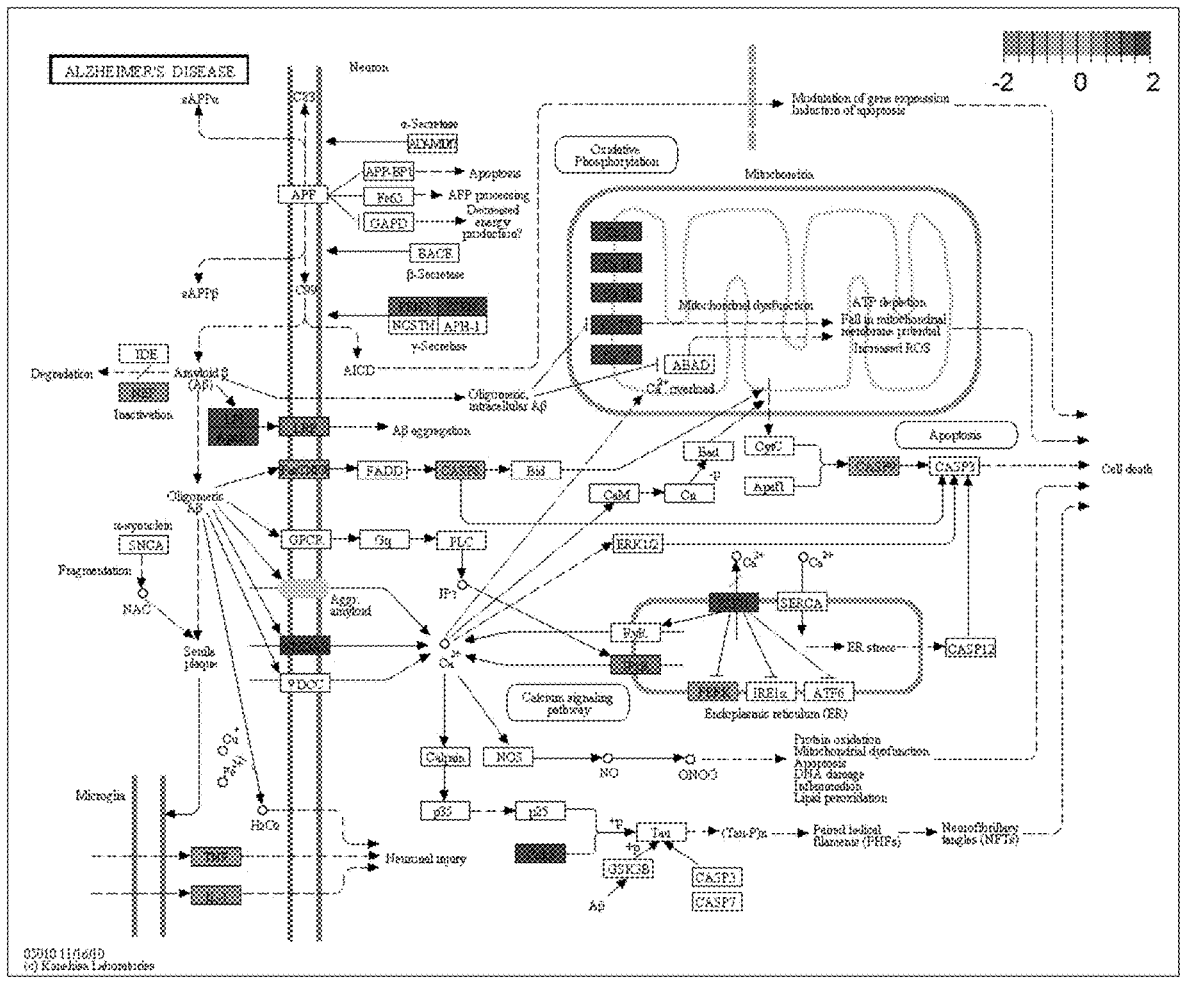
FIG. 31—MLPC derived stem-like cells PA6, 48 genes were significantly medicated Alzheimer's disease by KEGG database analysis. Red colour indicated up-regulation genes, green colour indicated down-regulation genes.
Figure 32:
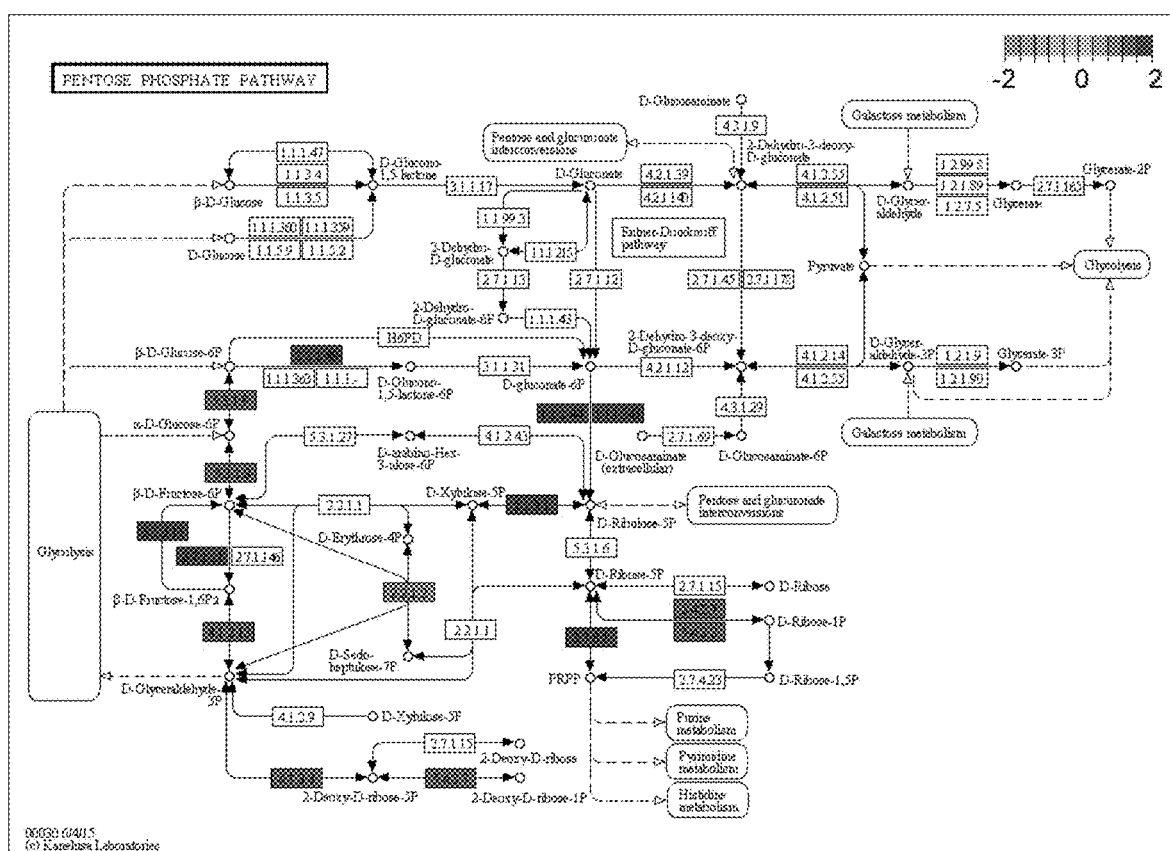
FIG. 32—MLPC derived stem-like cells PA6, 12 genes were significantly medicated pentose phosphate pathway by KEGG database analysis. Red colour indicated up-regulation genes, green colour indicated down-regulation genes.
Figure 33:
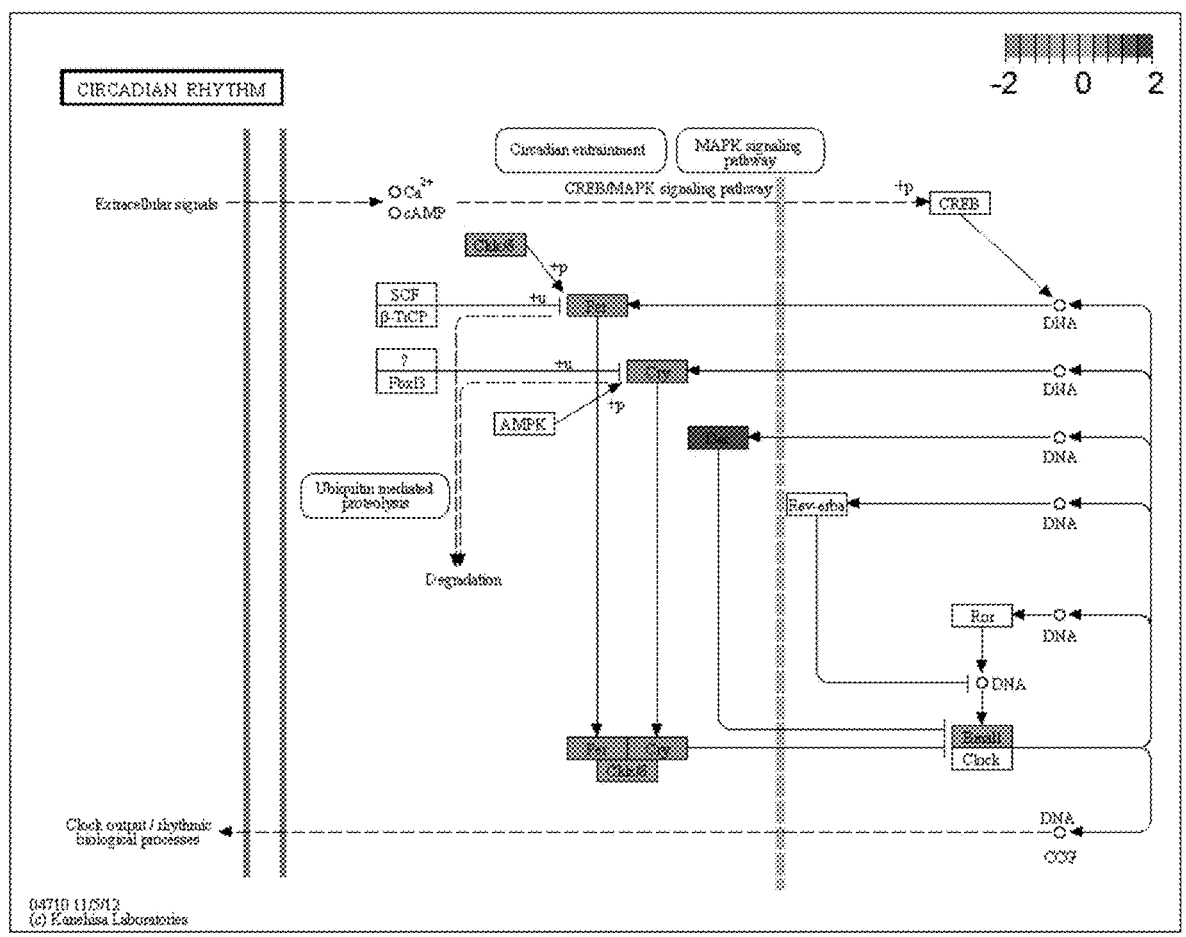
FIG. 33—MLPC derived stem-like cells PA6, 8 genes were significantly medicated Circadian rhythm pathway by KEGG database analysis. Red colour indicated up-regulation genes, green colour indicated down-regulation genes.
Figure 34:
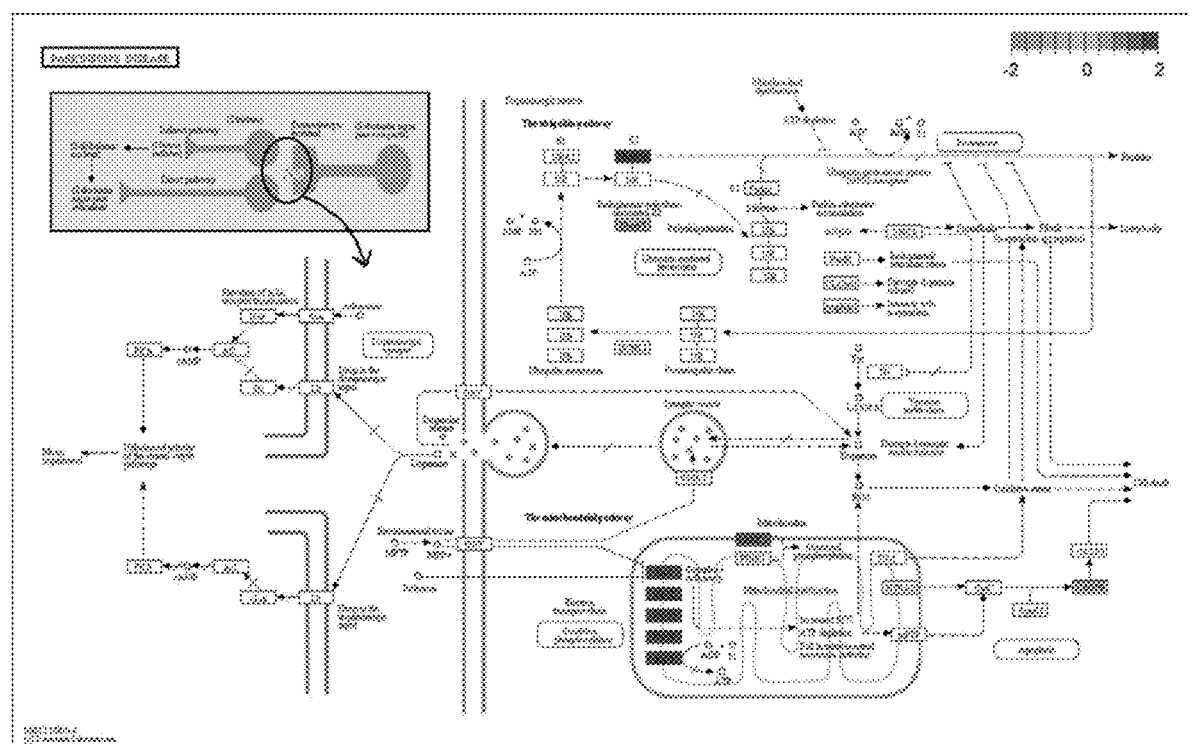
FIG. 34—MLPC derived stem-like cells PA6, 37 genes were significantly medicated Parkinson's disease by KEGG database analysis. Red colour indicated up-regulation genes, green colour indicated down-regulation genes.
Figure 35:
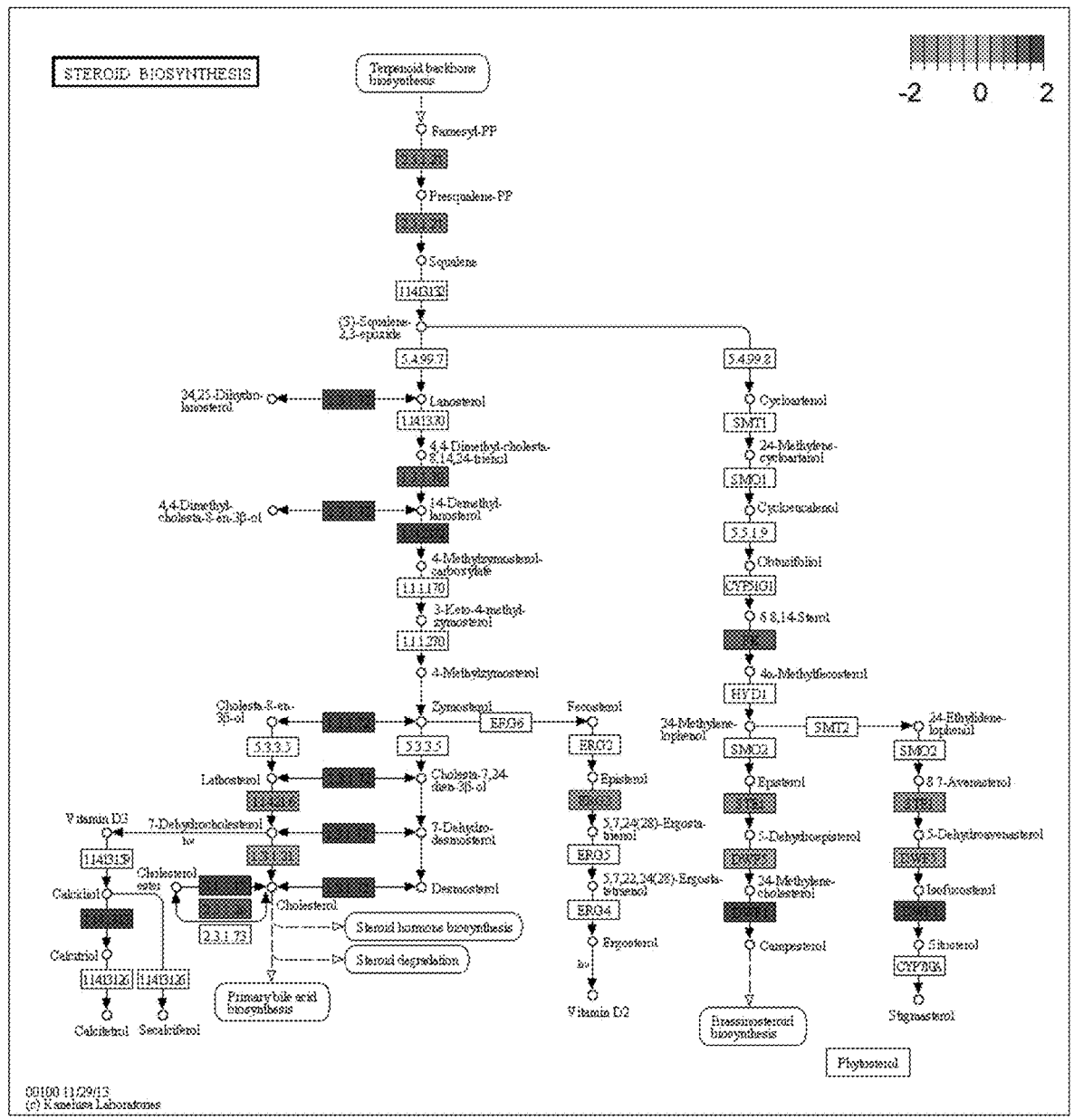
FIG. 35—MLPC derived stem-like cells PA6, 9 genes were significantly medicated steroid biosynthesis by KEGG database analysis. Red colour indicated up-regulation genes, green colour indicated down-regulation genes.
Figure 36:
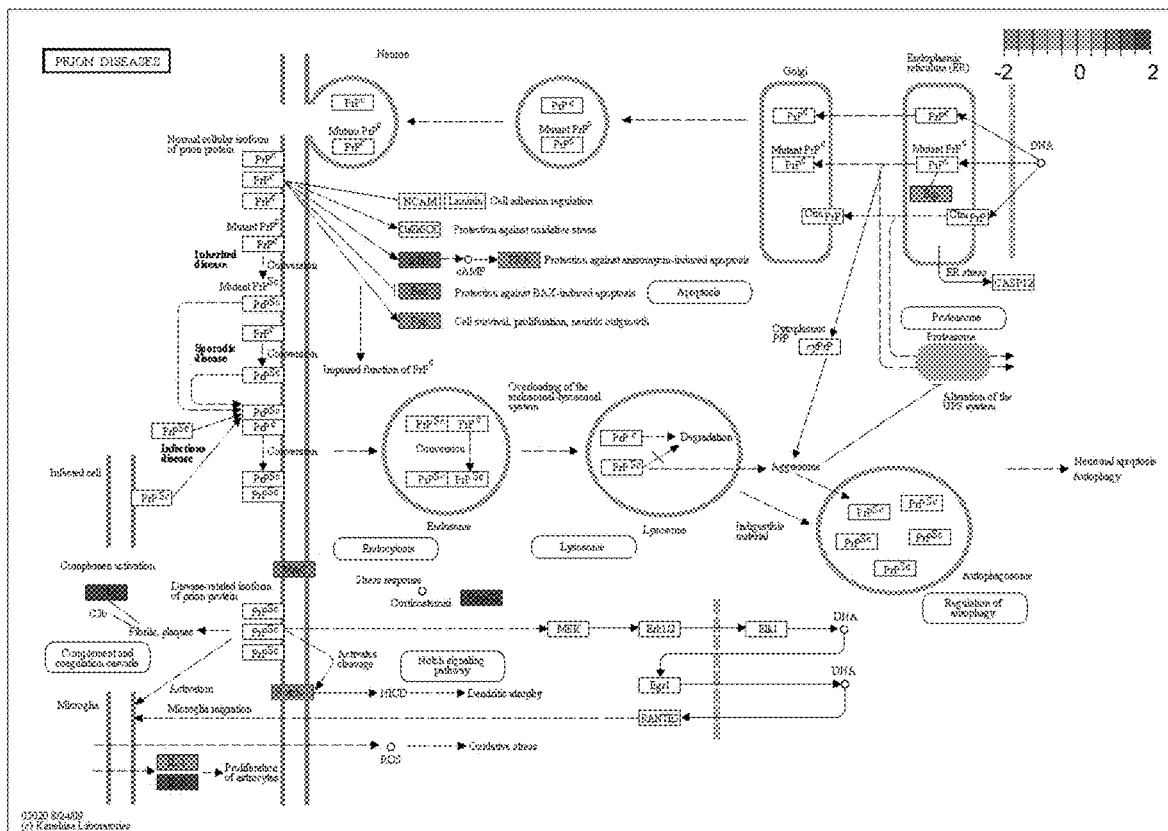
FIG. 36—MLPC derived stem-like cells PA6, 14 genes were significantly medicated Prion diseases by KEGG database analysis. Red colour indicated up-regulation genes, green colour indicated down-regulation genes.
Figure 37:
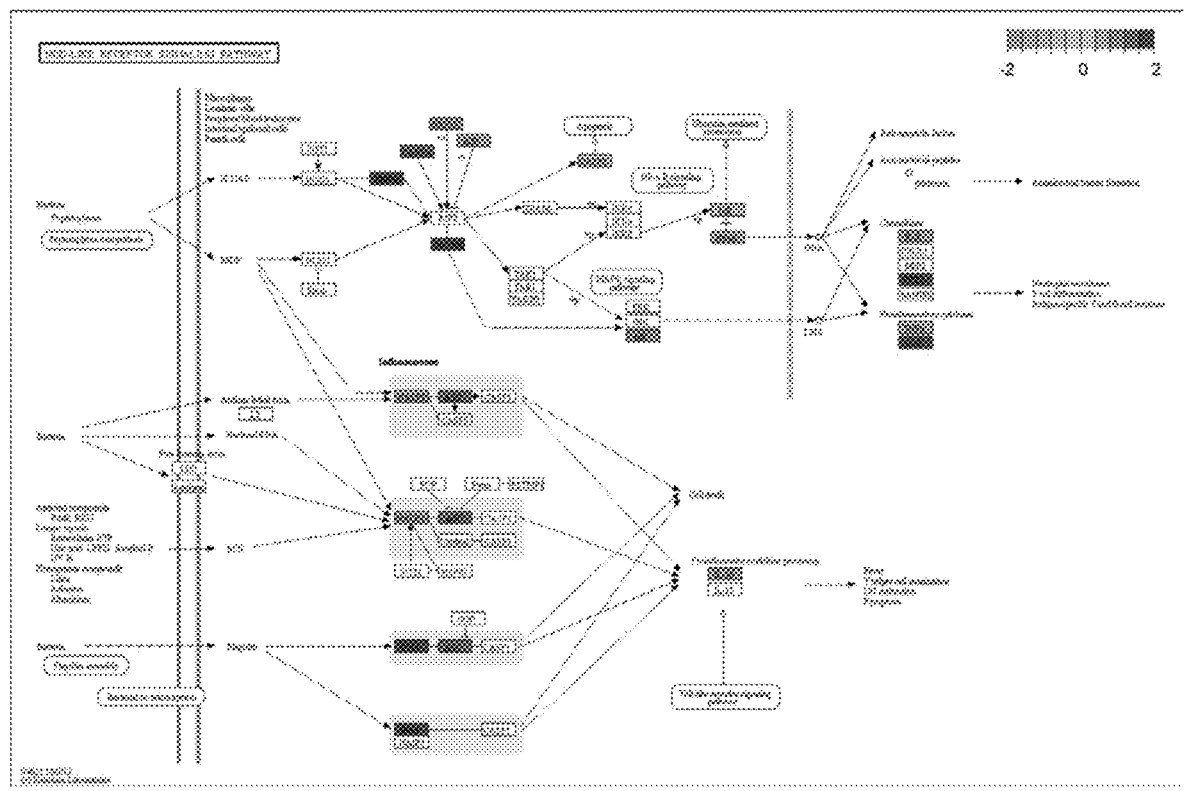
FIG. 37—MLPC derived stem-like cells PA6, 21 genes were significantly medicated NOD-like receptor signalling pathway by KEGG database analysis. Red colour indicated up-regulation genes, green colour indicated down-regulation genes.
Figure 38:
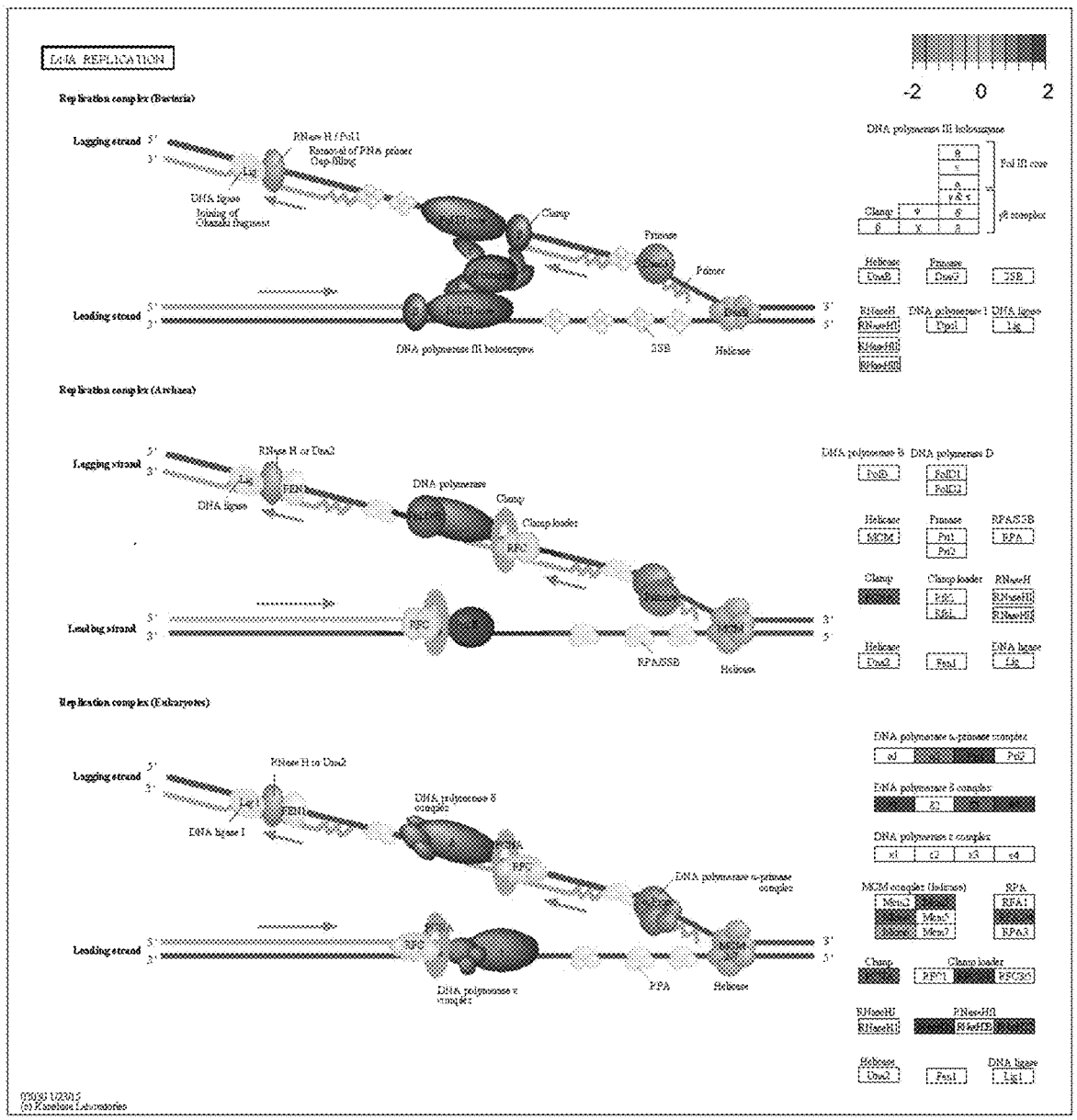
FIG. 38—MLPC derived stem-like cells PA6, 14 genes were significantly medicated DNA replication by KEGG database analysis. Red colour indicated up-regulation genes, green colour indicated down-regulation genes.
Figure 39:
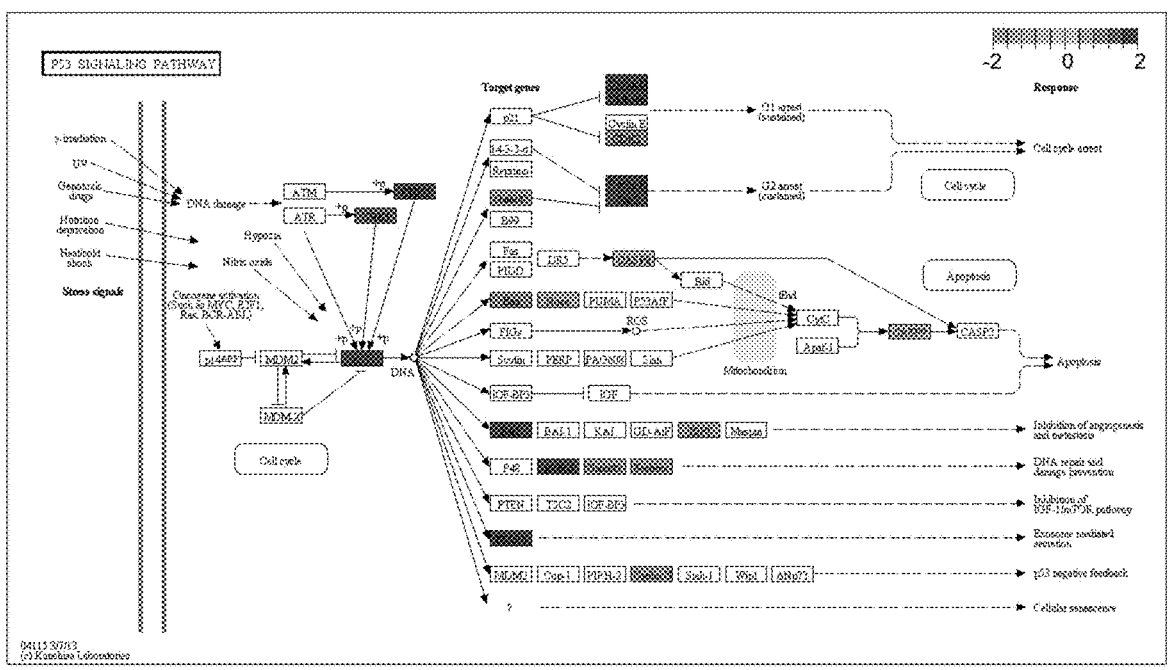
FIG. 39—MLPC derived stem-like cells PA6, 22 genes were significantly medicated p53 signalling pathway by KEGG database analysis. Red colour indicated up-regulation genes, green colour indicated down-regulation genes.
Figure 40:
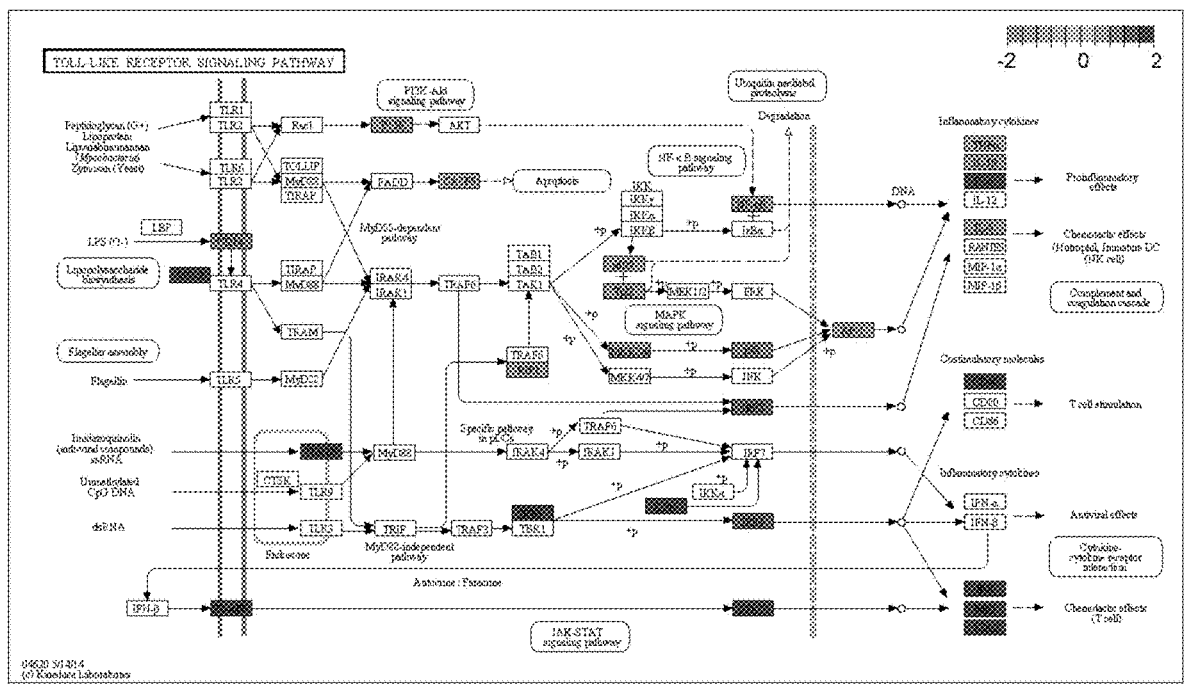
FIG. 40—MLPC derived stem-like cells PA6, 30 genes were significantly medicated Toll-like receptor signalling pathwayt by KEGG database analysis. Red colour indicated up-regulation genes, green colour indicated down-regulation genes.
Figure 41:
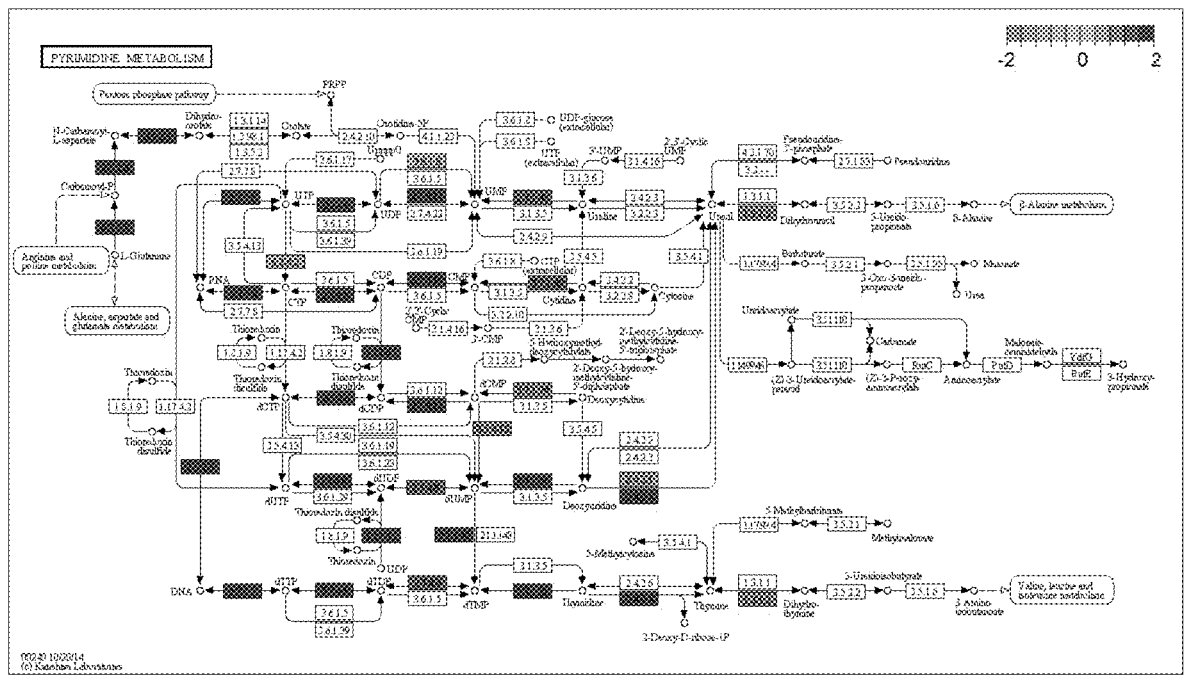
FIG. 41—MLPC derived stem-like cells PA6, 28 genes were significantly medicated pyrimidine metabolism by KEGG database analysis. Red colour indicated up-regulation genes, green colour indicated down-regulation genes.
Figure 42:
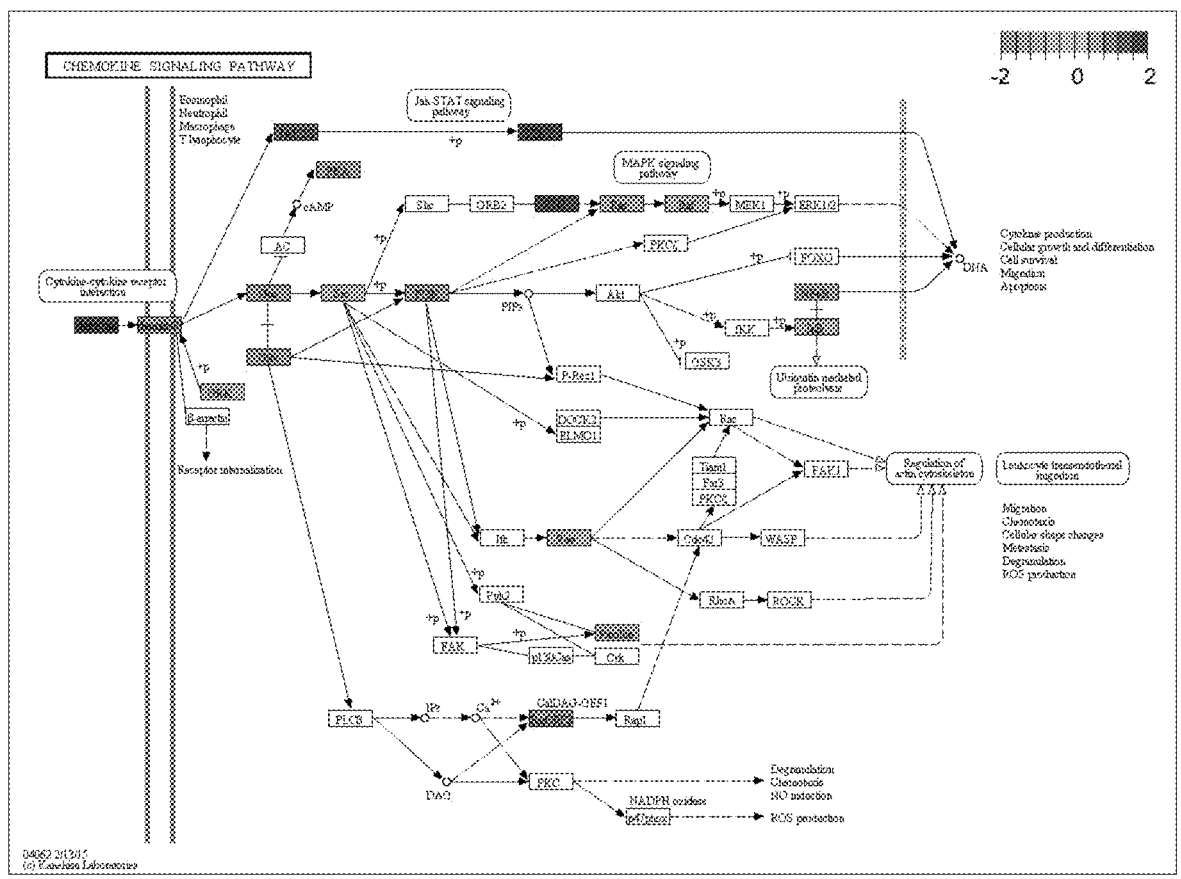
FIG. 42—MLPC derived stem-like cells PA6, 49 genes were significantly medicated chemokine signalling pathway by KEGG database analysis. Red colour indicated up-regulation genes, green colour indicated down-regulation genes.
Figure 43:
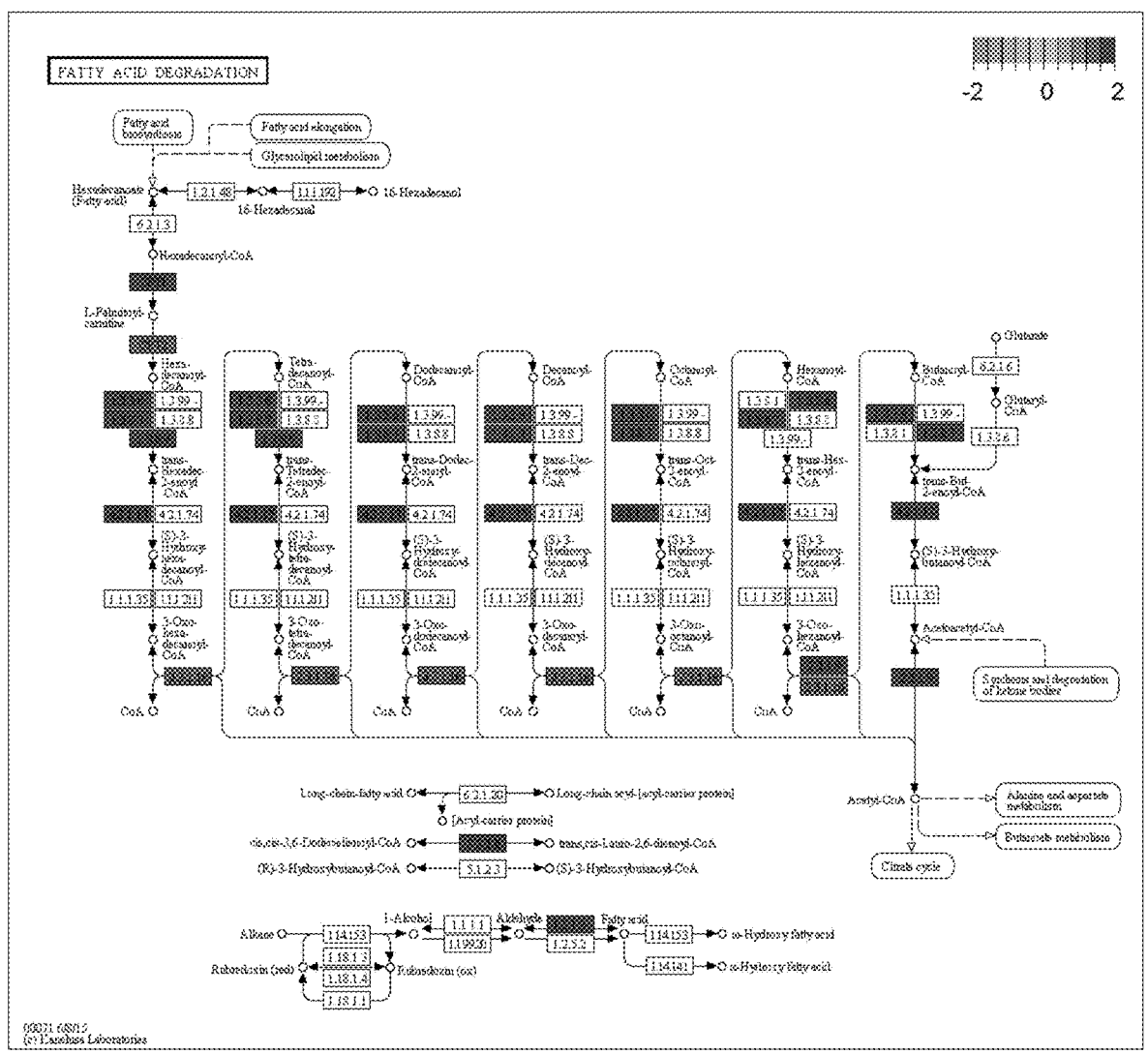
FIG. 43—MLPC derived stem-like cells PA6, 14 genes were significantly medicated fatty acid metabolism by KEGG database analysis. Red colour indicated up-regulation genes, green colour indicated down-regulation genes.
Figure 44:
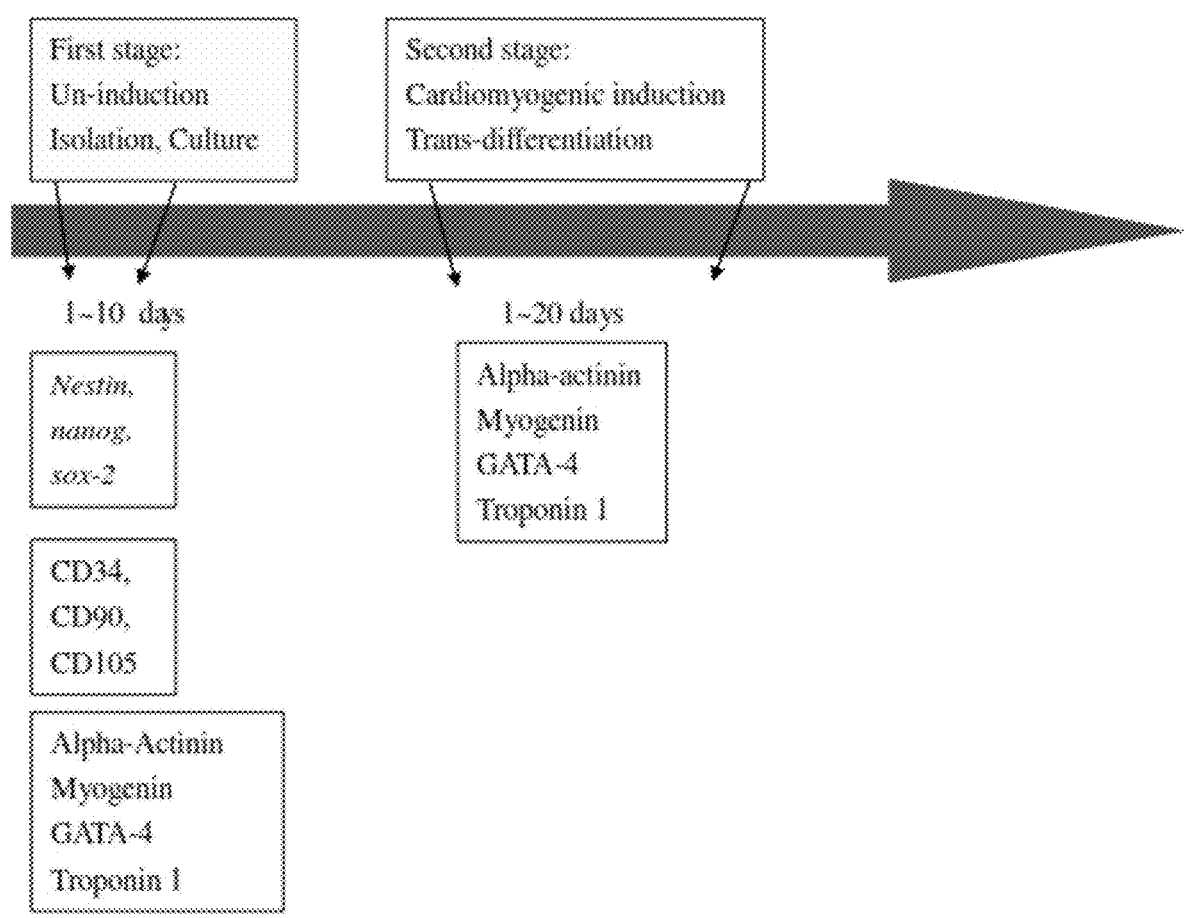
FIG. 44—Cardiomyogenic lineage trans-differentiation of MLPC strategies.
Figure 45:
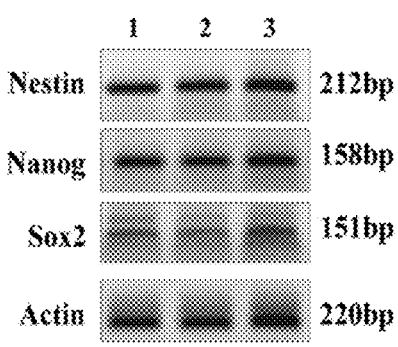
FIG. 45—Nestin, nanog and sox-2 genes of adherent cells of MLPC remark expression. Lane 1, 2, 3 were total, un-adherent and adherent cells of MLPC respectively. The PCR products are analyzed with 2% (w/v) agarose gel electrophoresis and stained with 1.5% RedSafe (iNtRON). PCR was performed in 20 microliter of a reaction mixture containing 2 micrograms cDNA and 500 nM each primers (Table 3).
Figure 48:
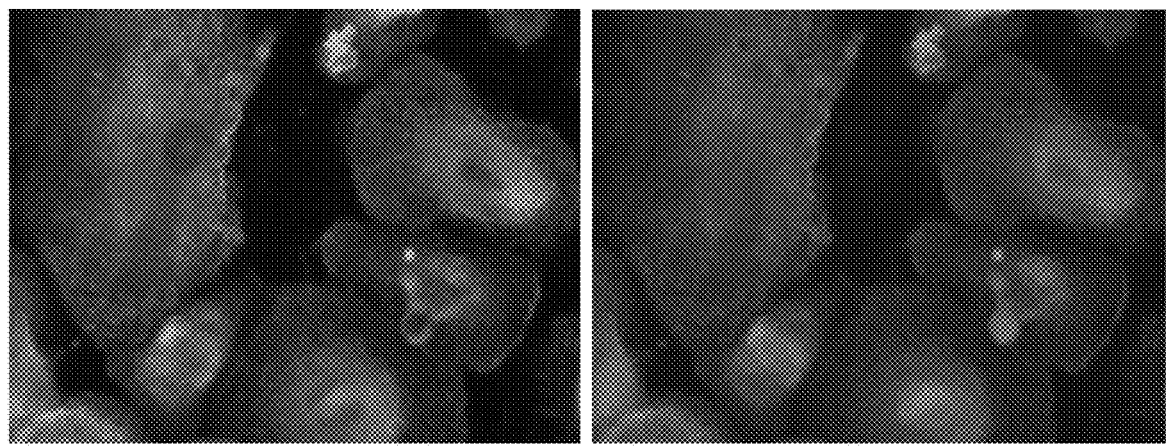
FIG. 48—Alpha-Actinin expressed (Alpha-Actinin-FITC) in MLPC in the first stage (A) and in the second stage (B)~(D) respectively. Left: fluorescence, Right: merged fluorescence & DAPI images. Original magnification: ×400.
Figure 50:
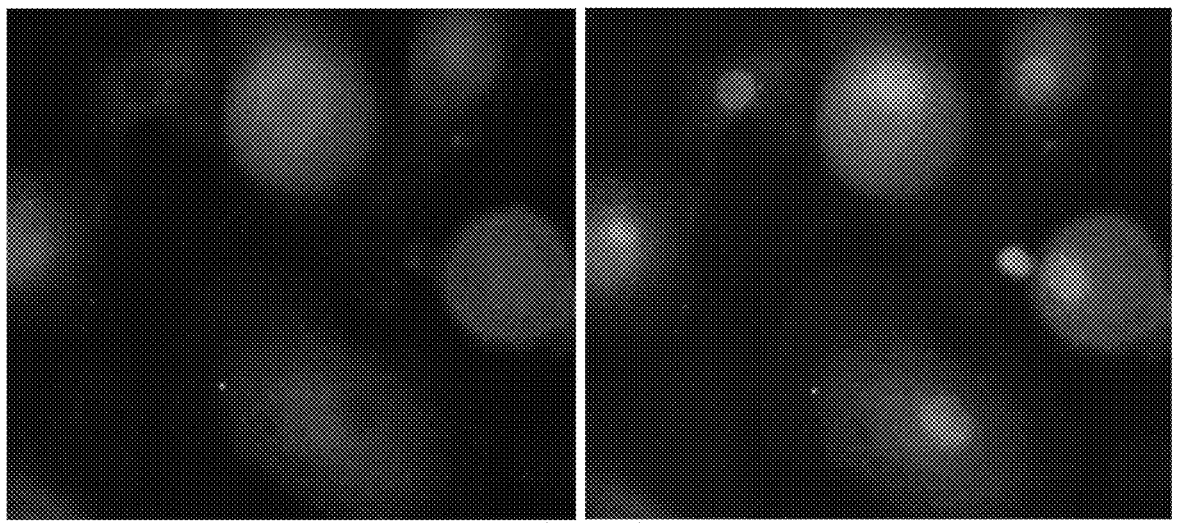
FIG. 50—Troponin I expressed (Troponin I-FITC) in MLPC in the first stage (A) and in the second stage (B)~(D) respectively. Left: fluorescence, Right: merged fluorescence & DAPI images. Original magnification: ×400.
Figure 51:
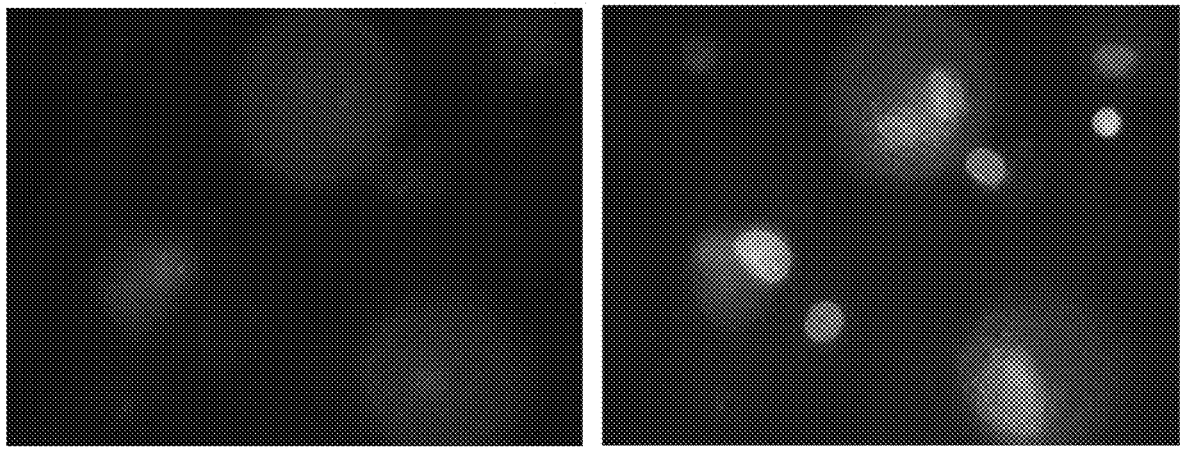
FIG. 51—GATA-4 expressed (GATA-4-FITC) in MLPC in the first stage (A) and in the second stage (B)~(D) respectively. Left: fluorescence, Right: merged fluorescence and DAPI images. Original magnification: ×400.
Figure 52:
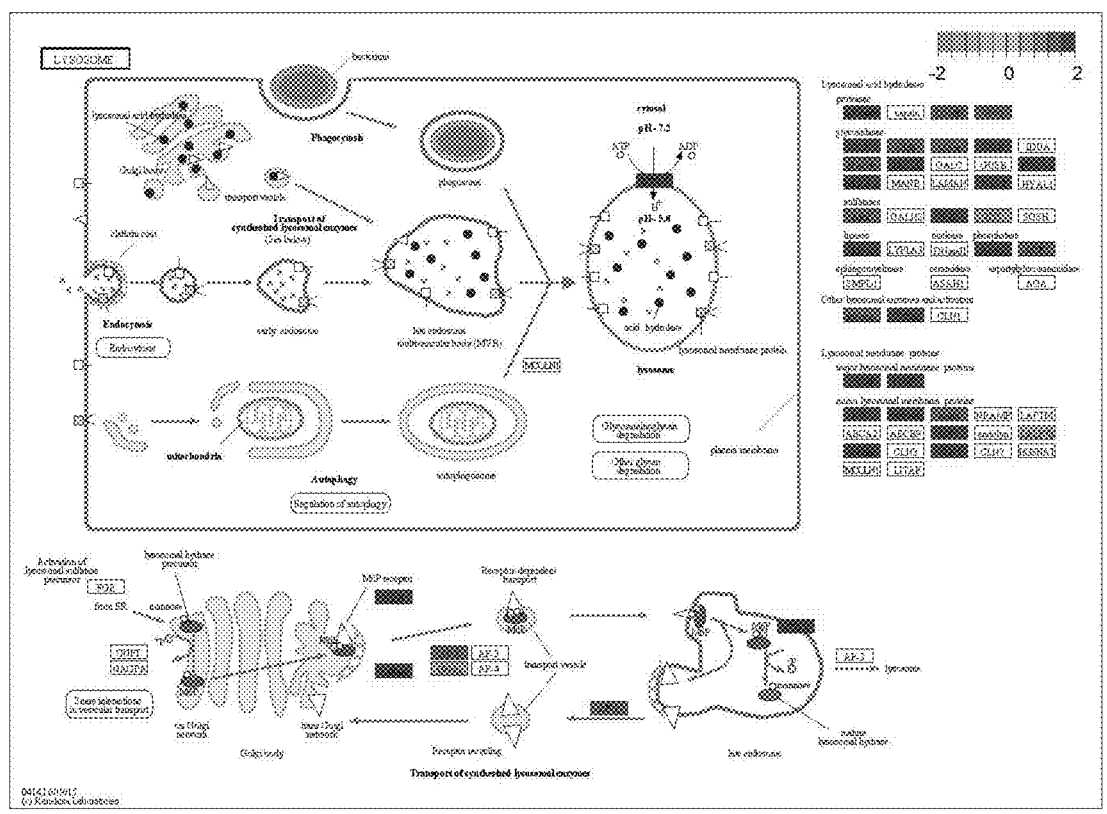

In induction condition of stage II period, observed cells became larger and flat from fibroblast-like morphology after 12 days induction (FIG. 18). Cells expressed alpha-fetoprotein (FIG. 19) and albumin (FIG. 20) between 8-12 days induction period, albumin had increase expression. Connexin 32 exhibited transient expression between 12 to 16 days, finally decrease on 19th day (FIG. 21). CYP1A1 protein markers is metabolic protein, which indicated hepatocyte's function on mature hepatocyte. In our differentiation of MLPC, CYP1A1 increased expression from 12 days to 19 days induction culture (FIG. 22). MLPC have the potential to differentiate into neo-hepatocyte cells, express liver functional markers.

8. Insights of Functional Regulations of MLPC by Microarray Analysis

In our studies, MLPC derived stem-like cells PA6, ATA6, and UATA6 compared with un-culture cells A0, which can show multiple functional regulations of pathway by genes analysis of microarray. Table 2 shown significantly pathways (p<0.05) of PA6 vs. A0, ATA6 vs. A0, and UATA6 vs. A0 results, which majority associated with lysosomes functions, metabolism regulation, neuron dysfunction diseases, steroid biosynthesis, cytokines and chemokines interaction.

Top one regulated pathway of PA6 and ATA6 was lysosomes (p value: 1.24E-04) by PA6 vs. A0 and ATA6 vs. A0 microarray data respectively, 34 genes of PA6 cells were up-regulated by Kyoto Encyclopedia of Genes and Genomes (KEGG) base analysis (Table 2). Lysosomes major function can storage various molecular for proteins degradation, including over 40 hydrolysis enzymes. MLPC derived stem-like cells PA6 can significantly increase hydrolase activity (p value: 2.04E-04) acting on glycosyl bonds, enhanced endocytosis, phagocytosis and autophagy functions. Furthermore, 34 genes of up regulation of PA6 cells can enhance glycosaminoglycan degradation (p value: 6.67E-08), glycosphingolipid biosynthesis (p value: 8.51E-05), phagosome (p value: 2.04E-04), rheumatoid arthritis (p value: 5.60E-04), and galactose metabolism (p value: 6.77E-04) by STRING network analysis.

Figure 53:
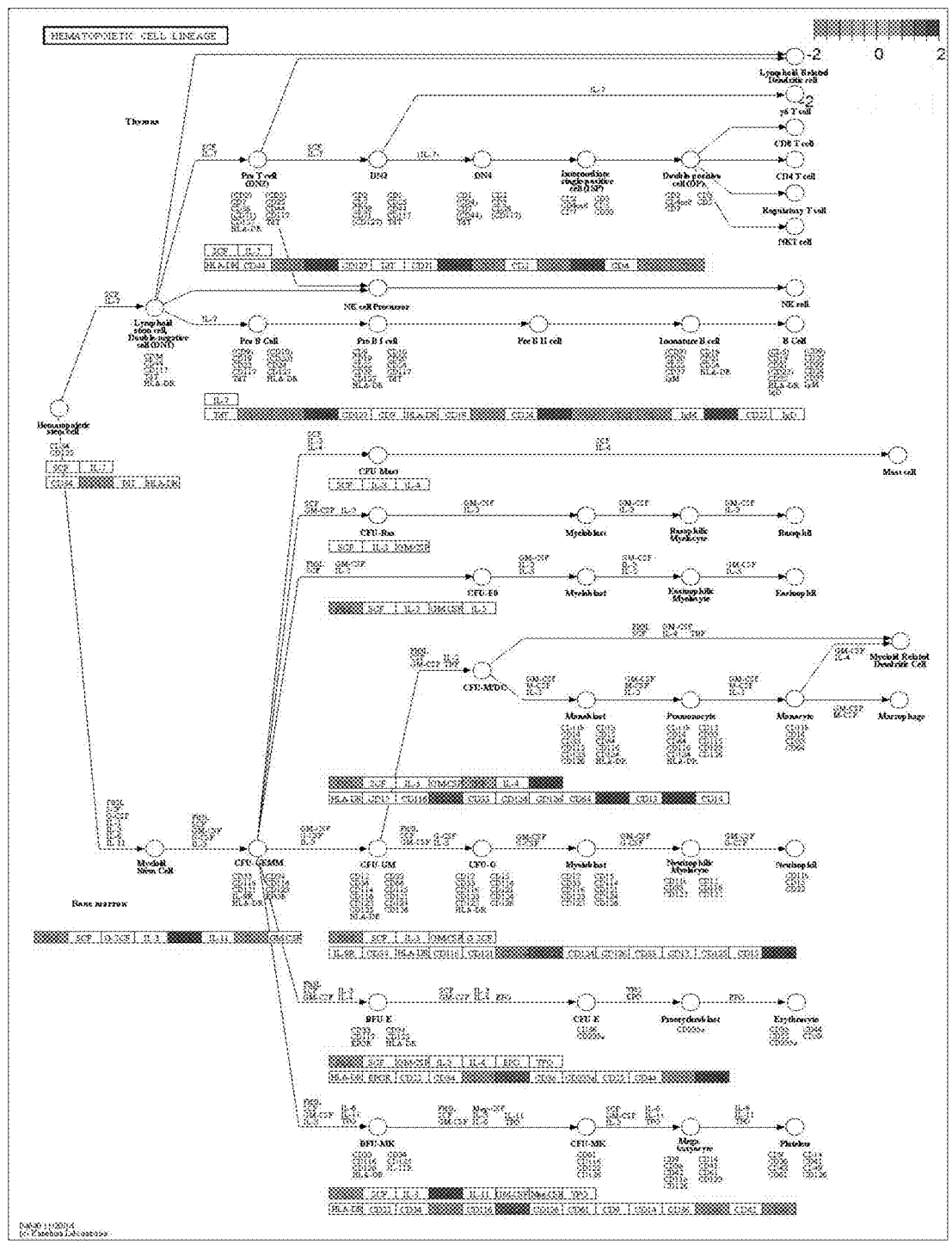
FIG. 53—MLPC derived stem-like cells ATA6, 36 genes were significantly involved Hematopoietic cell lineage by KEGG database analysis. Red colour indicated 11 genes of up regulation and green colour indicated 25 genes of down-regulation.
Figure 54:
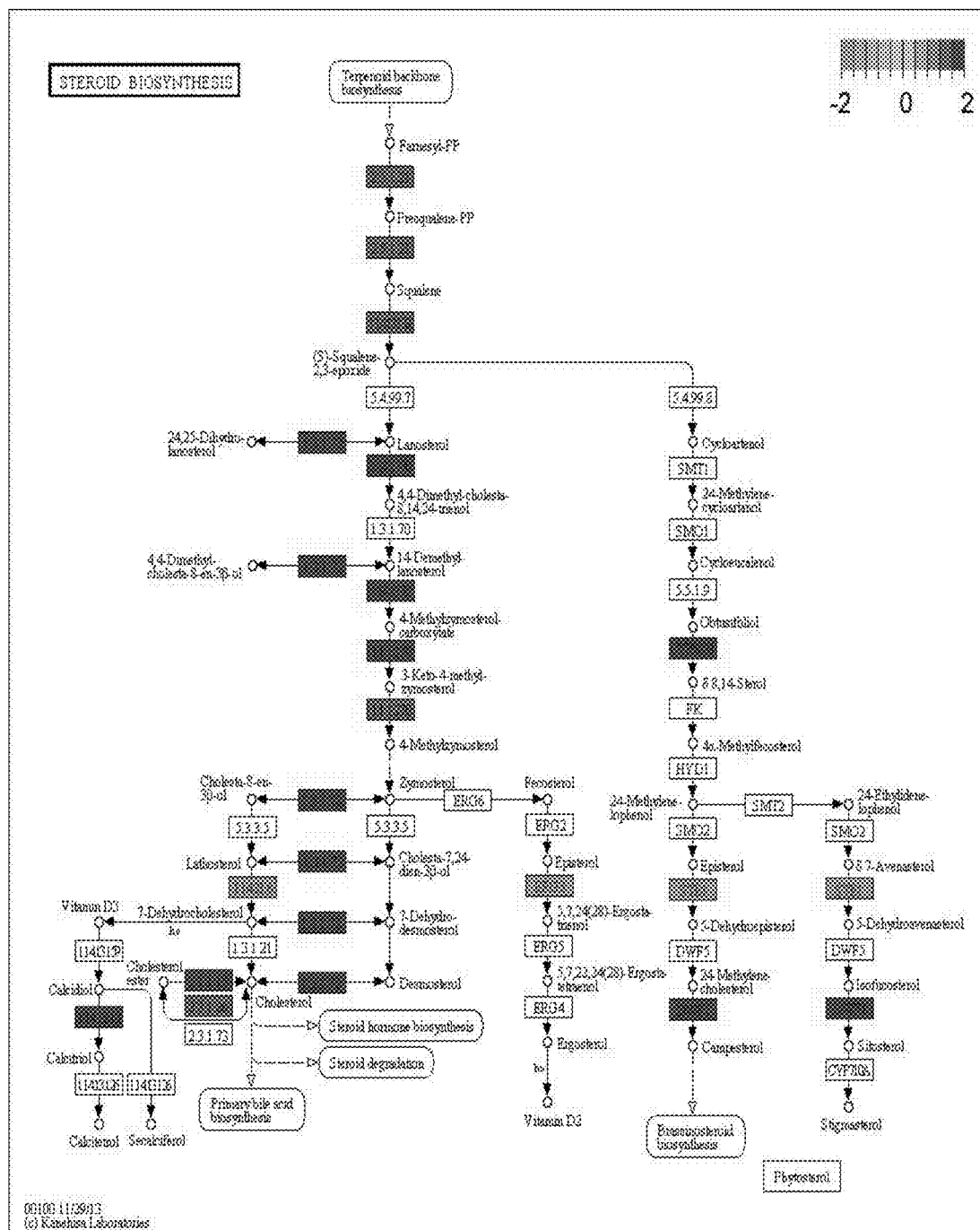
FIG. 54—MLPC derived stem-like cells ATA6, 11 genes were significantly involved steroid biosynthesis by KEGG database analysis. Red colour indicated 10 genes of up regulation and green colour indicated 1 genes of down-regulation.
Figure 55:
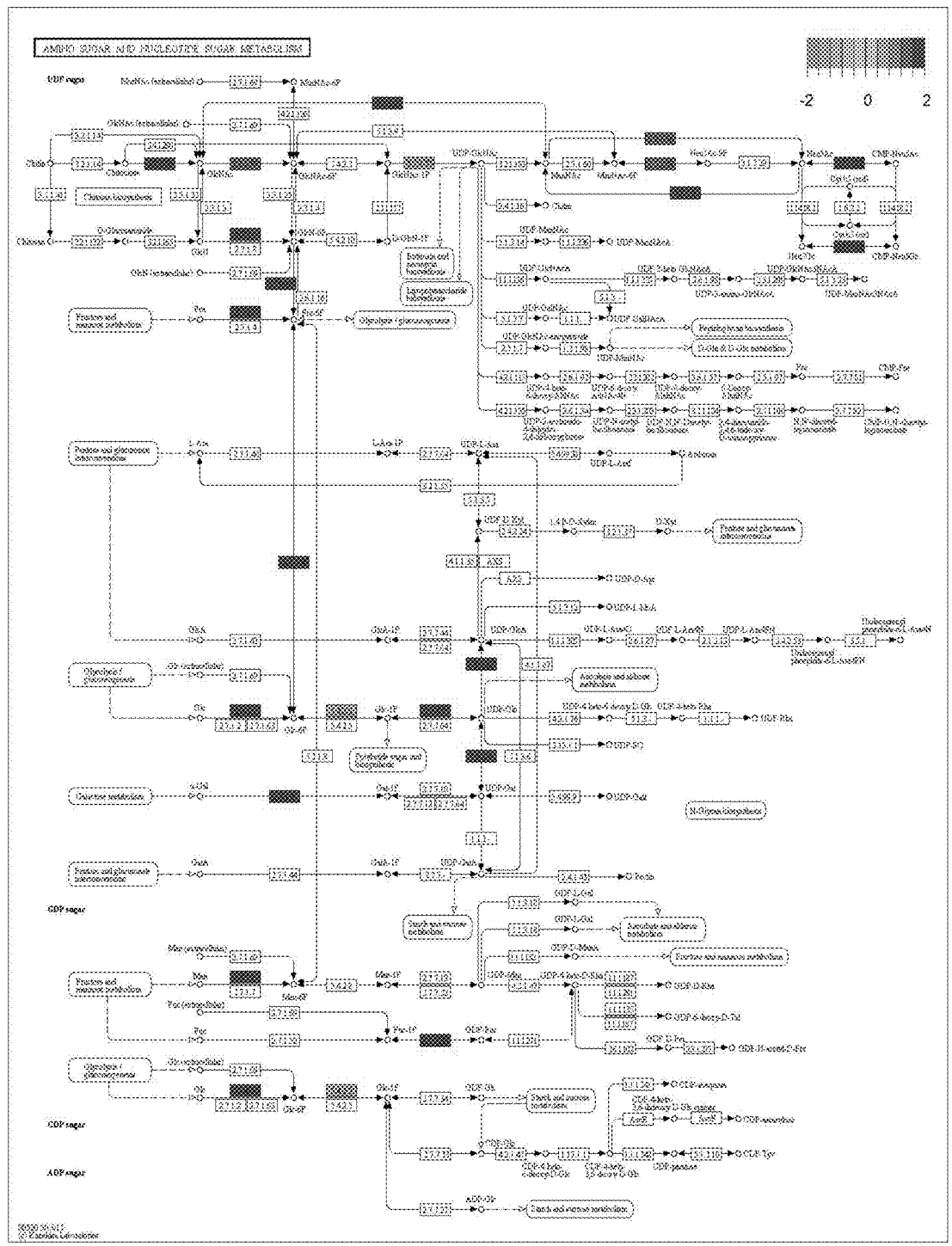
FIG. 55—MLPC derived stem-like cells ATA6, 20 genes were significantly involved amino sugar and nucleotide sugar metabolism by KEGG database analysis. Red colour indicated 18 genes of up regulation and green colour indicated 2 genes of down-regulation.
Figure 56:
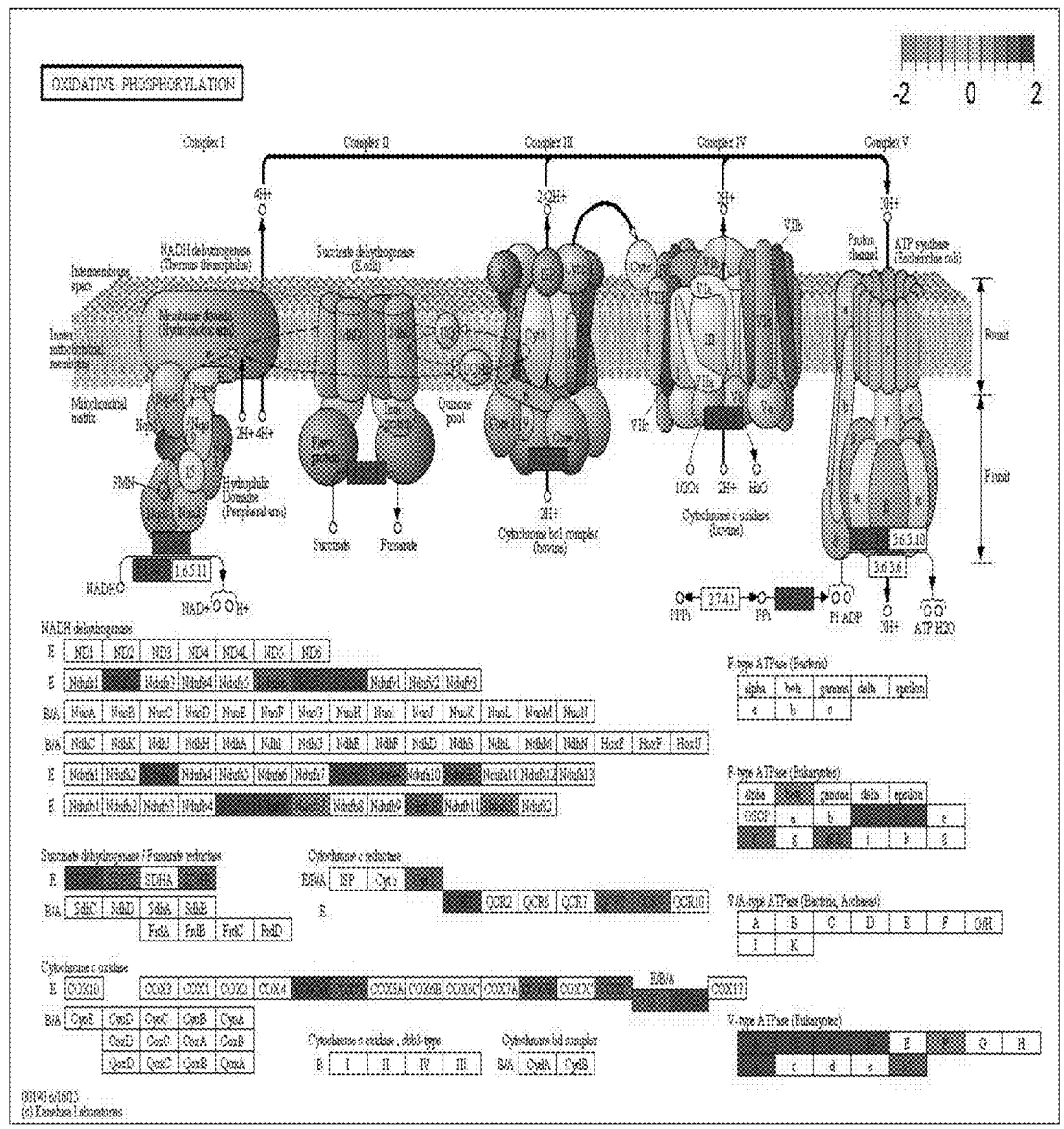
FIG. 56—MLPC derived stem-like cells ATA6, 44 genes were significantly involved oxidative phosphorylation by KEGG database analysis. Red colour indicated 44 genes of up regulation.
Figure 57:
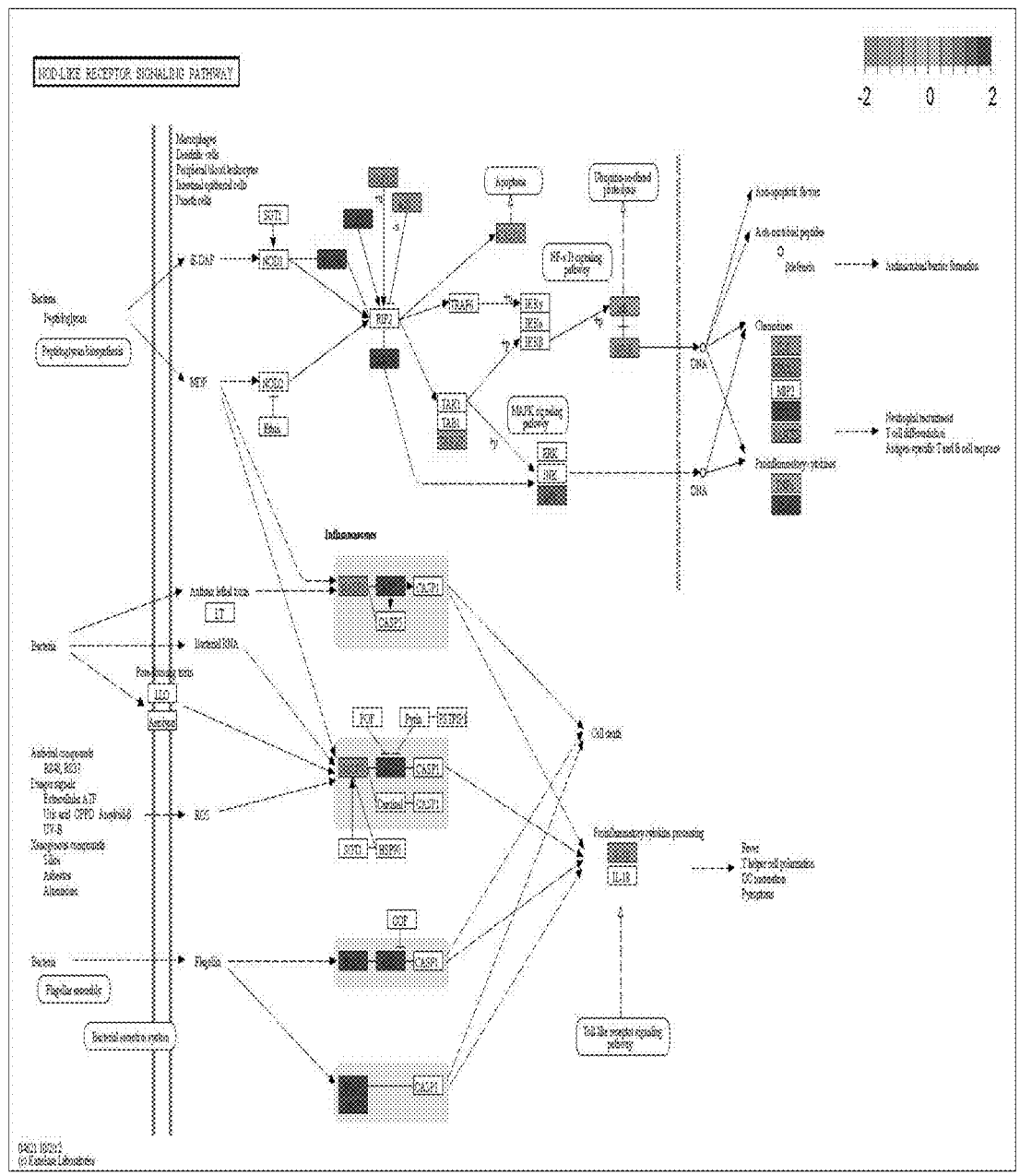
FIG. 57—MLPC derived stem-like cells ATA6, 25 genes were significantly involved NOD-like receptor signaling pathway by KEGG database analysis. Red colour indicated 12 genes of up regulation and green colour indicated 13 genes of down-regulation.
Figure 58:
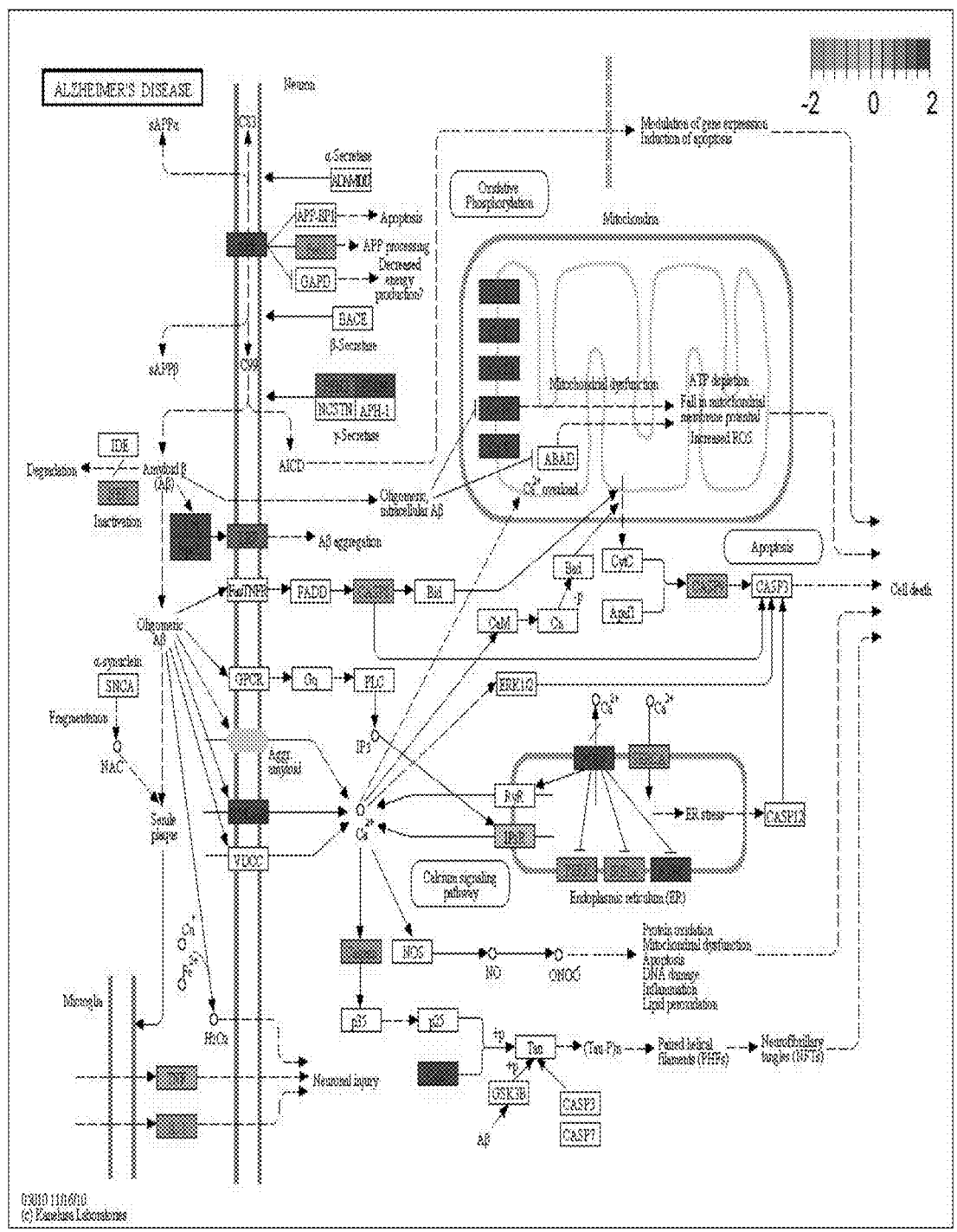
FIG. 58—MLPC derived stem-like cells ATA6, 52 genes were significantly involved Alzheimer's disease by KEGG database analysis. Red colour indicated 41 genes of up regulation and green colour indicated 11 genes of down-regulation.
Figure 59:
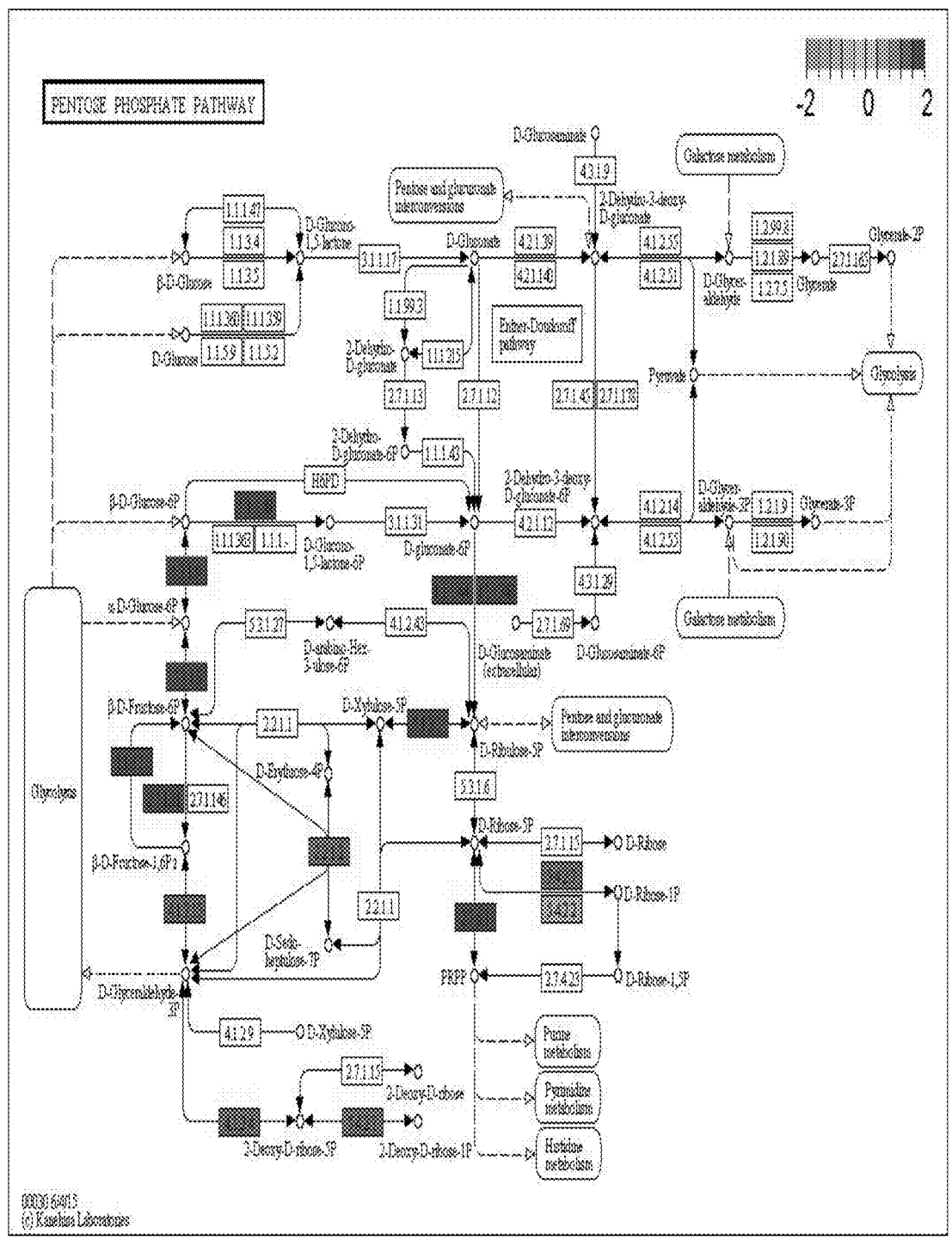
FIG. 59—MLPC derived stem-like cells ATA6, 13 genes were significantly involved pentose phosphate pathway by KEGG database analysis. Red colour indicated 12 genes of up regulation and green colour indicated 1 genes of down-regulation.
Figure 60:
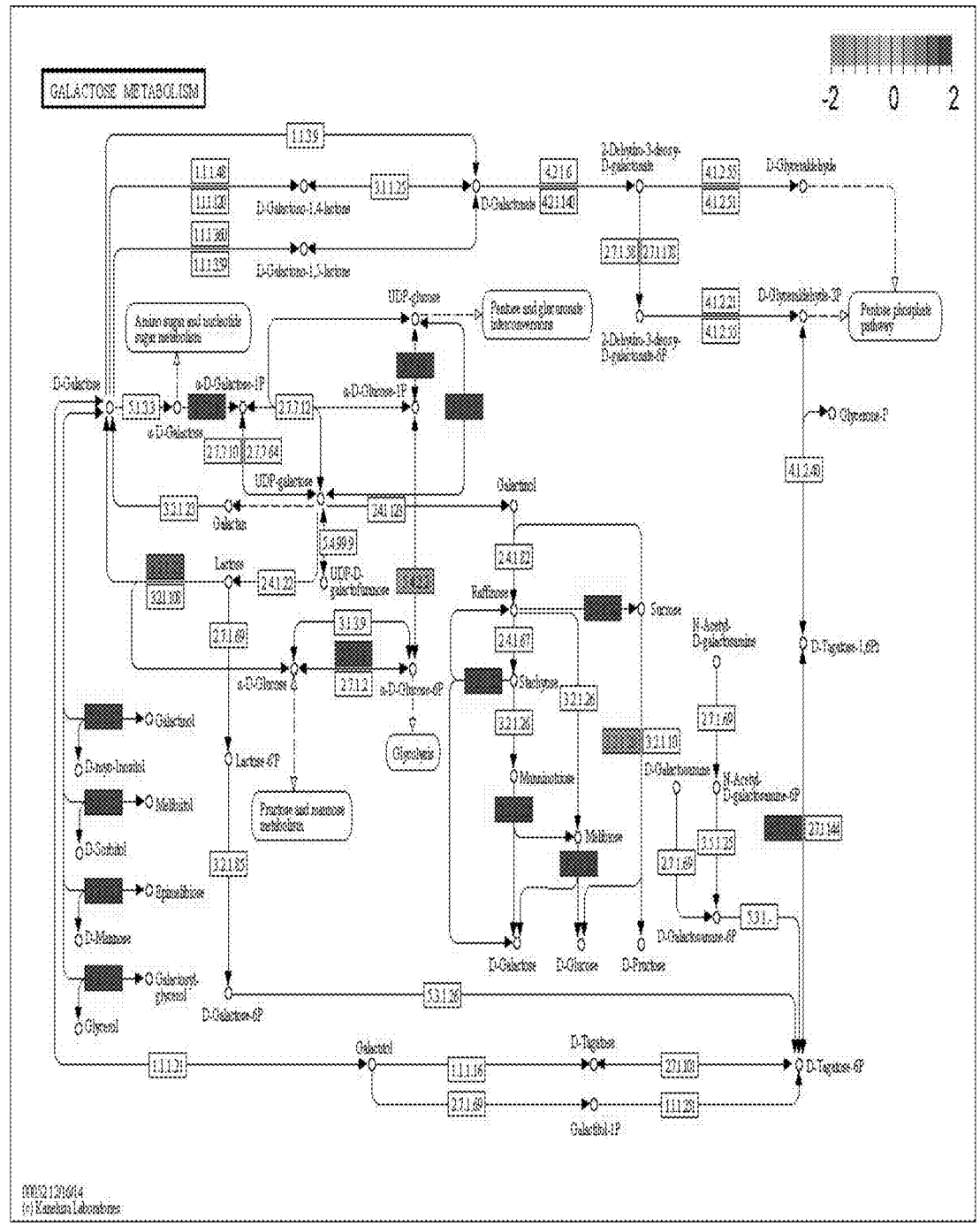
FIG. 60—MLPC derived stem-like cells ATA6, 13 genes were significantly involved galactose metabolism by KEGG database analysis. Red colour indicated 11 genes of up regulation and green colour indicated 2 genes of down-regulation.
Figure 61:
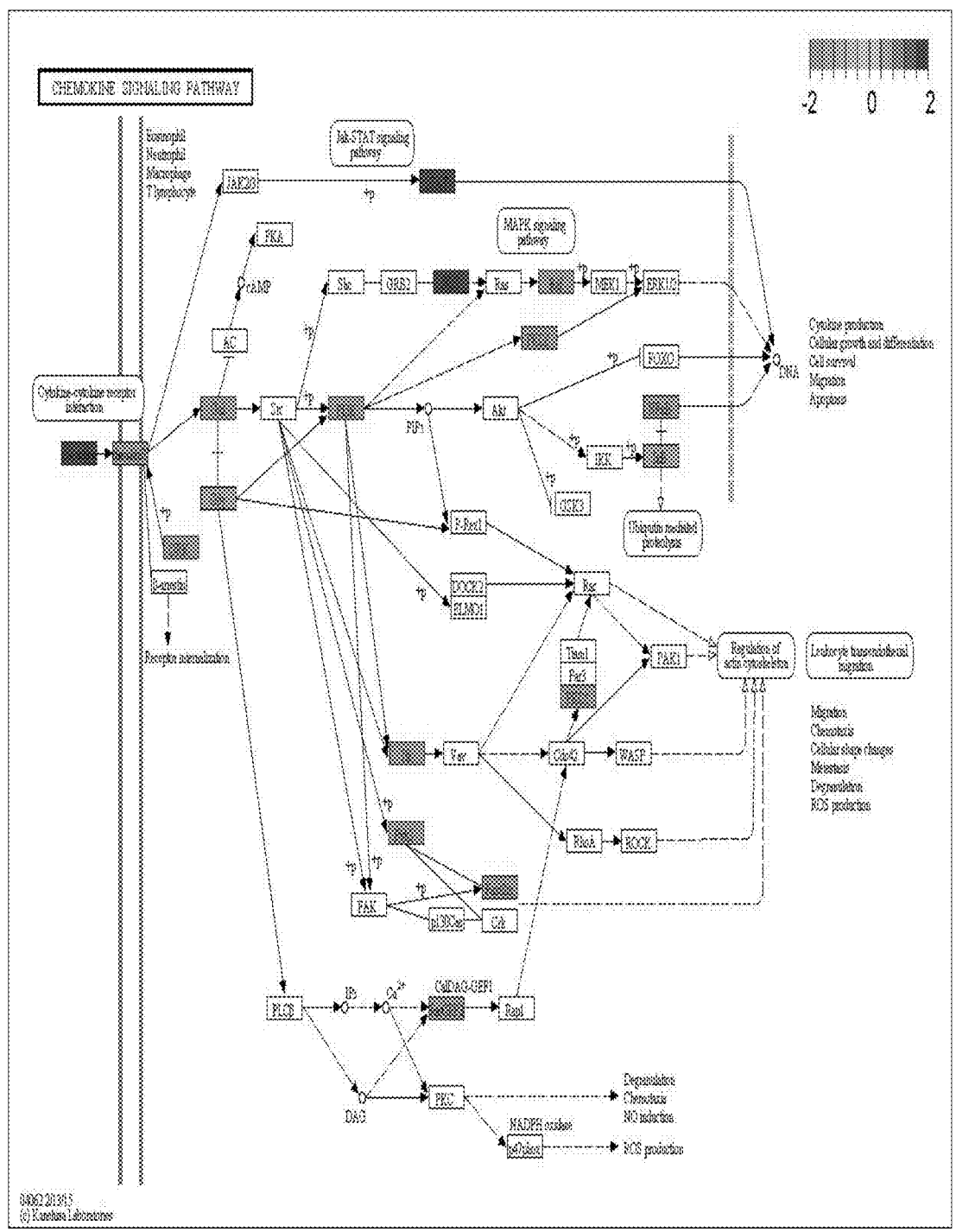
FIG. 61—MLPC derived stem-like cells ATA6, 56 genes were significantly involved chemokine signaling pathway by KEGG database analysis. Red colour indicated 23 genes of up regulation and green colour indicated 33 genes of down-regulation.
Figure 62:
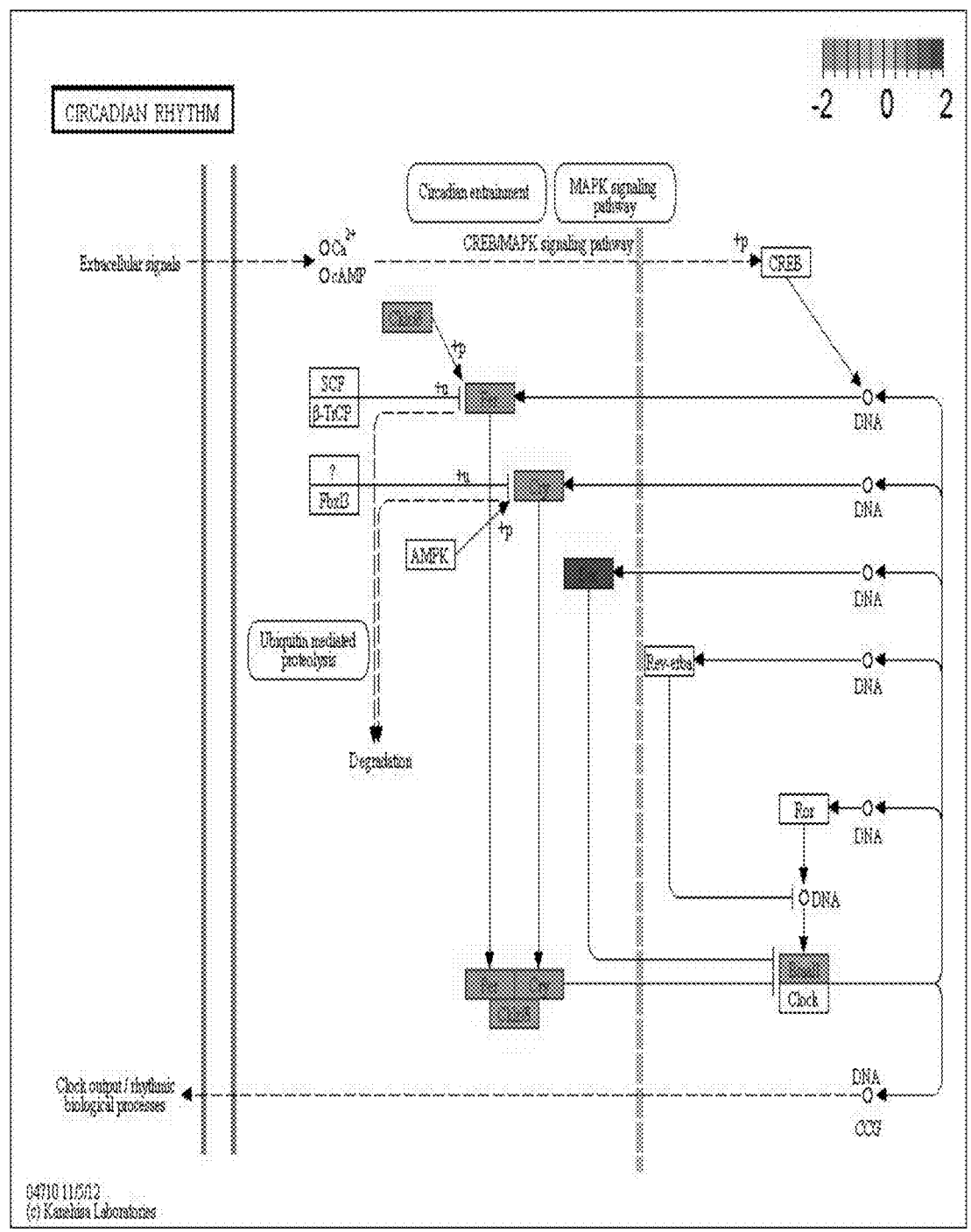
FIG. 62—MLPC derived stem-like cells ATA6, 8 genes were significantly involved Circadian rhythm by KEGG database analysis. Red colour indicated 1 genes of up regulation and green colour indicated 7 genes of down-regulation.
Figure 63:
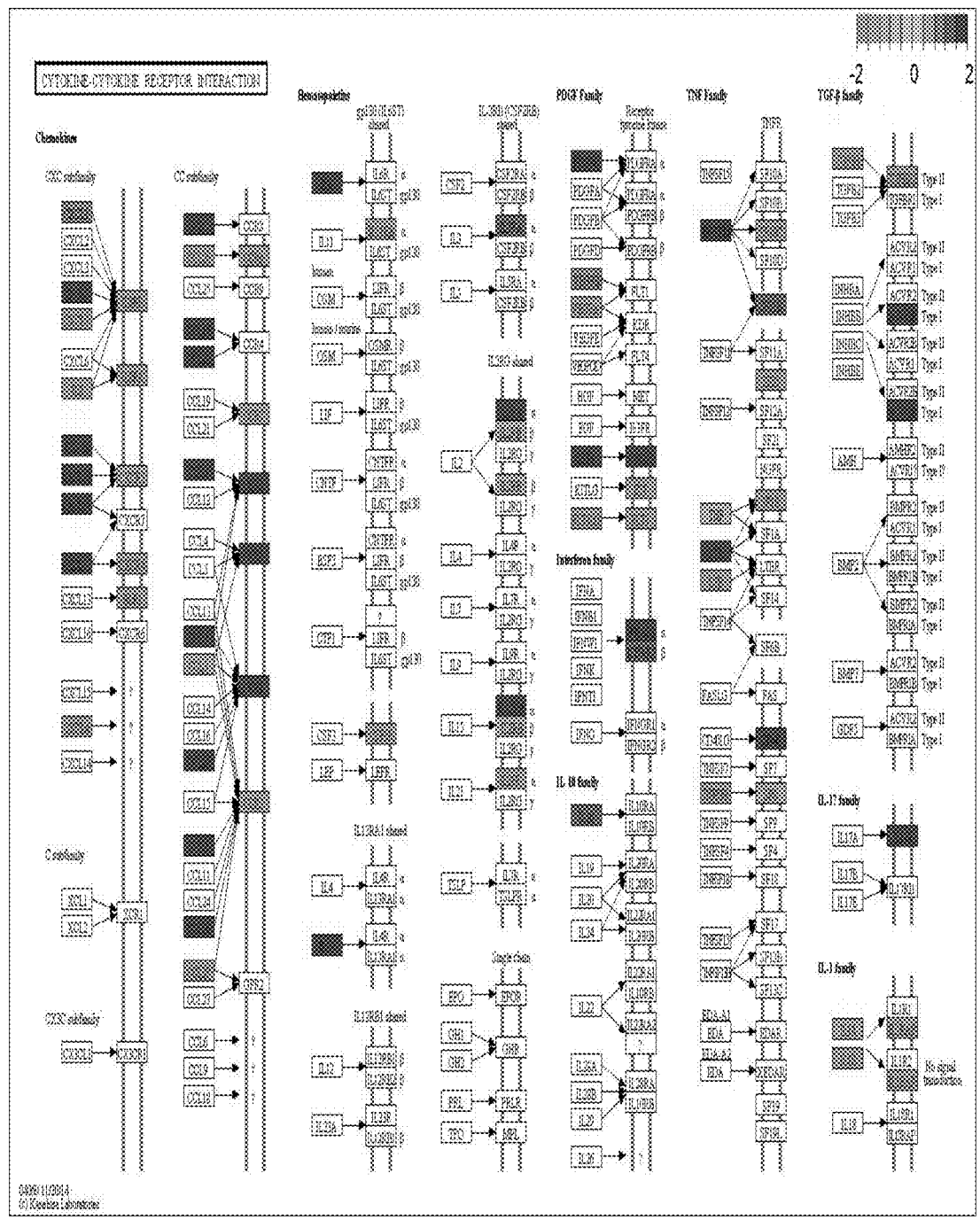
FIG. 63—MLPC derived stem-like cells ATA6, 73 genes were significantly involved cytokine-cytokine receptor interaction by KEGG database analysis. Red colour indicated 35 genes of up regulation and green colour indicated 38 genes of down-regulation.
Figure 64:
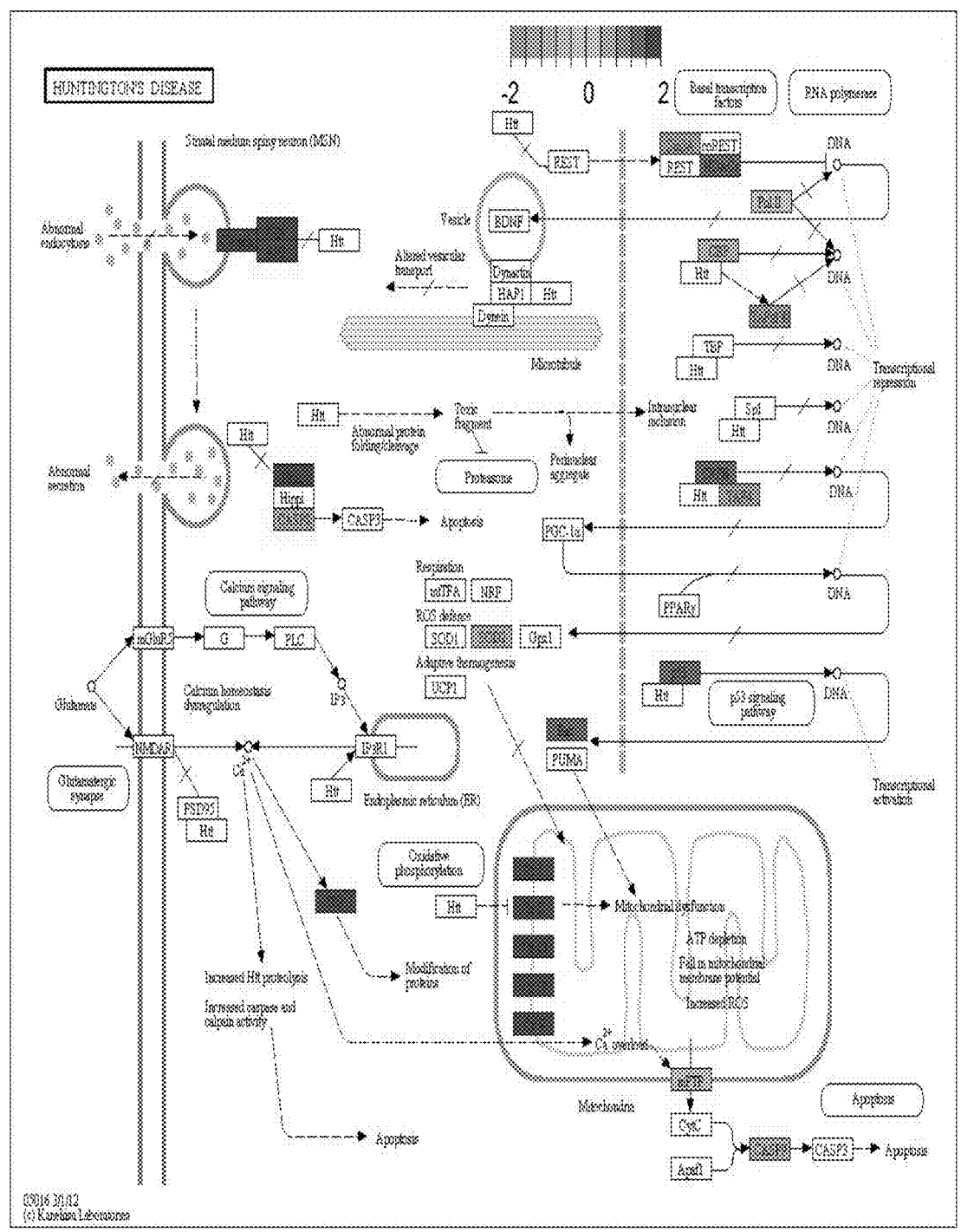
FIG. 64—MLPC derived stem-like cells ATA6, 52 genes were significantly involved Huntington's disease by KEGG database analysis. Red colour indicated 44 genes of up regulation and green colour indicated 11 genes of down-regulation.
Figure 65:
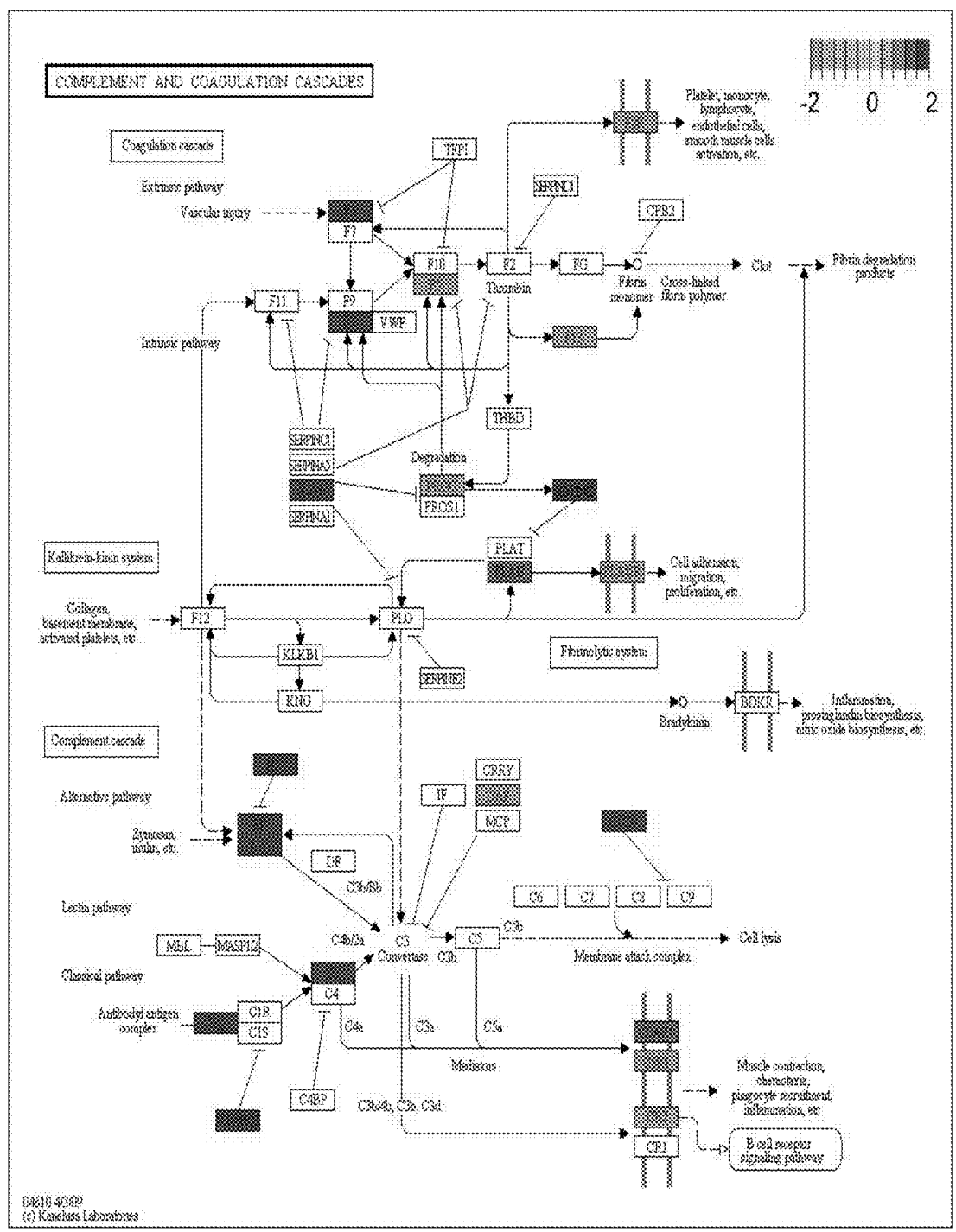
FIG. 65—MLPC derived stem-like cells ATA6, 24 genes were significantly involved complement and coagulation cascades by KEGG database analysis. Red colour indicated 16 genes of up regulation and green colour indicated 8 genes of down-regulation.
Figure 66:
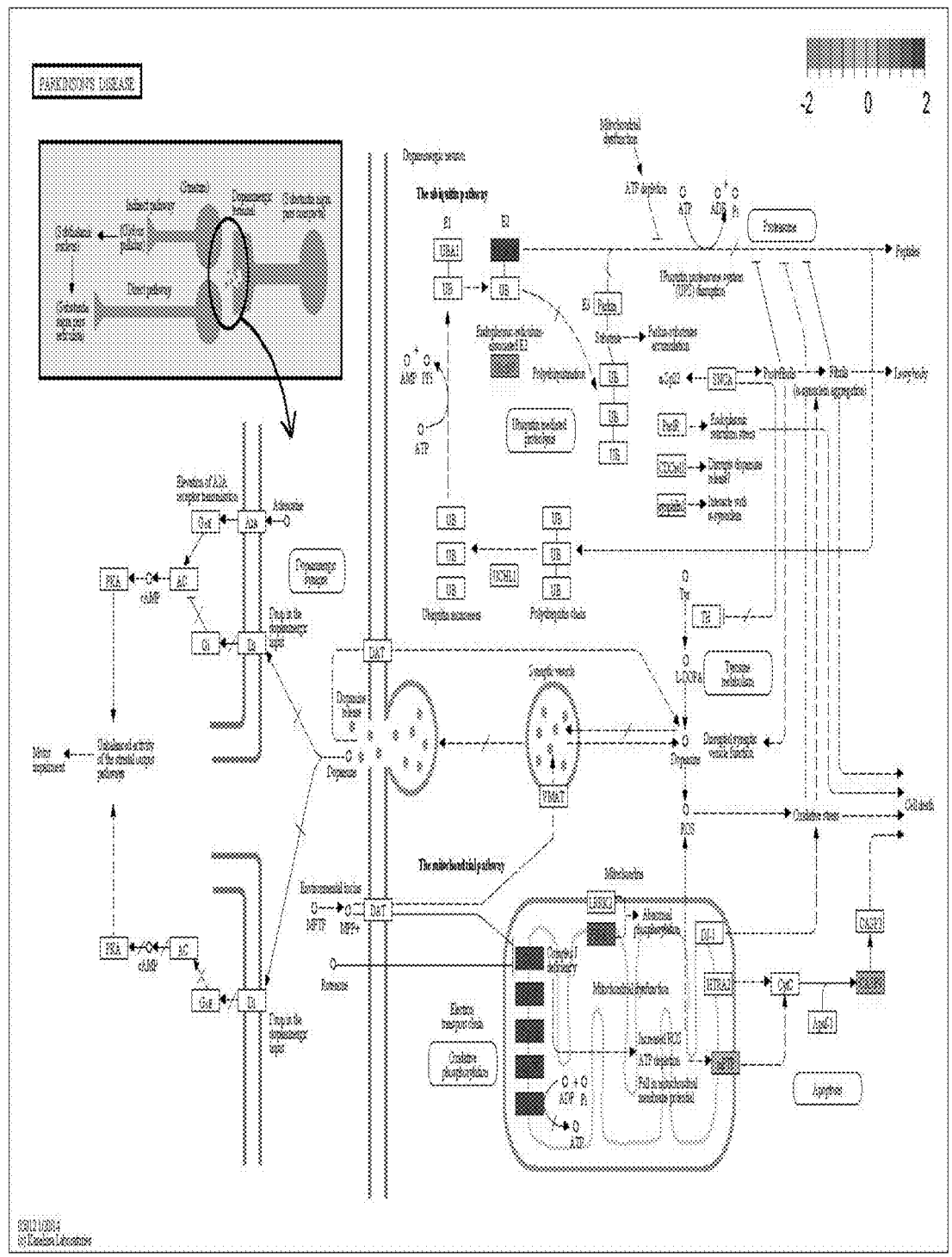
FIG. 66—MLPC derived stem-like cells ATA6, 39 were significantly involved Parkinson's disease by KEGG database analysis. Red colour indicated 36 genes of up regulation and green colour indicated 3 genes of down-regulation.
Figure 67:
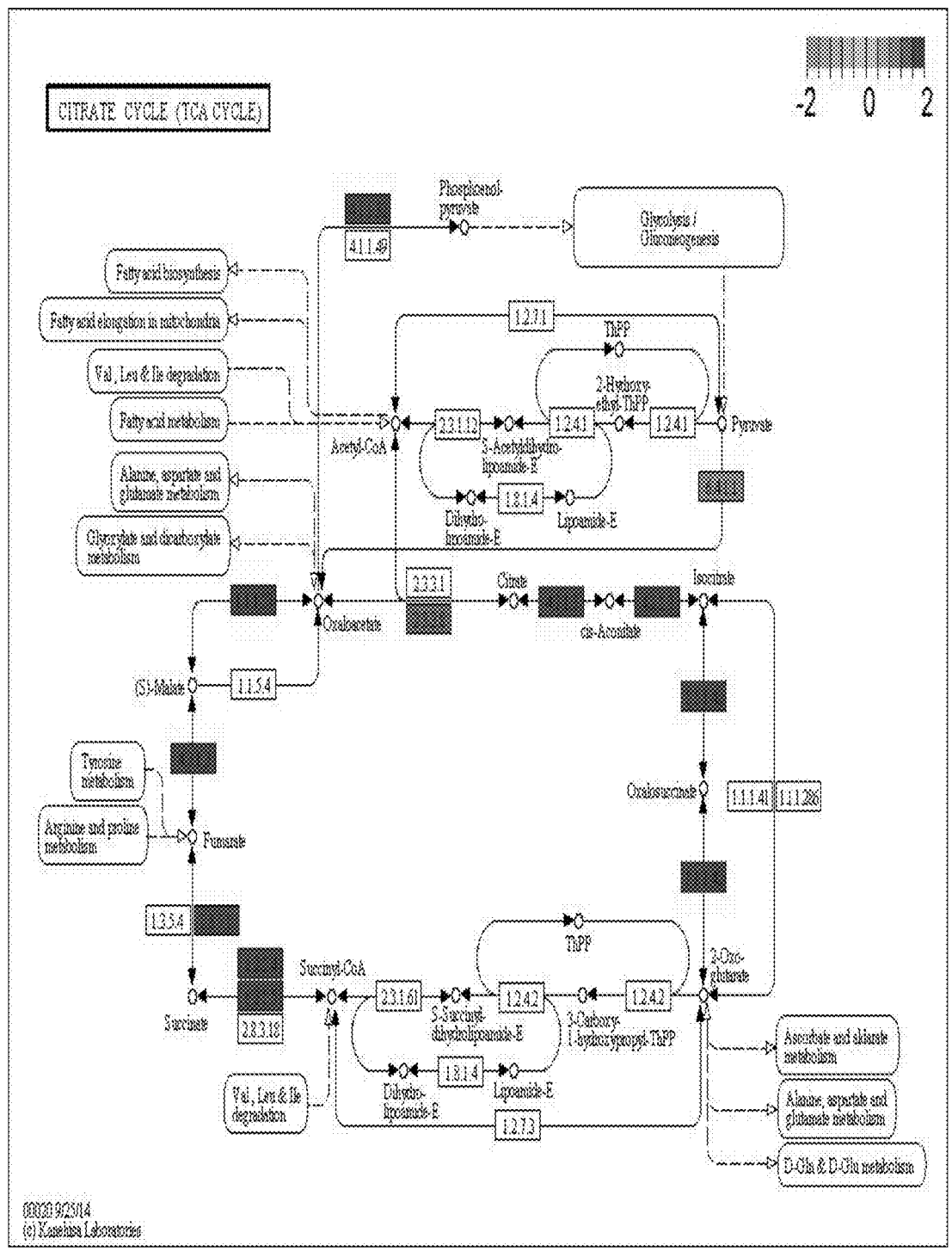
FIG. 67—MLPC derived stem-like cells ATA6, 13 genes were significantly involved citrate cycle (TCA cycle) by KEGG database analysis. Red colour indicated 13 genes of up regulation.
Figure 68:
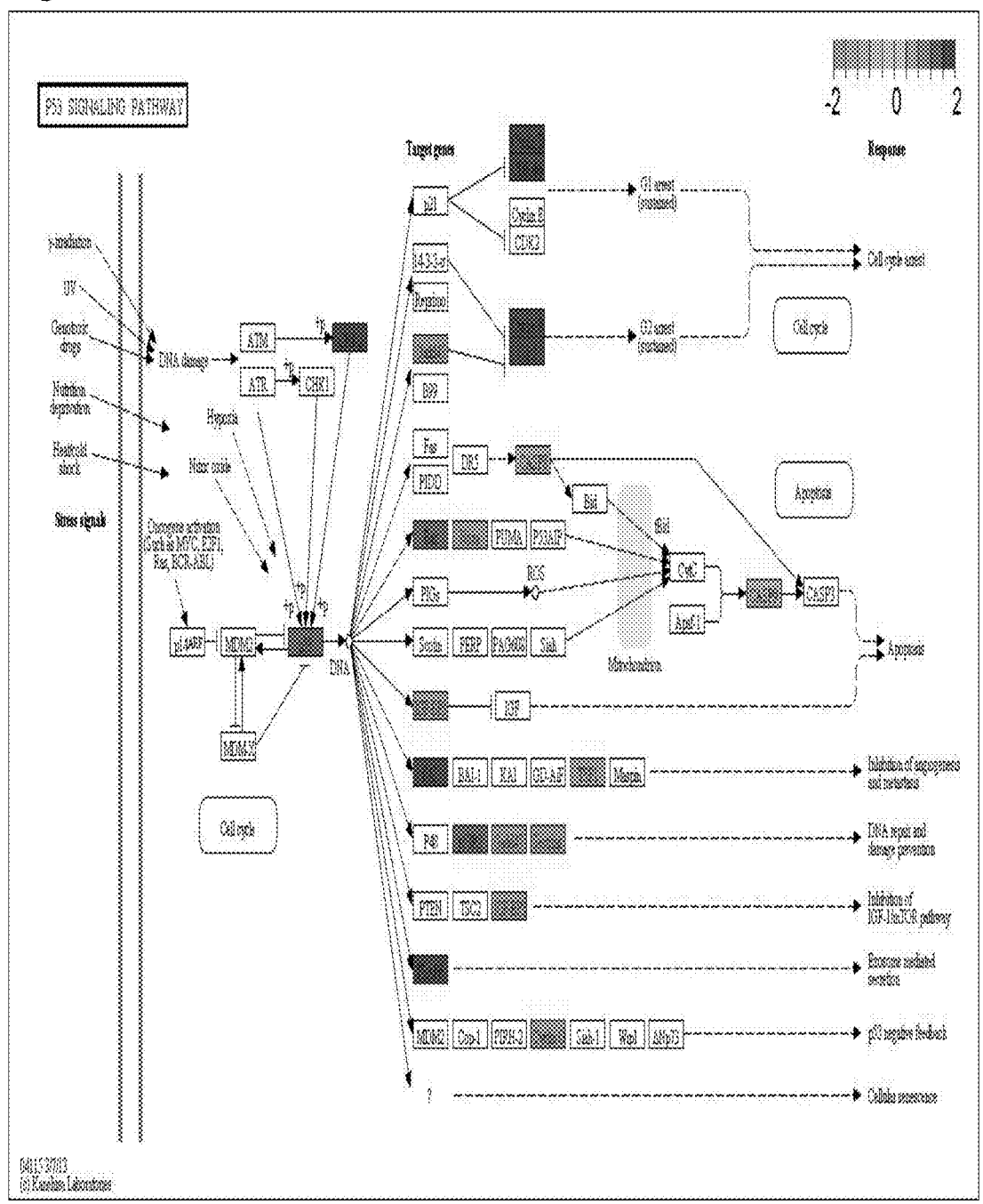
FIG. 68—MLPC derived stem-like cells ATA6, 23 genes were significantly involved p53 signaling pathway by KEGG database analysis. Red colour indicated 11 genes of up regulation and green colour indicated 12 genes of down-regulation.
Figure 69:
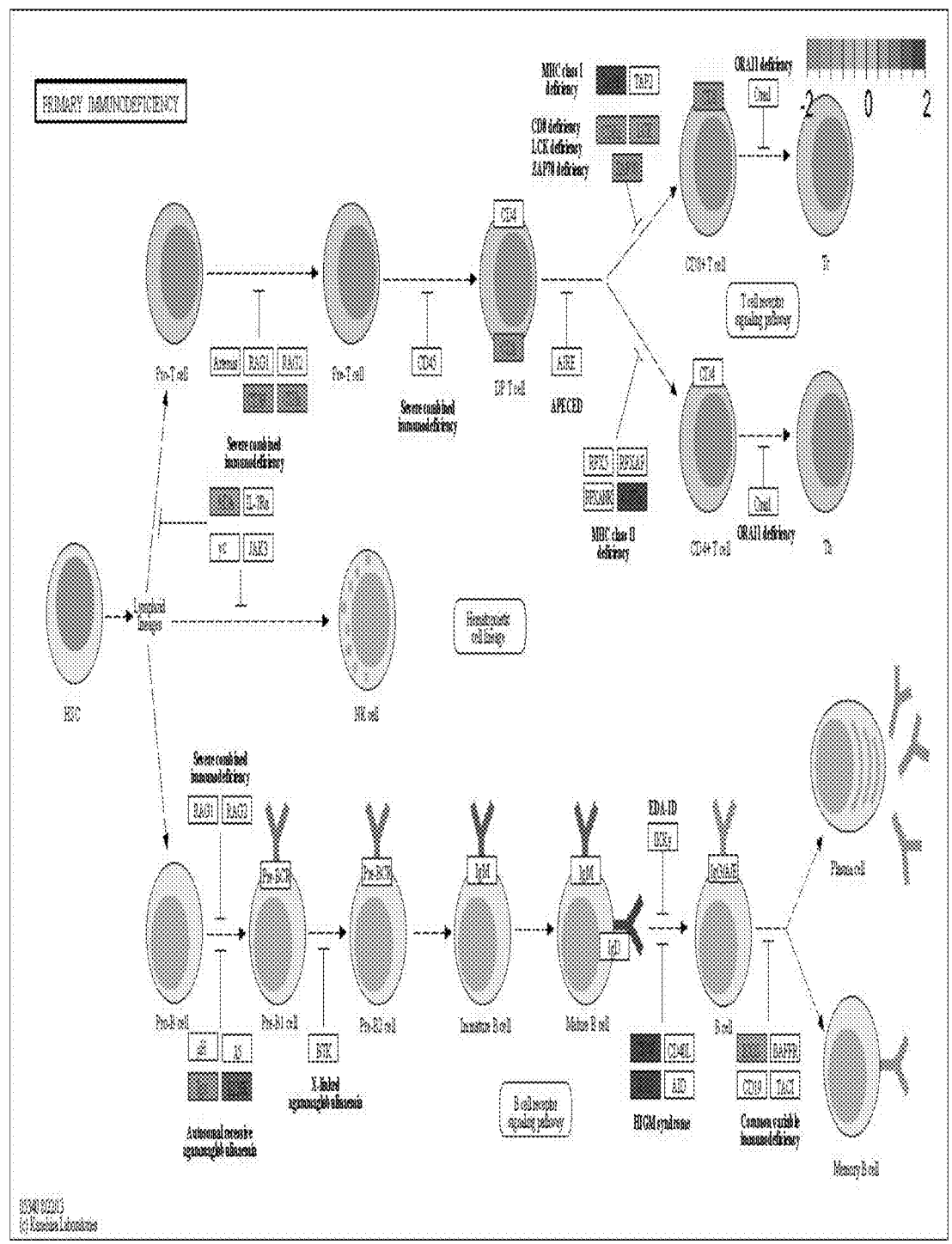
FIG. 69—MLPC derived stem-like cells ATA6, 14 genes were significantly involved primary immunodeficiency by KEGG database analysis. Red colour indicated 5 genes of up regulation and green colour indicated 9 genes of down-regulation.
Figure 70:
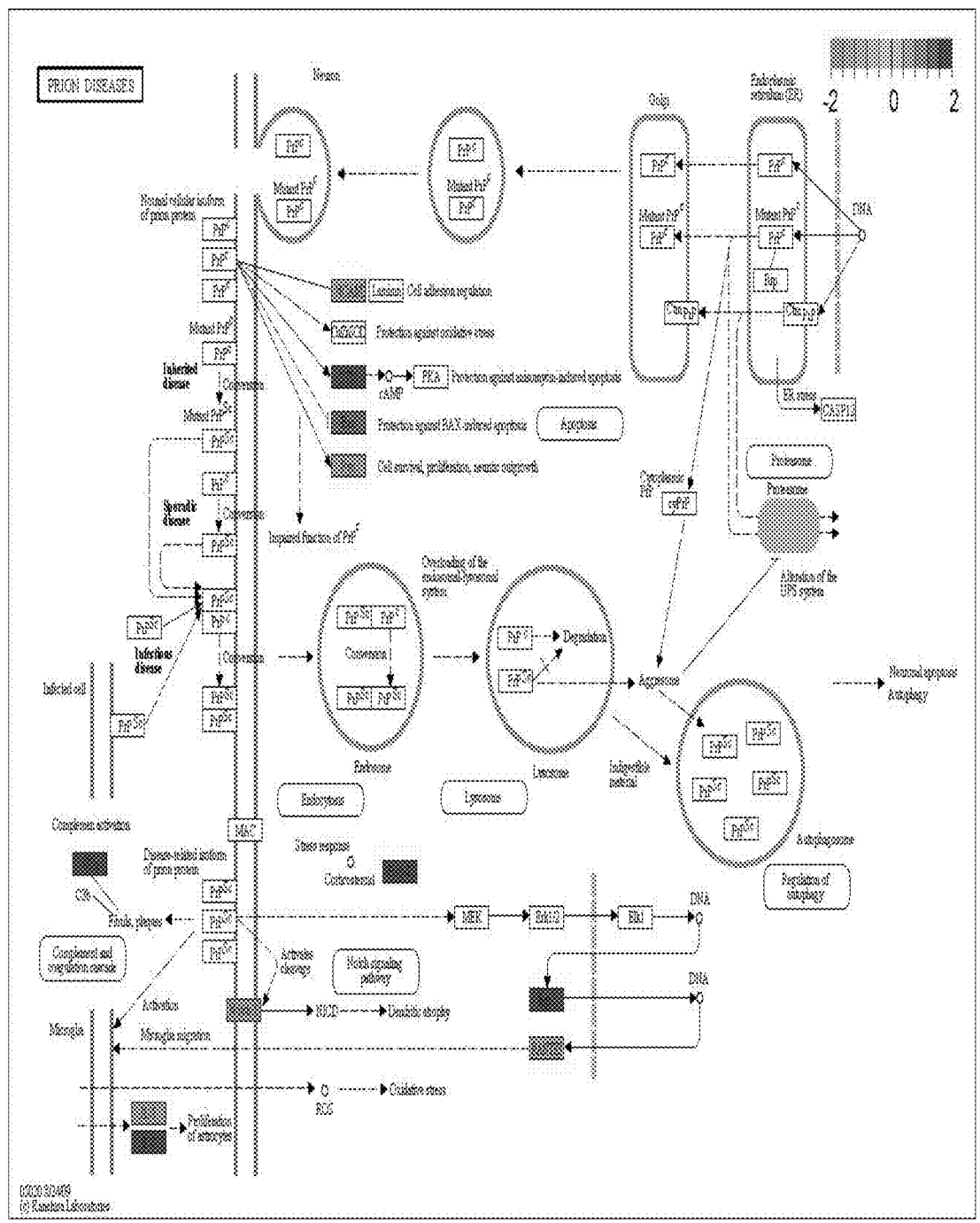
FIG. 70—MLPC derived stem-like cells ATA6, 15 genes were significantly involved Prion diseases by KEGG database analysis. Red colour indicated 9 genes of up regulation and green colour indicated 6 genes of down-regulation.
Figure 71:
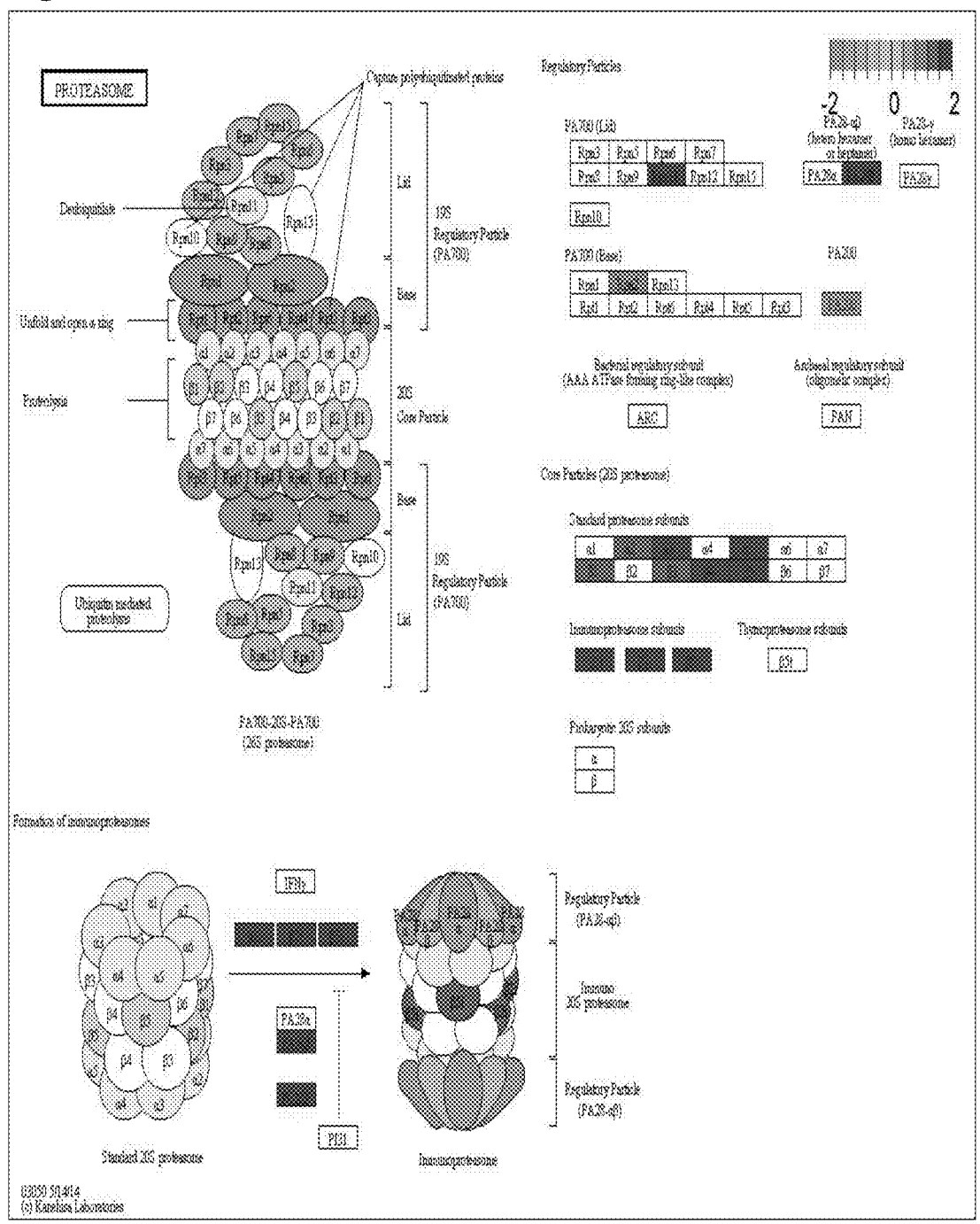
FIG. 71—MLPC derived stem-like cells ATA6, 17 genes were significantly involved proteasome by KEGG database analysis. Red colour indicated 16 genes of up regulation and green colour indicated 1 genes of down-regulation.
Figure 72:
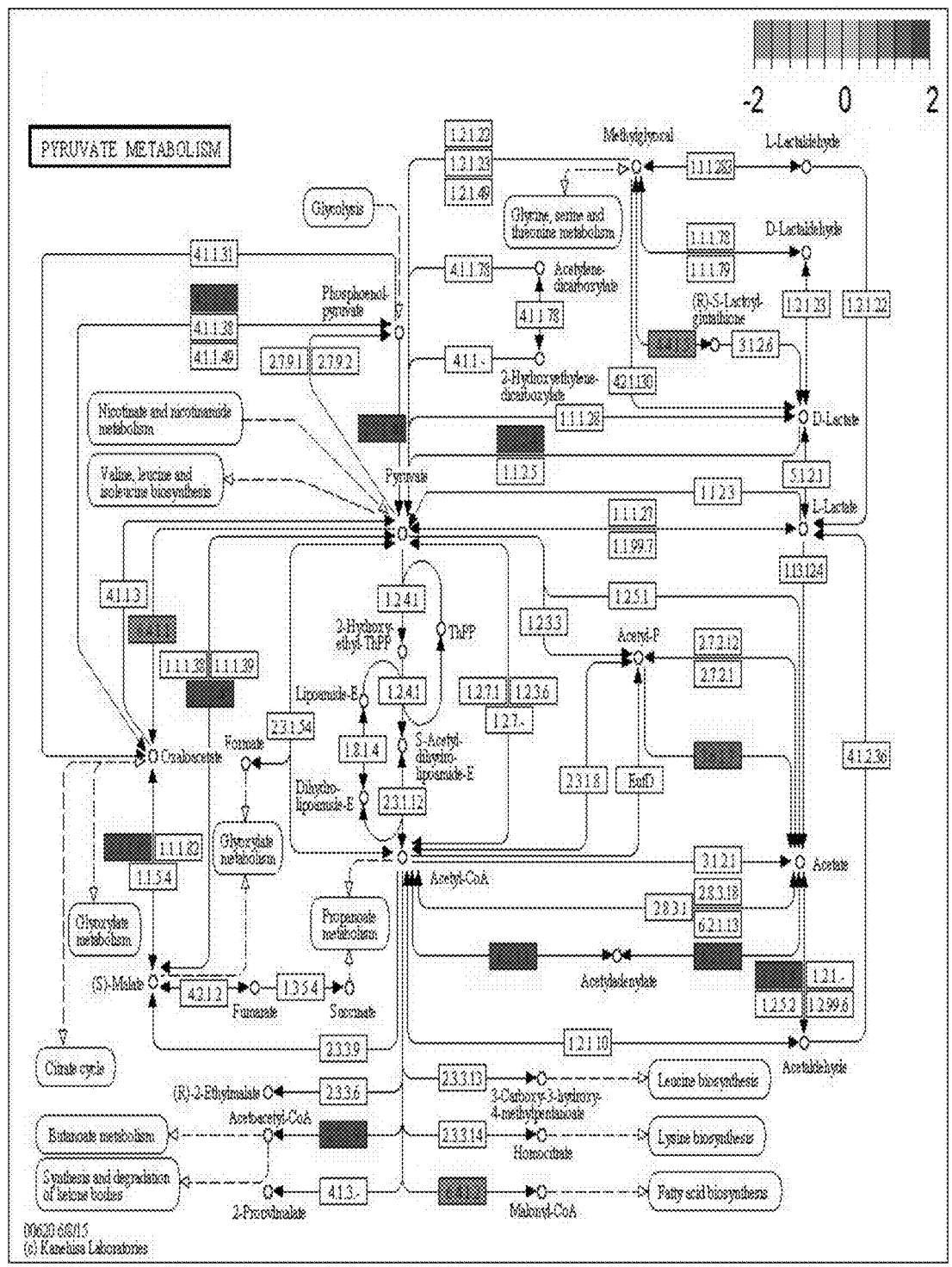
FIG. 72—MLPC derived stem-like cells ATA6, 15 genes were significantly involved pyruvate metabolism by KEGG database analysis. Red colour indicated 15 genes of up regulation.
Figure 73:
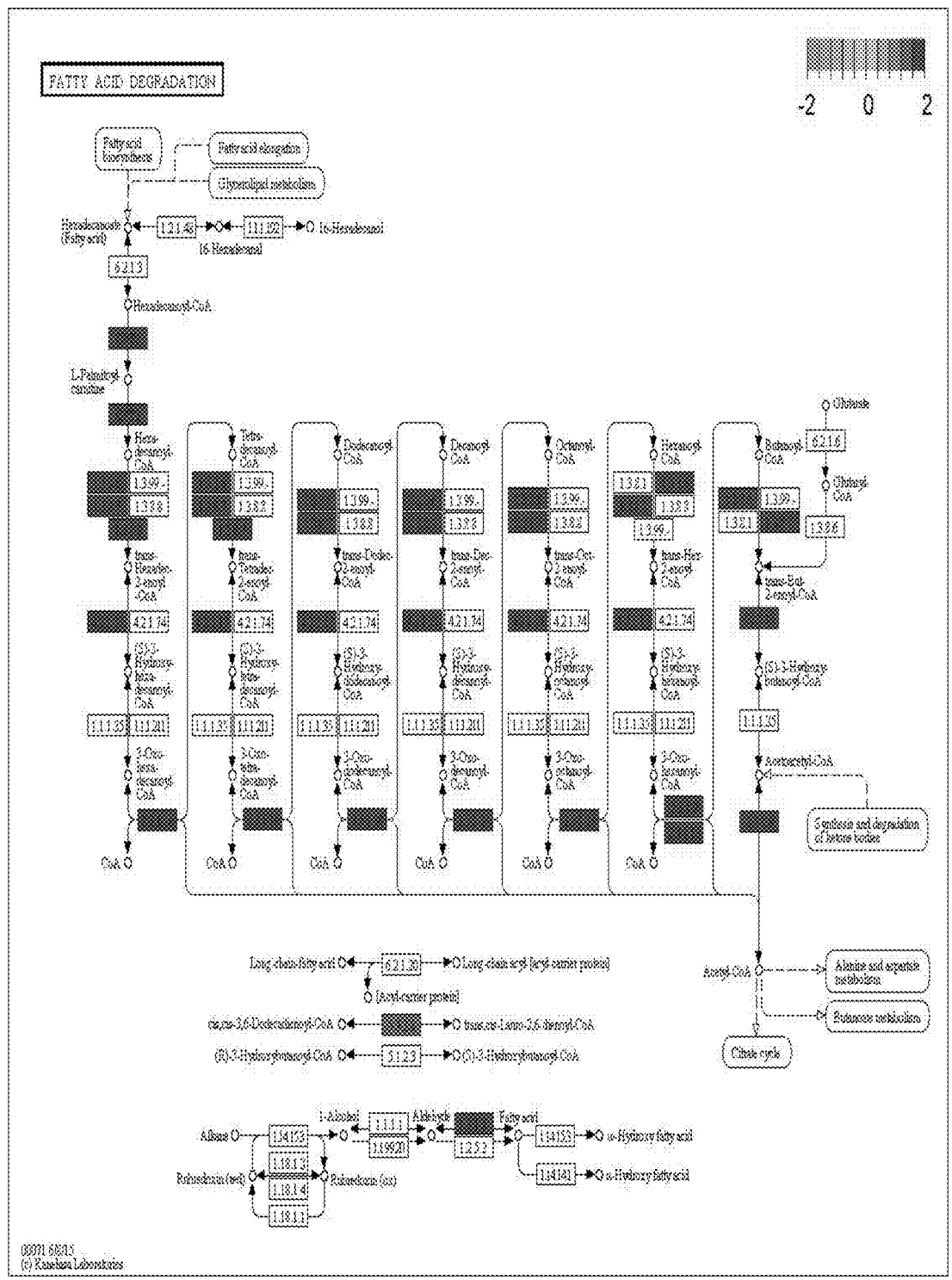
FIG. 73—MLPC derived stem-like cells ATA6, 15 genes were significantly involved fatty acid metabolism by KEGG database analysis. Red colour indicated 15 genes of up regulation.
Figure 74:
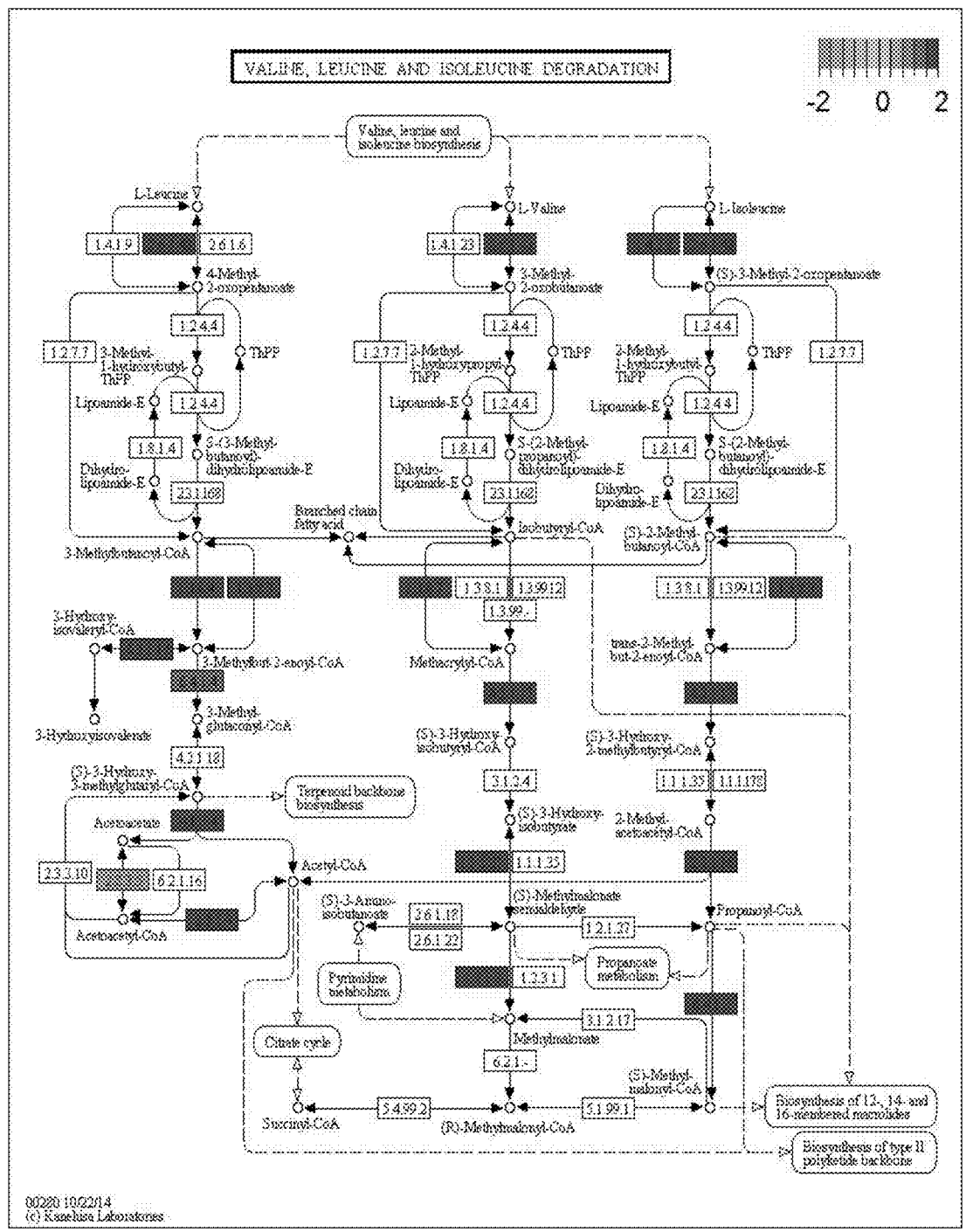
FIG. 74—MLPC derived stem-like cells ATA6, 16 genes were significantly involved valine, leucine and isoleucine degradation by KEGG database analysis. Red colour indicated 15 genes of up regulation and green colour indicated 1 genes of down-regulation.
Figure 75:
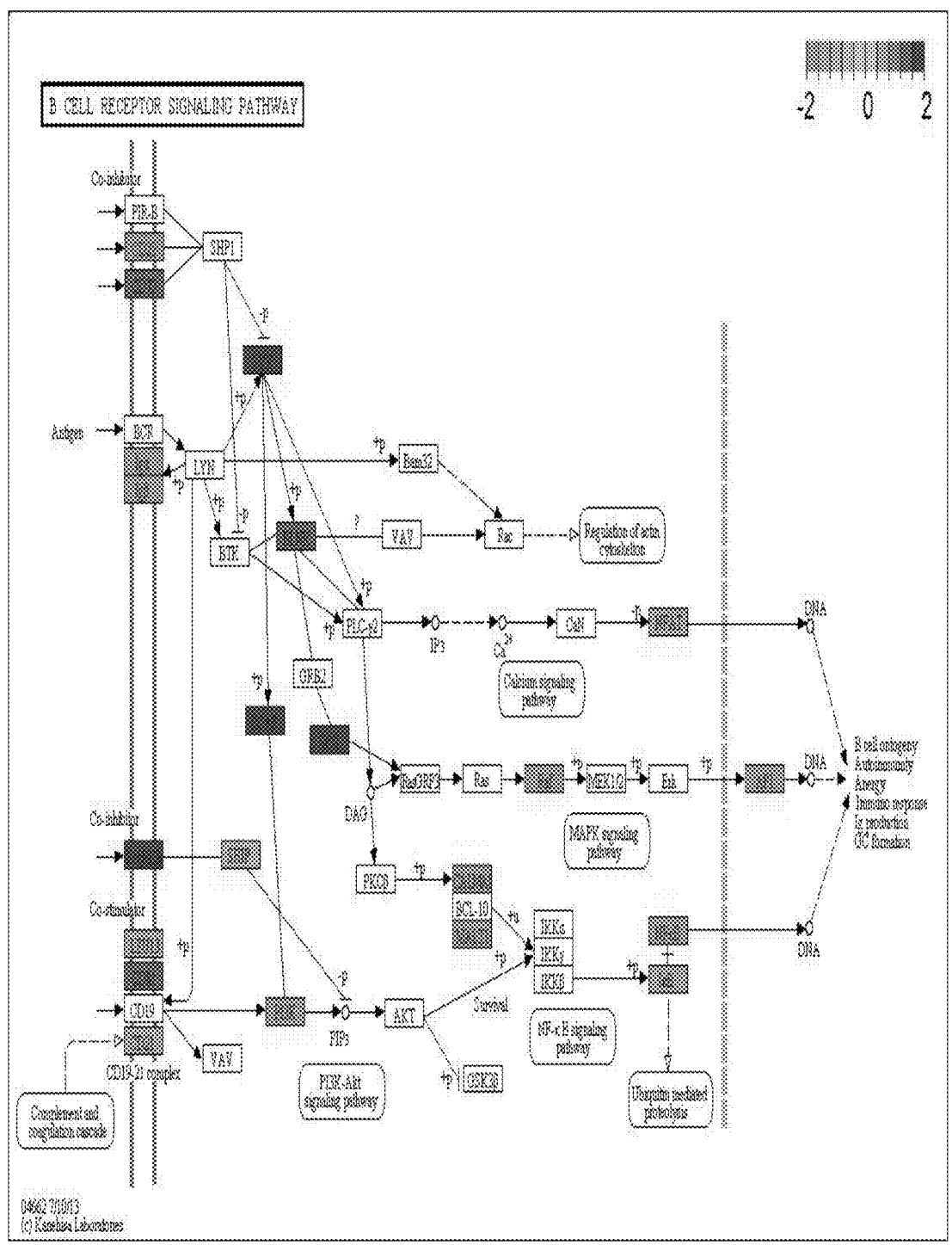
FIG. 75—MLPC derived stem-like cells ATA6, 24 genes were significantly involved B cell receptor signaling pathway by KEGG database analysis. Red colour indicated 7 genes of up regulation and green colour indicated 17 genes of down-regulation.
Figure 76:
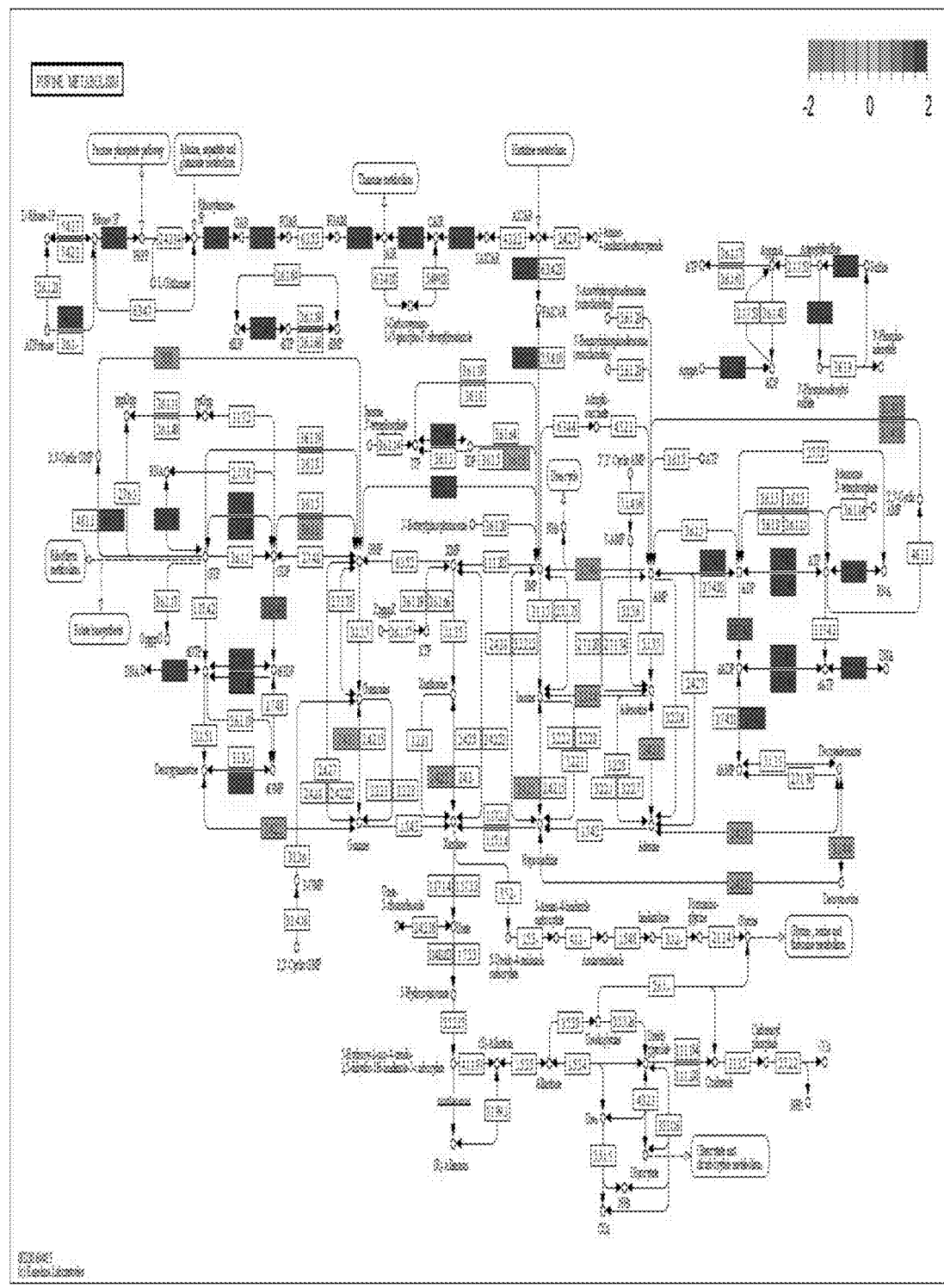
FIG. 76—MLPC derived stem-like cells ATA6, 43 genes were significantly involved purine metabolism by KEGG database analysis. Red colour indicated 30 genes of up regulation and green colour indicated 13 genes of down-regulation.
Figure 77:
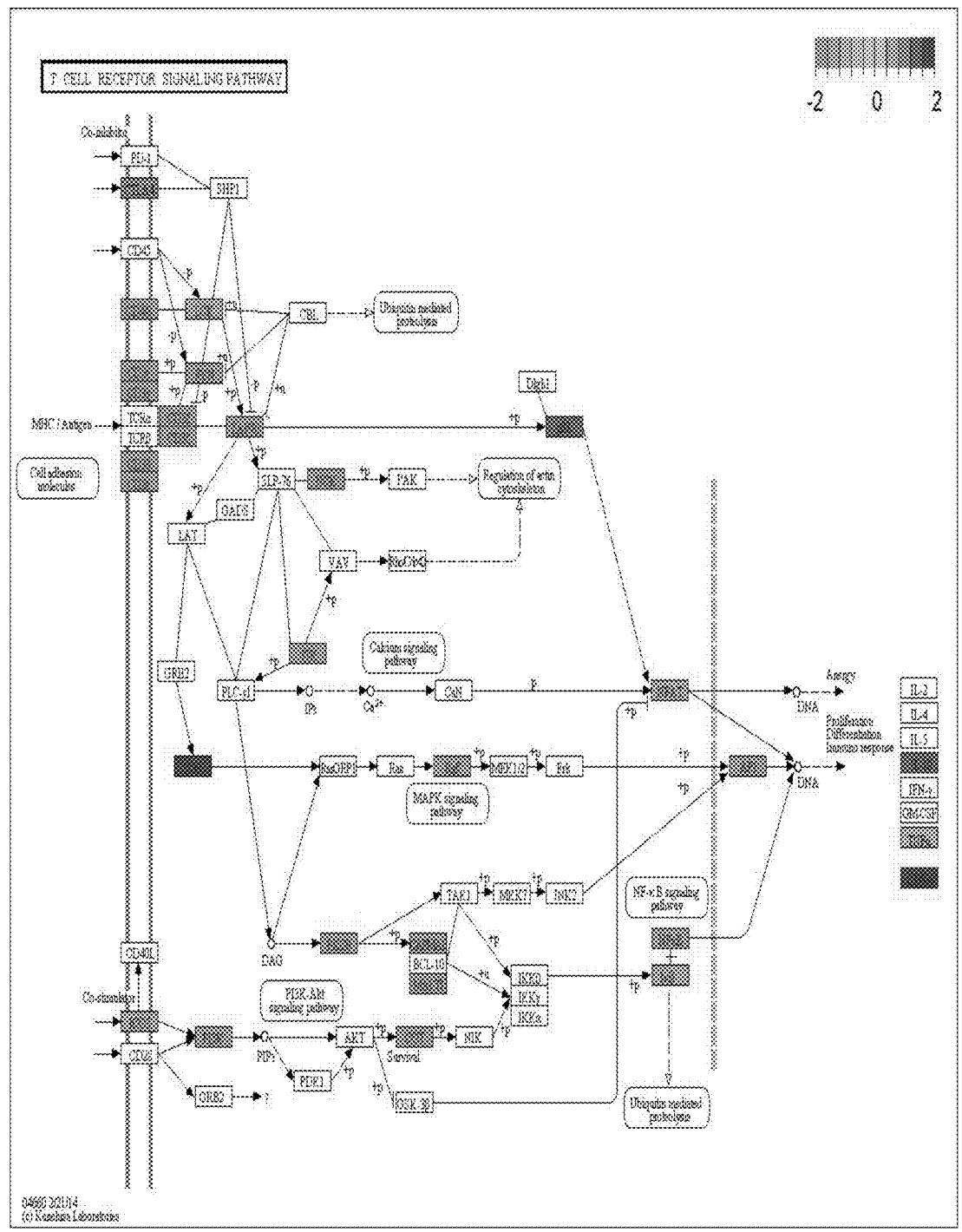
FIG. 77—MLPC derived stem-like cells ATA6, 32 genes were significantly involved T cell receptor signaling pathway by KEGG database analysis. Red colour indicated 5 genes of up regulation and green colour indicated 27 genes of down-regulation.
Figure 78:
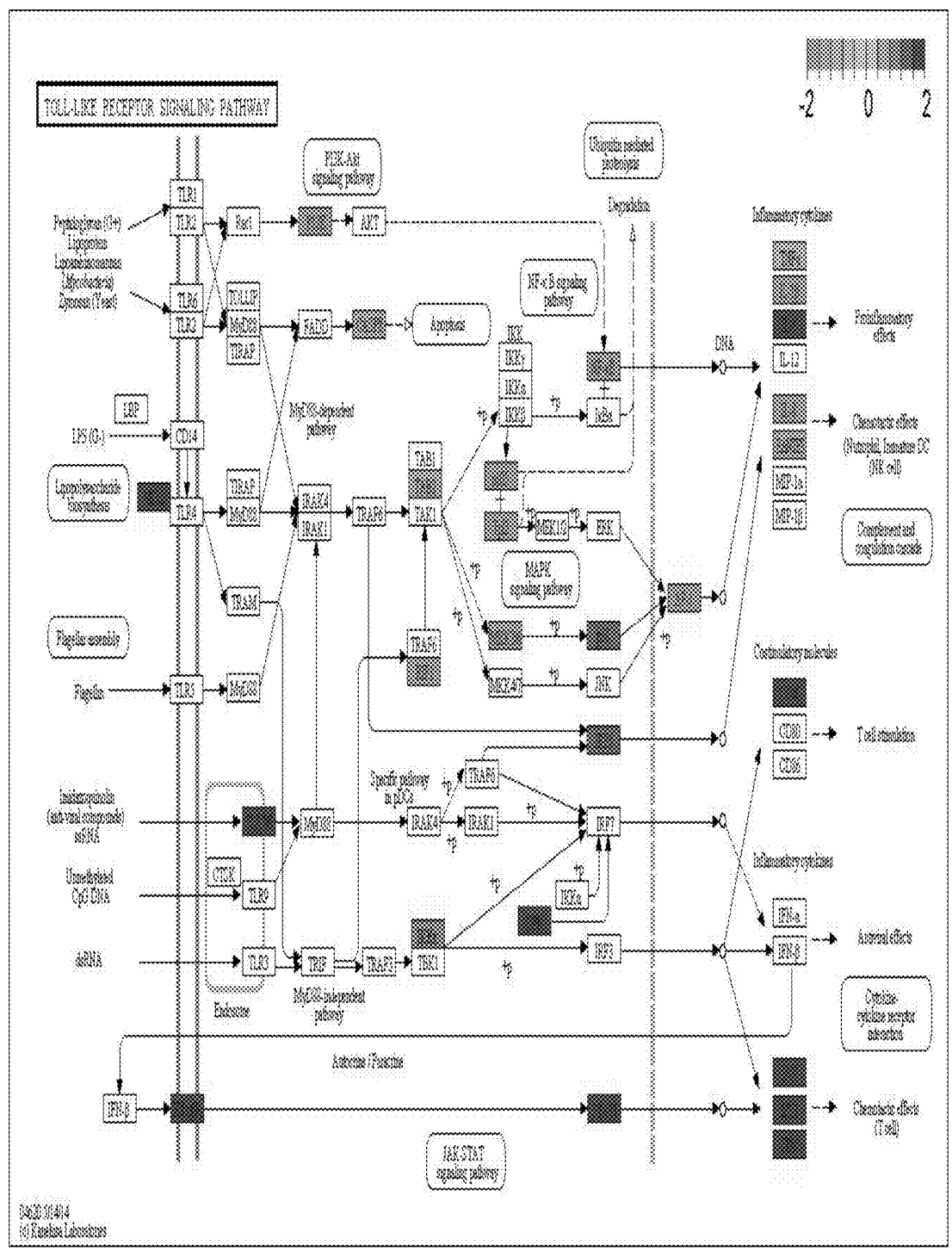
FIG. 78—MLPC derived stem-like cells ATA6, 30 genes were significantly involved Tol I -like receptor signaling pathway by KEGG database analysis. Red colour indicated 16 genes of up regulation and green colour indicated 14 genes of down-regulation.
Figure 79:
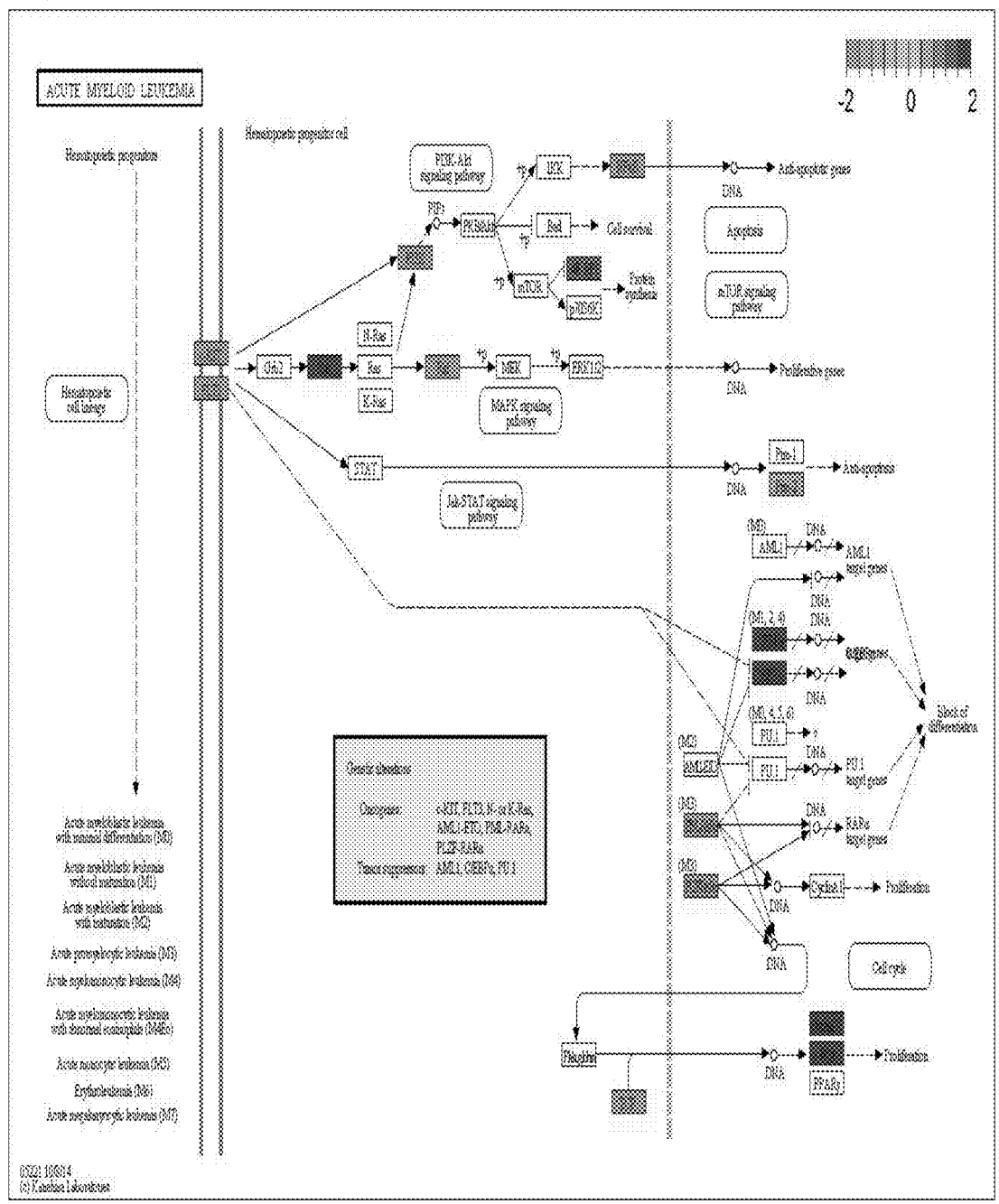
FIG. 79—MLPC derived stem-like cells ATA6, 19 genes were significantly involved acute myeloid leukemia by KEGG database analysis. Red colour indicated 6 genes of up regulation and green colour indicated 13 genes of down-regulation.
Figure 80:
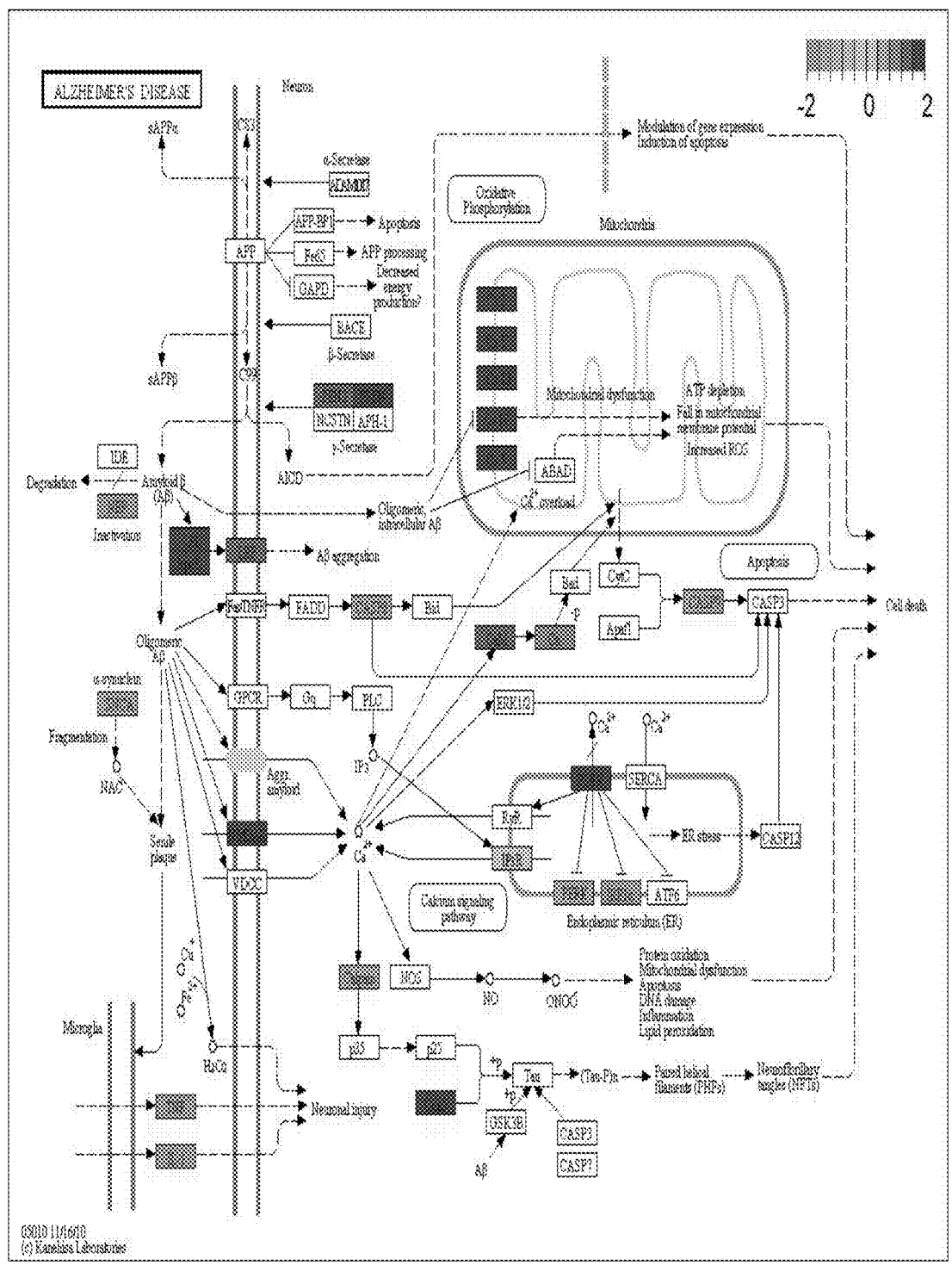
FIG. 80—MLPC derived stem-like cells UATA6, 51 genes were significantly involved Alzheimer's disease by KEGG database analysis. Red colour indicated 41 genes of up regulation and green colour indicated 10 genes of down-regulation.
Figure 81:
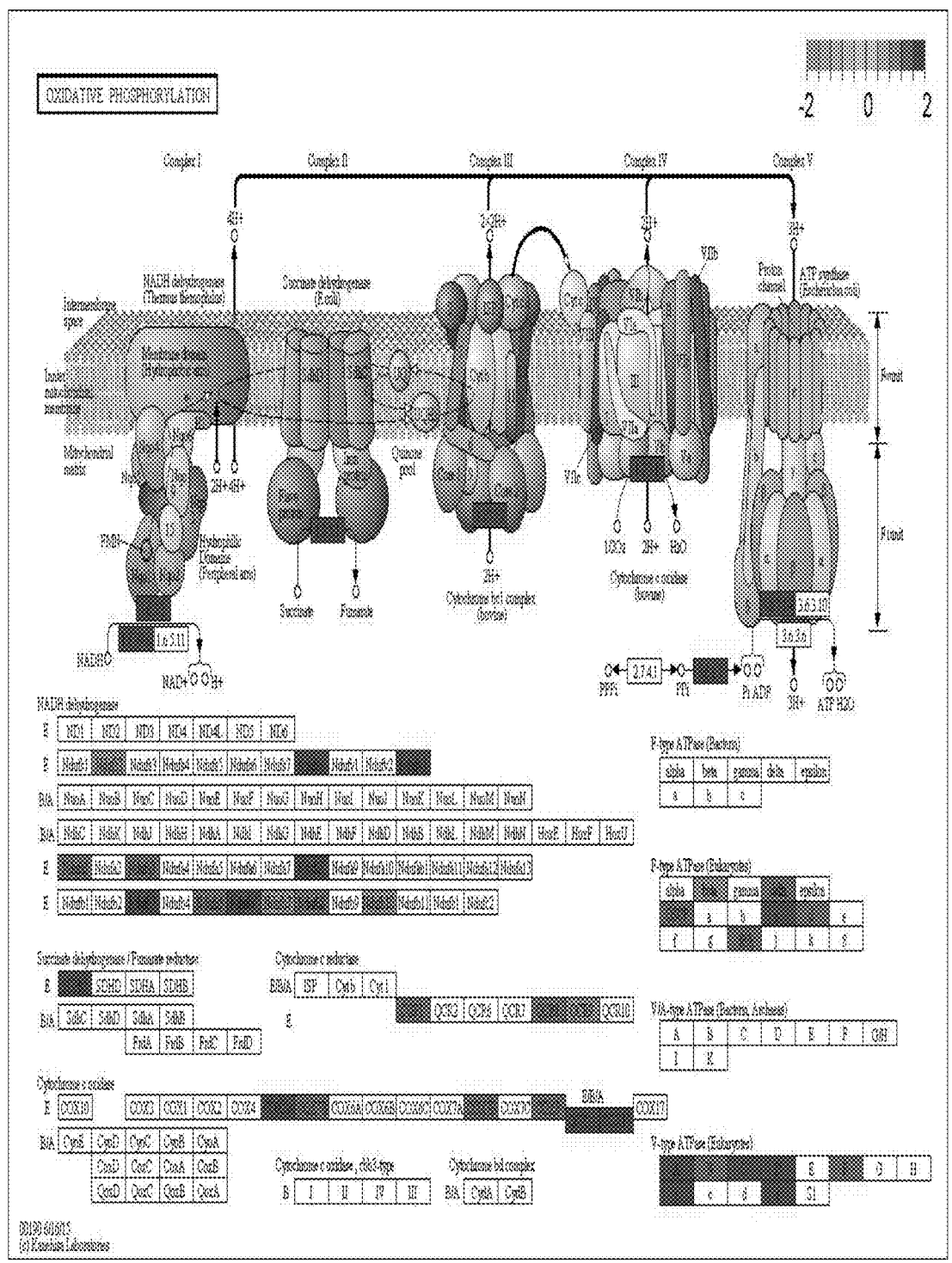
FIG. 81—MLPC derived stem-like cells UATA6, 41 genes were significantly involved oxidative phosphorylation by KEGG database analysis. Red colour indicated 41 genes of up regulation.
Figure 82:
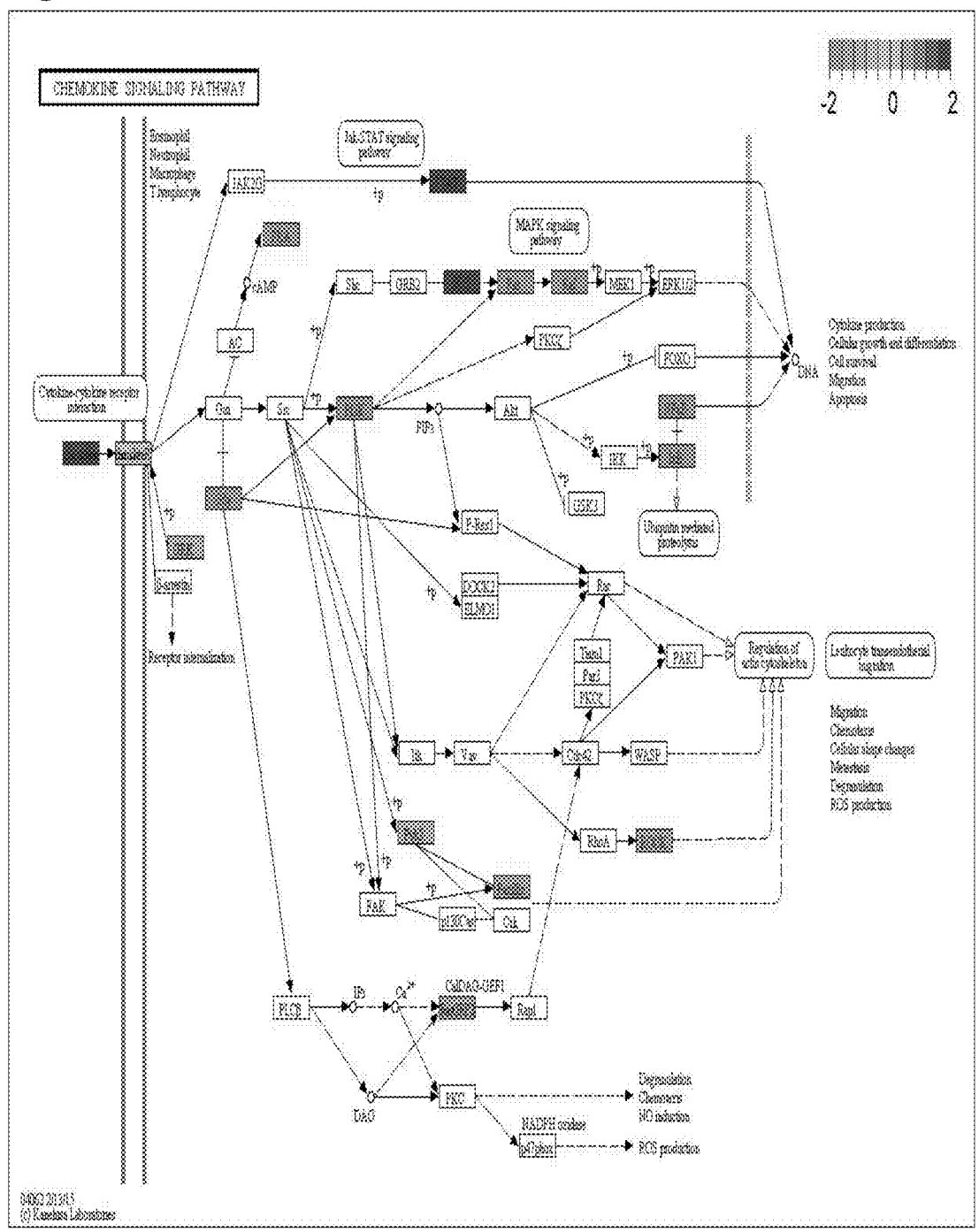
FIG. 82—MLPC derived stem-like cells UATA6, 54 genes were significantly involved chemokine signaling pathwaye by KEGG database analysis. Red colour indicated 25 genes of up regulation and green colour indicated 29 genes of down-regulation.
Figure 83:
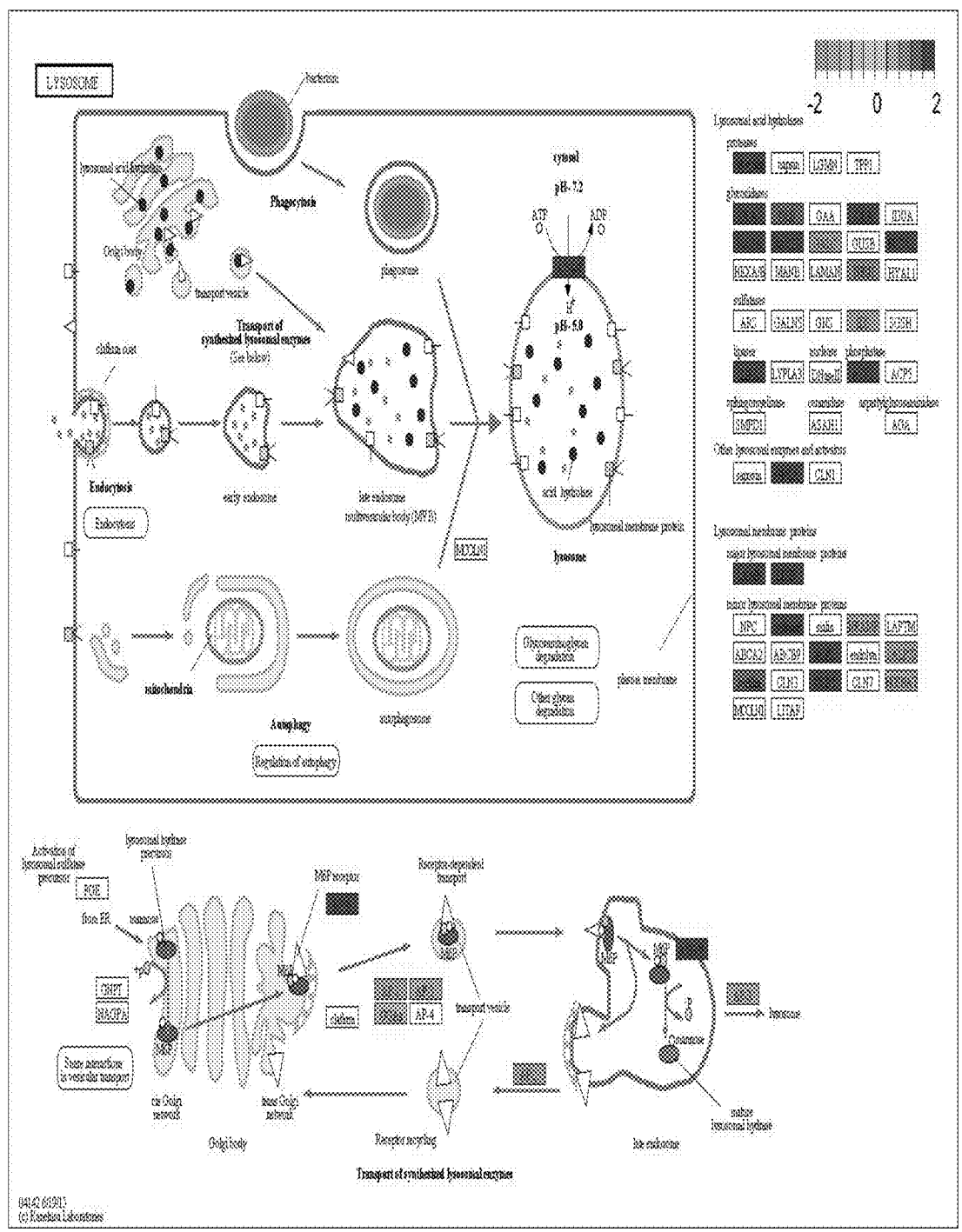
FIG. 83—MLPC derived stem-like cells UATA6, 37 genes were significantly involved lysosome by KEGG database analysis. Red colour indicated 28 genes of up regulation and green colour indicated 9 genes of down-regulation.
Figure 84:
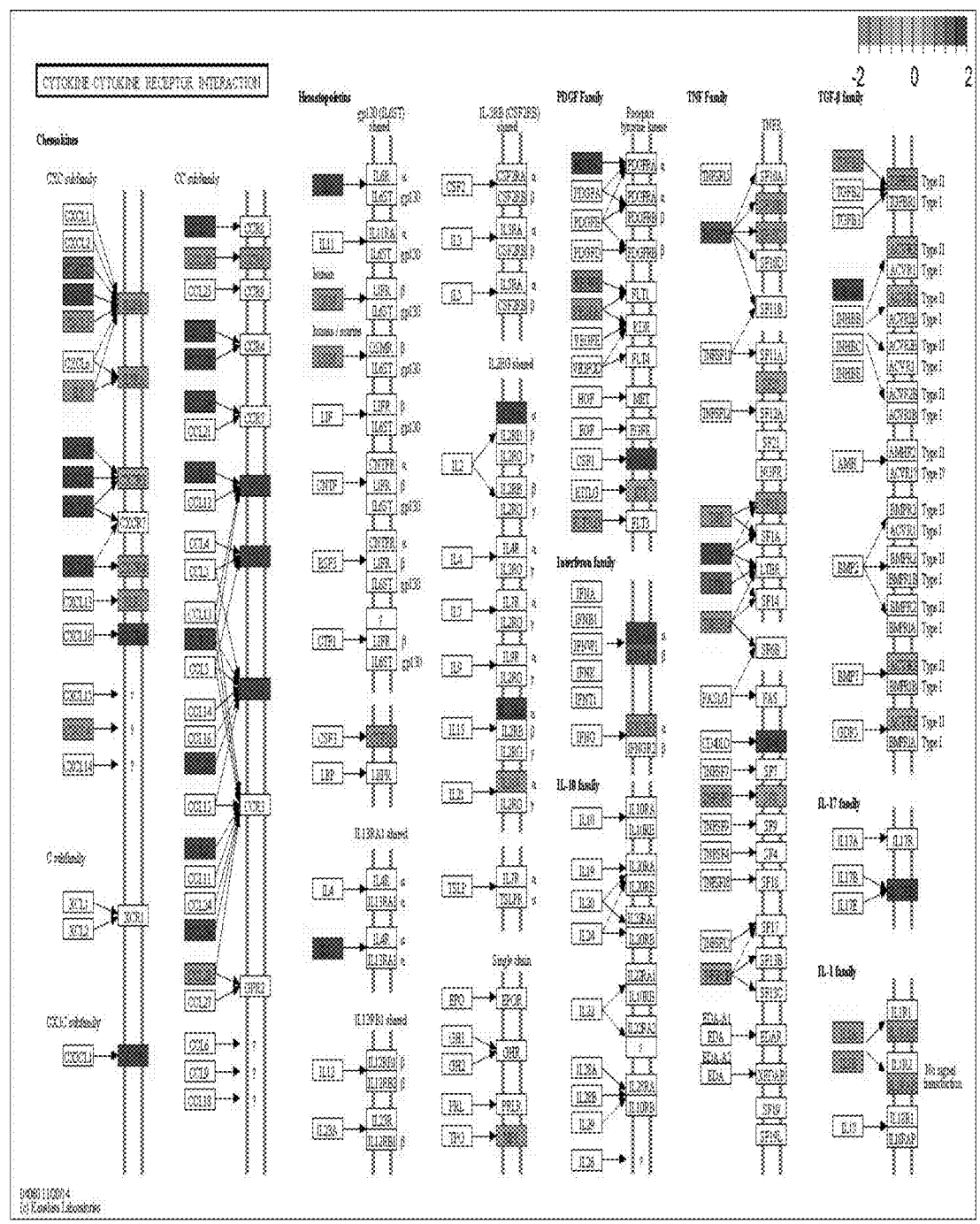
FIG. 84—MLPC derived stem-like cells UATA6, 71 genes were significantly involved cytokine-cytokine receptor interaction by KEGG database analysis. Red colour indicated 35 genes of up regulation and green colour indicated 36 genes of down-regulation.
Figure 85:
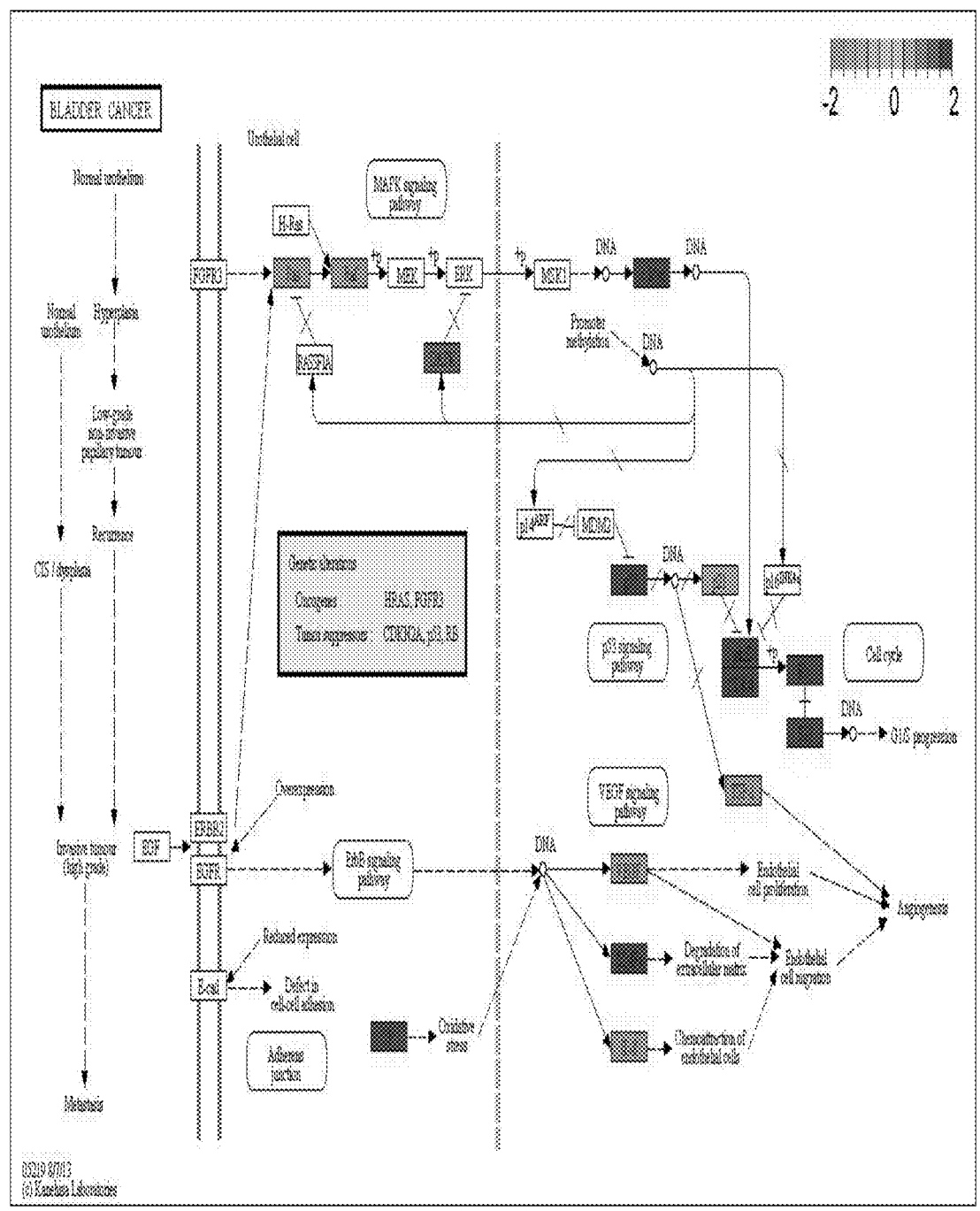
FIG. 85—MLPC derived stem-like cells UATA6, 17 genes were significantly involved bladder cancer by KEGG database analysis. Red colour indicated 10 genes of up regulation and green colour indicated 7 genes of down-regulation.
Figure 86:
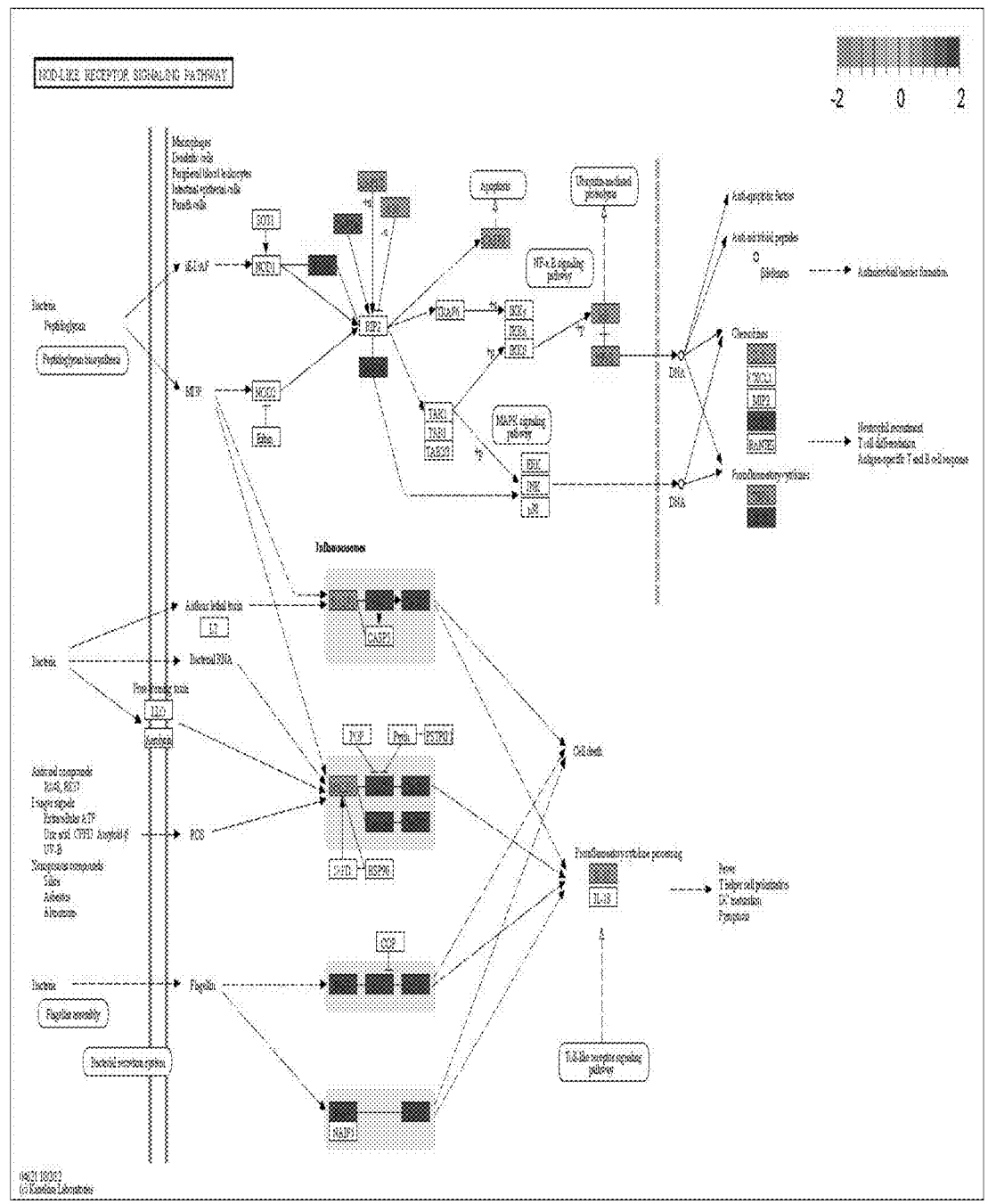
FIG. 86—MLPC derived stem-like cells UATA6, 22 genes were significantly involved NOD-like receptor signaling pathway by KEGG database analysis. Red colour indicated 11 genes of up regulation and green colour indicated 11 genes of down-regulation.
Figure 87:
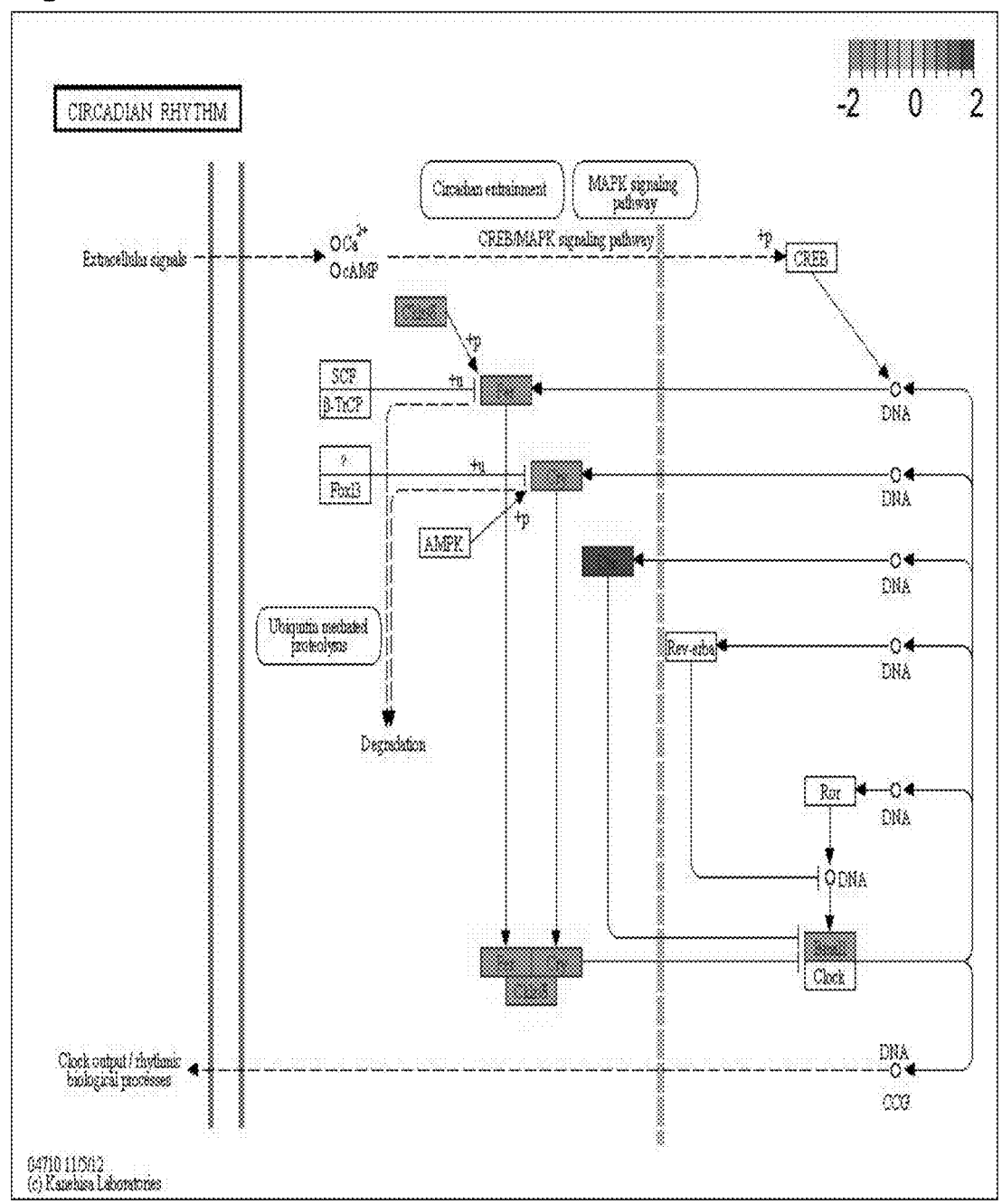
FIG. 87—MLPC derived stem-like cells UATA6, 8 genes were significantly involved Circadian rhythm by KEGG database analysis. Red colour indicated 7 genes of up regulation and green colour indicated 1 genes of down-regulation.
Figure 88:
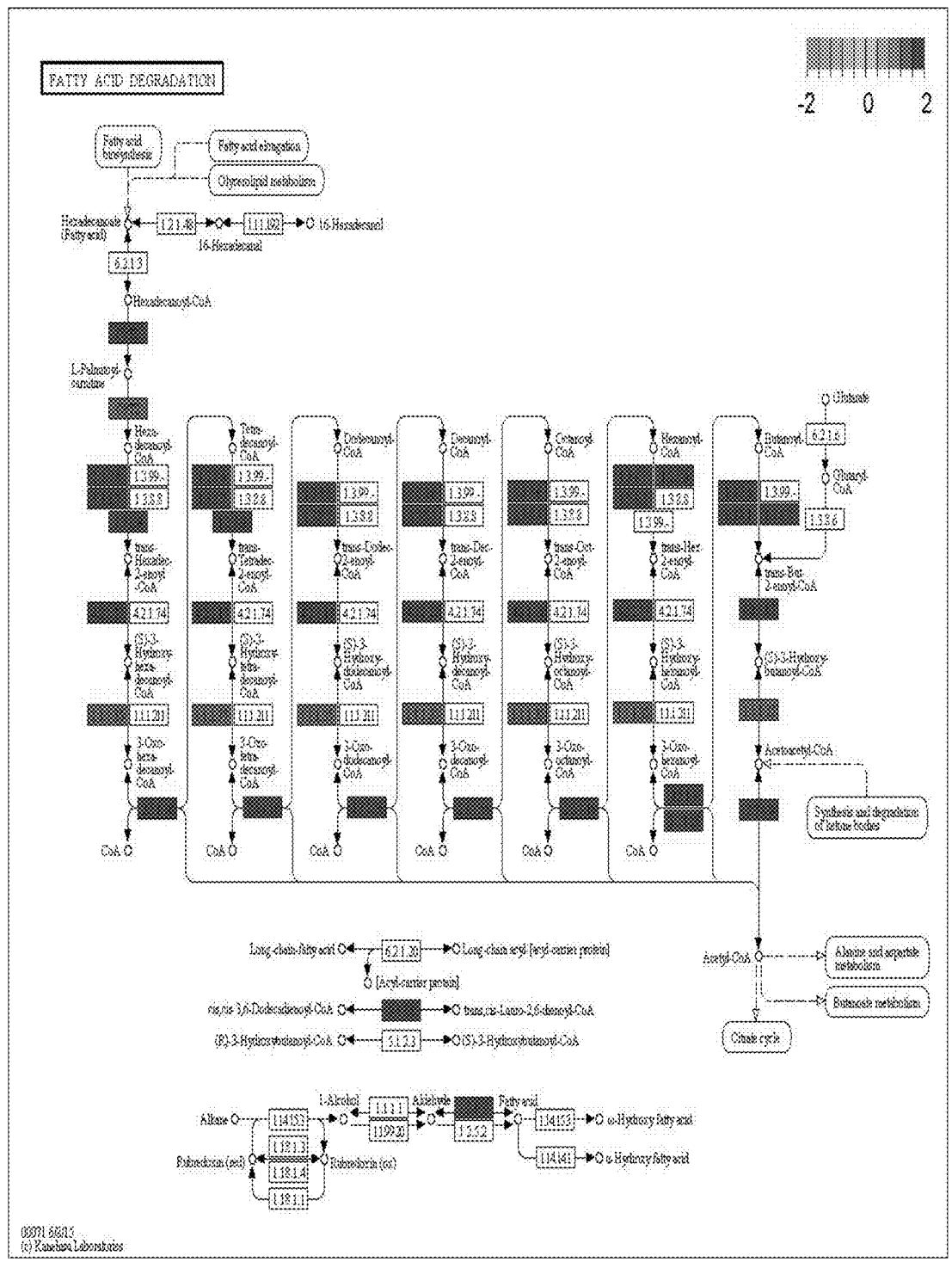
FIG. 88—MLPC derived stem-like cells UATA6, 16 genes were significantly involved Fatty acid metabolism by KEGG database analysis. Red colour indicated 16 genes of up regulation.
Figure 89:
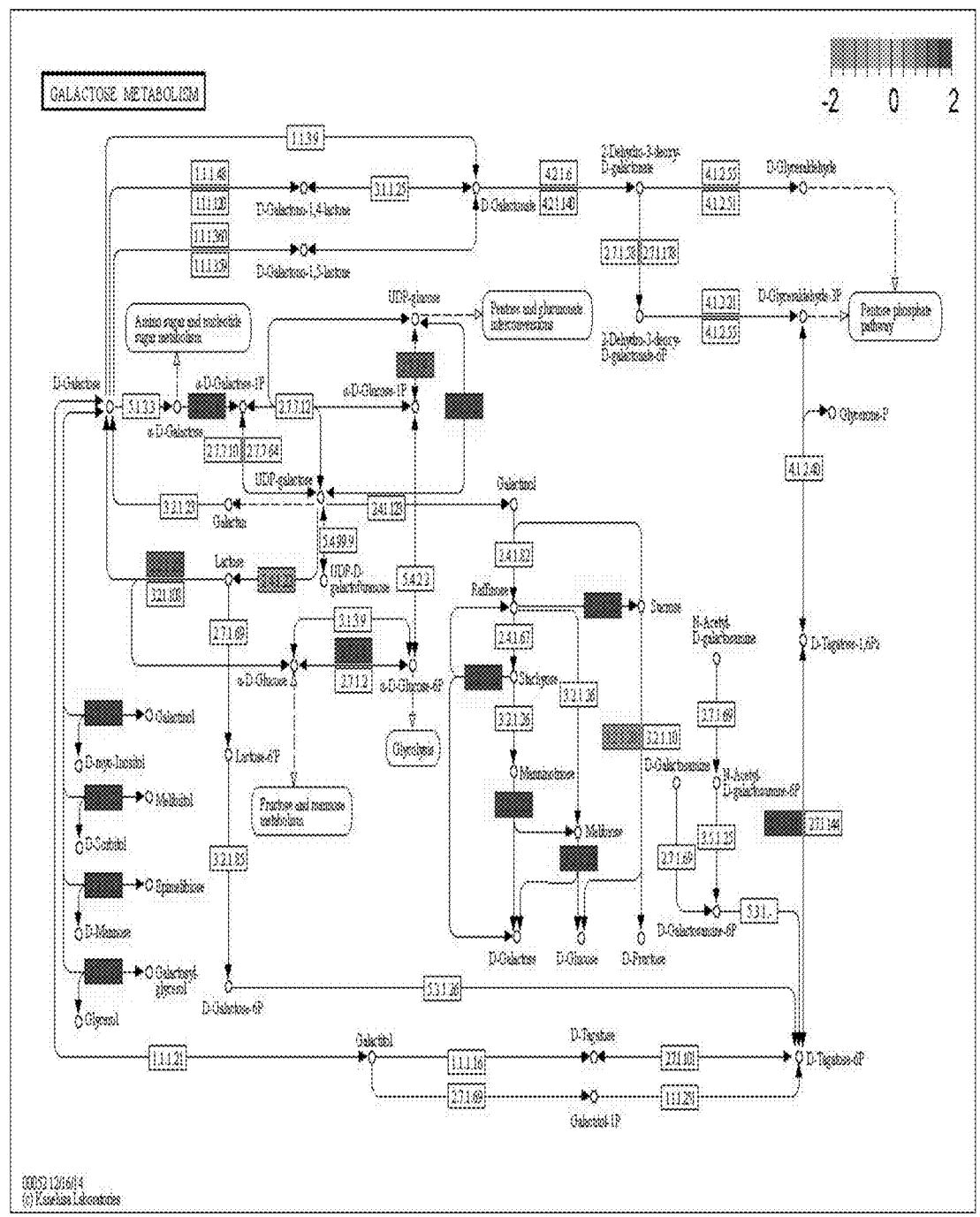
FIG. 89—MLPC derived stem-like cells UATA6, 12 genes were significantly involved galactose metabolism by KEGG database analysis. Red colour indicated 10 genes of up regulation and green colour indicated 2 genes of down-regulation.
Figure 90:
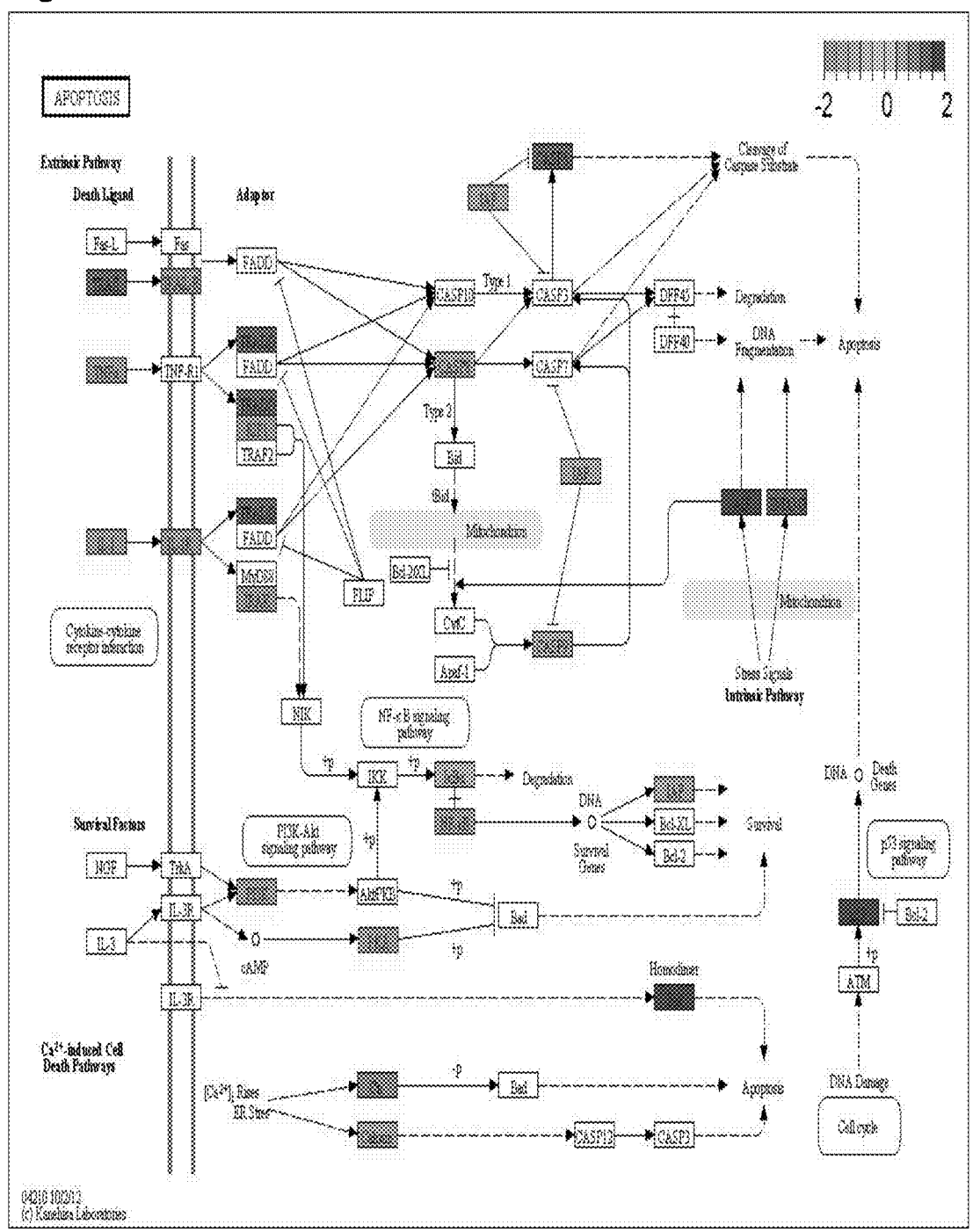
FIG. 90—MLPC derived stem-like cells UATA6, 28 genes were significantly involved apoptosis by KEGG database analysis. Red colour indicated 8 genes of up regulation and green colour indicated 20 genes of down-regulation.
Figure 91:
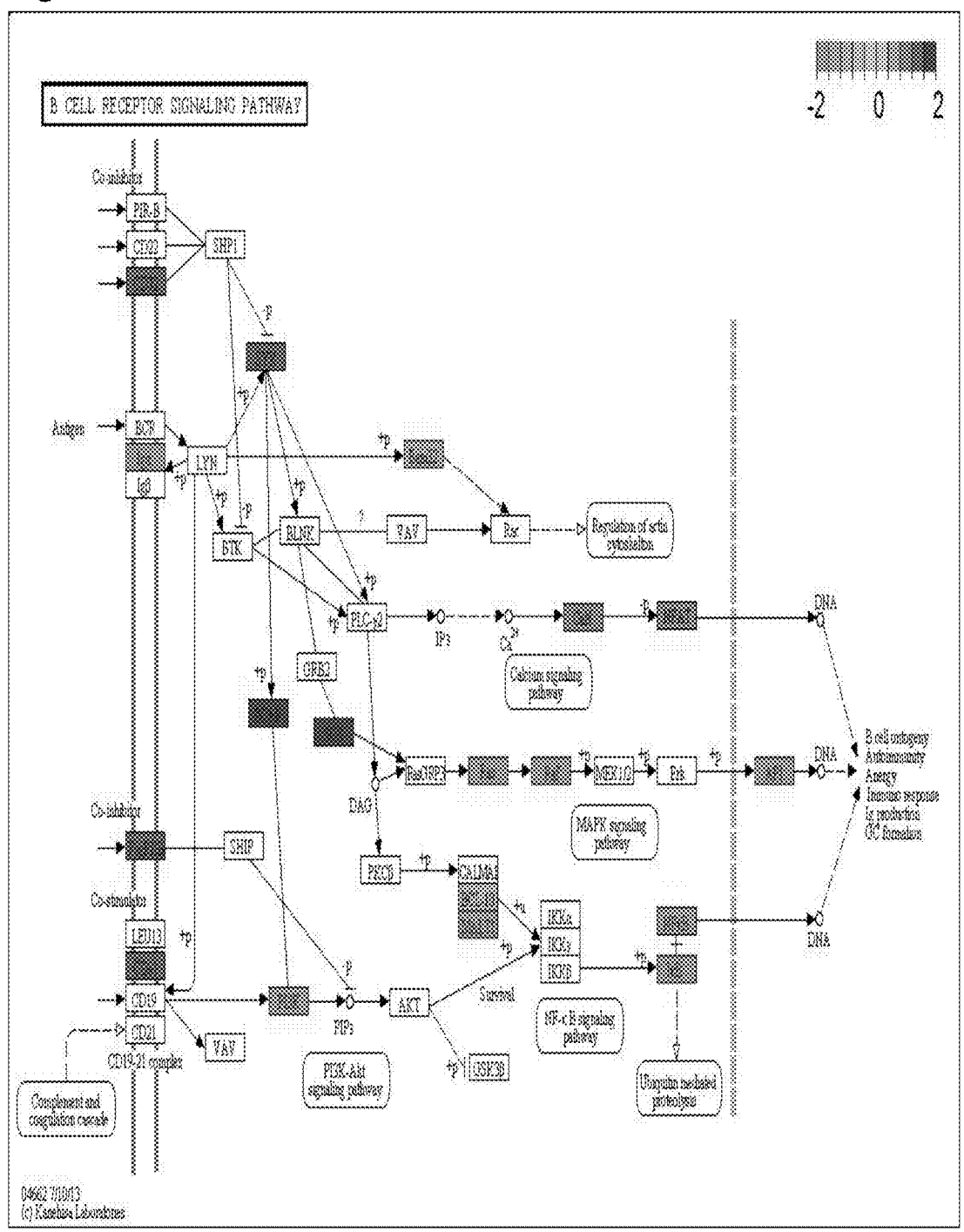
FIG. 91—MLPC derived stem-like cells UATA6, 25 genes were significantly involved B cell receptor signaling pathway by KEGG database analysis. Red colour indicated 9 genes of up regulation and green colour indicated 16 genes of down-regulation.
Figure 92:
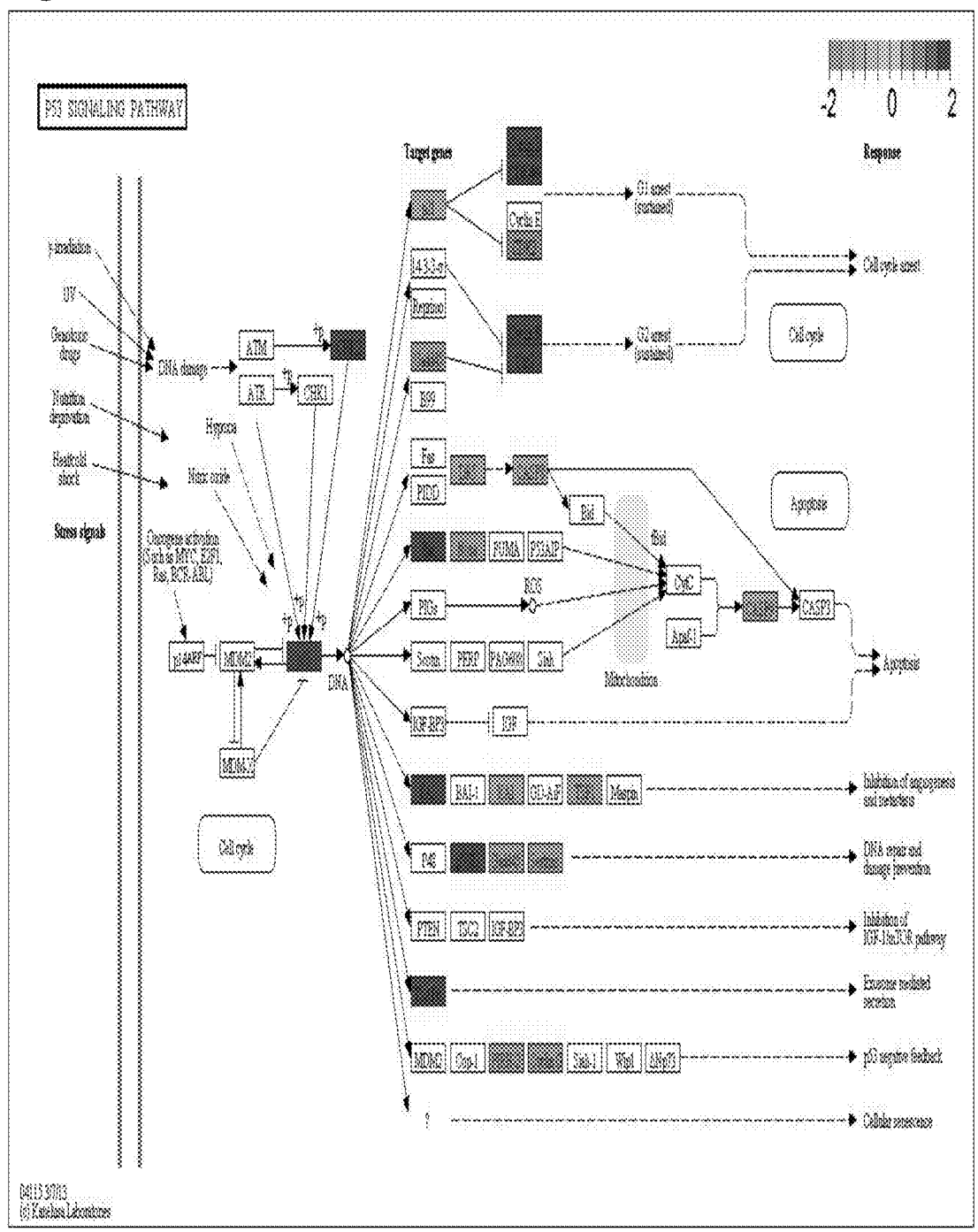
FIG. 92—MLPC derived stem-like cells UATA6, 23 genes were significantly involved p53 signaling pathway by KEGG database analysis. Red colour indicated 11 genes of up regulation and green colour indicated 12 genes of down-regulation.
Figure 93:
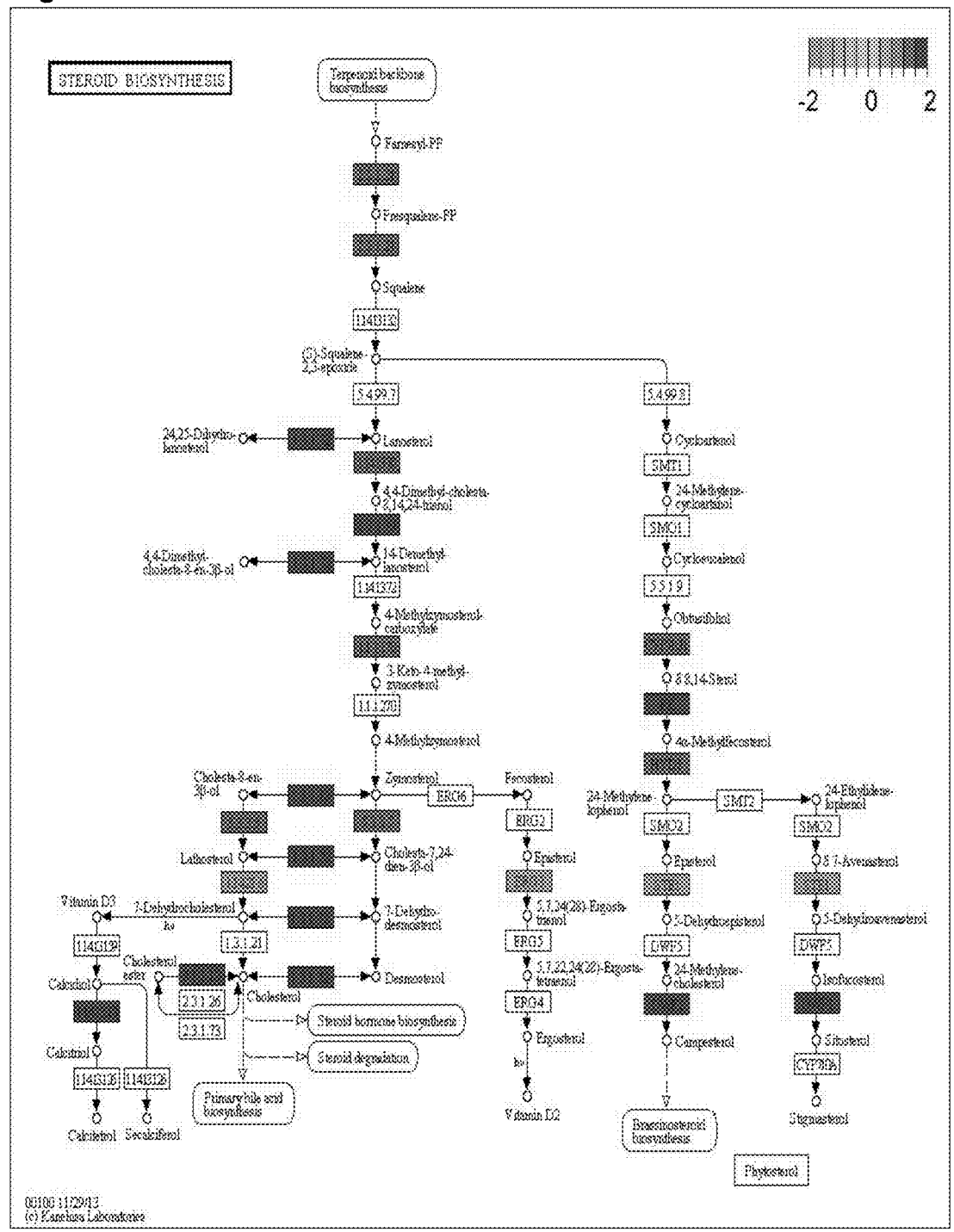
FIG. 93—MLPC derived stem-like cells UATA6, 9 genes were significantly involved steroid biosynthesis by KEGG database analysis. Red colour indicated 8 genes of up regulation and green colour indicated 1 genes of down-regulation.
Figure 94:
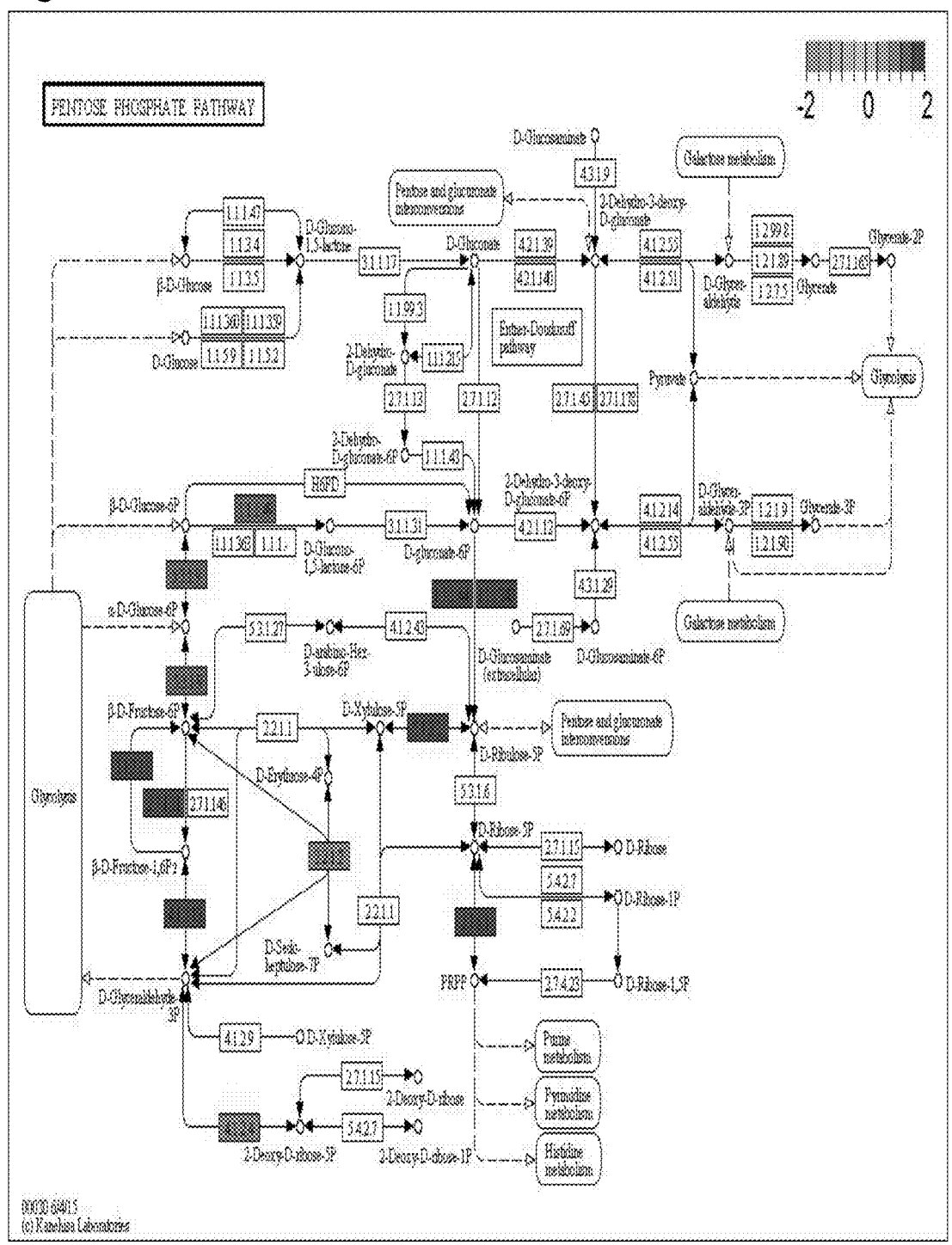
FIG. 94—MLPC derived stem-like cells UATA6, 11 genes were significantly involved pentose phosphate pathway by KEGG database analysis. Red colour indicated 11 genes of up regulation.
Figure 95:
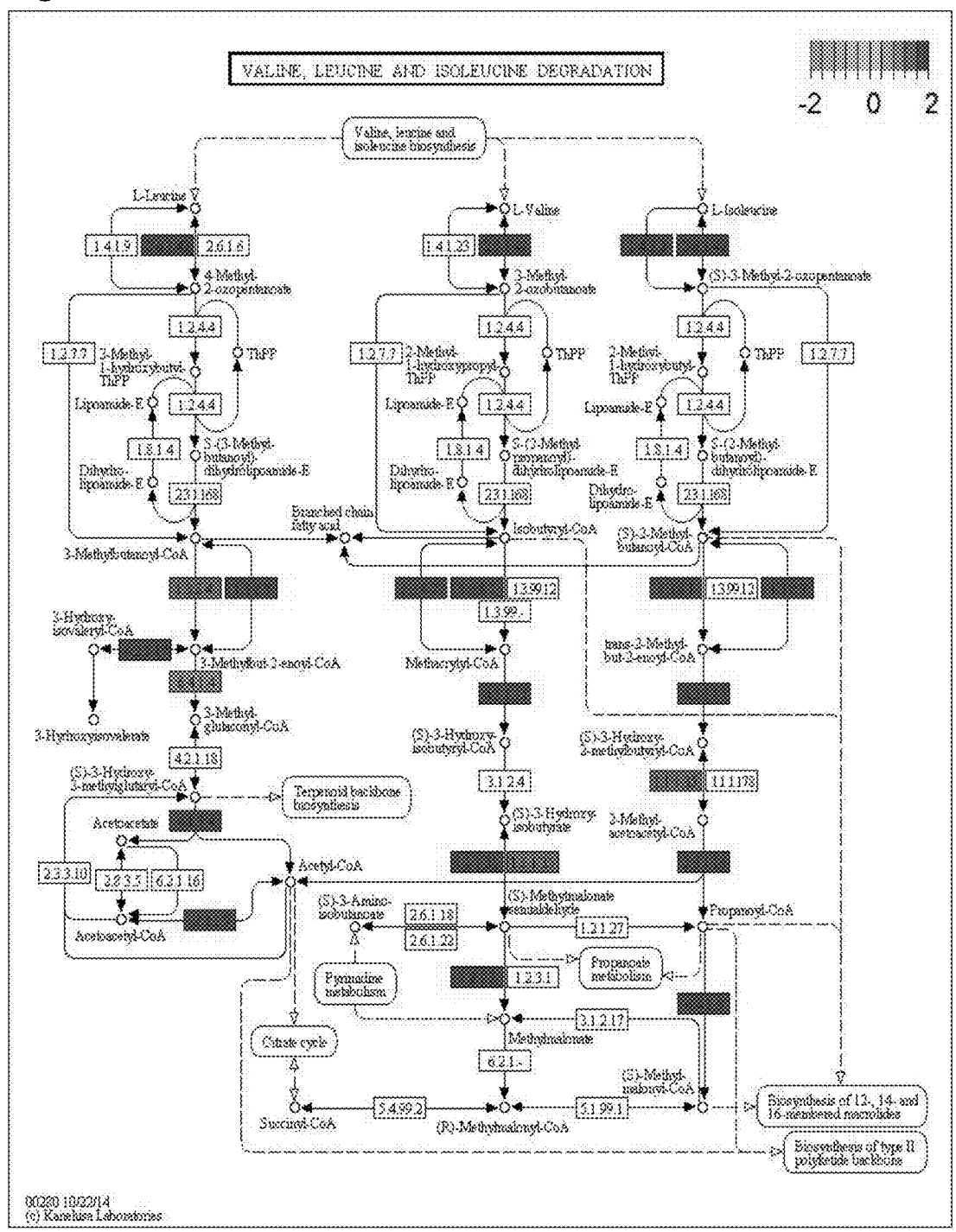
FIG. 95—MLPC derived stem-like cells UATA6, 16 genes were significantly involved valine, leucine and isoleucine degradation by KEGG database analysis. Red colour indicated 16 genes of up regulation.
Figure 96:
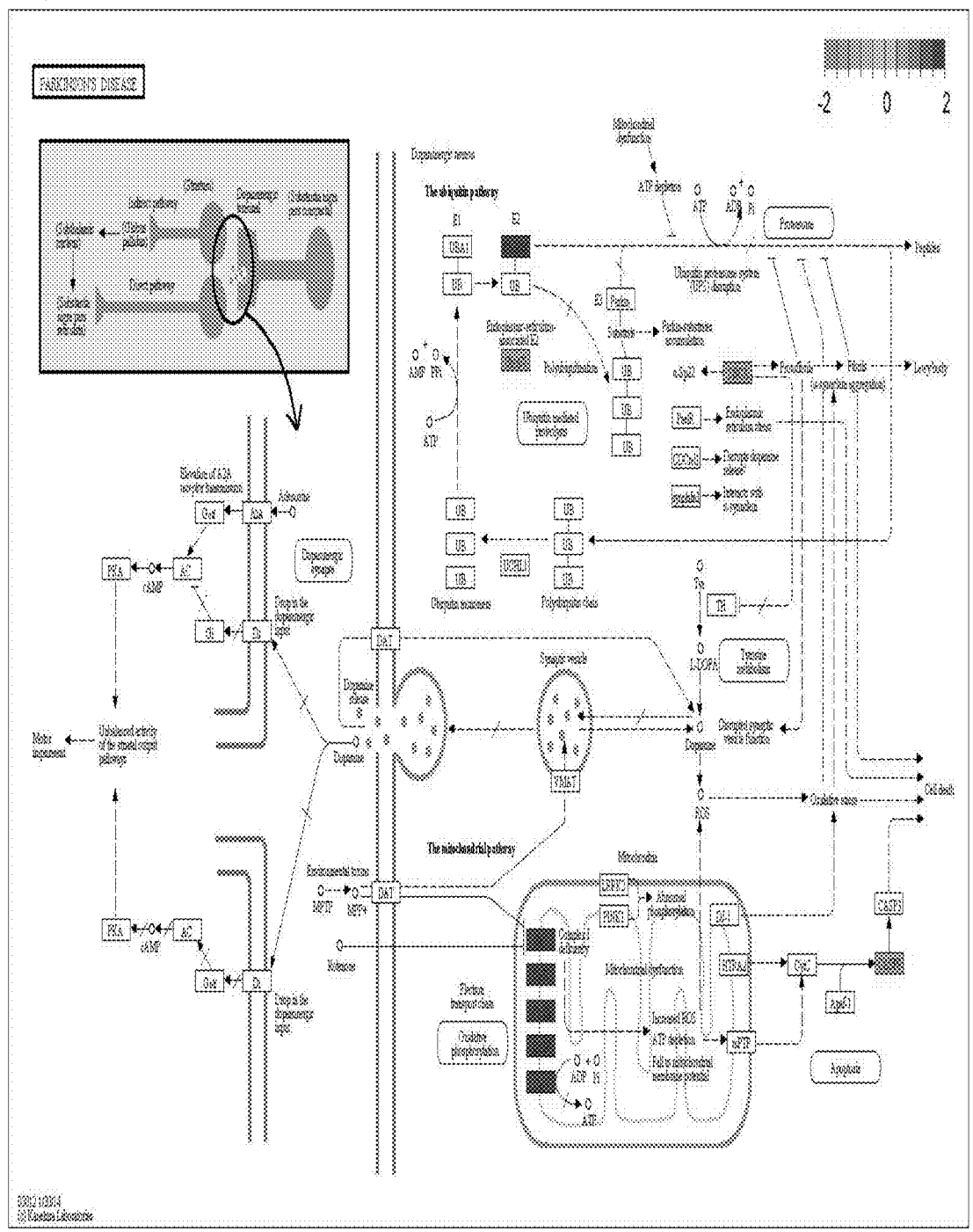
FIG. 96—MLPC derived stem-like cells UATA6, 36 genes were significantly involved Parkinson's disease by KEGG database analysis. Red colour indicated 33 genes of up regulation and green colour indicated 3 genes of down-regulation.
Figure 97:
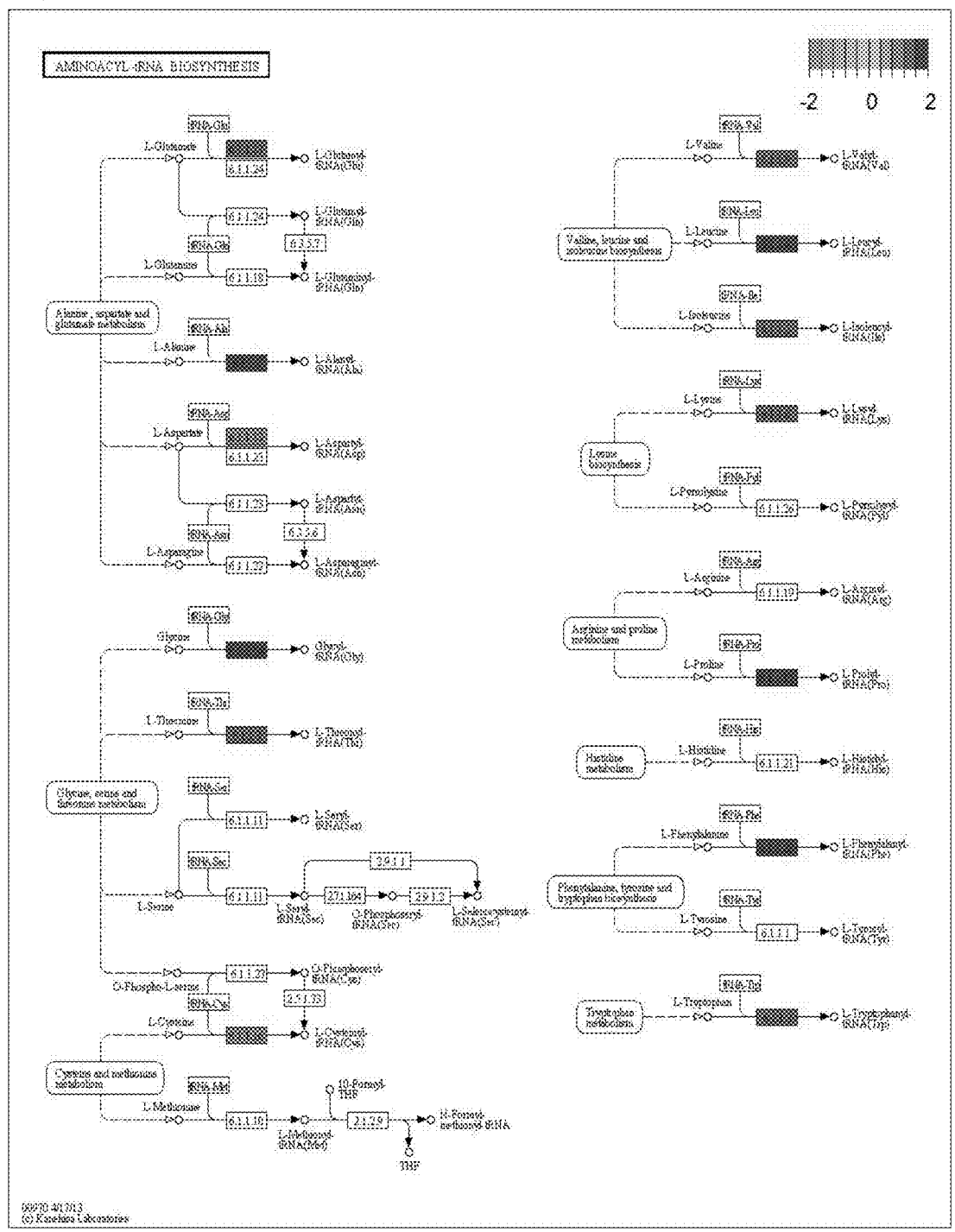
FIG. 97—MLPC derived stem-like cells UATA6, 15 genes were significantly involved aminoacyl-tRNA biosynthesis by KEGG database analysis. Red colour indicated 14 genes of up regulation and green colour indicated 1 genes of down-regulation.
Figure 98:
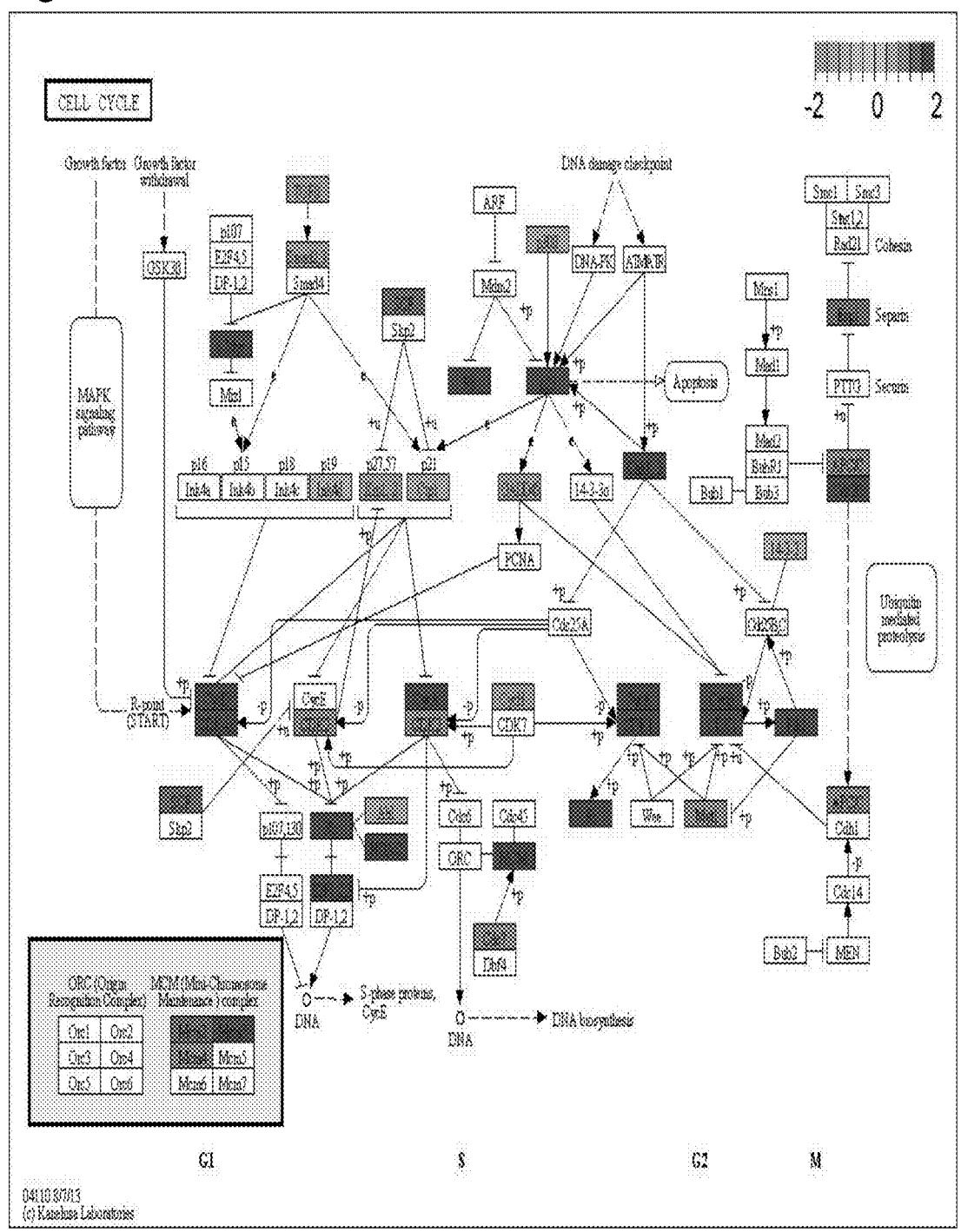
FIG. 98—MLPC derived stem-like cells UATA6, 35 genes were significantly involved cell cycle by KEGG database analysis. Red colour indicated 23 genes of up regulation and green colour indicated 12 genes of down-regulation.
Figure 99:
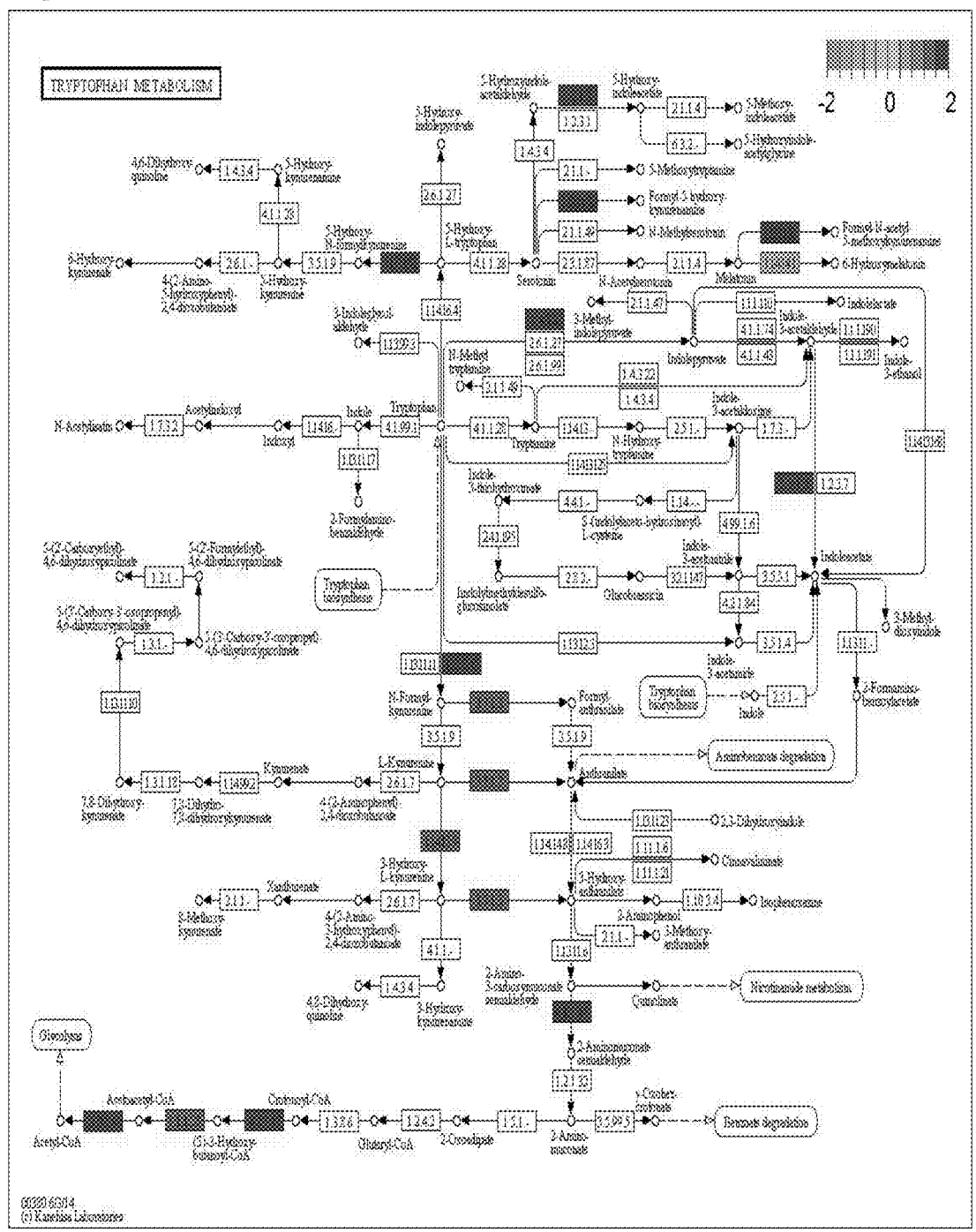
FIG. 99—MLPC derived stem-like cells UATA6, 14 genes were significantly involved tryptophan metabolism by KEGG database analysis. Red colour indicated 12 genes of up regulation and green colour indicated 2 genes of down-regulation.
Figure 100:
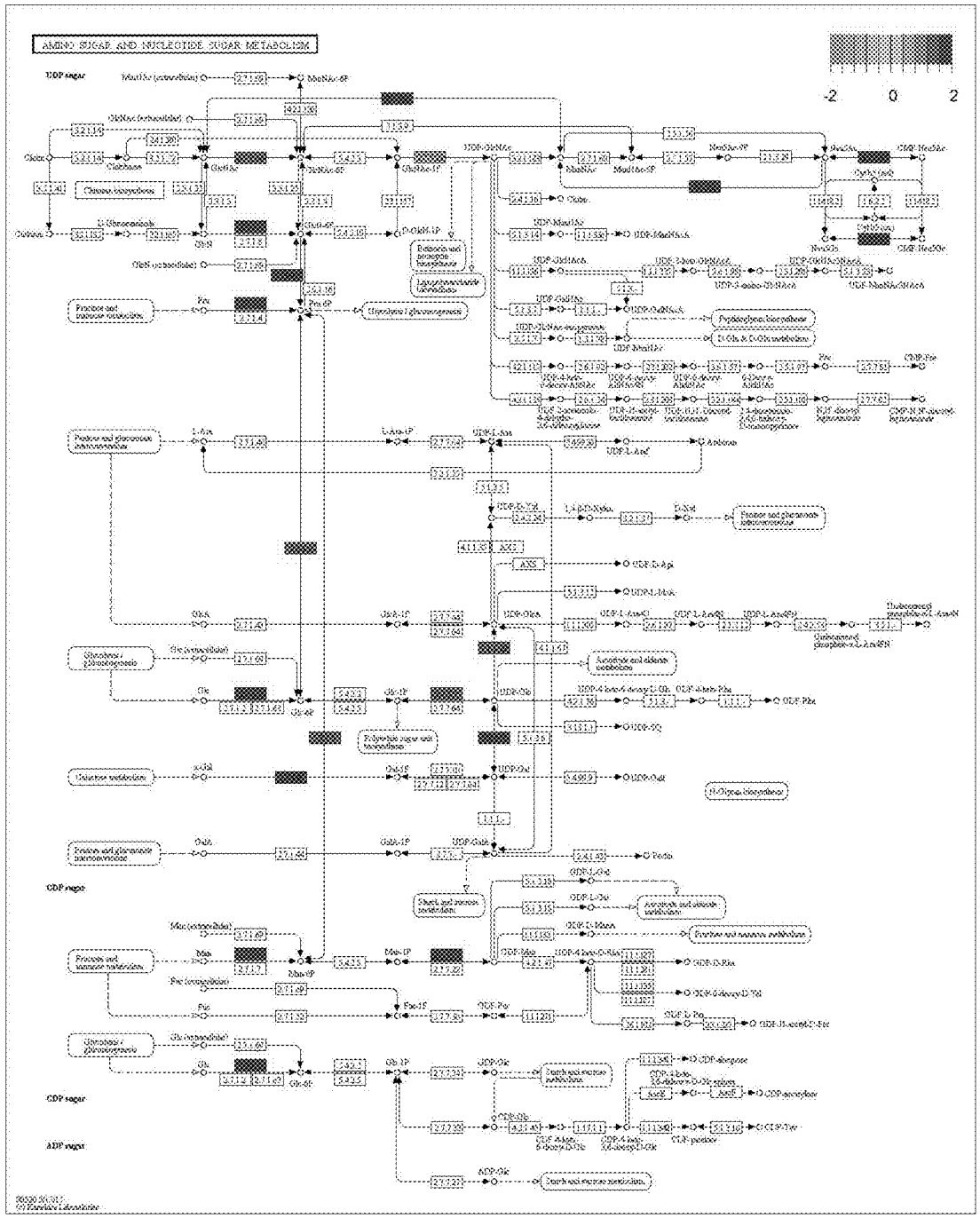
FIG. 100—MLPC derived stem-like cells UATA6, 15 genes were significantly involved amino sugar and nucleotide sugar metabolism by KEGG database analysis. Red colour indicated 14 genes of up regulation and green colour indicated 1 genes of down-regulation.
Figure 101:
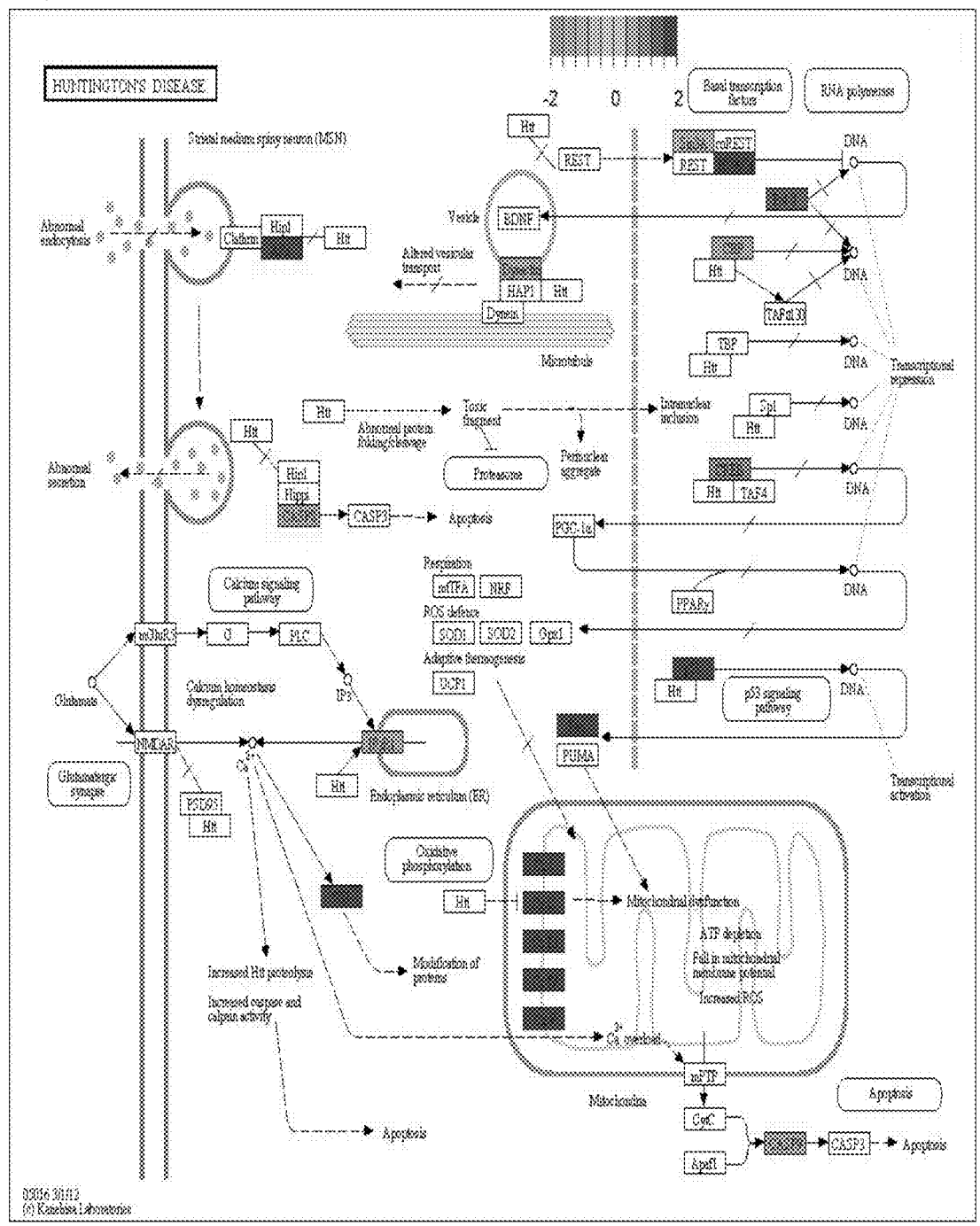
FIG. 101—MLPC derived stem-like cells UATA6, 46 genes were significantly involved Huntington's disease by KEGG database analysis. Red colour indicated 39 genes of up regulation and green colour indicated 7 genes of down-regulation.
Figure 102:
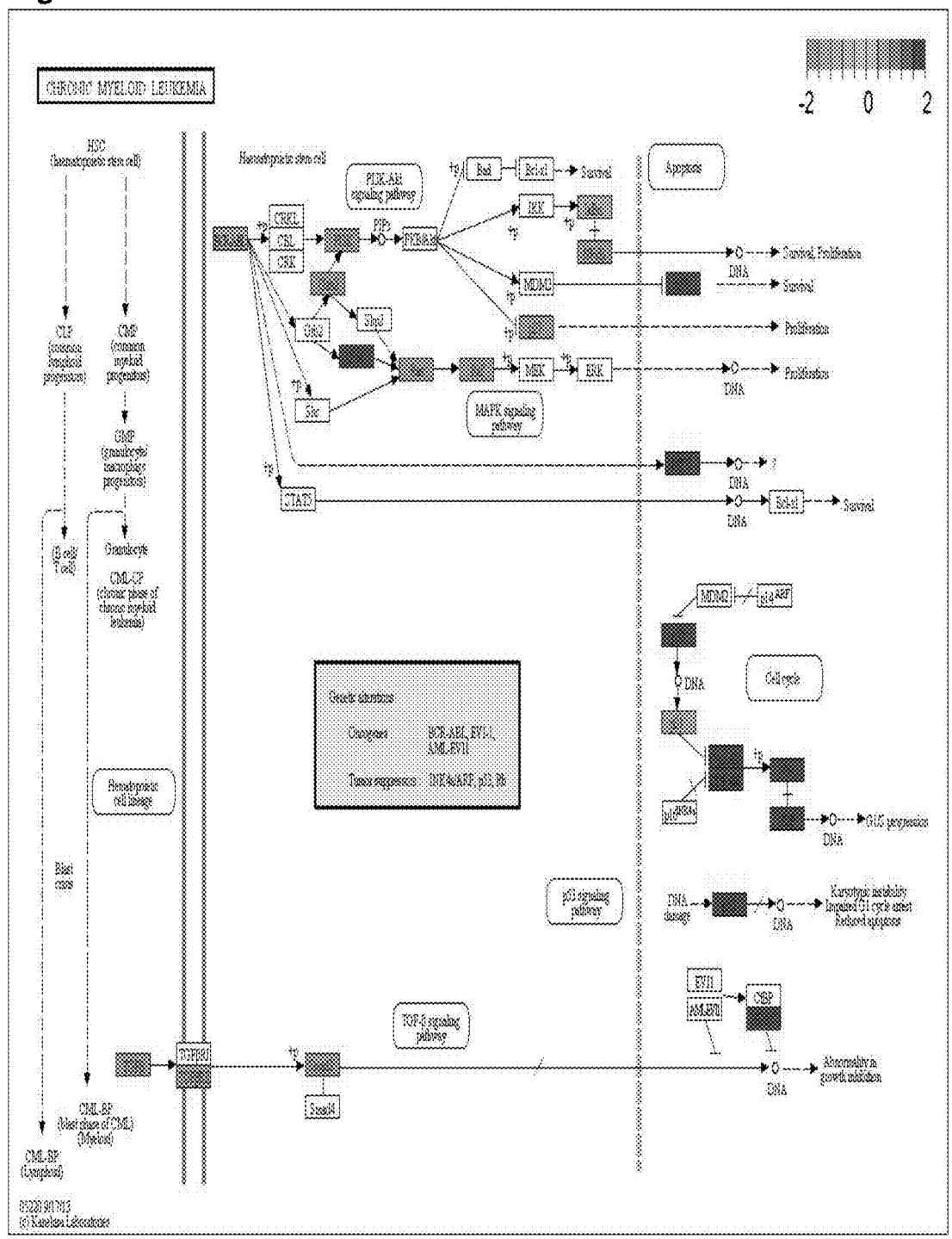
FIG. 102—MLPC derived stem-like cells UATA6, 22 genes were significantly involved chronic myeloid leukemia by KEGG database analysis. Red colour indicated 8 genes of up regulation and green colour indicated 14 genes of down-regulation.
Figure 106:
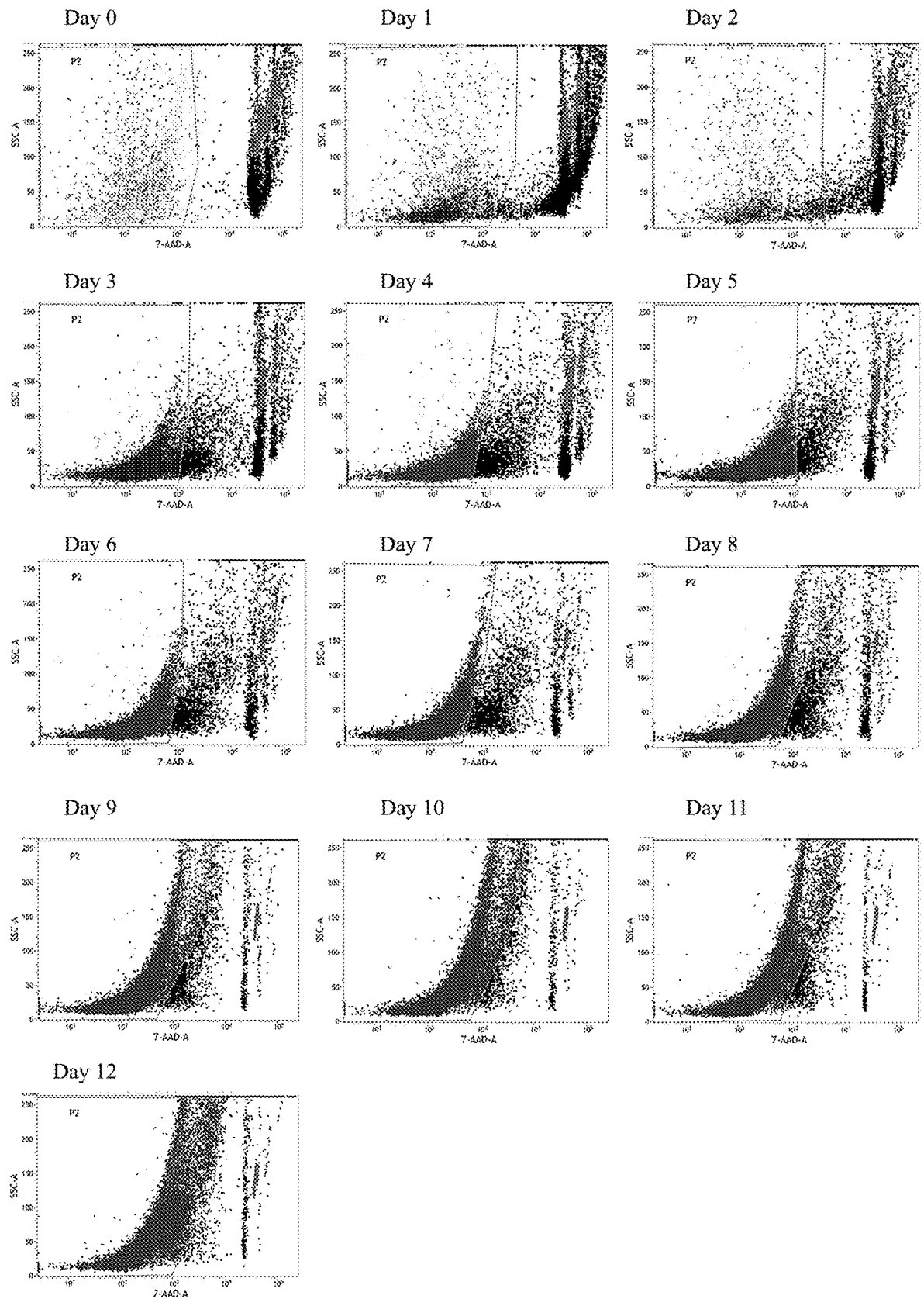
FIG. 106—CD45-FITC/7-AAD− of P population from day 0 to day 12.
Figure 107:
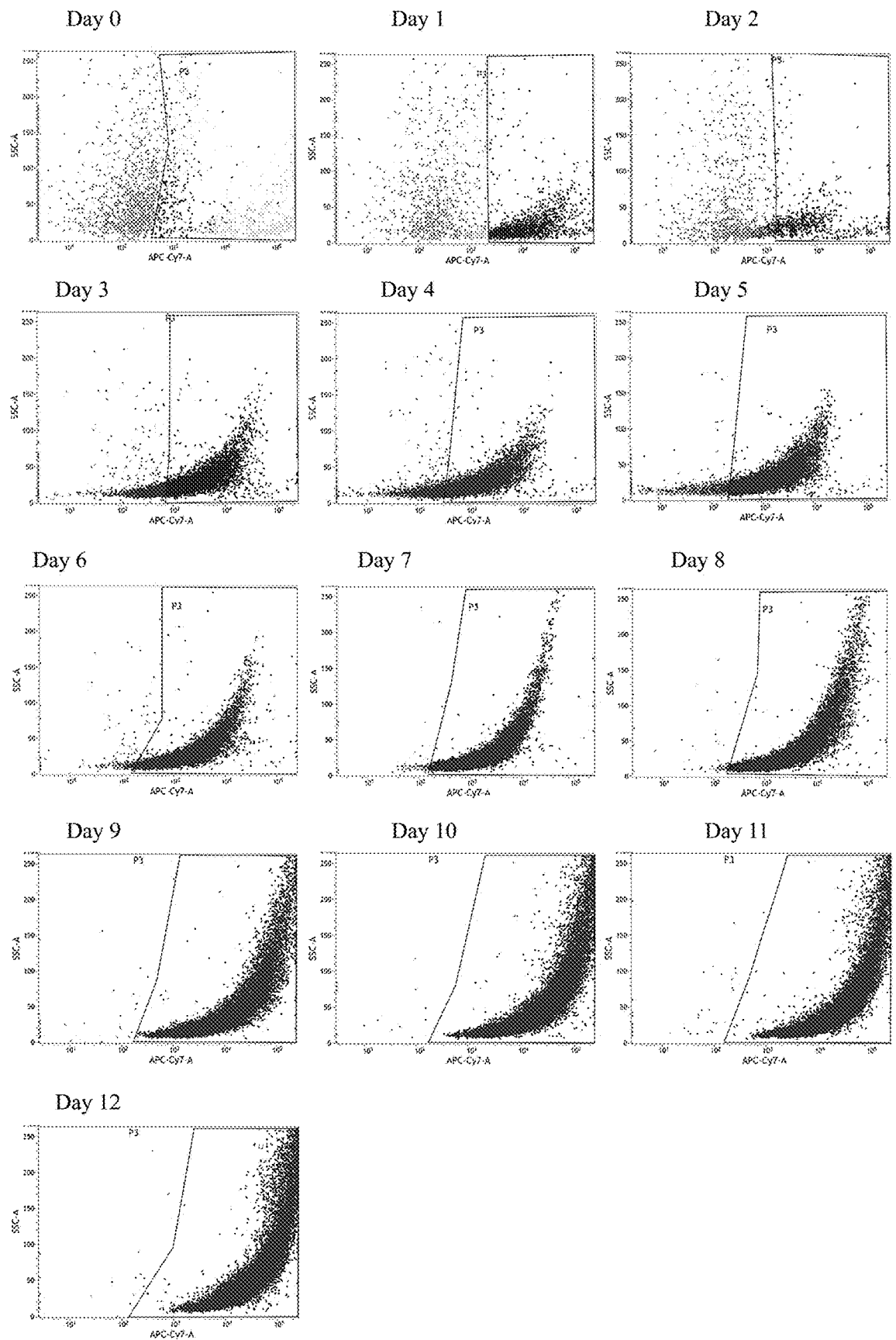
FIG. 107—CD117+-PECy7/CD45+/7-AAD− of P population from day 0 to day 12.
Figure 108:
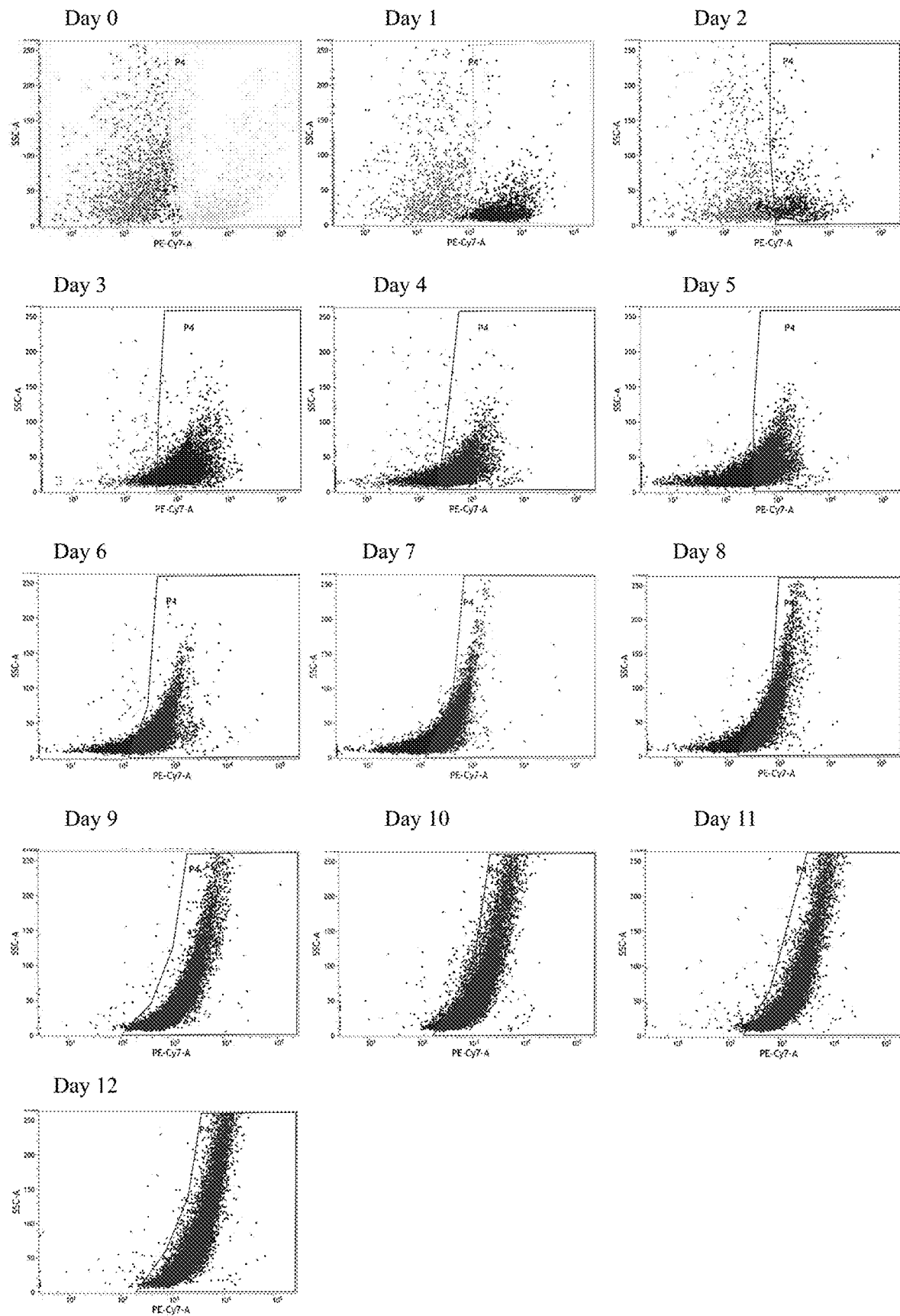
FIG. 108—Sca-1-APCCy7/CD45+/7-AAD− of P population from day 0 to day 12.
Figure 110:
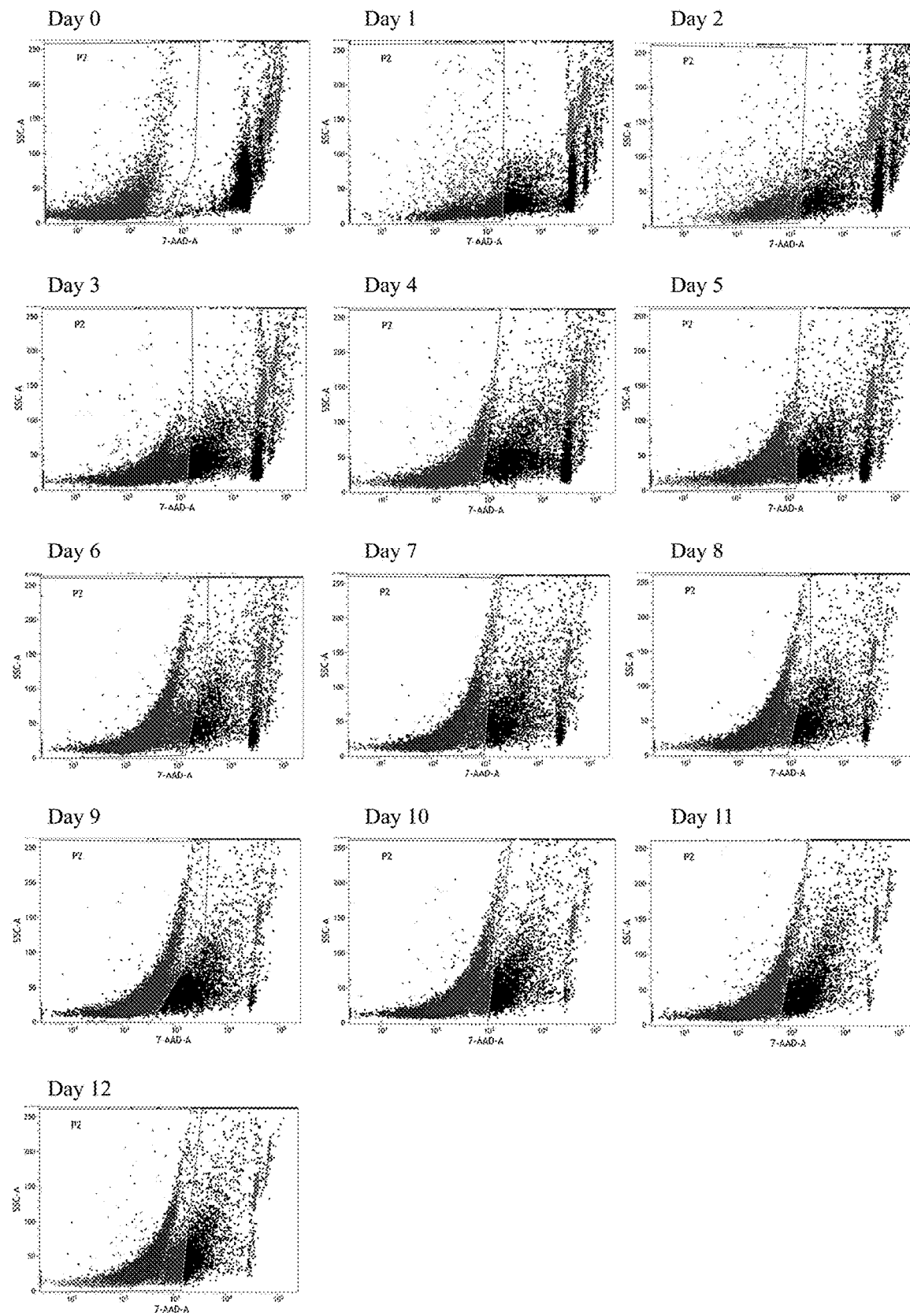
FIG. 110—CD45-FITC/7-AAD− of L population from day 0 to day 12.
Figure 111:
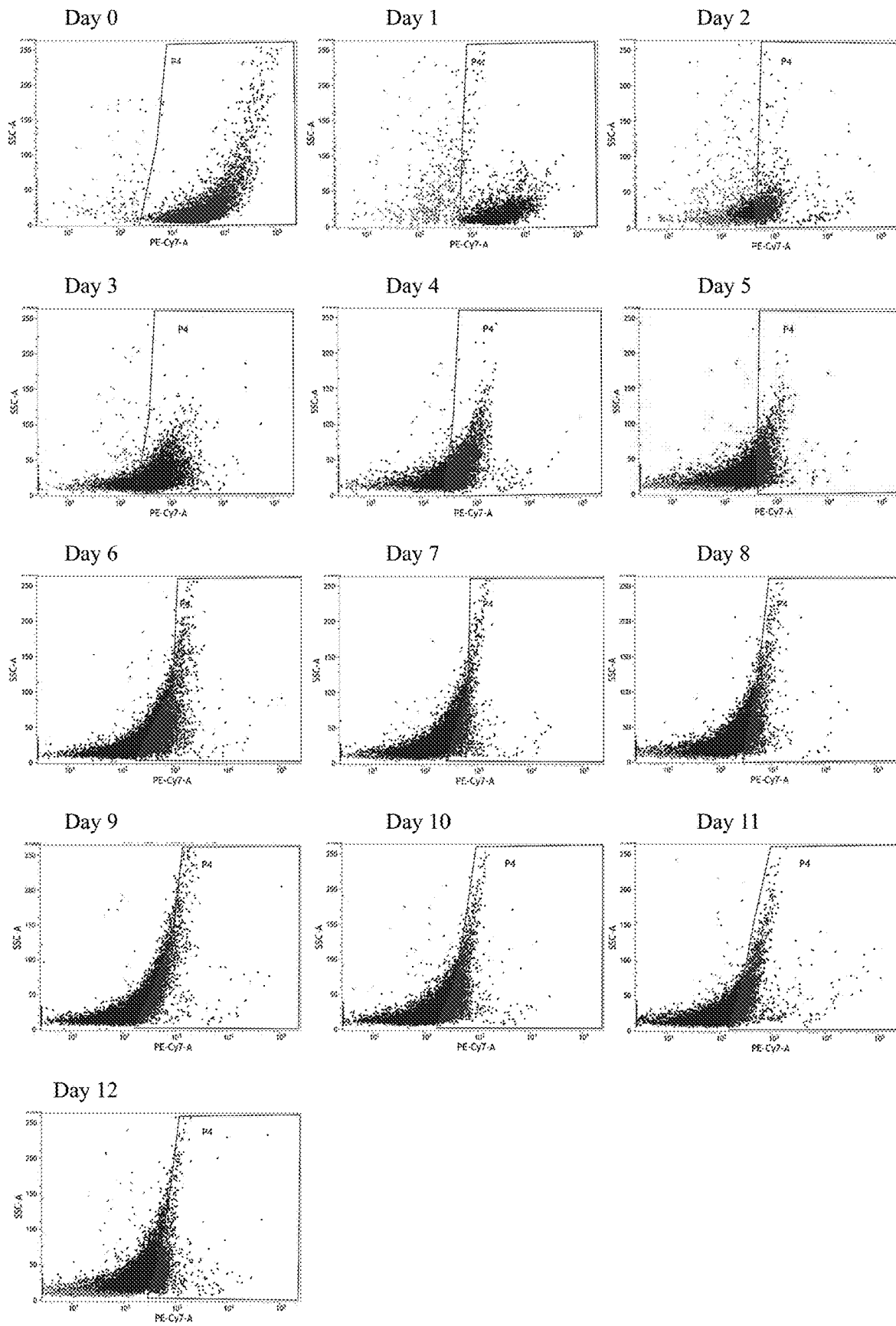
FIG. 111—CD117+-PECy7/CD45+/7-AAD− of L population from day 0 to day 12.
Figure 112:
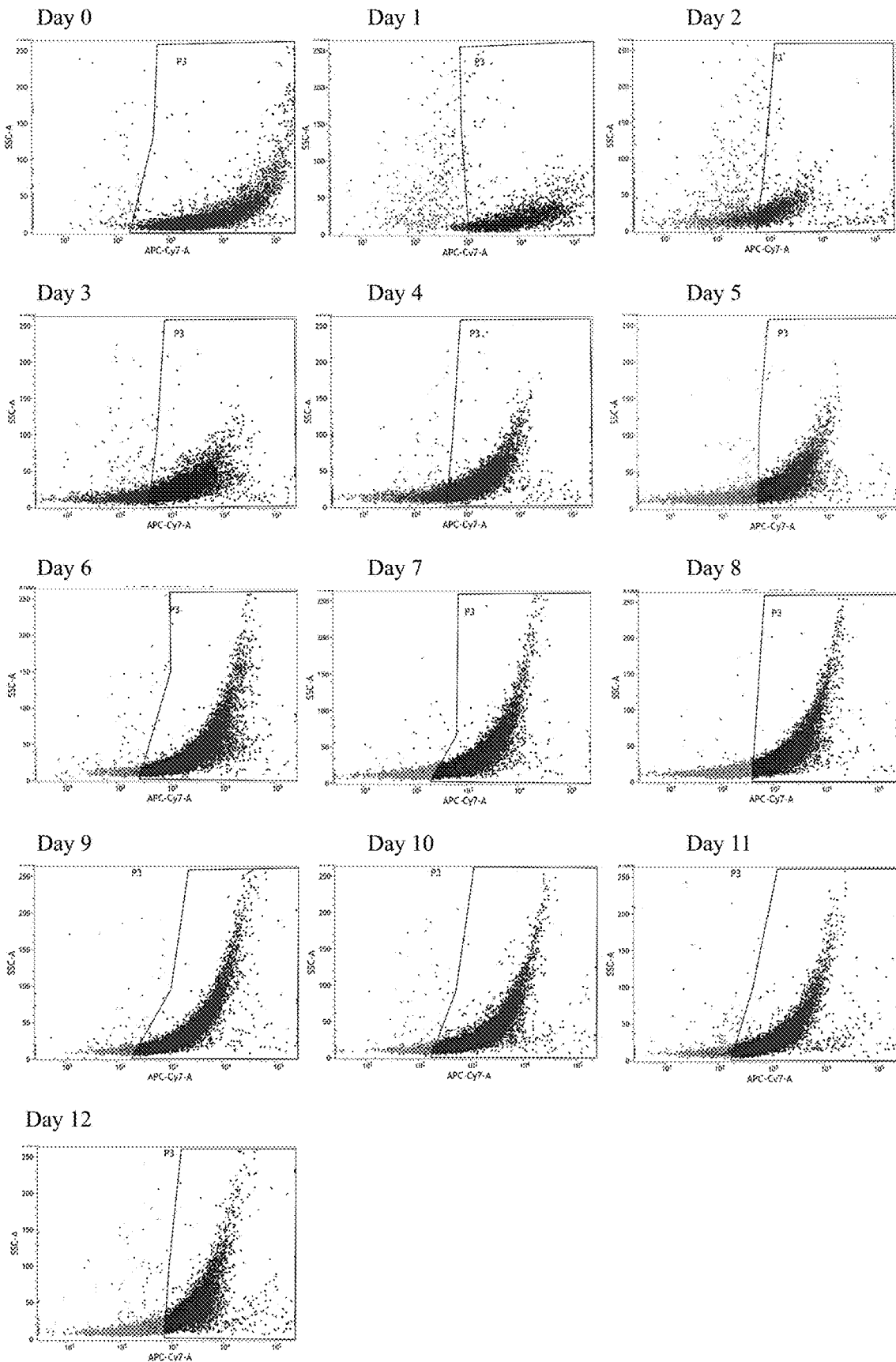
FIG. 112—Sca-1-APCCy7/CD45+/7-AAD− of L population from day 0 to day 12.

In the results of trans-differentiation, MLPC cells exhibited multi-differentiation potentials forming the three germ layers, endoderm, ectoderm and mesoderm lineages. In ATA6 vs. A0 microarray data, ATA6 cells significantly show 11 genes of up regulation and 25 genes of down regulation for hematopoietic cell lineage (p value: 2.39E-03) (FIG. 53).

11 genes of ATA6 cells included FCER2, CD1D, ITGAM, CSF1, CSF1R, CD59, IL2RA, CD38, IL3RA, IL6, and CD1B, showed positive regulation of mononuclear, leukocyte, lymphocyte, and T cell proliferation (p value<6.68E-04), immune response, antigen processing and presentation (p value<5.30E-03) by STRING database network analysis. These genes involved cytokine-cytokine receptor interaction, PI3K-Akt signaling pathway, Jak-STAT signaling pathway regulation (pathways p value<3.79E-03).

In summary PA6 vs. A0 results of microarray data by KEGG analysis as following, we list significantly regulated genes of pathways from Table 6 to Table 26. The involved genes were shown from FIG. 24 to FIG. 43 for every significant pathway.

In summary ATA6 vs. A0 results of microarray data by KEGG analysis as following, we list significantly regulated genes of pathways from Table 27 to Table 55. The involved genes were shown from FIG. 52 to FIG. 79 for every significant pathway.

In summary UATA6 vs. A0 results of microarray data by KEGG analysis as following, we list significantly regulated genes of pathways from Table 56 to Table 79. The involved genes were shown from FIG. 80 to FIG. 102 for every significant pathway. FIGS. 103 and 104 show differences in markers between MLPC and Leukocytes.

Example 2

Method of Producing MLPC from a Heterogenoeus Leukocyte Sample
1. Blood Sample

Approximately 250±30 mL of peripheral blood was taken from a patient and collected in a blood bag.
2. Separation Within 12 hours of collection, 250±30 ml of blood was separated using the closed tubing Spectra Optia® Apheresis System which uses a continuous-flow centrifuge and optical detection technology. A heterogeneous leukocyte sample was isolated. The separation method yields a fairly consistent recovery rate for each cell type. The sample included a minor proportion of red blood cells, typically less than 10% of the original amount of red blood cells in the blood sample.
3. Culturing The collected leucoytes were transferred via a closed system to a gas permeable culture bag and 50-100 mL of Nutriflex® peri solution and 25-50 mL 20% Human Serum Albumin was added. The final cell culture volume was up to 275-450 mL at a cell concentration of approximately $2.2 \times 10^5$-$3.6 \times 10^5$ cells/ml. In some cases, the plasma portion containing platelets were used as a diluent to achieve the preferred cell concentration and suspension viscosity.

The leukocyte culture was incubated for approximately 6 days at substantially 37° C. with 5% $CO_2$ and 90% relative humidity.
4. Harvesting After incubation the cells were removed and transferred into an infusion bag via a closed system. The culture bag was washed with 100 ml of 0.9% sodium chloride to ensure all adhered cells were removed.

A 5 ml sample of the resuspended cells was taken for identity and composition testing to determine the cell counts in each sample. The following test results were achieved for the sample. Approximately $1 \times 10^8$ cells were resuspended and of these approximately 48% were de-differentiated cells. The percentage of de-differentiated cells can vary between 12% and 70% and are more typically between 30% and 60%.

| Parameter | Specification | Test method |
|---|---|---|
| Viability | >60% Viable leukocytes including AMPC | Flow cytometry |
| Total CD45+ Cell Count | Approx. $1 \times 10^8$ cells (0.5-5 × $10^8$)/ 275-450 mL | Flow cytometry |
| Identification | Higher expression of CD34+ cells post-culture compared to pre-culture | Flow cytometry CD34markers |
| Impurities (non-leukocyte viable cells) | RBC recovery rate <6% | Haemocytometer |
| Total viable and total viable aerobic count | <1 CFR/100 μL | Biotest laboratories |
| Microbial growth | Not detected | British Pharmacopoeia |
| Endotoxin | <6 EU/mL | British Pharmacopoeia |
| Mycoplasma | Negative | Microgenetix laboratories (RT-PCR) |

5. In a further step, the cell suspension containing the de-differentiated cells were intravenously reintroduced to the patient.

Example 3

MLPC Production from a Heterogenous Leukocyte Suspension from a Blood Sample from an Individual To analyze the changes of CD117 and Sca-1 proteins expression from the day 0 to the day 12 culture process of peripheral blood derived Autologous Multilineage Potential Cells (AMPC). Expression of CD117 and Sca-1 proteins occurs only in pluripotent stem cells (ie. MLPC). Expression of 7-AAD$^-$ indicates whether the cell is alive and CD45+ is a lymphocyte marker.
Methods Approximately 350 ml of peripheral blood was collected from volunteer. The sample was separated from peripheral blood under ASCT's standard operating procedure (SOP), named AMPC (P), contained monocytes, lymphocytes, granulocytes and RBC. Another sample was the red blood cells of AMPC were removed by CD45 MicroBeads (MACS), named leukocyte (L), contained monocytes, lymphocytes, granulocytes. P and L samples were culture under ASCT's SOP.

P and L samples were respectively obtained respectively from the day 0 to the day 12 and were selected by CD45 MicroBeads. Then sampling cells were fixed by cooling 75% ethanol solution and stored on -20° C. until flow cytometry analysis. CD117 and Sca-1 proteins were analyzed by FACSVerse and normalized by Turcount™.
Results

TABLE 3.1

CD45+/7-AAD$^-$, CD117$^+$-PECy7 and Sca-1-APCCy7 cell numbers of P (Leukocytes and red blood cells) from the day 0 to the day 12

| Day | CD45+/7-AAD$^-$ ($\times 10^4$/ml) | CD117$^+$/CD45+/ 7-AAD$^-$ ($\times 10^4$/ml) | Sca-1+/CD45+/ 7-AAD$^-$ ($\times 10^4$/ml) |
|---|---|---|---|
| Day 0 | 0.49 ± 0.16 | 0.11 ± 0.01 | 0.14 ± 0.01 |
| Day 1 | 0.46 ± 0.13 | 0.26 ± 0.07 | 0.24 ± 0.06 |
| Day 2 | 0.63 ± 0.04 | 0.19 ± 0.02 | 0.19 ± 0.01 |
| Day 3 | 8.39 ± 0.07 | 6.79 ± 0.07 | 6.19 ± 0.25 |
| Day 4 | 9.06 ± 0.35 | 6.77 ± 0.32 | 7.53 ± 0.35 |

TABLE 3.1-continued

CD45+/7-AAD−, CD117+-PECy7 and Sca-1-APCCy7 cell numbers of P (Leukocytes and red blood cells) from the day 0 to the day 12

| Day | CD45+/7-AAD− (×10⁴/ml) | CD117+/CD45+/ 7-AAD− (×10⁴/ml) | Sca-1+/CD45+/ 7-AAD− (×10⁴/ml) |
|---|---|---|---|
| Day 5 | 26.00 ± 0.42 | 11.10 ± 0.48 | 21.30 ± 0.86 |
| Day 6 | 26.20 ± 0.45 | 20.60 ± 0.82 | 25.80 ± 0.39 |
| Day 7 | 102.00 ± 1.57 | 58.20 ± 0.96 | 101.00 ± 1.58 |
| Day 8 | 91.00 ± 1.47 | 58.10 ± 1.62 | 90.20 ± 1.65 |
| Day 9 | 115.00 ± 5.04 | 115.00 ± 5.01 | 115.00 ± 5.02 |
| Day 10 | 113.00 ± 5.58 | 111.00 ± 6.65 | 113.00 ± 5.39 |
| Day 11 | 96.90 ± 0.61 | 95.90 ± 0.56 | 96.70 ± 0.68 |
| Day 12 | 113.00 ± 1.62 | 112.00 ± 2.51 | 113.00 ± 2.09 |

TABLE 3.2

CD45+/7-AAD−, CD117+-PECy7 and Sca-1-APCCy7 growth ratio of P from the day 0 to the day 12

| Day | CD45+/7-AAD− | CD117+/CD45+/ 7-AAD− | Sca-1+/CD45+/ 7-AAD− |
|---|---|---|---|
| Day 0 | 1.00 | 1.00 | 1.00 |
| Day 1 | 0.95 | 2.39 | 1.69 |
| Day 2 | 1.29 | 1.77 | 1.35 |
| Day 3 | 17.30 | 62.91 | 43.21 |
| Day 4 | 18.67 | 62.68 | 52.60 |
| Day 5 | 53.61 | 102.84 | 149.05 |
| Day 6 | 54.00 | 190.60 | 180.58 |
| Day 7 | 209.29 | 539.17 | 703.55 |
| Day 8 | 187.63 | 537.99 | 629.96 |
| Day 9 | 237.29 | 1060.88 | 802.21 |
| Day 10 | 232.80 | 1024.66 | 786.85 |
| Day 11 | 199.66 | 887.96 | 675.41 |
| Day 12 | 233.49 | 1038.62 | 787.97 |

TABLE 3.3

CD45+/7-AAD−, CD117+-PECy7 and Sca-1-APCCy7 cell numbers of L from the day 0 to the day 12

| Day | CD45+/7-AAD− (×10⁴/ml) | CD117+/CD45+/ 7-AAD− (×10⁴/ml) | Sca-1+/CD45+/ 7-AAD− (×10⁴/ml) |
|---|---|---|---|
| Day 0 | 2.77 ± 0.18 | 2.71 ± 0.17 | 2.66 ± 0.22 |
| Day 1 | 0.30 ± 0.05 | 0.24 ± 0.38 | 0.23 ± 0.04 |
| Day 2 | 0.33 ± 0.10 | 0.09 ± 0.05 | 0.14 ± 0.03 |
| Day 3 | 3.51 ± 0.16 | 2.57 ± 0.18 | 2.49 ± 0.23 |
| Day 4 | 4.35 ± 0.05 | 2.15 ± 0.10 | 2.32 ± 0.52 |
| Day 5 | 8.25 ± 0.43 | 1.12 ± 0.04 | 3.25 ± 0.92 |
| Day 6 | 12.60 ± 0.31 | 4.44 ± 0.15 | 11.40 ± 0.26 |
| Day 7 | 21.10 ± 0.36 | 1.68 ± 0.23 | 16.10 ± 2.58 |
| Day 8 | 19.80 ± 4.25 | 2.22 ± 0.21 | 13.80 ± 1.35 |
| Day 9 | 13.20 ± 0.34 | 2.63 ± 0.02 | 12.00 ± 0.53 |
| Day 10 | 11.10 ± 0.42 | 3.23 ± 1.01 | 10.40 ± 0.54 |
| Day 11 | 8.58 ± 1.03 | 2.03 ± 0.13 | 7.75 ± 0.30 |
| Day 12 | 9.67 ± 0.56 | 0.90 ± 0.07 | 4.86 ± 0.09 |

TABLE 3.4

CD45+/7-AAD−, CD117+-PECy7 and Sca-1-APCCy7 growth ratio of L from the day 0 to the day 12

| Day | CD45+/7-AAD− | CD117+/CD45+/ 7-AAD− | Sca-1+/CD45+/ 7-AAD− |
|---|---|---|---|
| Day 0 | 1.00 | 1.00 | 1.00 |
| Day 1 | 0.11 | 0.09 | 0.09 |
| Day 2 | 0.12 | 0.03 | 0.05 |
| Day 3 | 1.27 | 0.95 | 0.94 |
| Day 4 | 1.57 | 0.79 | 0.87 |
| Day 5 | 2.98 | 0.41 | 1.23 |
| Day 6 | 4.54 | 1.64 | 4.29 |
| Day 7 | 7.62 | 0.62 | 6.05 |
| Day 8 | 7.14 | 0.82 | 5.19 |
| Day 9 | 4.77 | 0.97 | 4.53 |
| Day 10 | 4.00 | 1.19 | 3.93 |
| Day 11 | 0.43 | 0.91 | 0.56 |
| Day 12 | 3.49 | 0.33 | 1.83 |

FIGS. 105 to 112 show further results.

The results suggest that the majority of live leukocytes are de-differentiated to MLPC. The results suggest that the best days of incubation for de-differentiation are days 7 to 12. The results also suggest that without the presence of red blood cells (sample L) the de-differentiation to MLPC is reduced.

Example 4

MLPC Production with and without the Presence of Red Blood Cells

The experiments measured the difference in MLPC production where the leukocyte sample N69P contained red blood cells and the leukocyte sample N69L did not contain red blood cells.

Method

Approximately 350 mL of peripheral blood was collected and the sample was processed in a K5B cell separator. One third of the processed sample was cultured to protocol at a ratio of 70% K5B product+30% NP. This sample was labelled N69P, containing monocytes, lymphocytes, granulocytes, and erythrocytes.

The remaining two thirds of the processed sample was centrifuged at 3,000 rpm for 15 minutes, the pellet washed with PBS twice, and then resuspended in add 3 mL of PBS. CD45+ cells were then isolated from the resuspension with CD45 MicroBeads and the CD45+ cells isolate was cultured according to protocol at a ratio of 70% plasma+30% NP+CD45 isolate. This sample was labelled N69L, containing monocytes, lymphocytes, and granulocytes.

White blood cell counts and survival rates were analysed by flow cytometry on days 0, 6, and 7. Additionally, the white blood cell differential, red blood cells, and platelets were sent for cell count analysis at an external laboratory.

Results

TABLE 4.1

Cell counts of the N69P sample on days 0, 6, and 7 analysed by flow cytometry.

| Test Item | 0-day Culture (×10⁶) | 6-day Culture (×10⁶) | 7-day Culture (×10⁶) |
|---|---|---|---|
| CD45+ | 124 ± 1.64 | 103 ± 3.86 | 108 ± 11.2 |
| 7-AAD−CD45+ (Survival Rate) | 122 ± 1.86 (100%) | 87.8 ± 4.31 (72%) | 88.8 ± 8.96 (82%) |
| 7-AAD+CD45+ | 2.2 ± 0.24 | 15.6 ± 1.41 | 18.7 ± 2.37 |
| CD3+7-AAD−CD45+ | 93 ± 1.55 | 74.4 ± 5.04 | 80.9 ± 8.53 |
| CD14+7-AAD−CD45+ | 9.0 ± 1.00 | 1.95 ± 0.29 | 1.55 ± 0.08 |
| CD66abce+7-AAD−CD45+ | 77 ± 3.26 | 12.3 ± 0.374 | 19.6 ± 3.81 |

TABLE 4.2

White blood cell differential, red blood cell count, and platelet count of N69P analysed by external laboratory.

|  | Day 0 | Day 3 | Day 4 | Day 5 | Day 6 | Day 7 |
|---|---|---|---|---|---|---|
| WBC | 2.01E+08 | 1.42E+08 | 1.23E+08 | 1.10E+08 | 1.09E+08 | 9.44E+07 |
| Neutrophils | 2.71E+07 | 6.71E+07 | 6.41E+07 | 7.52E+07 | 8.89E+07 | 8.72E+07 |
| Lymphocytes | 1.50E+08 | 6.96E+07 | 5.52E+07 | 3.20E+07 | 1.60E+07 | 6.42E+06 |
| Monocytes | 2.41E+07 | 4.84E+06 | 3.20E+06 | 2.42E+06 | 3.16E+06 | 7.55E+05 |
| Eosinophils | 1.00E+00 | 8.54E+05 | 7.39E+05 | 7.73E+05 | 7.62E+05 | 0.00E+00 |
| Basophils | 1.00E+00 | 0.00E+00 | 0.00E+00 | 0.00E+00 | 0.00E+00 | 0.00E+00 |
| RBC | 2.64E+10 | 2.72E+10 | 2.64E+10 | 2.72E+10 | 2.56E+10 | 2.64E+10 |
| Platelet Count | 1.26E+10 | 9.36E+09 | 9.68E+09 | 8.48E+09 | 6.16E+09 | 4.64E+09 |

TABLE 4.3

Survival rates of cells of different subgroups in the N69P sample analysed by external laboratory.

|  | Day 3 (%) | Day 4 (%) | Day 5 (%) | Day 6 (%) | Day 7 (%) |
|---|---|---|---|---|---|
| WBC | 71 | 61 | 55 | 54 | 47 |
| Neutrophils | 247 | 236 | 277 | 328 | 322 |
| Lymphocytes | 47 | 37 | 21 | 11 | 4 |
| Monocytes | 20 | 13 | 10 | 13 | 3 |
| Eosinophils | 8.53E+05 | 7.39E+05 | 7.73E+05 | 7.62E+05 | 0 |
| Basophils | 0 | 0 | 0 | 0 | 0 |
| RBC | 103 | 100 | 103 | 97 | 100 |
| Platelet Count | 74 | 77 | 67 | 49 | 37 |

TABLE 4.4

Leukocyte composition of N69P sample on each day of culture analysed by external laboratory.

|  | Day 0 WBC Population (%) | Day 3 WBC Population (%) | Day 4 WBC Population (%) | Day 5 WBC Population (%) | Day 6 WBC Population (%) |
|---|---|---|---|---|---|
| WBC | 100 | 100 | 100 | 100 | 100 |
| Neutrophils | 13.5 | 47.1 | 52.0 | 68.1 | 81.7 |
| Lymphocytes | 74.5 | 48.9 | 44.8 | 29.0 | 14.7 |
| Monocytes | 12.0 | 3.4 | 2.6 | 2.2 | 2.9 |
| Eosinophils | 0.0 | 0.6 | 0.6 | 0.7 | 0.7 |
| Basophils | 0.0 | 0.0 | 0.0 | 0.0 | 0.0 |
| RBC | — | — | — | — | — |
| Platelet Count | — | — | — | — | — |

TABLE 4.5

Cell counts of the N69L sample on days 0, 6, and 7 analysed by flow cytometry (text in red indicates survival rate).

| Test Item | 0-day Culture (×10⁶) | 6-day Culture (×10⁶) | 7-day Culture (×10⁶) |
|---|---|---|---|
| CD45$^+$ | 115 ± 3.07 | 29.6 ± 0.32 | 28.6 ± 0.75 |
| 7-AAD$^-$CD45$^+$ (Survival Rate) | 91 ± 3.75 (100%) | 18.7 ± 0.24 (63%) | 19.6 ± 0.47 (68%) |
| 7-AAD$^+$CD45$^+$ | 25 ± 0.68 | 10.9 ± 0.10 | 8.99 ± 0.48 |
| CD3$^+$7-AAD$^-$CD45$^+$ | 84 ± 3.44 | 16.4 ± 0.26 | 14.8 ± 0.41 |
| CD14$^+$7-AAD$^-$CD45$^+$ | 21 ± 0.89 | 0.38 ± 0.09 | 0.34 ± 0.03 |
| CD66abce$^+$7-AAD$^-$CD45$^+$ | 48 ± 1.48 | 0.40 ± 0.05 | 1.55 ± 0.04 |

TABLE 4.6

White blood cell differential, red blood cell count, and platelet count of N69L analysed by external laboratory.

|  | Day 0 | Day 3 | Day 4 | Day 5 | Day 6 | Day 7 |
|---|---|---|---|---|---|---|
| WBC | 2.92E+08 | 4.64E+07 | 3.12E+07 | 3.68E+07 | 2.56E+07 | 2.72E+07 |
| Neutrophils | 6.54E+07 | 2.64E+07 | 2.48E+07 | 3.04E+07 | 2.24E_07 | 2.48E+07 |
| Lymphocytes | 1.92E_08 | 0.00E+00 | 0.00E+00 | 0.00E+00 | 0.00E+00 | 0.00E+00 |
| Monocytes | 3.45E+07 | 1.92E+07 | 5.58E+06 | 5.59E+06 | 3.20E+06 | 2.39E+06 |
| Eosinophils | 1.00E+00 | 7.89E+05 | 8.11E+05 | 8.10E+05 | 0.00E+00 | 0.00E+00 |
| Basophils | 0.00E+00 | 0.00E+00 | 0.00E+00 | 0.00E+00 | 0.00E+00 | 0.00E+00 |
| RBC | 0.00E+00 | 0.00E+00 | 0.00E+00 | 0.00E+00 | 0.00E+00 | 0.00E+00 |
| Platelet Count | 6.64E+09 | 3.20E+09 | 3.28E+09 | 3.20E+09 | 2.72E+09 | 2.56E+09 |

TABLE 4.7

Survival rates of cells of different subgroups in the N69L sample analysed by external laboratory.

|  | Day 3 (%) | Day 4 (%) | Day 5 (%) | Day 6 (%) | Day 7 (%) |
|---|---|---|---|---|---|
| WBC | 16 | 11 | 13 | 9 | 9 |
| Neutrophils | 40 | 38 | 46 | 34 | 38 |
| Lymphocytes | 0 | 0 | 0 | 0 | 0 |
| Monocytes | 56 | 16 | 16 | 9 | 7 |
| Eosinophils | 7.89E+05 | 8.11E+05 | 8.10E+05 | 0.00E+00 | 0 |
| Basophils | 0 | 0 | 0 | 0 | 0 |
| RBC | 0 | 0 | 0 | 0 | 0 |
| Platelet Count | 48 | 49 | 48 | 41 | 39 |

TABLE 4.8

Cell composition of N69L sample on each day of culture analysed by external laboratory.

|  | Day 0 WBC Population (%) | Day 3 WBC Population (%) | Day 4 WBC Population (%) | Day 5 WBC Population (%) | Day 6 WBC Population (%) |
|---|---|---|---|---|---|
| WBC | 100 | 100 | 100 | 100 | 100 |
| Neutrophils | 22.4 | 56.9 | 79.5 | 82.6 | 87.5 |
| Lymphocytes | 65.8 | 0.0 | 0.0 | 0.0 | 0.0 |
| Monocytes | 11.8 | 41.4 | 17.9 | 15.2 | 12.5 |
| Eosinophils | 0.0 | 1.7 | 2.6 | 2.2 | 0.0 |
| Basophils | 0.0 | 0.0 | 0.0 | 0.0 | 0.0 |
| RBC | — | — | — | — | — |
| Platelet Count | — | — | — | — | — |

The results suggest that in the presence of red blood cells, comparatively more neutrophils, lymphocytes, monocytes and basophils survived the de-differentiation process and more were de-differentiated to MLPC than a those in a similar sample which did not include red blood cells.

Example 5

Analysis of Pluripotency Gene Expression Over 6 Day AMPC Culture of Peripheral Blood Via Quantitative Real-Time Polymerase Chain Reaction The aim was to determine the changes of POU5F1 (oct4), sox-2, and nanog gene expression during the de-differentiation process of peripheral blood derived Autologous Multilineage Potential Cells (AMPC) where the blood was taken from two different individuals. The genes oct4, sox-2, and nanog are three pluripotency genes and are expressed by de-differentiated cells.

Methods

Approximately 120 ml of peripheral blood was collected from two different volunteers (sample 1 and sample 2). The leukocytes were separated from peripheral blood under ASCT's standard operating procedure. During AMPC culture periods, samples were obtained on day 0, day 3, day 4, day 5, and day 6 for qRT-PCR analysis.

To prepare the RNA extraction of samples, the red blood cells were lysed and dissolved into 1 ml Trizol™ reagent, then stored at −80° C. immediately. To normalize target genes expression of POU5F1 (oct4), sox-2, and nanog, actb was used as a reference gene. The day 0 sample was blank while the day 3, day 4, day 5, and day 6 samples were used as treatments. The changes in RNA expression were primarily analyzed by quantitative real-time polymerase chain reaction (qRT-PCR).

For reverse transcription of RNA, 2 μg of total RNA and ABI High-Capacity cDNA reverse transcription kits were used according to tables 5.1 and 5.2. The reaction condition was specified as the following: 25° C. for 10 min, 37° C. for 120 min, 85° C. for 5 min, then kept at 4° C.

For quantitative PCR, 20 μl RT products were diluted with 80 μl nuclease-free H2O to generate 5×-dilution RT products (20 ng/μl). Each reaction included 20 ng cDNA, 500 nM of forward and reverse primers, and BioRad iQ™ SYBR® Green Supermix (BioRad, 1708880). 10 μl reaction volumes were used according to the table below:

| SYBR® Green Supermix | Nuclease-free water | 5X-dilution RT product (20 ng/μl) | F + R primer (10 μM) | Total volume |
|---|---|---|---|---|
| 5.8 μl | 2.2 μl | 1 μl | 1 μl | 10 μl |

Each sample was tested in triplicate. A BIO-RAD CFX Connect real-time PCR machine was used with the following program: (95° C. for 20 sec), and 39 cycles (95° C. for 5 sec, 60° C. for 30 sec). BIO-RAD CFX Manager Version 3.0 software was used for experimental setup and data analysis. Target gene qPCR data were normalized to a reference gene actb.

TABLE 5.1

| Total RNA | 10 RT Buffer | dNTP Mix (100 mM) | RT Random Primers | Multi-Scribe™ Reverse Transcriptase | Total volume |
|---|---|---|---|---|---|
| 2 μg RNA in 14.2 μl nuclease-free H₂O | 2 μl | 0.8 μl | 2 μl | 1 μl | 20 μl |

Results

The results are shown in FIGS. 113 to 126.

Fold changes were relative to the control group to easily determine the degree of up- or down-regulation in the treatment group. The actb was the reference gene, day 0 sample (leukocytes) was used as the control, and samples of the remaining time points (AMPC) were used as treatments.

In summary the blood taken from different individuals showed a different MLPC profile after a blood sample had undergone the de-differentiation process. However high levels of de-differentiation appeared to occur on day 6 of incubation.

Example 6

Effect of Different Ratios of Leukoctye Subtypes in the Culture to Produce Autologous Multi-Lineage Potential Cells (AMPC)

Part 6.1: Analysis of Pluripotency Gene Expression Over 8 Day AMPC Culture of Granulocyte-Reduced, Lymphocyte and Monocyte Mixture via Quantitative Real-Time Polymerase Chain Reaction The aim was to determine the effect of a granulocyte-reduced, lymphocyte and monocyte mixture during the culture of Autologous Multilineage Potential Cells in expression of POU5F1 (oct4), sox-2, and nanog gene. The genes oct4, sox-2, and nanog are three pluripotency genes and are expressed by de-differentiated cells.

The expression pattern of pluripotency gene of leukocytes during AMPC culture showed similar expression patterns at different magnitudes for all three pluripotency genes oct4, sox-2, and nanog with the strongest expression of each gene on day 6 of AMPC culture. As AMPC cultures were produced from mixed leukocyte populations, the current example looked at the effect of reducing the population of a single leukocyte subtype to determine the effect on pluripotency gene expression. The results of using a granulocyte-reduced sample via Ficoll reagent compared with the results of a mixed leukocyte population in the production of an AMPC culture are provided below.

Methods

Approximately 300 ml of peripheral blood was collected from one male volunteer (N64). The leukocytes were separated and culture from peripheral blood under ASCT's standard operating procedure (SOP).

Approximately 40% of leukocytes were cultured directly on a 290AC bag, the product was named Sample 1 (A). In the remaining 60% of the sample, the lymphocytes and monocytes were isolated by Ficoll® reagent and the isolated cells were also cultured on 32AC bag. The product was named Sample 2 (F).

Samples from 1 (A) were retrieved on day 0, day 3, day 4, day 5, day 6, day, 7 and day 8 for qRT-PCR analysis. Samples were also retrieved from 2 (F) on day 0, day 3, day 4, day 5, and day 6 for qRT-PCR analysis.

To prepare RNA extraction of samples, the red blood cells were lysed and dissolved into 1 ml Trizol™ reagent, then stored at −80° C. immediately. For normalize target genes expression of POU5F1 (oct4), sox-2, and nanog, the actb was used as a reference gene. The day 0 was as blank, the day 3, day 4, day 5, day 6, 7, and day 8 were as treatments. The changes in RNA expression were primarily analyzed by quantitative real-time polymerase chain reaction (qRT-PCR).

For reverse transcription of RNA, 2 µg of total RNA was used by using ABI High-Capacity cDNA reverse transcription Kits. The reaction condition was performed with the following program: 25° C.→10 min, 37° C.→120 min, 85° C.→5 min, 4° C.→∞.

With Quantitative PCR, 20 µl RT products were diluted with 80 µl nuclease-free H$_2$O to generate 5×-dilution RT products (20 ng/µl). Each reaction included 20 ng cDNA, 500 nM of forward and reverse primers, and BioRad iQ™ SYBR® Green Supermix (BioRad, 1708880). 10 µl reaction volumes were used according to the table 6.1 below:

TABLE 6.1

| SYBR® Green Supermix | nuclease-free water | 5X-dilution RT product (20 ng/µl) | F + R primer (10 µM) | Total volume |
|---|---|---|---|---|
| 5.8 µl | 2.2 µl | 1 µl | 1 µl | 10 µl |

Each sample was tested in triplicate. A BIO-RAD CFX Connect real-time PCR machine was used with the following program: (95° C.→20 sec), and 39 cycles (95° C.→5 sec, 60° C.→30 sec). With data analysis, BIO-RAD CFX Manager Version 3.0 software was used for experimental setup and data analysis. Target gene qPCR data were normalized to a reference gene.

Results

Sample 1A were a mixed population of leukocytes and Sample 2F was a sample of lymphocytes and monocytes (without granulocytes).

Fold changes were relative to the control group to easily determine the degree of up- or down-regulation in the treatment group. The actb was as a reference gene, Day 0 sample (leukocytes) as a control and various day's sample (AMPC) as treatments.

With regard to the fold change (and thus pluripotency activity), sample 1 (unmodified leukocyte sample) showed activity on day 4 for oct4, sox-2, and nanog gene expression whereas sample 2 (granulocyte reduced leukocyte sample) showed pluripotency gene expression on each of days 3, 4, 5 and 6 for each of oct4, sox-2, and nanog genes. These results suggest that a mixed culture of different leukocytes subtypes produces AMPC profile that is different if one of the leukocyte subtypes is not present. These results suggest there is better production of MLPC when there is a substantially complete mixed leukocyte subtype from a blood sample. The melting curve data suggests that there is a specific PCR product generated from the primer and there is no non-specific amplification.

Part 6.2: Analysis of Pluripotency Gene Expression Over 7 Day AMPC Culture of a Leukocyte Mixture without Neutrophils via Quantitative Real-Time Polymerase Chain Reaction The aim was to determine the effect of a leukocyte sample lacking neutrophils during the culture of Autologous Multilineage Potential Cells in expression of POU5F1 (oct4), sox-2, and nanog gene. The genes oct4, sox-2, and nanog are three pluripotency genes and are expressed by de-differentiated cells.

Methods

Approximately 400 ml of peripheral blood was collected from a volunteer. The sample was separated from peripheral blood using standard operating procedure (SOP), and neutrophils were subsequent identified and removed from the sample by CD66abce MicroBeads (MACS). The subsequent sample, containing monocytes, lymphocytes, and RBC, was labeled N78. The final cell composition in the sample is shown in Tables 6.2 and 6.3 below:

TABLE 6.2

White blood cell (WBC) populations of N78 on Day 0

| Components | Cell numbers | Population (%)$^a$ |
|---|---|---|
| WBC | 2.46E+08 | 100% |
| Neutrophils | 2.39E+07 | 10% |
| Lymphocytes | 1.72E+08 | 70% |
| Monocytes | 5.07E+07 | 20% |
| Eosinophils | 0.00E+00 | 0% |
| Basophils | 0.00E+00 | 0% |

$^a$% = (cell numbers/WBC) × 100%

TABLE 6.3

Total blood cell population of N78 on Day 0

| Components | Cell numbers | Population (%)$^a$ |
|---|---|---|
| WBC | 2.46E+08 | 1.38% |
| Neutrophils | 2.39E+07 | 0.13% |
| Lymphocytes | 1.72E+08 | 0.96% |
| Monocytes | 5.07E+07 | 0.29% |
| Eosinophils | 0.00E+00 | 0.00% |
| Basophils | 0.00E+00 | 0.00% |

TABLE 6.3-continued

Total blood cell population of N78 on Day 0

| Components | Cell numbers | Population (%)$^a$ |
|---|---|---|
| RBC | 1.76E+10 | 98.62% |
| Total numbers | 1.78E+10 | 100% |

$^a$% = (cell numbers/total numbers) × 100%

Samples from N78 were obtained on day 0, day 3, day 4, day 5, day 6, and day 7 for qRT-PCR analysis of the oct4, sox2, and nanog gene expressions.

To prepare the RNA extraction of samples, the red blood cells were lysed and dissolved into 1 ml Trizol™ reagent, then stored at −80° C. immediately. To normalize target genes expression of POU5F1 (oct4), sox-2, and nanog, actb was used as a reference gene. The day 0 sample was used as a blank for comparison with the remaining treatment samples. The changes in RNA expression were analysed by quantitative real-time polymerase chain reaction (qRT-PCR) as per standard procedures.

Results

Fold changes were relative to the control group (day 0) for easy determination of the degree of up- or down-regulation in the treatment group. The actb gene was the reference gene, day 0 sample (leukocytes) was used as the control, and samples of the remaining time points (AMPC) were treatment groups. The expression profile of the POU5F1 (oct4), sox-2, and nanog genes was different in a leukocyte culture where neutrophils were removed compared with the expression profile of a mixed leukocyte culture (see example 5). These results confirm that a mixed culture of different leukocytes subtypes produces an AMPC profile that is different if one of the leukocyte subtypes is not present. The melting curve data suggests that there is a specific PCR product generated from the primer and there is no non-specific amplification.

Example 7

Kidney Disease Case Study: Autologous Multi-Lineage Potential Cells (AMPC) and Kidney Correlation Study A patient (male 78 years old) who had stage three kidney disease had undergone AMPC treatment. Kidney disease is categorised into five varying stages of severity, with stage one reflecting normal kidney function and stage five representing kidney failure. These stages of kidney function are measured using the estimated glomerular filtration rate (eGFR). A higher eGFR indicates better kidney function with the values of eGFR ranging from 0 to 100.

On 1 May 2013, a test was conducted on the patient that showed an eGFR of 52.5, indicating the patient to be at stage three kidney disease. Stage three kidney disease is indicative of 30% to 59% of a healthy body's kidney function. Patients at this stage require treatment to prevent further damage to the kidney. An AMPC intervention was then introduced on 7 Sep. 2013. The eGFR values were measured again on 28 Oct. 2013 and 31 Dec. 2013 to be at 57 in both instances. A second AMPC intervention was introduced on 14 Apr. 2014 and eGFR values were measured twice more on 10 Jul. 2013 and 28 Jan. 2015 to be 56.9 in both instances. A third measurement was taken nine months after the second AMPC intervention on 24 Apr. 2015 to be at an eGFR value of 62.4. This indicates an improvement of kidney function from stage three kidney disease to stage two kidney disease. Stage two kidney disease reflects approximately 60% of a healthy body's kidney function. Patients at this stage need to have their kidney functions monitored twice a year to prevent deterioration of kidney function.

| Date | Event | Estimated Glomerular Filtration Rate(eGFR) | Stage of Kidney Disease |
|---|---|---|---|
| 1 May 2013 | eGFR Measurement | 52.5 | Stage 3 |
| 7 Sep. 2013 | AMPC Intervention | | |
| 28 Oct. 2013 | eGFR Measurement | 57.0 | Stage 3 |
| 31 Dec. 2013 | eGFR Measurement | 57.0 | Stage 3 |
| 14 Apr. 2014 | AMPC Intervention | | |
| 10 Jul. 2014 | eGFR Measurement | 56.9 | Stage 3 |
| 28 Jan. 2015 | eGFR Measurement | 56.9 | Stage 3 |
| 24 Apr. 2015 | eGFR Measurement | 62.4 | Stage 2 |

The AMPC intervention administered in this example was shown to positively affect kidney function after two reinfusion procedures. Kidney function in the patient was improved after the AMPC treatments.

Example 8

Cancer Case Study: Autologous Stem Cell Treatment Via Peripheral Blood Harvest in a 35 Year Old Terminally-Ill Thymus Cancer Patient This case study is of a 35 year old male who was terminally ill with stage 4 metastatic Thymus gland cancer. The patient underwent three AMPC treatment interventions and experienced a dramatic increase in white blood cell count over a period of six months. He was injected with three rounds of autologous stem cells prepared in accordance with Example 2.

Initial pathology reports of the patient on 10 Apr. 2013 detected the presence of myelocytes in the bloodstream and lymphocyte levels of 3%, which was well below that of a standard, healthy individual. Myelocytes should not be present in the bloodstream of a healthy individual—they are precursor blood cells usually found in the bone marrow. Continual damage to the bone marrow through chemotherapy may have caused the escape of myelocytes into the bloodstream, where they will lose the ability to turn into useful blood cells.

On arrival he was wheel-chair bound, severely anemic and neutropenic. He had previously received surgical resection of his tumour and chemotherapy. His left lung was complete collapsed and there was a cardiac metastatic identified upon echo-cardiography. 250 ml of his blood was drawn via venipuncture with a 16 gauge catheter and then transported to the labs of Autologous Stem Cell Technology for the autologous conversion of stem cells.

Reinfusion of $2.3 \times 10^8$ of the patient's stem cells took place on 13 Apr. 2013. The objective of this treatment was to restore his bone marrow and strengthen his immune system which was reduced after several rounds of chemotherapy. No adverse events were noted post treatment.

After treatment, the myelocytes were no longer detected in the bloodstream on 19 Apr. 2013. Lymphocyte levels were also dramatically increased to 10%, restoring the patient's lymphocyte levels back to normal. This suggested that the patient's thymus function had improved. The high lymphocyte levels indicate that cancer cells were present and were attempted to be controlled by the increased lymphocyte production.

A second AMPC intervention was then introduced on 29 Apr. 2013 and lymphocyte levels were measured on 3 May 2013 and 10 May 2013 to have stabilised at normal levels of 5% and 6% respectively.

Post treatment, the patient was able to walk unassisted and reported an increase in appetite and an increase in energy levels.

The third and final 250 ml of blood was drawn from the patient with reinfusion of $3.6 \times 10^8$ stem cells taking place.

After 3 stem cell treatments, his hemoglobin improved to the point where he did not need to have routine packed red blood cell transfusions. His overall strength and vitality improved to the point where he could walk unassisted. His oxygen saturation was noted to be remarkably improved post stem cell treatments. He continued to improve in all pathology parameters and imaging reports from his Taiwanese doctors showed tumor regression around the heart and blood vessels. His abdominal distension from malignant ascites improved post treatment. His peripheral oedema subsequently also diminished as kidney and liver functions improved.

Example 9

Acute Myeloid Leukaemia Case Study: Autologous Multi-Lineage Potential Cells (AMPC) and Acute Myeloid Leukaemia (AML)

Acute Myeloid Leukaemia is a form of cancer characterised by the bone marrow's inability to produce normal, mature blood cells. AML is not a single disease, but rather a group of diseases caused by the same mechanisms.

In individuals with AML, the bone marrow produces white blood cells that are immature, called myeloblasts. This production occurs for prolonged periods, causing a build up of excess myeloblasts in the bone marrow. This compounds the condition further as the bone marrow function is exacerbated by the interference.

Consequently, normal blood cells cannot be produced by the bone marrow to deliver oxygen, causing even more fatigue to existing white blood cells.

Eventually, the excess myeloblasts spill into the bloodstream from the bone marrow. This is detrimental to the body as the immature myeloblasts cannot properly fight off infection. AML is essentially a positive feedback loop of harm caused to the bone marrow and immune system. Additionally, the bloodstream also provides myeloblasts access to other parts of the body, allowing the rapid spread of AML.

A patient, female aged 57, was diagnosed with AML on the August of 2011. Before the patient underwent AMPC treatment, she exhibited abnormally low white blood cell counts of $2.5 \times 1000$/UI that indicated poor immune function. Additionally, the haemoglobin level and red blood cells were also presented at 11.4 g/dL and 32% respectively, which indicated poor oxygen circulation in the body. The segmented neutrophils, which are the primary white blood cells for fighting infections, were also below the normal standard at 30%.

The patient then underwent AMPC treatment early November 2013. Approximately four months after the treatment, improvements in immune and red blood cell function were observed. The white blood cell counts were increased to $6.4 \times 1000$/UI. Improvements were also seen in haemoglobin and red blood cell levels at 13.3 g/dL and 38.3% respectively. The level of segmented neutrophils had also been restored to normal levels at 57%.

Example 10

Male Infertility Case Study: Autologous Multi-Lineage Potential Cells (AMPC) and Male Infertility A male patient, aged 45, suffered from of severe oligozoospermia in 2011 with 100% abnormal morphology on semen analysis. Further investigation revealed a high degree of sperm DNA damage (DNA fragmentation rate of 29%) and chromosome abnormality (aneuploidy rate of 33%). Several initial IVF attempts utilising intracytoplasmic sperm injection (ICSI) did not result in any ova being fertilised. The third attempt in July 2013 remained unsuccessful even after obtaining sperm via a microsurgical epididymal sperm aspiration (MESA) procedure.

The patient underwent testosterone therapy for 6 months in 2013, which resulted in complete azoospermia on sperm analysis. The cause of male infertility was completely unknown. He was also prescribed high-dose antioxidant therapy, zinc, and folic acids. Testosterone supplements were then discontinued on May 2013 and replaced with 100 mg Clomiphene daily for 3 months. He then underwent a peripheral autologous stem cell reinfusion in June 2013.

His subsequent sperm counts showed improved sperm morphology, progressive sperm motility and normal volume. He underwent a fourth IVF cycle in January 2014, where his sperm was able to fertilise 5 ova and resulted in normal day 3 eight-cell embryos. His sperm could also be thawed without complication.

Example 11

Female Infertility Case Study: Autologous Multi-Lineage Potential Cells (AMPC) and Female Infertility A female patient, aged 51, had undergone AMPC treatment for thin endometrium. Previous measurements of the lining via ultrasound showed a thickness of 4.5 mm to 5.5 mm. The patient has had a history of the condition and had undergone a series of fertility treatments including 25 stimulation cycles for IVF. She had also taken hormone medication for oestrogen and progesterone; and also medication to stimulate blood circulation to the uterus—aspirin, Clexane, and Viagra. G-CSF therapies were also sought by the patient to no significant benefit.

On 17 Apr. 2015, the patient underwent AMPC treatment along with low-dose oestrogen medication for thin endometrium. A 2 mg tablet of oestrogen was to be taken twice daily by the patient, achieving a maintenance dose of 4 mg. The endometrium thickness was then measured on 1 May 2015, on the fourteenth day of the cycle to be at 4.3 mm.

The same course of medication was continued and a second measurement was taken on 29 May 2015 which was the fourteenth day of the second menstrual cycle. The measurement of the lining was shown to be 6.2 mm.

Even though the patient had been through a series of treatments—therefore causing drastic hormonal changes to the body—the endometrial lining still showed an increase in thickness after AMPC reinfusion. This was achieved with only a low, maintenance dose of oestrogen. While the thickness of the lining remains inadequate for pregnancy, the endometrial thickness showed an increase from 4.3 mm to 6.2 mm. This thickness was only previously exceeded by the patient once with G-CSF therapy and excessive hormone medication, the outcome of which still remains unsuitable for pregnancy. The lining of the endometrium was able to achieve its highest thickness with low doses of oestrogen on the second month. These results suggest that AMPC treatment can be used to increase the thickness of the endometrium lining and assist women in being able to become pregnant.

Advantages

The multilineage potential cells of the present invention are useful in a wide range of clinical and research settings. These uses include the therapeutic or prophylactic treatment of a range of conditions either via the administration of the multilineage potential cells of the invention.

Variations

It will of course be realized that while the foregoing has been given by way of illustrative example of this invention, all such and other modifications and variations thereto as would be apparent to persons skilled in the art are deemed to fall within the broad scope and ambit of this invention as is herein set forth.

Throughout the description and claims of this specification the word "comprise" and variations of that word such as "comprises" and "comprising", are not intended to exclude other additives, components, integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

The invention claimed is:

1. A method of producing multilineage potential cells derived from a heterogeneous population of leukocyte subtypes, comprising:
separating leukocytes from red blood cells and plasma in a blood sample to form a suspension of leukocytes which comprises a heterogenous population of leukocyte subtypes;
reintroducing up to 10% of the red blood cells and the plasma to the leukocyte suspension, thereby generating a mixed cell-type suspension; and
cultivating the mixed cell-type suspension for 1 to 12 days at substantially 37° C. in a humidified incubator with between 1% to 10% $CO_2$ to form a cell suspension comprising multilineage potential cells.

2. A method of producing multilineage potential cells derived from a heterogeneous population of leukocyte subtypes, comprising:
separating leukocytes from red blood cells and plasma in a blood sample to form a suspension of leukocytes which comprise a heterogenous population of leukocyte subtypes;
reintroducing up to 10% of the red blood cells and the plasma to the leukocyte suspension, thereby generating a mixed cell-type suspension; and
cultivating the mixed cell-type suspension for 5 to 6 days at 5% $CO_2$ with 90% humidity and at substantially 37° C. in nutrient medium containing serum albumin.

3. A method as claimed in claim 1, wherein the leukocyte suspension is a heterogeneous population in relative proportions which mimics the natural in vivo differential ratios of somatic peripheral blood leukocyte subpopulations.

4. A method as claimed in claim 1, wherein the heterogeneous population of leukocytes is incubated in a plastic container that allows the leukocyte cells to adhere to its surface and the concentration of the leukocytes is at a level where the cells are able to adhere to the container.

5. A method of making a medicament for the treatment of a condition in a mammal, the method comprising using a population of multilineage potential cells, which cells have been generated in accordance with the method as claimed in claim 1.

6. A method as claimed in claim 1, wherein one or more agents are added to assist with de-differentiation to a particular phenotype and are selected from the group consisting of: osteogenic induction medium including dexamethasone, β-glycerophosphate, and ascorbic acid 2-phosphate to form osteoblasts; a co-culture induction system where induction cells secrete neural growth factors to form neuroectodermal cells; cardiomyogenic lineage induction medium including human insulin, human EGF, and human β-FGF to form cardiomyogenic cells; and a neo-hepatocyte lineage induction medium including dexamethasone, human HGF, and human β-FGF to form neo-hepatocytes.

7. A method as claimed in claim 2, wherein the leukocyte suspension is a heterogeneous population in relative proportions which mimics the natural in vivo differential ratios of somatic peripheral blood leukocyte subpopulations.

8. A method as claimed in claim 2, wherein the heterogeneous population of leukocytes is incubated in a plastic container that allows the leukocyte cells to adhere to its surface and the concentration of the leukocytes is at a level where the cells are able to adhere to the container.

9. A method as claimed in claim 2, wherein one or more agents are added to assist with de-differentiation to a particular phenotype and are selected from the group consisting of: osteogenic induction medium including dexamethasone, β-glycerophosphate, and ascorbic acid 2-phosphate to form osteoblasts; a co-culture induction system where induction cells secrete neural growth factors to form neuroectodermal cells; cardiomyogenic lineage induction medium including human insulin, human EGF, and human β-FGF to form cardiomyogenic cells; and a neo-hepatocyte lineage induction medium including dexamethasone, human HGF, and human β-FGF to form neo-hepatocytes.

* * * * *